US010925878B2

(12) United States Patent
Strum et al.

(10) Patent No.: US 10,925,878 B2
(45) Date of Patent: Feb. 23, 2021

(54) HSPC-SPARING TREATMENTS FOR RB-POSITIVE ABNORMAL CELLULAR PROLIFERATION

(71) Applicant: G1 Therapeutics, Inc., Research Triangle Park, NC (US)

(72) Inventors: Jay Copeland Strum, Hillsborough, NC (US); John Emerson Bisi, Chapel Hill, NC (US); Patrick Joseph Roberts, Durham, NC (US); Francis Xavier Tavares, Durham, NC (US)

(73) Assignee: G1 Therapeutics, Inc., Research Triangle Park, NC (US)

( * ) Notice: Subject to any disclaimer, the term of this patent is extended or adjusted under 35 U.S.C. 154(b) by 0 days.

(21) Appl. No.: 16/178,419

(22) Filed: Nov. 1, 2018

(65) Prior Publication Data

US 2019/0070185 A1 Mar. 7, 2019

Related U.S. Application Data

(63) Continuation of application No. 16/112,362, filed on Aug. 24, 2018, now Pat. No. 10,434,104, which is a continuation of application No. 15/387,083, filed on Dec. 21, 2016, now Pat. No. 10,076,523, which is a continuation of application No. 14/214,048, filed on Mar. 14, 2014, now Pat. No. 9,527,857.

(60) Provisional application No. 61/949,786, filed on Mar. 7, 2014, provisional application No. 61/911,354, filed on Dec. 3, 2013, provisional application No. 61/861,374, filed on Aug. 1, 2013, provisional application No. 61/798,772, filed on Mar. 15, 2013.

(51) Int. Cl.
| | |
|---|---|
| A61K 31/527 | (2006.01) |
| C07D 487/14 | (2006.01) |
| A61K 45/06 | (2006.01) |
| A61K 31/519 | (2006.01) |
| A61K 31/5377 | (2006.01) |
| A61P 35/04 | (2006.01) |
| A61P 35/00 | (2006.01) |
| A61K 31/555 | (2006.01) |
| A61K 31/7048 | (2006.01) |
| A61K 9/00 | (2006.01) |

(52) U.S. Cl.
CPC ......... *A61K 31/527* (2013.01); *A61K 9/0053* (2013.01); *A61K 31/519* (2013.01); *A61K 31/5377* (2013.01); *A61K 31/555* (2013.01); *A61K 31/7048* (2013.01); *A61K 45/06* (2013.01); *A61P 35/00* (2018.01); *A61P 35/04* (2018.01); *C07D 487/14* (2013.01)

(58) Field of Classification Search
CPC ............. A61K 31/519; A61K 31/5377; A61K 31/527; A61K 31/7048; A61K 31/555; A61K 9/0053; A61K 45/06; A61P 35/00; A61P 35/04; C07D 487/14
See application file for complete search history.

(56) References Cited

U.S. PATENT DOCUMENTS

| | | | |
|---|---|---|---|
| 5,591,855 A | 1/1997 | Hudkins et al. | |
| 5,628,984 A | 5/1997 | Boucher | |
| 6,291,504 B1 | 9/2001 | Nugiel et al. | |
| 6,369,086 B1 | 4/2002 | Davis | |
| 6,610,684 B2 | 8/2003 | Zaharevitz et al. | |
| 6,667,346 B2 | 12/2003 | Reddy et al. | |
| 6,936,612 B2 | 8/2005 | Barvian et al. | |
| 6,962,993 B2 | 11/2005 | Blumenkopf et al. | |
| 6,982,277 B2 | 1/2006 | Gudkov et al. | |
| 7,208,489 B2 | 4/2007 | Barvain et al. | |
| 7,345,171 B2 | 3/2008 | Beylin et al. | |
| 7,482,354 B2 | 1/2009 | Traquandi et al. | |
| 7,855,211 B2 | 12/2010 | Coates et al. | |
| 7,977,347 B2 | 7/2011 | Qian et al. | |
| 8,598,186 B2 | 12/2013 | Tavares et al. | |
| 8,598,197 B2 | 12/2013 | Tavares et al. | |
| 8,691,830 B2 | 4/2014 | Tavares et al. | |
| 8,822,683 B2 | 9/2014 | Tavares et al. | |
| 8,829,012 B2 | 9/2014 | Tavares et al. | |
| 9,260,442 B2 | 2/2016 | Tavares | |
| 9,464,092 B2 * | 10/2016 | Strum | A61P 35/04 |
| 9,487,530 B2 * | 11/2016 | Strum | A61P 35/04 |
| 9,527,857 B2 * | 12/2016 | Strum | A61P 35/04 |
| 9,616,062 B2 | 4/2017 | Sharpless et al. | |
| 9,717,735 B2 * | 8/2017 | Strum | A61K 31/5377 |
| 9,808,461 B2 | 11/2017 | DiRocco et al. | |
| 9,931,345 B2 * | 4/2018 | Strum | A61P 35/04 |
| 10,076,523 B2 * | 9/2018 | Strum | A61P 35/04 |
| 10,085,992 B2 * | 10/2018 | Strum | A61P 35/04 |
| 10,231,969 B2 * | 3/2019 | Strum | A61K 31/519 |

(Continued)

FOREIGN PATENT DOCUMENTS

| | | |
|---|---|---|
| CA | 2656290 | 1/2008 |
| CN | 1278794 | 1/2001 |

(Continued)

OTHER PUBLICATIONS

Giacinti et al., "RB and cell cycle progression", 2006, Oncogene, 25(38), pp. 5520-5227. (Year: 2006).*

(Continued)

*Primary Examiner* — My-Chau T. Tran
(74) *Attorney, Agent, or Firm* — Knowles Intellectual Property Strategies, LLC

(57) ABSTRACT

This invention is in the area of improved compounds for and methods of treating selected RB-positive cancers and other Rb-positive abnormal cellular proliferative disorders while minimizing the deleterious effects on healthy cells, for example healthy Hematopoietic Stem Cells and Progenitor Cells (HSPCs), associated with current treatment modalities. In one aspect, improved treatment of select RB-positive cancers is disclosed using specific compounds disclosed herein. In certain embodiments, the compounds described herein act as highly selective and, in certain embodiments, short, transiently-acting cyclin-dependent kinase 4/6 (CDK 4/6) inhibitors when administered to subjects.

85 Claims, 51 Drawing Sheets

(56) References Cited

U.S. PATENT DOCUMENTS

| | | |
|---|---|---|
| 2002/0042412 A1 | 4/2002 | Zaharevitz et al. |
| 2003/0069430 A1 | 4/2003 | Davis et al. |
| 2003/0073668 A1 | 4/2003 | Booth et al. |
| 2003/0224522 A1 | 12/2003 | de Jong et al. |
| 2003/0229026 A1 | 12/2003 | Al-Awar et al. |
| 2004/0006074 A1 | 1/2004 | Kelley et al. |
| 2004/0048915 A1 | 3/2004 | Engler et al. |
| 2004/0236084 A1 | 11/2004 | Biwersi et al. |
| 2005/0222163 A1 | 10/2005 | Eck et al. |
| 2005/0267073 A1 | 12/2005 | Dairi et al. |
| 2007/0027147 A1 | 2/2007 | Hayama et al. |
| 2007/0179118 A1 | 8/2007 | Barvian et al. |
| 2007/0207143 A1 | 9/2007 | Dang et al. |
| 2007/0212736 A1 | 9/2007 | Chen-Kiang et al. |
| 2007/0270362 A1 | 11/2007 | Harlan et al. |
| 2008/0085890 A1 | 4/2008 | Tsou et al. |
| 2008/0161355 A1 | 7/2008 | Curry et al. |
| 2008/0182853 A1 | 7/2008 | Kruman et al. |
| 2011/0009353 A1 | 1/2011 | Chen-Kiang et al. |
| 2011/0224221 A1 | 9/2011 | Sharpless et al. |
| 2011/0224227 A1 | 9/2011 | Sharpless et al. |
| 2011/0312909 A1 | 12/2011 | Ciomei et al. |
| 2012/0100100 A1 | 4/2012 | Sharpless et al. |
| 2013/0289031 A1 | 10/2013 | Sanofi |
| 2014/0037622 A1 | 2/2014 | Boshoff et al. |
| 2014/0080838 A1 | 3/2014 | Wendel et al. |
| 2014/0107114 A1 | 4/2014 | Kim et al. |
| 2014/0271460 A1 | 9/2014 | Sharpless et al. |
| 2014/0274896 A1 | 9/2014 | Sharpless et al. |
| 2014/0275066 A1 | 9/2014 | Sharpless et al. |
| 2014/0275067 A1 | 9/2014 | Sharpless et al. |
| 2015/0031880 A1 | 1/2015 | Tavares et al. |
| 2015/0210769 A1 | 7/2015 | Freeman et al. |
| 2015/0297606 A1 | 10/2015 | Strum et al. |
| 2015/0297607 A1 | 10/2015 | Strum et al. |
| 2015/0297608 A1 | 10/2015 | Strum et al. |
| 2015/0299212 A1 | 10/2015 | Strum et al. |
| 2016/0045509 A1 | 2/2016 | Strum et al. |
| 2016/0108054 A1 | 4/2016 | Tavares |
| 2016/0332989 A1 | 11/2016 | Wu et al. |

FOREIGN PATENT DOCUMENTS

| | | |
|---|---|---|
| CN | 1379668 | 11/2002 |
| JP | 2001-517652 | 10/2001 |
| JP | 2005-519909 | 7/2005 |
| JP | 2007-530425 | 11/2007 |
| JP | 2007-530654 | 11/2007 |
| WO | WO 1998/033798 | 8/1998 |
| WO | WO 1999/015500 | 4/1999 |
| WO | WO 2001/012188 | 2/2001 |
| WO | WO 2002/044174 | 6/2002 |
| WO | WO 2003/062236 A1 | 7/2003 |
| WO | WO 2005/005426 | 1/2005 |
| WO | WO 2005/040166 A1 | 5/2005 |
| WO | WO 2005/052147 | 6/2005 |
| WO | WO 2015/084892 A1 | 6/2005 |
| WO | WO 2005/094830 A1 | 10/2005 |
| WO | WO 2005/105213 A2 | 11/2005 |
| WO | WO 2006/074985 | 7/2006 |
| WO | WO 2006/127587 | 11/2006 |
| WO | WO 2007/025090 | 3/2007 |
| WO | WO 2007/048847 A2 | 5/2007 |
| WO | WO 2007/065820 | 6/2007 |
| WO | WO 2007/124252 A2 | 11/2007 |
| WO | WO 2008/005538 | 1/2008 |
| WO | WO 2008/079933 | 7/2008 |
| WO | WO 2009/003003 A2 | 12/2008 |
| WO | WO 2009/061345 | 5/2009 |
| WO | WO 2009/085185 A1 | 7/2009 |
| WO | WO 2010/012777 A1 | 2/2010 |
| WO | WO 2010/020675 | 2/2010 |
| WO | WO 2010/039997 A2 | 4/2010 |
| WO | WO 2010/051127 A2 | 5/2010 |
| WO | WO 2010/132725 A2 | 11/2010 |
| WO | WO 2011/101409 | 8/2011 |
| WO | WO 2011/101417 | 8/2011 |
| WO | WO 2011/103485 A1 | 8/2011 |
| WO | WO 2012/061156 | 5/2012 |
| WO | WO 2012/068381 A2 | 5/2012 |
| WO | WO 2012/129344 | 9/2012 |
| WO | WO 2013/006532 A1 | 1/2013 |
| WO | WO 2013/014448 A1 | 1/2013 |
| WO | WO 2013/148748 A1 | 10/2013 |
| WO | WO 2013/163239 A1 | 10/2013 |
| WO | WO 2014/085318 A1 | 6/2014 |
| WO | WO 2014/144326 A1 | 9/2014 |
| WO | WO 2014/144596 A2 | 9/2014 |
| WO | WO 2014/144740 A2 | 9/2014 |
| WO | WO 2014/144847 A2 | 9/2014 |
| WO | WO 2014/168975 A1 | 10/2014 |
| WO | WO 2015/061407 A1 | 4/2015 |
| WO | WO 2015/161283 A1 | 10/2015 |
| WO | WO 2015/161285 A1 | 10/2015 |
| WO | WO 2015/161287 A1 | 10/2015 |
| WO | WO 2015/161288 A1 | 10/2015 |
| WO | WO 2016/040848 A1 | 3/2016 |
| WO | WO 2016/040858 A1 | 3/2016 |
| WO | WO 2016/126889 A1 | 8/2016 |

OTHER PUBLICATIONS

Nicholas J. Dyson, "RB1: a prototype tumor suppressor and an enigma", 2016, Genes Dev., vol. 30, pp. 1492-1502. (Year: 2016).*

Sherr et al., "The RB and p53 pathways in cancer", 2002, Cancer Cell, 2(2), pp. 103-112. (doi.org/10.1016/S1535-6108(02) 00102-2) (Year: 2002).*

Meuwissen et al., "Induction of small cell lung cancer by somatic inactivation of both Trp53 and Rb1 in a conditional mouse model", 2003, Cancer Cell, 4(3), pp. 181-189. (doi.org/10.1016/S1535-6108(03)00220-4) (Year: 2003).*

An, H. X. et al. "Gene amplification and overexpression of CDK4 in sporadic breast carcinomas is associated with high tumor cell proliferation" American Journal of Pathology, 1999; 154: 113-118.

Anderson, M. S. and J. A. Bluestone "The NOD mouse: a model of immune dysregulation" Annu Rev Immunol, 2005; 23: 447-485.

Barginear, M. F. and D. R. Budman "Trastuzumab-DM1: A review of the novel immuno-conjugate for HER2-overexpressing breast cancer" The Open Breast Cancer Journal, 2009; 1: 25-30.

Baughn, L. B. et al. "A novel orally active small molecule potently induces G1 arrest in primary myeloma cells and prevents tumor growth by specific inhibition of cyclin-dependent kinase 4/6" Cancer Res, Aug. 1, 2006; 66(15): 7661-7667.

Berge et al. "Pharmaceutical Salts" J. Pharm. Sci., 1977; 66(1): 1-19.

Bernhard, E. J. et al. "Reducing the radiation-induced G2 delay causes HeLa cells to undergo apoptosis instead of mitotic death" Int J Radiat Biol., May 1996; 69(5): 575-584.

Blagosklonny, M. V. and A. B. Pardee "Exploiting cancer cell cycling for selective protection of normal cells" Cancer Res, Jun. 1, 2001; 61(11): 4301-4305.

Brookes et al. "INK4a-deficient human diploid fibroblasts are resistant to RAS-induced senescence" EMBO J., Jun. 17, 2002; 21(12): 2936-2945.

Bucher, N. and C. D. Britten "G2 checkpoint abrogation and checkpoint kinase-1 targeting in the treatment of cancer" Br J Cancer, Feb. 12, 2008; 98(3): 523-528.

Burdelya et al. "An agonist of toll-like receptor 5 has radioprotective activity in mouse and primate models" Science, Apr. 11, 2008; 320(5873): 226-230.

Casi, G. and D. Neri "Antibody-drug conjugates: basic concepts, examples and future perspectives" Journal of Controlled Release, 2012; 161(2): 422-428.

Chart, R.V. "Targeted cancer therapy: conferring specificity to cytotoxic drugs" Accounts of Chemical Research, 2008; 41(1): 98-107.

Chen, X. et al. "Protection of normal proliferating cells against chemotherapy by staurosporine-mediated, selective, and reversible G1 arrest" J Natl Cancer Inst., Dec. 20, 2000; 92(24): 1999-2008.

(56) References Cited

OTHER PUBLICATIONS

Chin et al. "Cooperative effects of INK4a and ras in melanoma susceptibility in vivo" Genes & Development, 1997; 11: 2822-2834.

Chu et al. "Discovery of [4-Amino-2-(1-methanesulfonylpiperidin-4-ylamino)pyrimidin-5-yl](2,3-difluoro-6-methoxyphenyl)methanone (R547), a potent and selective cyclin-dependent kinase inhibitor with significant in vivo antitumor activity" J Med Chem, Nov. 2, 2006; 49(22): 6549-6560.

Curtin et al. "Distinct Sets of Genetic Alterations in Melanoma" N Engl J Med 2005; 353: 2135-2147.

Daniotti et al. "BRAF alterations are associated with complex mutational profiles in malignant melanoma" Oncogene, 2004; 23: 5968-5977.

Davis, S. T. et al. "Prevention of chemotherapy-induced alopecia in rats by CDK inhibitors" Science, Jan. 5, 2001; 291(5501): 134-137.

Davis, S.T. et al. "Retraction" Science, Dec. 20, 2002; 298(5602): 2327.

Davis, T. A. et al. "Genistein induces radioprotection by hematopoietic stem cell quiescence" Int J Radiat Biol, Sep. 2008; 84(9): 713-726.

Decker et al. "Expression of Cyclin E in resting and activated B-chronic lymphocytic leukemia cells: cyclin E/cdk2 as protential therapeutic target" British Journal of Hematology, Jan. 13, 2004, 125, 141-148.

Deep, G. et al. "New Combination Therapies with Cell Cycle Agents" Current Opinion in Investigational Drugs, 2008; 9: 591-605.

Dickson, M. A. and G. K. Schwartz "Development of cell-cycle inhibitors for cancer therapy" Curr Oncol, Mar. 2009; 16(2): 36-43.

Dickson, Mark, et al. "Phase II Trial of the CDK4 Inhibitor PD0332991 in Patients With Advanced CDK4-Amplified Well-Differentiated or Dedifferentiated Liposarcoma." J Clin Oncol. Jun. 1, 2013; 31(16): 2024-2028.

Diehl, J. A. "Cycling to Cancer with Cyclin D1" Cancer Biology and Therapy, 2002; 1(3): 226-231.

El-Diery, W. S. "Meeting report: The international conference on tumor progression and therapeutic resistance" Cancer Res, Jun. 1, 2005; 65(11): 4475-4484.

Elkind, M.M. and H. Sutton "Radiation response of mammalian cells grown in culture. 1. Repair of x-ray damage in surviving Chinese hamster cells" Radiat Res., 1960; 13: 556-593.

Elkind, M.M. and H. Sutton "X-ray damage and recovery in mammalian cells in culture" Nature, 1959; 184: 1293-1295.

Engler et al. "Novel, potent and selective cyclin D1/CDK4 inhibitors: indolo[6,7-a]pyrrolo[3,4-c]carbazoles" Bioorg Med Chem Lett, Jul. 21, 2003; 13(14): 2261-2267.

Finn et al. "PD 0332991, a selective cyclin D kinase 4/6 inhibitor, preferentially inhibits proliferation of luminal estrogen receptor-positive human breast cancer cell lines in vitro" Breast Cancer Research, Oct. 29, 2009; 11(5): R77.

Finn et al. "Results of a randomized phase 2 study of PD 0332991, a cyclin-dependent kinase (CDK) 4/6 inhibitor, in combination with letrozole vs letrozole alone for first-line treatment of ER+/HER2— advanced breast cancer (BC)" Cancer Res, 2012; 72(24 Suppl): Abstract nr S1-6.

Firer, M. A. and G. J. Gellerman Targeted drug delivery for cancer therapy: the other side of antibodies, J. Hematol. Oncol., 2012; 5: 70. [retrieved from http://www.jhoonline.org/content/5/1/70 on Jul. 16, 2014].

Franken et al. "Clonogenic assay of cells in vitro" Nature Protocols, 2006; 1: 2315-2319.

Fry, D. W. et al. "Specific inhibition of cyclin-dependent kinase 4/6 by PD 0332991 and associated antitumor activity in human tumor xenografts" Mol Cancer Ther., Nov. 2004; 3(11): 1427-1438.

Goldberg et al. "Pyrazinoindolone inhibitors of MAPKAP-K2" Bioogranic & Medicinal Chemistry Letters, Dec. 23, 2007, 18, 938-941.

Guillard et al., "Synthesis and biological evaluations of new pyrrolo[2,3-b]pyrimidine as SDI analogs" Heterocyles, 2008, vol. 75(5), pp. 1163-1189.

Hallahan, D. E. et al. "Inhibition of protein kinases sensitizes human tumor cells to ionizing radiation" Radiat Res., Mar. 1992; 129(3): 345-350.

Hara, E. et al. "Regulation of p16CDKN2 expression and its implications for cell immortalization and senescence" Mol Cell Biol, Mar. 1996; 16(3): 859-867.

Herodin, F. et al. "Short-term injection of antiapoptotic cytokine combinations soon after lethal gamma—irradiation promotes survival" Blood, Apr. 1, 2003; 101(7): 2609-2616.

Hershman, D et al. "Acute myeloid leukemia or myelodysplastic syndrome following use of granulocyte colony-stimulating factors during breast cancer adjuvant chemotherapy" J Natl Cancer Inst, Feb. 7, 2007; 99(3): 196-205.

Hibbs, M. L. et al. "Multiple defects in the immune system of Lyn-deficient mice, culminating in autoimmune disease" Cell, Oct. 20, 1995; 83(2): 301-311.

Hirose, Y. et al. "Abrogation of the Chkl-mediated G(2) checkpoint pathway potentiates temozolomide-induced toxicity in a p53-independent manner in human glioblastoma cells" Cancer Res, Aug. 1, 2001; 61(15): 5843-5849.

Honma, T. et al. "A novel approach for the development of selective Cdk4 inhibitors: library design based on locations of Cdk4 specific amino acid residues" J Med Chem, Dec. 20, 2001; 44(26): 4628-4640.

Honma, T. et al. "Structure-based generation of a new class of potent Cdk4 inhibitors: new de novo design strategy and library design" J Med Chem, Dec. 20, 2001; 44(26): 4615-4627.

Humphreys, B.D. et al. "Intrinsic epithelial cells repair the kidney after injury" Cell Stem Cell, 2008; 2: 284-291.

Humphreys, B.D. et al. "Repair of injured proximal tubule does not involve specialized progenitors" Proc Natl Acad Sci USA, 2011; 108: 9226-9231.

Ikuta, M. et al. "Crystallographic approach to identification of cyclin-dependent kinase 4 (CDK4)-specific inhibitors by using CDK4 mimic CDK2 protein" J Biol Chem, Jul. 20, 2001; 276(29): 27548-27554.

Johnson, D. G. and C. L. Walker "Cyclins and Cell Cycle Checkpoints" Annual Review of Pharmacology and Toxicology, Apr. 1999; 39: 295-312.

Johnson, N. and G. Shapiro "Cyclin-dependent kinase 4/6 inhibition in cancer therapy" Cell Cycle, Nov. 1, 2012; 11(21): 3913-3918.

Johnson, S.M., et al. "Mitigation of hematologic radiation toxicity in mice through pharmacological quiescence induced by CDK4/6 inhibition" J Clin Invest, Jul. 2010; 120(7): 2528-2536.

Karaman, M. W. et al. "A quantitative analysis of kinase inhibitor selectivity" Nat Biotechnol., Jan. 2008; 26(1): 127-132.

Khuri, F. R. "Weighing the hazards of erythropoiesis stimulation in patients with cancer" N Engl J Med, Jun. 14, 2007; 356(24): 2445-2448.

Kiel et al. "SLAM Family Receptors Distinguish Hematopoietic Stem and Progenitor Cells and Reveal Endothelial Niches for Stem Cells" Cell, 2005; 121: 1109-1121.

Kim, S. et al. "Enhancement of radiation effects by flavopiridol in uterine cervix cancer cells" Cancer Res Treat, Jun. 2005; 37(3): 191-195.

Knockaert et al. "Pharmacological inhibitors of cyclin-dependent kinases" Trends Pharmacol Sci, Sep. 2002; 23(9): 417-425.

Konecny, Gottfried E., et al., Expression of p16 and Retinoblastoma Determines Responses to CDK4/6 Inhibition in Ovarian Cancer, Clinical Cancer Research, 2011, vol. 17, No. 6, p. 1591-1602.

Kubinyi (3D QSAR in Drug Design: Ligand-Protein Interactions and Molecular Similarity, vol. 2-3, Springer, 1998, 800 pages). p. 243-244.

Kubo, et al. "The p16 status of tumor cell lines identifies small molecule inhibitors specific for cyclin-dependent kinase 4" Clin Cancer Res, 1999; 5: 4279-4286.

Lambert, J. M. Drug-conjugated antibodies for the treatment of cancer British Journal of Clinical Pharmacology, 2013; 76(2): 248-262.

Landis, M.W. et al. Cyclin D1-dependent kinase activity in murine development and mammary tumorigenesis. Cancer Cell, 2006; 9: 13-22.

(56) References Cited

OTHER PUBLICATIONS

Laredo, J. et al. "Effect of the protein kinase C inhibitor staurosporine on chemosensitivity to daunorubicin of normal and leukemic fresh myeloid cells" Blood, Jul. 1, 1994; 84(1): 229-237.

Le Deley et al. "Anthracyclines, Mitoxantrone, Radiotherapy, and Granulocyte Colony-Stimulating Factor: Risk Factors for Leukemia and Myelodysplastic Syndrome After Breast Cancer" J Clin Oncol, 2007; 25: 292-300.

Little, J.B. "Repair of sub-lethal and potentially lethal radiation damage in plateau phase cultures of human cells" Nature, 1969; 224(5221): 804-806.

Lohmann and Gallie "Retinoblastoma" Gene Reviews (2000), retrieved from http://www.ncbi.nlm.nih.gov/books/NBK1452/ on Jul. 10, 2014.

Lopus, M. Antibody-DM1 conjugates as cancer therapeutics, Cancer Letters, 2011; 307(2): 113-118.

Luo, Y. et al. "Blocking Chk1 expression induces apoptosis and abrogates the G2 checkpoint mechanism" Neoplasia, Sep.-Oct. 2001; 3(5): 411-419.

Malumbres, M. and M. Barbacid "Cell cycle, CDKs and cancer: a changing paradigm" Nature Reviews Cancer, Mar. 2009; 9(3): 153-166.

Malumbres, M. and M. Barbacid "Mammalian cyclin-dependent kinases" Trends Biochem. Sci., Nov. 2005; 30(11): 630-641.

McInnes, C. "Progress in the evaluation of CDK inhibitors as anti-tumor agents" Drug Discov Today, Oct. 2008; 13(19-20): 875-881.

Meng et al. "Ionizing Radiation and Busulfan Induce Premature Senescence in Murine Bone Marrow Hematopoietic Cells" Cancer Res, 2003; 63: 5414-5419.

Menu, E. et al. "A novel therapeutic combination using PD 0332991 and bortezomib: study in the 5T33MM myeloma model" Cancer Res, Jul. 15, 2008; 68(14): 5519-5523.

Michaud, Karine et al. "Pharmacologic inhibition of cdk4/6 arrests the growth of glioblastoma multiforme intracranial xenografts" Cancer Res, Apr. 15, 2011; 70: 3228-3238.

Morgan, D.O. "Cyclin-dependent Kinases: Engines, Clocks, and Microprocessors" Annual Review of Cell and Developmental Biology, 1997; 13: 261-291.

Na Nakorn et al. "Myeloerythroid-restricted progenitors are sufficient to confer radioprotection and provide the majority of day 8 CFU-S" J Clin Invest, 2002; 109: 1579-1585.

Newland, A. M. "Brentuximab vedotin: a CD30-directed antibody-cytotoxic drug conjugate" Pharmacotherapy, Jan. 2013; 33(1): 93-104.

O'Dwyer, et al. "A phase I dose escalation trial of a daily oral CDK 4/6 inhibitor PD-0332991" J Clin Oncol, 2007; 25(18S): 3550. [Abstract].

Ojeda, F. et al. "Role of protein kinase-C in thymocyte apoptosis induced by irradiation" Int J Radiat Biol., May 1992; 61(5): 663-667.

Park et al. "Toxicogenetics in drug development" Toxicology Letters, Mar. 31, 2001, 120, 281-291.

Parsam et al. "A comprehensive, sensitive and economical approach for the detection of mutations in the RB1 gene in retinoblastoma" Journal of Genetics, Dec. 2009; 88(4): 517-527.

Passegué et al. "Global analysis of proliferation and cell cycle gene expression in the regulation of hematopoietic stem and progenitor cell fates" J Exp Med, 2005; 202: 1599-1611.

Pawlik, T. M. and K. Keyomarsi "Role of cell cycle in mediating sensitivity to radiotherapy" Int J Radiat Oncol Biol Phys, Jul. 15, 2004; 59(4): 928-942.

Presser, Armin and Antje Hüfner "Trimethylsilyldiazomethane—A Mild and Efficient Reagent for the Methylation of Carboxylic Acids and Alcohols in Natural Products" Monatshefte für Chemie, 2204, 135(8): 1015-1022.

Ramsey, M. R. et al. "Expression of p16Ink4a compensates for p18Ink4c loss in cyclin-dependent kinase 4/6-dependent tumors and tissues" Cancer Res, May 15, 2007; 67(10): 4732-4741.

Reddy, H. K. et al. "Cyclin-dependent kinase 4 expression is essential for neu-induced breast tumorigenesis" Cancer Research, 2005; 65: 10174-10178.

Roberts et al. "Multiple Roles of Cyclin-Dependent Kinase 4/6 Inhibitors in Cancer Therapy" JNCI, 2012; 104(6):476-487.

Ruas et al. "CDK4 and CDK6 Delay Senescence by Kinase-Dependent and p16INK4a-Independent Mechanisms" Molecular and Cellular Biology, Jun. 2007; 27(12): 4273-4282.

Samady, L. et al. "Activation of CDK4 gene expression in human breast cancer cells by the Brn-3b POU family transcription factor" Cancer Biology & Therapy, 2004; 3: 317-323.

Sanchez-Martinez, C. et al. "Aryl[a]pyrrolo[3,4-c]carbazoles as selective cyclin D1-CDK4 inhibitors" Bioorg Med Chem Lett, Nov. 3, 2003; 13(21): 3835-3839.

Sanchez-Martinez, C. et al. "Studies on cyclin-dependent kinase inhibitors: indolo-[2,3-a]pyrrolo[3,4-c]carbazoles versus bis-indolylmaleimides" Bioorg Med Chem Lett, Nov. 3, 2003; 13(21): 3841-3846.

Sapra, P. and B. Shor "Monoclonal antibody-based therapies in cancer: advances and challenges" Pharmacology & Therapeutics, 2013; 138(3): 452-469.

Sarkar et al. "Nonsolvent Application of Ionic Liquids: Organo-Catalysis by 1-Alkyl-3-methylimidazolium Cation Based Room-Temperature Ionic Liquids for Chemoselective N-tert-Butyloxycarbonylation of Amines and the Influence of the C-2 Hydrogen on Catalytic Efficiency" Journal of Organic Chemistry, 2011; 76(17): 7132-7140.

Sawai, Catherine M., et al., "Therapeutic Targeting of the Cyclin D3:CDK4/6 Complex in T Cell Leukemia," Cancer Cell, Oct. 16, 2012, vol. 22, pp. 452-465.

Schliemann, C. and D. Neri "Antibody-based targeting of the tumor vasculature" Biochimica et Biophysica Acta, 2007; 1776(2): 175-192.

Schmidt, M. and Z. Fan "Protection against chemotherapy-induced cytotoxicity by cyclin-dependent kinase inhibitors (CKI) in CKI-responsive cells" Oncogene, Sep. 27, 2001; 20(43): 6164-6171.

Schönauer, K. and E. Zibral "Reactions with organophosphorus compounds, 50.: Trimethylsilylethoxymethylene triphenylphosphorane, a novel reagent for the homologation of carbonyl compounds." Tetrahedron Letters, 1983; 24: 573-576.

Schwartz, G.K. et al. "Phase I study of PD 0332991, a cyclin-dependent kinase inhibitor, administered in 3-week cycles (Schedule 2/1)" Br J Cancer, Jun. 7, 2011; 104(12): 1862-1868.

Seed, T. M. "Radiation protectants: current status and future prospects" Health Phys, Nov. 2005; 89(5): 531-545.

Sharma, P.S. et al. "Inhibitors of cyclin dependent kinases: useful targets for cancer treatment" Curr. Cancer Drug Targets, Feb. 2008; 8(1): 53-75.

Sharpless et al. "Both products of the mouse Ink4a/Arf locus suppress melanoma formation in vivo" Oncogene, Aug. 7, 2003; 22(32): 5055-5059.

Sherr, C. J., "Cancer Cell Cycles" Science, Dec. 6, 1996; 274(5293): 1672-1677.

Shields et al. "Lack of Extracellular Signal-Regulated Kinase Mitogen-Activated Protein Kinase Signaling Shows a New Type of Melanoma" Cancer Res, 2007; 67: 1502-1512.

Shimamura, T. et al. "Identification of potent 5-pyrimidinyl-2-aminothiazole CDK4, 6 inhibitors with significant selectivity over CDK1, 2, 5, 7, and 9" Bioorg Med Chem Lett., Jul. 15, 2006; 16(14): 3751-3754.

Sielecki et al "Quinazolines as cyclin dependent kinase inhibitors" Bioogranic & Medicinal Chemistry Letters, May 7, 2001, 11, 1157-1160.

Sinclair, W.K. and R.A. Morton "X-ray sensitivity during the cell generation cycle of cultured Chinese hamster cells" Radiat Res., Nov. 1966; 29(3): 450-474.

Soni, R. et al. "Selective in vivo and in vitro effects of a small molecule inhibitor of cyclin-dependent kinase 4" J Natl Cancer Inst, Mar. 21, 2001; 93(6): 436-446.

Stone, S. et al. "Reversible, p16-mediated cell cycle arrest as protection from chemotherapy" Cancer Research, Jul. 15, 1996; 56(14): 3199-3202.

Sun, Y. et al. "Antibody-drug conjugates as targeted cancer therapeutics" Acta Pharmaceutica Sinica, 2009; 44(9): 943-952.

(56) References Cited

OTHER PUBLICATIONS

Takano, Y. et al. Cyclin D1 overexpression in invasive breast cancers: correlation with cyclin-dependent kinase 4 and oestrogen receptor overexpression, and lack of correlation with mitotic activity Journal of Cancer Research and Clinical Oncology, 1999; 125: 505-512.
Teicher, B. A. and R. V. Chari "Antibody conjugate therapeutics: challenges and potential" Clinical Cancer Research, 2011; 17(20): 6389-6397.
Terasima, T. and Li Tolmach "X-ray sensitivity and DNA synthesis in synchronous populations of HeLa cells" Science, 1963, 140: 490-492.
Teyssier, F. et al. "Cell cycle regulation after exposure to ionizing radiation" Bull Cancer., Apr. 1999; 86(4): 345-357. [Abstract].
Toogood, P.L. et al. "Discovery of a potent and selective inhibitor of cyclin-dependent kinase 4/6" J Med Chem, Apr. 7, 2005; 48(7): 2388-2406.
Tsou, H. R. et al. "4-(Phenylaminomethylene)isoquinoline-1,3(2H,4H)-diones as potent and selective inhibitors of the cyclin-dependent kinase 4 (CDK4)" J Med Chem, Jun. 26, 2008; 51(12): 3507-3525.
Tsou, H. R. et al. "Discovery of 4-(benzylaminomethylene)isoquinoline-1,3-(2H,4H)-diones and 4-[(pyridylmethyl)aminomethylene]isoquinoline-1,3-(2H,4H)-diones as potent and selective inhibitors of the cyclin-dependent kinase 4" J Med Chem, Apr. 23, 2009; 52(8): 2289-2310.
Tu, S. et al. "New potential inhibitors of cyclin-dependent kinase 4: design and synthesis of pyrido[2,3-d]pyrimidine derivatives under microwave irradiation" Bioorg Med Chem Lett, Jul. 1, 2006; 16(13): 3578-3581.
Uckun, F. M. et al. "In vivo radioprotective effects of recombinant human granulocyte colony-stimulating factor in lethally irradiated mice" Blood, Feb. 1, 1990; 75(3): 638-645.
Vanderwel, S.N. et al. "Pyrido[2,3-d]pyrimidin-7-ones as specific inhibitors of cyclin-dependent kinase 4" J Med Chem., Apr. 7, 2005; 48(7): 2371-2387.
Vlachakis, D. and S. Kossida "Antibody Drug Conjugate bioinformatics: drug delivery through the letterbox" Comput. Math. Methods Med., 2013; 2013: 282398. Published online on Jun. 19, 2013. [retrieved from http://dx.doi.org/10.1155/2013/282398 on Jul. 16, 2014].
Walker et al. "Virtually 100% of melanoma cell lines harbor alterations at the DNA level within CDKN2A, CDKN2B, or one of their downstream targets" Genes Chromosomes & Cancer, 1998; 22: 157-163.
Wang et al. "Loss of p21 increases sensitivity to ionizing radiation and delays the onset of lymphoma in atm-deficient mice" Proc Natl Acad Sci, USA, 1997; 94: 14590-14595.
Wang, R. H. et al. "Protein kinase inhibitor staurosporine enhances cytotoxicity of antitumor drugs to cancer cells" Yao Xue Xue Bao, 1996; 31(6): 411-415. [Abstract].
Weiss and Landauer "History and development of radiation-protective agents" International Journal of Radiation Biology, Jul. 2009; 85: 539-573.
Wermuth, The Practice of Medicinal Chemistry, 2d ed. (2003), 768 pages. Chs. 9-10.
White, J.D. et al. "Transformations of Quinic Acid. Asymmetric Synthesis and Absolute Configuration of Mycosporin I and Mycosporingly" Journal of Organic Chemistry, 1995, 60(12): 3600-3611.
Wilson et al. "Hematopoietic Stem Cells Reversibly Switch from Dormancy to Self-Renewal during Homeostasis and Repair" Cell, 2008; 135: 1118-1129.
Yu, Q. et al. "Requirement for CDK4 kinase function in breast cancer" Cancer Cell, 2006; 9: 23-32.
Yu, Q. et al. "Specific protection against breast cancers by cyclin D1 ablation" Nature, 2001; 411: 1017-1021.
Zhang, W. et al. "Sensitization of C6 glioma cells to radiation by staurosporine, a potent protein kinase C inhibitor" J Neurooncol., Jan. 1993; 15(1): 1-7.
Zhu, G. et al. "Synthesis, structure-activity relationship, and biological studies of indolocarbazoles as potent cyclin D1-CDK4 inhibitors" J Med Chem., May 22, 2003; 46(11): 2027-2030.
Zhu, G. et al. "Synthesis of quinolinyl/isoquinolinyl[a]pyrrolo [3,4-c] carbazoles as cyclin D1/CDK4 inhibitors" Bioorg Med Chem Lett, Apr. 7, 2003; 13(7): 1231-1235.
Blachly et al., "Emerging Drug Profile: Cyclin-Dependent Kinase Inhibitors," Leuk Lymphoma. Oct. 2013; 54(10): 2133-2143. doi:10.3109/10428194.2013.783911.
Bose et al., "Cyclin-dependent kinase inhibitor therapy for hematologic malignancies," Expert Opin Investigating Drugs. Jun. 2013; 22(6): 723-738. doi:10.1517/13543784.2013.7.
Boss Ds, et al. "Safety, tolerability, pharmacokinetics and pharmacodynamics of the oral cyclin-dependent kinase inhibitor AZD5438 when administered at intermittent and continuous dosing schedules in patients with advanced solid tumours." Ann. Oncol. 2010; 21: 884-894. Published online Oct. 13, 2009.
Choi, YJ et al., "The Requirement for Cyclin D Function in Tumor Maintenance," Cancer Cell. 2012; 22: 438-451.
Choi, YJ et al. "Signaling Through Cyclin D-dependent kinases," Oncogene (2014) 33, 1890-1903; doi:10.1038/onc.2013.137; published online May 6, 2013.
Gojo I, et al. "Phase II study of the cyclin-dependent kinase (CDK) inhibitor dinaciclib (SCH 727965) in patients with advanced acute leukemias." ASH Annual Meeting Abstracts. 2010; 116: 3287.
Hamilton et al., Synergistic Anticancer Activity of Topotecan-Cyclin-Dependent Kinase Inhibitor Combinations Against Drug-Resistant Small Cell Lung Cancer (SCLC) Cell Lines. J. Cancer Therapy, 2013 4,47-53.
Hamilton et al., Synergism of cyclin-dependent kinase inhibitors with camptothecin derivatives in small cell lung cancer cell lines. Molecules (2014), 19, 2077-2088.
McClendon, et al. CDK4/6 inhibition antagonizes the cytotoxic response to anthracycline therapy. Cell Cycle 11:14, 2747-2755; Jul. 15, 2012.
McInnes, Progress in the evaluation of CDK inhibitors as anti-tumor agents, Drug Discovery Today vol. 13, Nos. 19/20 Oct. 2008.
Mita MM, et al. "Randomized Phase II trial of the cyclin-dependent kinase inhibitor dinaciclib (MK-7965) versus capecitabine in patients with advanced breast cancer." Clin. Breast Cancer. 2014; 14:169-176.
Rader et al., Dual CDK4/CDK6 inhibition induces cell-cycle arrest and senescence in Neuroblastoma. Clin Cancer Res; 19(22); 6173-82; 2013.
Sawai CM, et al. "Therapeutic targeting of the cyclin D3:CDK4/6 complex in T cell leukemia." Cancer Cell. 2012; 22: 452-465.
Tan et al., Trilaciclib plus chemotherapy versus chemotherapy alone in patients with metastatic triple-negative breast cancer; a multi-center, randomized, open-label, phase 2 trial. Lancet Oncol 2019; 20: 1587-601.
Tong et al. "Phase I and Pharmacologic Study of SNS-032, a Potent and Selective Cdk2, 7, and 9 Inhibitor, in Patients With Advanced Chronic Lymphocytic Leukemia and Multiple Myeloma," J Clin Oncol Jun. 20, 2010, 28:3015-3022.
Weiss et al., Myelopreservation with the CDK4/6 inhibitor trilaciclibin patients with small-cell lung cancer receiving first-linechemotherapy: a phase Ib/randomized phase II trial. Annals of Oncology30: 1613-1621, 2019.
G1 Therapeutics, Inc. Corporate Presentation (Jan. 13, 2020).
Bisi et al., Preclinical Characterization of G1T28: A Novel CDK4/6 Inhibitor for Reduction of Chemotherapy-Induced Myelosuppression, Mol. Cancer Therap. (2016) (15)5: 783-793.
Bisi et al., Preclinical development of G1T38: a novel, potent and selective inhibitor of cyclin dependent kinases 4/6 for use as an oral antineoplastic in patients with CDK4/6 sensitive tumors, Oncotarget. Mar 15, 2017: doi:10.18632/oncotarget.16216.
Deng et al., "New Strategies in the Treatment of Mantle Cell Lymphoma" Clinical Cancer Research, 2012; 18(13): 3499-3508.
Giacinti et al., "RB and cell cycle progression", Oncogene, 2006, 25, 5220-5227.
Guo et al. "Staurosporine modulates radiosensitivity and radiation-induced apoptosis in U937 cells" Int J Radiat Biol., Feb. 2006; 82(2): 97-109.

(56) References Cited

OTHER PUBLICATIONS

He et al., "Transient CDK4/6 inhibition protects hematopoietic stem cells from chemotherapy-induced exhaustion", Science Translational Medicine, 2017, 9, eaa13986.
Johnson et al., Cyclin-dependent kinases (cdks) and the DNA damage response: rationale for cdk inhibitor-chemotherapy combinations as an anticancer strategy for solid tumors, Expert Opin Ther Targets. Nov. 2010; 14(11): 1199-1212.
NCT02079636—A Study of Abemaciclib (LY2835219) in Combination With Another Anticancer Drug in Participants With Lung Cancer (NSCLC); Mar. 6, 2014.
Rocha Lima Caio Max S Rocha et al., "G1T28, a cyclin dependent kinase 4/6 inhibitor, in combination with etoposide and carboplatin for extensive stage small cell lung cancer (ES-SCLC): preliminary results", Cancer Research, 2016, 76(14), CT151, XP002799585; & 107th Annual Meeting of the American Association of Cancer Research (AACR), New Orleans, LA Apr. 16-20, 2016.
Sorrentino Jessica et al., "Trilaciclib (G1T28), a CDK 4/6 inhibitor, enhances the efficacy of combination therapy and immune checkpoint inhibitor treatment in preclinical models", Cancer Research, 2017, 77(13), Supplement 1, XP002799587.
Sorrentino Jessica et al., "G1T28, a novel Cdk 4/6 inhibitor, protects murine hematopoietic stem and progenitor cells from cytotoxic chemotherapy", Cancer Research, 2015, 75(15), 941, XP002799586; & 106th Annual Meeting of the American Association for Cancer Research (AACR), Philadelphia, PA, Apr. 18-22, 2015.
Tong et al., "Phase I and pharmacologic study of SNS-032, a potent and selective CDK2, 7 and 9 inhibitors in patients with advanced chronic lymphocytic leukemia and multiple myeloma", Journal of Clinical Oncology, 2010, 28(18), 3015-3022.

\* cited by examiner

| Test Compound | Species | Half-Life (minutes) |
|---|---|---|
| Compound T | Human | >60 (66) |
| | Monkey | 30 |
| | Dog | 5 |
| | Rat | >60 (73) |
| | Mouse | 28 |
| PD0332991 | Human | >60 |
| | Monkey | >60 |
| | Dog | >60 |
| | Rat | >60 |
| | Mouse | >60 |

FIG. 7

| | Complete Response | Partial Response | Stable Disease | Progressive Disease | ORR % (CR+PR+SD/PD) | Mean % Change in Tumor Vol |
|---|---|---|---|---|---|---|
| No Treatment | 0 | 0 | 0 | 9 | 0 (0/9) | 500 |
| Compound T | 1 | 5 | 1 | 0 | 100 (7/0) | -70 |
| Compound GG | 1 | 4 | 1 | 1 | 85 (6/1) | -67 |
| Compound U | 1 | 2 | 5 | 0 | 100 (8/0) | -40 |

FIG. 10

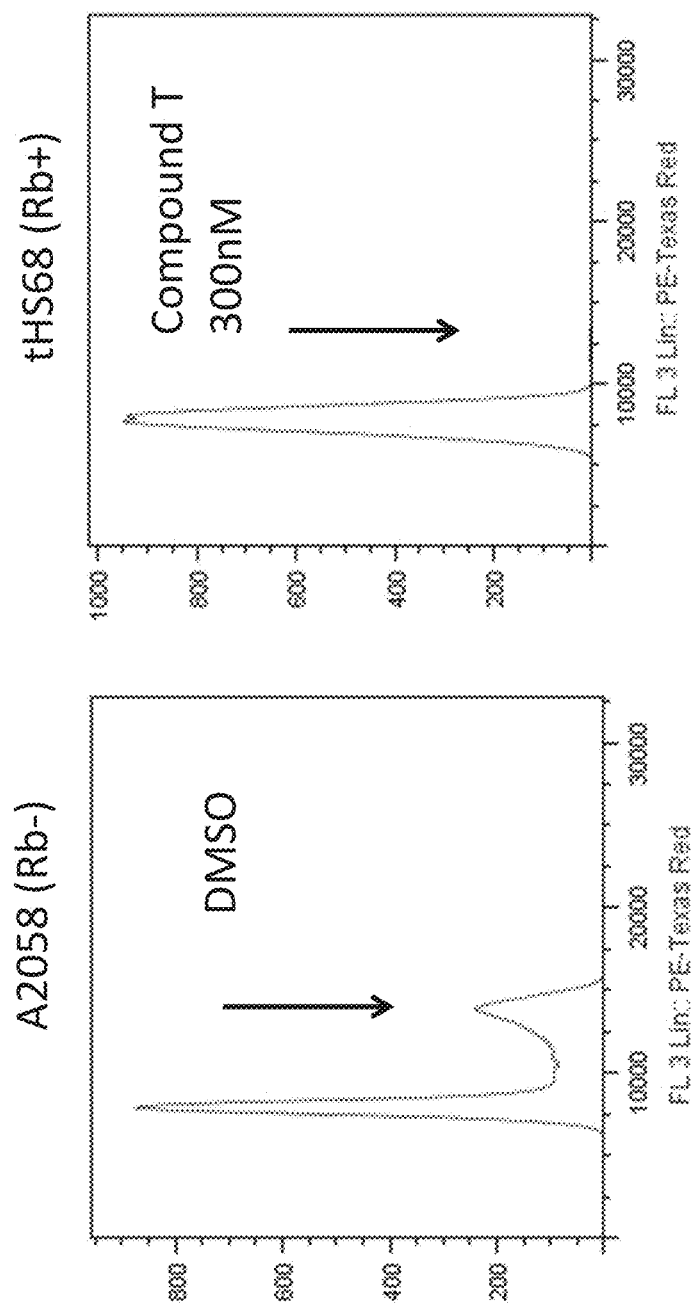

HSPC-SPARING TREATMENTS FOR RB-POSITIVE ABNORMAL CELLULAR PROLIFERATION

RELATED APPLICATIONS

This application is a continuation of U.S. application Ser. No. 16/112,362, filed Aug. 24, 2018, which is a continuation of U.S. application Ser. No. 15/387,083, filed Dec. 21, 2016, which is related to and claims benefit of U.S. application Ser. No. 14/214,048, filed Mar. 14, 2014, now U.S. Pat. No. 9,527,857, issued Dec. 27, 2016, which is related to and claims benefit of provisional U.S. Application No. 61/798,772, filed Mar. 15, 2013, provisional U.S. Application No. 61/861,374, filed on Aug. 1, 2013, provisional U.S. Application 61/911,354, filed on Dec. 3, 2013, and provisional U.S. Application No. 61/949,786, filed on Mar. 7, 2014. The entirety of each of these applications is hereby incorporated by reference for all purposes.

GOVERNMENT INTEREST

The U.S. Government has rights in this invention by virtue of support under Grant No. 5R44AI084284 awarded by the National Institute of Allergy and Infectious Diseases.

FIELD

This invention is in the area of improved compounds for and methods of treating selected RB-positive cancers and other Rb-positive abnormal cellular proliferative disorders while minimizing the deleterious effects on healthy cells, for example healthy Hematopoietic Stem Cells and Progenitor Cells (HSPCs), associated with current treatment modalities. In one aspect, improved treatment of select RB-positive cancers is disclosed using specific compounds disclosed herein. In certain embodiments, the compounds described herein act as highly selective and, in certain embodiments, short, transiently-acting cyclin-dependent kinase 4/6 (CDK 4/6) inhibitors when administered to subjects.

BACKGROUND

The regulation of the cell cycle is governed and controlled by specific proteins, which are activated and deactivated mainly through phosphorylation/dephosphorylation processes in a precisely timed manner. The key proteins that coordinate the initiation, progression, and completion of cell-cycle program are cyclin dependent kinases (CDKs). Cyclin-dependent kinases belong to the serine-threonine protein kinase family. They are heterodimeric complexes composed of a catalytic kinase subunit and a regulatory cyclin subunit. CDK activity is controlled by association with their corresponding regulatory subunits (cyclins) and CDK inhibitor proteins (Cip & Kip proteins, INK4s), by their phosphorylation state, and by ubiquitin-mediated proteolytic degradation (see D. G. Johnson, C. L. Walker, Annu. Rev. Pharmacol. Toxicol 39 (1999) 295-312; D. O. Morgan, Annu. Rev. Cell Dev. Biol. 13 (1997) 261-291; C. J. Sherr, Science 274 (1996) 1672-1677; T. Shimamura et al., Bioorg. Med. Chem. Lett. 16 (2006) 3751-3754).

There are four CDKs that are significantly involved in cellular proliferation: CDK1, which predominantly regulates the transition from G2 to M phase, and CDK2, CDK4, and CDK6, which regulate the transition from G1 to S phase (Malumbres M, Barbacid M. Cell cycle, CDKs and cancer: a changing paradigm. Nat. Rev. Cancer 2009; 9(3):153-166).

In early to mid G1 phase, when the cell is responsive to mitogenic stimuli, activation of CDK4-cyclin D and CDK6-cyclin D induces phosphorylation of the retinoblastoma protein (pRb). Phosphorylation of pRb releases the transcription factor E2F, which enters the nucleus to activate transcription of other cyclins which promote further progression of the cell cycle (see J. A. Diehl, Cancer Biol. Ther. 1 (2002) 226-231; C. J. Sherr, Cell 73 (1993) 1059-1065). CDK4 and CDK6 are closely related proteins with basically indistinguishable biochemical properties (see M. Malumbres, M. Barbacid, Trends Biochem. Sci. 30 (2005) 630-641).

A number of CDK 4/6 inhibitors have been identified, including specific pyrido[2,3-d]pyrimidines, 2-anilinopyrimidines, diaryl ureas, benzoyl-2,4-diaminothiazoles, indolo[6,7-a]pyrrolo[3,4-c]carbazoles, and oxindoles (see P. S. Sharma, R. Sharma, R. Tyagi, Curr. Cancer Drug Targets 8 (2008) 53-75). For example, WO 03/062236 identifies a series of 2-(pyridin-2-ylamino-pyrido[2,3]pyrimidin-7-ones for the treatment of Rb positive cancers that show selectivity for CDK4/6, including 6-acetyl-8-cyclopentyl-5-methyl-2-(5-piperazin-1-yl-pyridin-2-ylammino)-8H-pyrido-[2,3-d]-pyrimidin-7-one (PD0332991), which is currently being tested by Pfizer in late stage clinical trials as an antineoplastic agent against estrogen-positive, HER2-negative breast cancer. VanderWel et al. describe an iodine-containing pyrido[2,3-d]pyrimidine-7-one (CKIA) as a potent and selective CDK4 inhibitor (see VanderWel et al., J. Med. Chem. 48 (2005) 2371-2387). WO 99/15500 filed by Glaxo Group Ltd discloses protein kinase and serine/threonine kinase inhibitors. WO 2010/020675 filed by Novartis AG describes pyrrolopyrimidine compounds as CDK inhibitors. WO 2011/101409 also filed by Novartis describes pyrrolopyrimidines with CDK 4/6 inhibitory activity. WO 2005/052147 filed by Novartis and WO 2006/074985 filed by Janssen Pharma disclose additional CDK4 inhibitors. WO 2012/061156 filed by Tavares and assigned to G1 Therapeutics describes CDK inhibitors. WO 2013/148748 filed by Francis Tavares and assigned to G1 Therapeutics describes Lactam Kinase Inhibitors.

While selective CDK4/6 inhibitors are generally designed to target CDK4/6-replication dependent cancers, the very fact that they inhibit CDK4/6 activity may also result in deleterious effects to CDK4/6-dependent healthy cells, for example their growth inhibition. CDK4/6 activity is necessary for the production of healthy blood cells by the bone marrow, as healthy hematopoietic stem and progenitor cells (HSPCs) require the activity of CDK4/6 for proliferation (see Roberts et al. Multiple Roles of Cyclin-Dependent Kinase 4/6 Inhibitors in Cancer Therapy. JNCI 2012; 104 (6):476-487). Healthy hematopoietic stem cells give rise to progenitor cells which in turn give rise to all the differentiated components of blood as shown in FIG. 1 (e.g., lymphocytes, erythrocytes, platelets, granulocytes, monocytes). Healthy hematopoietic cells display a gradient dependency on CDK4/6 activity for proliferation during myeloid/erythroid differentiation (see Johnson et al. Mitigation of hematological radiation toxicity in mice through pharmacological quiescence induced by CDK4/6 inhibition. J Clin. Invest. 2010; 120(7): 2528-2536). Accordingly, the least differentiated cells (e.g., healthy hematopoietic stem cells (HSCs), multi-potent progenitors (MPPs), and common myeloid progenitors (CMP)) appear to be the most dependent on CDK4/6 activity for proliferation, and therefore the most deleteriously affected by the use of a CDK4/6 inhibitor to treat a CDK4/6 replication dependent cancer or other proliferative disorder.

Accordingly, there is an ongoing need for improved compounds, methods, and regimes to treat patients with select Rb-positive cancers and abnormal cellular proliferative disorders while minimizing the treatment's effect on healthy cells such as HSPCs.

SUMMARY OF THE INVENTION

Improved compounds, methods, and compositions are provided to treat select Rb-positive abnormal cellular proliferation including an Rb-positive cancer while minimizing the treatment's deleterious effects on healthy cells, such as healthy HSPCs and other CDK4/6-replication dependent healthy cells by administration of an effective amount of a compound described herein.

In one embodiment of the invention, a compound is selected from the compounds of Formula I, II, III, IV, or V as described herein, or a pharmaceutically acceptable composition, salt, isotopic analog, or prodrug thereof. In one non-limiting example, a compound can be selected from the compounds of Table 1 below, or a pharmaceutically acceptable composition, salt, isotopic analog, or prodrug thereof.

In one embodiment, the Rb-positive cancer can be Rb-positive adenocarcinoma. The Rb-positive cancer can be Rb-positive adenocarcinoma of the colon. The Rb-positive cancer can also be Rb-positive adenocarcinoma of the rectum.

Alternatively, the Rb-positive cancer can be a Rb-positive analastic astrocytoma.

The Rb-positive cancer can be Rb-positive breast cancer. In one embodiment, the Rb-positive cancer is Rb-positive estrogen-receptor positive, HER2-negative advanced breast cancer. Alternatively, the Rb-positive cancer can be Rb-positive estrogen receptor-negative breast cancer. The Rb-positive cancer can be Rb-positive estrogen receptor positive breast cancer. The Rb-positive cancer can be Rb-positive late-line metastatic breast cancer. The Rb-positive cancer can be Rb-positive luminal A breast cancer. The Rb-positive cancer can be Rb-positive luminal B breast cancer. The Rb-positive cancer can be Rb-positive Her2-negative breast cancer or Rb-positive HER2-positive breast cancer. The Rb-positive cancer is Rb-positive male breast cancer. In one embodiment, the Rb-positive cancer is Rb-positive progesterone receptor-negative breast cancer. The Rb-positive cancer can be Rb-positive progesterone receptor-positive breast cancer. The Rb-positive cancer can be Rb-positive recurrent breast cancer. In one embodiment, the Rb-positive cancer is Rb-positive stage IV breast cancers. In one embodiment, the Rb-positive cancer is Rb-positive advanced HER2-positive breast cancer.

The Rb-positive cancer can be Rb-positive bronchial cancer. The Rb-positive cancer can be Rb-positive colon cancer. The Rb-positive cancer can be Rb-positive recurrent colon cancer. The Rb-positive cancer can be Rb-positive stage IV colon cancers. In one embodiment, the Rb-positive cancer is Rb-positive colorectal cancer.

In one embodiment, the Rb-positive cancer is Rb-positive endometrial cancer.

The Rb-positive cancer can be Rb-positive extragonadal seminoma. The Rb-positive cancer can be Rb-positive stage III extragonadal seminoma. The Rb-positive cancer can be Rb-positive stage IV extragonadal seminoma.

The Rb-positive cancer can be Rb-positive germ cell cancer. The Rb-positive cancer can be Rb-positive central nervous system germ cell tumor. The Rb-positive cancer can be Rb-positive familial testicular germ cell tumor. The Rb-positive cancer can be Rb-positive recurrent gonadal germ cell tumor. The Rb-positive cancer can be Rb-positive recurrent extragonadal non-seminomatous germ cell tumor. The Rb-positive cancer can be Rb-positive extragonadal seminomatous germ cell tumor. The Rb-positive cancer can be Rb-positive recurrent malignant testicular germ cell tumors. The Rb-positive cancer can be Rb-positive recurrent ovarian germ cell tumors. The Rb-positive cancer can be Rb-positive stage III malignant testicular germ cell tumors. The Rb-positive cancer can be Rb-positive stage III ovarian germ cell tumors. The Rb-positive cancer can be Rb-positive stage IV ovarian germ cell tumors. The Rb-positive cancer can be Rb-positive stage III extragonadal non-seminomatous germ cell tumors. The Rb-positive cancer can be Rb-positive stage IV extragonadal non-seminomatous germ cell tumors. In one embodiment, the Rb-positive cancer is Rb-positive germ cell cancer. In one embodiment, the Rb-positive cancer is Rb-positive cisplatin-refractory, unresectable germ cell cancer.

In one embodiment, the Rb-positive cancer is Rb-positive glioblastoma.

In one embodiment, the Rb-positive cancer is Rb-positive liver cancer. The Rb-positive cancer can be Rb-positive hepatocellular cancer.

The Rb-positive cancer can be Rb-positive lung cancer. In one embodiment, the Rb-positive cancer is Rb-positive non-small cell lung cancer. In one embodiment, the Rb-positive cancer is Rb-positive KRAS mutant non-small cell lung cancer.

The Rb-positive cancer can be Rb-positive melanoma. In one embodiment, the Rb-positive cancer is Rb-positive recurrent melanomas. In one embodiment, the Rb-positive cancer is Rb-positive stage IV melanomas.

The Rb-positive cancer can be Rb-positive ovarian cancer. In one embodiment, the Rb-positive cancer is Rb-positive ovarian epithelial carcinoma.

The Rb-positive cancer can be Rb-positive pancreatic cancer.

The Rb-positive cancer can be Rb-positive prostate cancer.

In one embodiment, the Rb-positive cancer is Rb-positive rectal cancer. The Rb-positive cancer can be Rb-positive recurrent rectal cancer. The Rb-positive cancer can be Rb-positive stage IV rectal cancers.

The Rb-positive cancer can be Rb-positive sarcoma. The Rb-positive cancer can be Rb-positive gliosarcoma. The Rb-positive cancer can be Rb-positive liposarcoma. The Rb-positive cancer can be Rb-positive fibrosarcoma. The Rb-positive cancer can be Rb-positive myxosarcoma. In one embodiment, the Rb-positive cancer can be Rb-positive chondrosarcoma. The Rb-positive cancer can be Rb-positive osteosarcoma.

The Rb-positive cancer can be Rb-positive malignant fibrous histiocytoma. The Rb-positive cancer can be Rb-positive hemangiosarcoma. The Rb-positive cancer can be Rb-positive angiosarcoma. The Rb-positive cancer can be Rb-positive lymphangiosarcoma. The Rb-positive cancer can be Rb-positive mesothelioma. The Rb-positive cancer can be Rb-positive leiomyosarcoma. The Rb-positive cancer can be Rb-positive rhabdomyosarcoma. The Rb-positive cancer can be a Rb-positive meningioma. The Rb-positive cancer can be a Rb-positive schwannoma.

In one embodiment, the Rb-positive cancer is a Rb-positive pheochromocytoma. The Rb-positive cancer can be a Rb-positive Islet cell carcinoma. The Rb-positive cancer can be Rb-positive carcinoid. The Rb-positive cancer can be a Rb-positive paraganglioma.

In one embodiment, the Rb-positive cancer is Rb-positive squamous cell carcinoma. The Rb-positive cancer can be Rb-positive adenocarcinoma. The Rb-positive cancer can be Rb-positive hepatocellular carcinoma. The Rb-positive cancer can be Rb-positive renal cell carcinoma. The Rb-positive cancer can be Rb-positive cholangiocarcinoma.

The Rb-positive cancer can be Rb-positive refractory solid tumors.

The Rb-positive cancer can be Rb-positive neuroblastoma.

The Rb-positive cancer can be Rb-positive medulloblastoma.

In one embodiment, the Rb-positive cancer is a Teratoma. The Rb-positive cancer can be Rb-positive ovarian immature teratoma. The Rb-positive cancer can be a Rb-positive ovarian mature teratoma. The Rb-positive cancer can be a Rb-positive ovarian specialized teratoma. The Rb-positive cancer can be Rb-positive testicular immature teratoma. The Rb-positive cancer can be Rb-positive testicular mature teratoma. The Rb-positive cancer can be Rb-positive teratoma. The Rb-positive cancer can be Rb-positive ovarian monodermal teratoma.

The Rb-positive cancer can be Rb-positive testicular cancer.

In one embodiment, the Rb-positive cancer is Rb-positive vaginal cancer.

In one embodiment, the Rb-positive cancer is selected from an Rb-positive carcinoma, sarcoma, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

In one embodiment, the subject is suffering from a Rb-positive abnormal cellular proliferation disorder. In one embodiment, the Rb-positive abnormal cellular proliferation disorder is non-cancerous.

In certain embodiments, a compound described herein, when used to treat a select Rb-positive cellular proliferation disorder, such as a cancer, allows for a rapid reentry of healthy cells into the normal cell-cycle and a fast reconstitution of damaged tissue and progeny cells such as hematological cells. In this aspect, the compounds described herein when used to treat Rb-positive cancers eliminate, reduce, and/or minimize the drug holidays and dose delays associated with the current anti-neoplastic use of CDK4/6 inhibitors, allowing for the quick recovery of damaged blood cells through the replication and differentiation of progenitor and parent cells. Specifically, the invention includes administering to a patient having a cancer such as an Rb-positive cancer an effective amount of a compound described herein, wherein the compound has a pharmacokinetic and enzymatic half-life that provides for a transient, reversible G1 arrest of CDK4/6-replication dependent cells. The compound can be any of those described in this application. Non-limiting examples of active compounds are described in Table 1, or a pharmaceutically acceptable composition, salt, isotopic analog, or prodrug thereof as provided below.

In one embodiment, a compound described herein may be useful in an improved method for treating a cancer such as an Rb-positive cancer, wherein such methods have reduced or minimized effects on CDK4/6-replication dependent healthy cells due in part because they (i) utilize compounds that exhibit a pharmacokinetic and enzymatic half-life which provide for a relatively short, transient and reversible G1-arresting effect on CDK4/6-replication dependent healthy cells and (ii) allow for a rapid, reentry into the cell cycle for the healthy cells following the cessation of administration or dissipation of therapeutically effective levels in the subject. Using a compound described herein allows for, for example, a reduction in the replication delay of the HSPCs due to CDK4/6 inhibition and/or accelerated hematopoietic cell lineage recovery following cessation of CDK4/6 inhibitory activity and/or reduced hematological deficiency because the utilized compound is short-acting, and reduces the length of off-cycle periods or drug holidays associated with current CDK4/6 inhibitor treatment modalities which reduces or minimizes the facilitation of tumor drug resistance. In certain embodiments, the use of a compound described herein allows for the continuous treatment of the subject over a longer time period without the need for an off-cycle or drug holiday.

The timely resumption of CDK4/6-replication dependent healthy cell proliferation is necessary for tissue repair, and an overly long period of healthy cell cell-cycle arrest, for example HSPC cell-cycle arrest, is undesirable. Despite reports indicating that the selective CDK4/6 inhibitor PD0332991 is an effective inhibitor of Rb-positive breast cancers, it has been discovered that such inhibitor may not be the most ideal compound for use as a chemotherapeutic due to the excessive myelosuppressive effects of the compound. For example, PD0332991 has a relatively long-acting intra-cellular effect (see Roberts et al. Multiple Roles of Cyclin-Dependent Kinase 4/6 Inhibitors in Cancer Therapy. JCNI 2012; 104(6):476-487 (FIG. 2A)), extending the transiency of G1 arrest of healthy cells such as HSPCs leading to dose limiting myelosuppression. Such a long acting effect delays, for example, the proliferation of HSPC cell lineages necessary to reconstitute the hematological cell lines that have been growth inhibited due to a treatment which may inhibit CDK4/6 activity, and thus, Rb phosphorylation in Rb competent cells. While desirable for its anti-neoplastic effects, the long-acting G1 arrest provided by PD0332991 requires an extended off-cycle period in order to reconstitute the erythroid, platelet, and myeloid cells (monocyte and granulocyte) adversely effected by acute HSPC G1-arrest in order to limit myelosuppressive and allow a hematologic replication period. The use of a compound described herein as anti-neoplastic agent for the treatment of select Rb-positive cancers may eliminate, reduce, or minimize the required length of off-cycle periods or drug holidays, allowing for a longer effective CDK4/6 inhibitory time period on the cancer over the course of an anti-neoplastic regime.

Thus in one embodiment, the invention includes administering a compound described herein, including one selected from Table 1 in an effective amount to a host suffering from a Rb-positive cancer in a treatment regime, wherein (either alone or in any combination thereof, each of which is considered specifically and independently described): i) a substantial portion of the CDK4/6-replication dependent healthy cells (e.g. at least 80% or greater), for example HSPCs, return to or approach pre-treatment baseline cell cycle activity (i.e., reenter the cell-cycle) in less than 24 hours, 30 hours or 36 hours from the last administration of a compound described herein in humans; ii) a substantial portion of the CDK4/6-replication dependent healthy cells, for example HSPCs, reenter the cell-cycle synchronously in less than 24 hours, 30 hours, or 36 hours from the last administration of a compound described herein; (iii) the dissipation of the compound's inhibitory effect on CDK4/6-replication dependent healthy cells, for example HSPCs, occurs in less than 24 hours, 30 hours, or 36 hours from the administration of the compound; (iv) a substantial portion of the CDK4/6-replication dependent healthy cells, for example HSPCs, return to or approach pre-treatment baseline cell cycle activity (i.e., reenter the cell-cycle) in less than 24 hours, 30 hours, or 36 hours from the dissipation of the compound's CDK4/6 inhibitory effect; or (vi) a substantial portion of the CDK4/6-replication dependent healthy cells, for example HSPCs, return to or approach pre-treatment baseline cell cycle activity (i.e. reenter the cell-cycle) within less than about 24 hours, about 30 hours, or about 36 hours from the point in which the administered compound's concentration level in the subject's blood drops below a therapeutic effective concentration.

In a central embodiment of the invention, a compound described herein can be administered in a concerted regimen with another agent such as a non-DNA-damaging, targeted anti-neoplastic agent or a hematopoietic growth factor agent for beneficial, additive, or synergistic effect against the abnormal cellular proliferation. It has been recently reported that the untimely administration of hematopoietic growth factors can have serious side effects. For example, the use of the EPO family of growth factors has been associated with arterial hypertension, cerebral convulsions, hypertensive encephalopathy, thromboembolism, iron deficiency, influenza like syndromes and venous thrombosis. The G-CSF family of growth factors has been associated with spleen enlargement and rupture, respiratory distress syndrome, allergic reactions and sickle cell complications. By combining the administration of a compound described herein and methods of the present invention with the timely administration of hematopoietic growth factors, for example, at the time point wherein the affected cells are no longer under growth arrest, it is possible for the health care practitioner to decrease the amount of the growth factor to minimize the unwanted adverse effects while achieving the desired therapeutic benefit. In one embodiment, the growth factor is administered upon cessation of the effect of the inhibitory effect of the compound on the CDK4/6 replication dependent healthy cells, for example HSPCs. Thus, in this embodiment, the use of a selective CDK4/6 inhibitor described herein in an anti-neoplastic therapeutic regime may allow the subject to receive a reduced amount of growth factor because the targeted hematopoietic cells will have reentered the cell cycle quicker than when other CDK4/6 inhibitors, for example PD0332991. In addition, allowing rapid cell-cycle reentry following G1 arrest by using a compound described herein provides for the ability to time the administration of hematopoietic growth factors to assist in the reconstitution of hematopoietic cell lines to maximize the growth factor effect. As such, in one embodiment, the use of a compound or method described herein is combined with the use of a hematopoietic growth factor including, but not limited to, granulocyte colony stimulating factor (G-CSF), granulocyte-macrophage colony stimulating factor (GM-CSF), thrombopoietin, interleukin (IL)-12, steel factor, and erythropoietin (EPO), or a derivative thereof.

In one embodiment, the CDK4/6 inhibitor is administered prior to administration of the hematopoietic growth factor. In one embodiment, the hematopoietic growth factor administration is timed so that the CDK4/6 inhibitor's effect on HSPCs has dissipated. In one embodiment, the use of a compound described herein is combined in a therapeutic regime with at least one other chemotherapeutic agent, and can be one that does not rely on proliferation or advancement through the cell-cycle for anti-proliferative activity. Such agent may include, but is not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof). Examples of mTOR inhibitors include but are not limited to rapamycin and its analogs, everolimus (Afinitor), temsirolimus, ridaforolimus, sirolimus, and deforolimus. Examples of P13 kinase inhibitors include but are not limited to Wortmannin, demethoxyviridin, perifosine, idelalisib, PX-866, IPI-145, BAY 80-6946, BEZ235, RP6503, TGR 1202 (RP5264), MLN1117 (INK1117), Pictilisib, Buparlisib, SAR245408 (XL147), SAR245409 (XL765), Palomid 529, ZSTK474, PWT33597, RP6530, CUDC-907, and AEZS-136. Examples of MEK inhibitors include but are not limited to Tametinib, Selumetinib, MEK162, GDC-0973 (XL518), and PD0325901. Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol.

In certain embodiments, a compound described herein is administered to the subject prior to treatment with another chemotherapeutic agent, during treatment with another chemotherapeutic agent, after administration of another chemotherapeutic agent, or a combination thereof. In one embodiment, a compound described herein is administered to the subject less than about 24 hours, 20 hours, 16 hours, 12 hours, 8 hours, or 4 hours or less prior to treatment with the other chemotherapeutic agent in order to sensitize the Rb-positive cancer to the chemotherapeutic agent. In one embodiment, the compound is administered up to 4 hours prior to treatment with the other chemotherapeutic agent.

In one embodiment, a compound described herein is administered in a manner that allows the drug facile access to the blood stream, for example via intravenous injection or sublingual, intraaortal, or other efficient blood-stream accessing route. In one embodiment, a compound described herein is administered in an orally administrable formulation. In other embodiments, a compound described herein is administered via topical, transdermal, or other desired administrative routes.

In one embodiment, a compound described herein is administered to the subject less than about 24 hours, 20 hours, 16 hours, 12 hours, 8 hours, or 4 hours or less prior to treatment with the hematopoietic growth factor. In one embodiment, the compound is administered up to 4 hours prior to treatment with the hematopoietic growth factor or other chemotherapeutic agent.

The compounds useful in the present invention show a marked selectivity for the inhibition of CDK4 and/or CDK6 in comparison to other CDKs, for example CDK2. For example, compounds useful in the present invention provide for a dose-dependent G1-arresting effect on a subject's Rb-positive cancer cells, and the methods provided for herein are sufficient to afford chemotherapeutic treatment and growth inhibition of RB-positive cancer cells while not affecting CDK4/6-replication independent cells.

In one embodiment, the use of a compound described herein results in the G1-arresting effect dissipates such that the subject's CDK4/6-replication dependent healthy cells return to their pre-administration baseline cell-cycle activity within less than about 12 hours, 14 hours, 16 hours, 18 hours, 20 hours, 24 hours, 30 hours, 36 hours, or 40 hours.

In one embodiment, the G1-arresting effect dissipates such that the subject's CDK4/6-replication dependent healthy cells return to their pre-administration baseline cell-cycle activity within less than about 24 hours, 30 hours, 36 hours, or 40 hours, or within about 48 hours of the cessation of administration. In one embodiment, the CDK4/6-replication dependent healthy cells are HSPCs. In one embodiment, the use of a CDK4/6 inhibitor described herein results in the G1-arresting effect dissipating so that the subject's CDK4/6-replication dependent healthy cells return to or approach their pre-administration baseline cell-cycle activity within less than about 24 hours, 30 hours, 36 hours, 40 hours, or within less than about 48 hours from the point in which the CDK4/6 inhibitor's concentration level in the subject's blood drops below a therapeutic effective concentration. In one embodiment, the G1-arresting effect dissipates so that the subject's CDK4/6-replication dependent healthy cells return to their pre-administration baseline cell-cycle activity within about within less than about 24 hours, 30 hours, 36 hours, 40 hours, or 48 hours of the from the point in which the CDK4/6 inhibitor's concentration level in the subject's blood drops below a therapeutic effective concentration.

In one embodiment, a compound described herein and useful in the described methods may be synchronous in its off-effect, that is, upon dissipation of the G1 arresting effect, CDK4/6-replication dependent healthy cells exposed to a compound described herein reenter the cell-cycle in a similarly timed fashion. CDK4/6-replication dependent healthy cells that reenter the cell-cycle do so such that the normal proportion of cells in G1 and S are reestablished quickly and efficiently, within less than about 24 hours, 30 hours, 36 hours, 40 hours, or within about 48 hours of the from point in which the compound's concentration level in the subject's blood drops below a therapeutic effective concentration.

The rapid cell-cycle reentry associated with the compound's rapid off-effect advantageously allow for a larger number of CDK4/6-replication dependent healthy cells to begin replicating upon dissipation of the G1 arrest compared with other CDK4/6 inhibitors such as PD0332991. Accordingly, CDK4/6-replication dependent healthy cells, such as HSPCs, can quickly begin to replicate during an off-cycle period or during administration periods.

The use of a compound as described herein in a therapeutic regime targeting CDK4/6-replication dependent cancers can result in reduced anemia, reduced lymphopenia, reduced thrombocytopenia, or reduced neutropenia compared to that typically expected after, common after, or associated with treatment with currently available antineoplastic chemotherapeutic agents. The use of the compounds as described herein may result in a faster recovery from bone marrow suppression associated with long-term use of CDK4/6 inhibitors, such as myelosuppression, anemia, lymphopenia, thrombocytopenia, or neutropenia, following the cessation of use of the CDK4/6 inhibitor. In some embodiments, the use of a compound as described herein results in reduced bone marrow suppression associated with long-term use of CDK4/6 inhibitors, such as myelosuppression, anemia, lymphopenia, leukopenia, thrombocytopenia, or granulocytopenias such as neutropenia.

In some embodiments, the subject or host is a mammal, including a human. The compound can be administered to the subject by any desired route, including intravenous, sublingual, buccal, oral, intraaortal, topical, intranasal, parenteral, transdermal, systemic, intramuscular, or via inhalation.

In summary, the present invention includes the following features:

A) Optimal compounds, methods, and compositions as chemotherapeutics which minimize the deleterious effects on CDK4/6 replication dependent healthy cells, for example hematopoietic stem and progenitor cells (HSPCs), in a subject undergoing treatment for a select Rb-positive cancer, comprising administering an effective amount of a compound of Formula I, II, III, IV, or V, including a compound selected from Table 1 as described herein;

B) Optimal compounds, methods, and compositions as chemotherapeutics which minimize the deleterious effects on CDK4/6 replication dependent healthy cells, for example hematopoietic stem and progenitor cells (HSPCs), in a subject undergoing treatment for a Rb-positive cancer, comprising administering an effective amount of a selective compound described herein, wherein a substantial portion of the healthy cells return to or approach pre-treatment baseline cell cycle activity (i.e., reenter the cell-cycle) within less than about 24 hours, 30 hours, 36 hours, or about 40 hours from the last administration of the CDK4/6 inhibitor and wherein the CDK4/6 inhibitor has an $IC_{50}$ concentration for CDK4 inhibition that is more than about 1500 times less than its $IC_{50}$ concentration for CDK2 inhibition. In certain embodiments, the CDK4/6 replication dependent healthy cells are HSPCs. In certain embodiments, the CDK4/6 replication dependent healthy cells are renal epithelial cells;

C) Optimal compounds, methods, and composition as chemotherapeutics which minimize the deleterious effect on CDK4/6 replication dependent healthy cells in a subject undergoing treatment for a Rb-positive cancer comprising administering an effective amount of a compound described herein, wherein a substantial portion of the CDK-replication dependent healthy cells synchronously reenter the cell-cycle within less than about 24 hours, 30 hours, 36 hours, or about 40 hours following the dissipation of the compound's CDK4/6 inhibitory effect, wherein the compound has an $IC_{50}$ concentration for CDK4 inhibition that is more than 1500 times less than its $IC_{50}$ concentration for CDK2 inhibition. In certain embodiments, the CDK4/6 replication dependent healthy cells are HSPCs. In certain embodiments, the CDK4/6 replication dependent healthy cells are renal epithelial cells;

D) Optimal compounds, methods, and compositions as chemotherapeutics which minimize the deleterious effects on CDK4/6 replication dependent healthy cells in a subject, the method comprising administering to a subject with a Rb-positive abnormal cellular proliferative disorder an effective amount of a selective CDK4/6 inhibitor selected from the group consisting of a compound described herein. In certain embodiments, the subject's healthy cells return to or approach pre-treatment baseline cell cycle activity (i.e. reenter the cell-cycle) within less than about 24 hours, about 30 hours, about 36 hours, or about 40 hours from the point in which the compound's concentration level in the subject's blood drops below a therapeutic effective concentration. In certain embodiments, the CDK4/6 replication dependent healthy cells are HSPCs. In certain embodiments, the CDK4/6 replication dependent healthy cells are renal epithelial cells.

E) A compound as described herein, or a pharmaceutically acceptable composition, salt, isotopic analog, or prodrug thereof, for use as a chemotherapeutic in the treatment of an Rb-positive abnormal cellular proliferation disorder, including Rb-positive cancers;

F) A compound as described herein, or a pharmaceutically acceptable composition, salt, isotopic analog, and prodrug thereof, for use as a chemotherapeutic regimen for the treatment of an Rb-positive abnormal cellular proliferation disorder, including Rb-positive cancers, which minimizes the deleterious effects on CDK4/6-replication dependent healthy cells, for example HSPCs or renal cells;

G) A compound as described herein, or a pharmaceutically acceptable composition, salt, isotopic analog, and prodrug thereof, for use in combination with hematopoietic growth factors in a subject undergoing a therapeutic regime to treat Rb-positive abnormal cellular proliferation disorder, including Rb-positive cancers;

H) Compounds as described herein, or a pharmaceutically acceptable composition, salt, isotopic analog, or prodrug thereof, for use in combination with a second chemotherapeutic agent in a subject undergoing a therapeutic regime to treat a Rb-positive abnormal cellular proliferation disorder, including Rb-positive cancers;

I) Use of a compound described herein, or a pharmaceutically acceptable composition, salt, isotopic analog, or prodrug thereof, in the manufacture of a medicament for use as a chemotherapeutic to treat a subject with a Rb-positive abnormal cellular proliferation disorder, including Rb-positive cancers;

J) Use of a compound described herein, or a pharmaceutically acceptable composition, salts, isotopic analog, or prodrug thereof, in the manufacture of a medicament for use as chemotherapeutic to treat a subject with a Rb-positive cellular proliferation disorder, including a Rb-positive cancer that, when exposed to a CDK4/6 inhibitor, is growth arrested or growth inhibited;

K) Processes for the preparation of therapeutic products that contain an effective amount of a compound described herein, for use in the treatment of a subject having a Rb-positive abnormal cellular proliferation disorder, such as cancer, and;

L) A method for manufacturing a medicament selected from the compounds described herein intended for therapeutic use as a chemotherapeutic on the treatment of a Rb-positive abnormal cellular proliferation disorder, such as a cancer, responsive to a CDK4/6 inhibitor.

BRIEF DESCRIPTION OF THE DRAWINGS

FIG. 7 provides the half-life (minutes) of compound T and PD0332991 in human and animal (monkey, dog, rat, and mouse) liver microsomes. As described in Example 158, PD0332991 has a half-life greater than 60 minutes in each of the species tested. Compound T was determined to have a shorter half-life than PD0332991 in each of the species tested.

FIG. 10 is a table showing the objective response rate (ORR) of MMTV-c-neu (Rb-positive) tumors in mice treated with compounds T, GG, or U in the MMTV-c-neu luminal breast cancer (Rb-positive) model. All three compounds were administered orally via medicated diets (100 mg/kg/day). Medicated diets were administered for 28 consecutive days and then stopped. RECIST criteria were used to assess objective response rates. The objective response rates (ORR) were categorized based on the percentage change in tumor volume, using the following categories: CR (complete response)=100% response; PR (partial response) =at least a 30% decrease; SD (stable disease)=no change (not a PR and not a PD); and PD (progressive disease)=20% increase. As described in Example 160, continuous treatment with compounds T, GG, or U led to a marked reduction in tumor volume during a 28 day course of therapy.

FIG. 29D is a graph of the number of A2058 cells (CDK4/6-independent cell line) vs. the DNA content of the cells (as measured by propidium iodide). Cells were treated with DMSO for 24 hours, harvested, and analyzed for cell cycle distribution.

FIG. 29E is a graph of the number of tHS68 cells (CDK4/6-dependent cell line) vs. the DNA content of the cells (as measured by propidium iodide) after treatment with Compound T. Cells were treated with Compound T (300 nM) for 24 hours, harvested, and analyzed for cell cycle distribution. As described in Example 161, treatment of tHS68 cells with Compound T causes a loss of the S-phase peak (indicated by arrow).

DETAILED DESCRIPTION OF THE INVENTION

Figure 1:
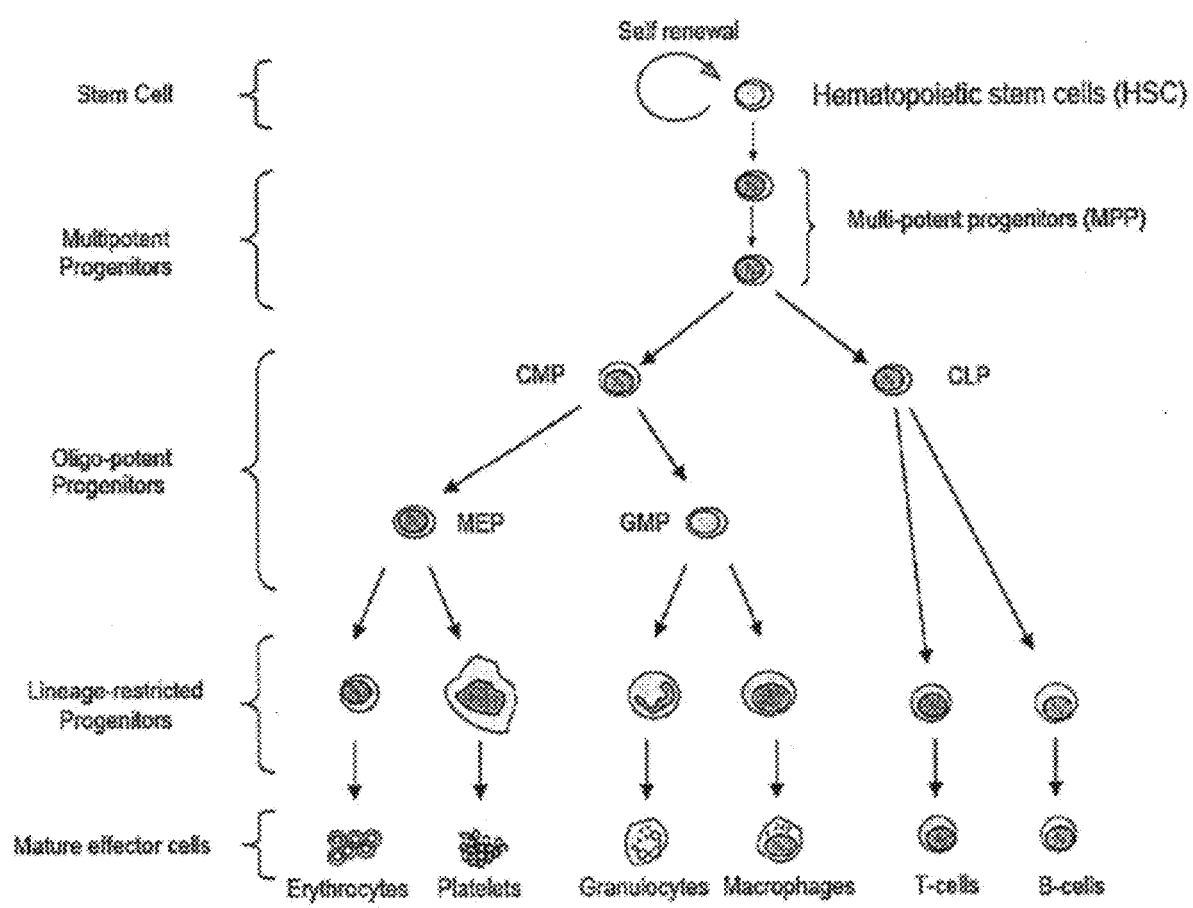
FIG. 1 is a schematic drawing of hematopoiesis showing the hierarchical proliferation of healthy hematopoietic stem cells (HSC) and healthy hematopoietic progenitor cells with increasing differentiation upon proliferation.

Improved compounds, methods, and compositions are provided as chemotherapeutics for the treatment of select Rb-positive cancers which minimize or reduce the deleterious effects on CDK4/6 replication dependent healthy cells, such as hematopoietic stem cells and/or progenitor cells (HSPCs), due to CDK4/6 growth arrest, in subjects, typically humans.

Definitions

Unless otherwise stated, the following terms used in this application, including the specification and claims, have the definitions given below. As used in the specification and the appended claims, the singular forms "a," "an" and "the" include plural referents unless the context clearly dictates otherwise. Definition of standard chemistry terms may be found in reference works, including Carey and Sundberg (2007) *Advanced Organic Chemistry* 5$^{th}$ Ed. Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology. Conventional methods of organic chemistry include those included in *March's Advanced Organic Chemistry: Reactions, Mechanisms, and Structure*, 6$^{th}$ *Edition*, M. B. Smith and J. March, John Wiley & Sons, Inc., Hoboken, N.J., 2007.

The term "alkyl," either alone or within other terms such as "haloalkyl" and "alkylamino," embraces linear or branched radicals having one to about twelve carbon atoms. "Lower alkyl" radicals have one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylene" embraces bridging divalent linear and branched alkyl radicals. Examples include methylene, ethylene, propylene, isopropylene and the like.

The term "alkenyl" embraces linear or branched radicals having at least one carbon-carbon double bond of two to about twelve carbon atoms. "Lower alkenyl" radicals having two to about six carbon atoms. Examples of alkenyl radicals include ethenyl, propenyl, allyl, propenyl, butenyl and 4-methylbutenyl. The terms "alkenyl" and "lower alkenyl," embrace radicals having "cis" and "trans" orientations, or alternatively, "E" and "Z" orientations.

The term "alkynyl" denotes linear or branched radicals having at least one carbon-carbon triple bond and having two to about twelve carbon atoms. "Lower alkynyl" radicals having two to about six carbon atoms. Examples of such radicals include propargyl, butynyl, and the like.

Alkyl, alkenyl, and alkynyl radicals may be optionally substituted with one or more functional groups such as halo, hydroxy, nitro, amino, cyano, haloalkyl, aryl, heteroaryl, heterocyclo and the like.

The term "alkylamino" embraces "N-alkylamino" and "N,N-dialkylamino" where amino groups are independently substituted with one alkyl radical and with two alkyl radicals, respectively. "Lower alkylamino" radicals have one or two alkyl radicals of one to six carbon atoms attached to a nitrogen atom. Suitable alkylamino radicals may be mono or dialkylamino such as N-methylamino, N-ethylamino, N,N-dimethylamino, N,N-diethylamino and the like.

The term "halo" means halogens such as fluorine, chlorine, bromine or iodine atoms.

The term "haloalkyl" embraces radicals wherein any one or more of the alkyl carbon atoms is substituted with one or more halo as defined above. Examples include monohaloalkyl, dihaloalkyl and polyhaloalkyl radicals including perhaloalkyl. A monohaloalkyl radical, for one example, may have an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means an alkyl radical having all hydrogen atoms replaced with fluoro atoms. Examples include trifluoromethyl and pentafluoroethyl.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 or more substituents such as lower alkyl, hydroxyl, halo, haloalkyl, nitro, cyano, alkoxy, lower alkylamino, and the like. An aryl group may be optionally substituted with one or more functional groups such as halo, hydroxy, nitro, amino, cyano, haloalkyl, aryl, heteroaryl, heterocyclo and the like.

The term "heterocyclyl" (or "heterocyclo") embraces saturated, and partially saturated heteroatom-containing ring radicals, where the heteroatoms may be selected from nitrogen, sulfur and oxygen. Heterocyclic rings comprise monocyclic 6-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like.

Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclo groups include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

Heterocyclo groups also includes radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl].

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heteroarylalkyl" denotes alkyl radicals substituted with a heteroaryl group. Examples include pyridylmethyl and thienylethyl.

The term "sulfonyl", whether used alone or linked to other terms such as alkylsulfonyl, denotes respectively divalent radicals —SO$_2$—.

The terms "carboxy" or "carboxyl", whether used alone or with other terms, such as "carboxyalkyl", denotes —C(O)—OH.

The term "carbonyl", whether used alone or with other terms, such as "aminocarbonyl", denotes —C(O)—.

The term "aminocarbonyl" denotes an amide group of the Formula —C(O)—NH$_2$.

The terms "heterocycloalkyl" embrace heterocyclic-substituted alkyl radicals. Examples include piperidylmethyl and morpholinylethyl.

The term "arylalkyl" embraces aryl-substituted alkyl radicals. Examples include benzyl, diphenylmethyl and phenylethyl. The aryl in said aralkyl may be additionally substituted with halo, alkyl, alkoxy, halkoalkyl and haloalkoxy.

The term "cycloalkyl" includes saturated carbocyclic groups of 3 to 10 carbons. Lower cycloalkyl groups include $C_3$-$C_6$ rings. Examples include cyclopentyl, cyclopropyl, and cyclohexyl. Cycloalkyl groups may be optionally substituted with one or more functional groups such as halo, hydroxy, nitro, amino, cyano, haloalkyl, aryl, heteroaryl, heterocyclo and the like.

The term "cycloalkylalkyl" embraces cycloalkyl-substituted alkyl radicals. "Lower cycloalkylalkyl" radicals are cycloalkyl radicals attached to alkyl radicals having one to six carbon atoms. Examples of include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Examples include cyclopentenyl, cyclopentadienyl, cyclohexenyl and cycloheptadienyl.

The term "comprising" is meant to be open ended, including the indicated component but not excluding other elements.

The term "oxo" as used herein contemplates an oxygen atom attached with a double bond.

The term "nitro" as used herein contemplates —$NO_2$.

The term "cyano" as used herein contemplates —CN.

As used herein, the term "prodrug" means a compound which when administered to a host in vivo is converted into the parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

Throughout the specification and claims, a given chemical formula or name shall encompass all optical and stereoisomers, as well as racemic mixtures where such isomers and mixtures exist, unless otherwise noted.

The current invention is directed to an HSPC-sparing strategy during the treatment of Rb-positive proliferation disorders. According, as used herein, the term "HSPCs" is meant to describe healthy hematopoietic stem and/or hematopoietic progenitor cells, as opposed to diseased HSPCs or cells of related hematological origin. HSPCs include hematopoietic stem cells, such as long term hematopoietic stem cells (LT-HSCs) and short term hematopoietic stem cells (ST-HSCs), and hematopoietic progenitor cells, including multipotent progenitors (MPPs), common myeloid progenitors (CMPs), common lymphoid progenitors (CLPs), granulocyte-monocyte progenitors (GMPs) and megakaryocyte-erythroid progenitors (MEPs).

In some embodiments, a CDK4/6-replication dependent healthy cell is a hematopoietic stem progenitor cell. In some embodiments, the CDK4/6-replication dependent healthy cell may be a cell in a non-hematopoietic tissue, such as, but not limited to, the liver, kidney, pancreas, brain, lung, adrenals, intestine, gut, stomach, skin, auditory system, bone, bladder, ovaries, uterus, testicles, gallbladder, thyroid, heart, pancreatic islets, blood vessels, and the like.

The term "selective CDK4/6 inhibitor" used in the context of the compounds described herein includes compounds that inhibit CDK4 activity, CDK6 activity, or both CDK4 and CDK6 activity at an $IC_{50}$ molar concentration at least about 500, or 1000, or 1500, or 1800, or 2000 times less than the $IC_{50}$ molar concentration necessary to inhibit to the same degree of CDK2 activity in a standard phosphorylation assay.

As used herein the term "chemotherapy" or "chemotherapeutic agent" refers to treatment with a cytostatic or cytotoxic agent (i.e., a compound) to reduce or eliminate the growth or proliferation of undesirable cells, for example cancer cells. Thus, as used herein, "chemotherapy" or "chemotherapeutic agent" refers to a cytotoxic or cytostatic agent used to treat a proliferative disorder, for example cancer.

By "induces G1-arrest" is meant that the inhibitor compound induces a quiescent state in a substantial portion of a cell population at the G1 phase of the cell cycle.

By "hematological deficiency" is meant reduced hematological cell lineage counts or the insufficient production of blood cells (i.e., myelodysplasia) and/or lymphocytes (i.e., lymphopenia, the reduction in the number of circulating lymphocytes, such as B- and T-cells). Hematological deficiency can be observed, for example, as myelosuppression in form of anemia, reduction in platelet count (i.e., thrombocytopenia), reduction in white blood cell count (i.e., leukopenia), or the reduction in granulocytes (e.g., neutropenia).

By "synchronous reentry into the cell cycle" is meant that CDK4/6-replication dependent healthy cells, for example HSPCs, in G1-arrest due to the effect of a CDK4/6 inhibitor compound reenter the cell-cycle within relatively the same collective timeframe or at relatively the same rate upon dissipation of the compound's effect. Comparatively, by "asynchronous reentry into the cell cycle" is meant that the healthy cells, for example HSPCs, in G1 arrest due to the effect of a CDK4/6 inhibitor compound within relatively different collective timeframes or at relatively different rates upon dissipation of the compound's effect such as PD0332991.

By "off-cycle" or "drug holiday" is meant a time period during which the subject is not administered or exposed to a chemotherapeutic. For example, in a treatment regime wherein the subject is administered the chemotherapeutic for 21 straight days and is not administered the chemotherapeutic for 7 days, and the regime is repeated a number of times, the 7 day period of non-administration is considered the "off-cycle" or "drug holiday." Off-target and drug holiday may also refer to an interruption in a treatment regime wherein the subject is not administered the chemotherapeutic for a time due to a deleterious side effect, for example, myelosuppression.

The subject treated is typically a human subject, although it is to be understood the methods described herein are effective with respect to other animals, such as mammals and vertebrate species. More particularly, the term subject can include animals used in assays such as those used in preclinical testing including but not limited to mice, rats, monkeys, dogs, pigs and rabbits; as well as domesticated swine (pigs and hogs), ruminants, equine, poultry, felines, bovines, murines, canines, and the like.

Active Compounds

In one embodiment, the invention is directed to compounds or the use of such compounds of Formula I, II, III, IV, or V:

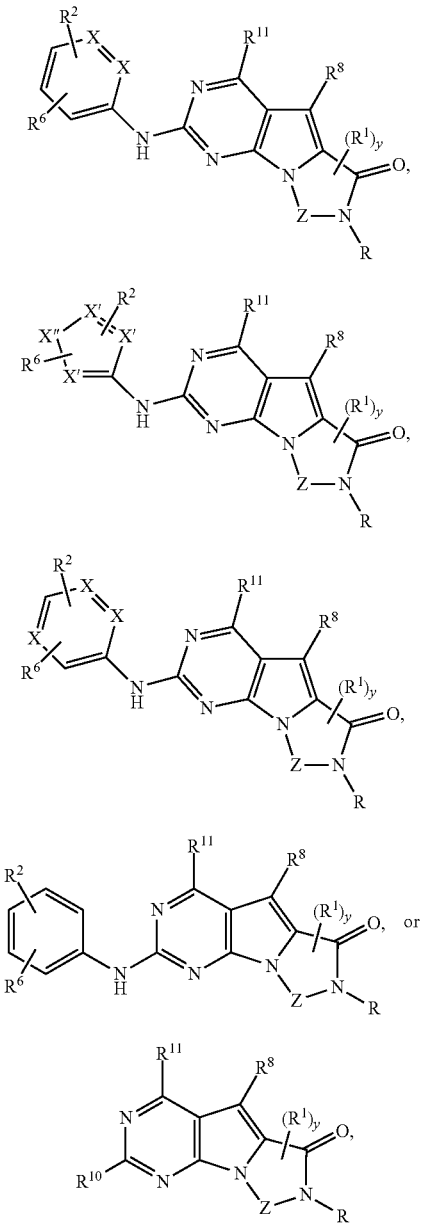

or a pharmaceutically acceptable salt thereof;
wherein:
Z is —$(CH_2)_x$— wherein x is 1, 2, 3 or 4 or —O—$(CH_2)_z$— wherein z is 2, 3 or 4;
each X is independently CH or N;
each X' is independently, CH or N;
X" is independently $CH_2$, S or NH, arranged such that the moiety is a stable 5-membered ring; R, $R^8$, and $R^{11}$ are independently H, $C_1$-$C_3$ alkyl or haloalkyl, cycloalkyl or cycloalkyl containing one or more heteroatoms selected from N, O or S; -(alkylene)m-$C_3$-$C_8$ cycloalkyl, -(alkylene)$_m$-aryl, -(alkylene)$_m$-heterocyclo, -(alkylene)$_m$-heteroaryl, -(alkylene)$_m$-$NR^3R^4$, -(alkylene)$_m$-C(0)-$NR^3R^4$; -(alkylene)$_m$-O—$R^5$, -(alkylene)$_m$-S(0)n-$R^5$, or -(alkylene)$_m$-S(0)n-$NR^3R^4$ any of which may be optionally independently substituted with one or more R groups as allowed by valance, and wherein two $R^x$ groups bound to the same or adjacent atoms may optionally combine to form a ring;
each $R^1$ is independently aryl, alkyl, cycloalkyl or haloalkyl, wherein each of said alkyl, cycloalkyl and haloalkyl groups optionally includes O or N heteroatoms in place of a carbon in the chain and two $R^1$'s on adjacent ring atoms or on the same ring atom together with the ring atom(s) to which they are attached optionally form a 3-8-membered cycle;
y is 0, 1, 2, 3 or 4;
$R^2$ is -(alkylene)$_m$-heterocyclo, -(alkylene)$_m$-heteroaryl, -(alkylene)$_m$-$NR^3R^4$, (alkylene)$_m$-C(O)—$NR^3R^4$; -(alkylene)$_m$-C(O)—O-alkyl; -(alkylene)$_m$-O—$R^5$, (alkylene)$_m$-S(O)$_n$—$R^5$, or -(alkylene)$_m$-S(O)$_n$—$NR^3R^4$ any of which may be optionally independently substituted with one or more $R^x$ groups as allowed by valance, and wherein two $R^x$ groups bound to the same or adjacent atom may optionally combine to form a ring and wherein m is 0 or 1 and n is 0, 1 or 2;
$R^3$ and $R^4$ at each occurrence are independently:
  (i) hydrogen or
  (ii) alkyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance, and wherein two $R^x$ groups bound to the same or adjacent atom may optionally combine to form a ring; or $R^3$ and $R^4$ together with the nitrogen atom to which they are attached may combine to form a heterocyclo ring optionally independently substituted with one or more $R^x$ groups as allowed by valance, and wherein two $R^x$ groups bound to the same or adjacent atom may optionally combine to form a ring;
$R^5$ and $R^{5*}$ at each occurrence is:
  (i) hydrogen or
  (ii) alkyl, alkenyl, alkynyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance;
$R^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-$OR^5$, -(alkylene)$_m$-O-alkylene-$OR^5$, -(alkylene)$_m$-S(O)$_n$—$R^5$, -(alkylene)$_m$-$NR^3R^4$, -(alkylene)$_m$-CN, -(alkylene)$_m$-C(O)—$R^5$, -(alkylene)$_m$-C(S)—$R^5$, -(alkylene)$_m$-C(O)—$OR^5$, -(alkylene)$_m$-O—C(O)—$R^5$, -(alkylene)$_m$-C(S)—$OR^5$, -(alkylene)$_m$-C(O)-(alkylene)$_m$-$NR^3R^4$, -(alkylene)$_m$-C(S)—$NR^3R^4$, -(alkylene)$_m$-N($R^3$)—C(O)—$NR^3R^4$, -(alkylene)$_m$-N($R^3$)—C(S)—$NR^3R^4$, -(alkylene)$_m$-N($R^3$)—C(O)—$R^5$, -(alkylene)$_m$-N($R^3$)—C(S)—$R^5$, -(alkylene)$_m$-O—C(O)—$NR^3R^4$, -(alkylene)$_m$-O—C(S)—$NR^3R^4$, -(alkylene)$_m$-S0$_2$-$NR^3R^4$, -(alkylene)$_m$-N($R^3$)—SO$_2$—$R^5$, -(alkylene)$_m$-N($R^3$)—SO$_2$—$NR^3R^4$, -(alkylene)$_m$-N($R^3$)—C(O)—$OR^5$) -(alkylene)$_m$-N($R^3$)—C(S)—$OR^5$, or -(alkylene)$_m$-N($R^3$)—SO$_2$—$R^5$; wherein:
said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-CN, -(alkylene)$_m$-$OR^5$, -(alkylene)$_m$-S(O)$_n$$R^{5*}$, -(alkylene)$_m$-$NR^{3*}R^{4*}$, -(alkylene)$_m$-C(O)—$R^{5*}$, -(alkylene)$_m$-C(=S)$R^{5*}$, -(alkylene)$_m$-C(=O)O $R^{5*}$, -(alkylene)$_m$-OC(=O)$R^{5*}$, -(alkylene)$_m$-C(S)—OR$^{5*}$, -(alkylene)$_m$-C(O)—NR$^{3*}$R$^{4*}$, -(alkylene)$_m$-C(S)—NR$^{3*}$R$^{4*}$, -(alkylene)$_m$-N(R$^{3*}$)—C(O)—NR$^{3*}$R$^{4*}$, -(alkylene)$_m$-N(R$^{3*}$)—C(S)—NR$^{3*}$R$^{4*}$, -(alkylene)$_m$-N(R$^{3*}$)—C(O)—R$^{5*}$, -(alkylene)$_m$-N(R$^{3*}$)—C(S)—R$^{5*}$, -(alkylene)$_m$-O—C(O)—NR$^{3*}$R$^{4*}$, -(alkylene)$_m$-O—C(S)—NR$^{3*}$R$^{4*}$, -(alkylene)$_m$-SO2-NR$^{3*}$R$^{4*}$, -(alkylene)$_m$-N(R$^{3*}$)—SO$_2$—R$^{5*}$, -(alkylene)$_m$-N(R$^{3*}$)—SO$_2$—NR$^{3*}$R$^{4*}$, -(alkylene)$_m$-N(R$^{3*}$)—C(O)—OR$^{5*}$, -(alkylene)$_m$-N(R$^{3*}$)—C(S)—OR$^{5*}$, or -(alkylene)$_m$-N(R$^{3*}$)—SO$_2$—R$^{5*}$, n is 0, 1 or 2, and
m is 0 or 1;

R$^{3*}$ and R$^{4*}$ at each occurrence are independently:
(i) hydrogen or
(ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance; or R$^{3*}$ and R$^{4*}$ together with the nitrogen atom to which they are attached may combine to form a heterocyclo ring optionally independently substituted with one or more R$^x$ groups as allowed by valance; and R$^6$ is H or lower alkyl, -(alkylene)$_m$-heterocyclo, -(alkylene)$_m$-heteroaryl, -(alkylene)$_m$-NR$^3$R$^4$, -(alkylene)$_m$-C(0)-NR$^3$R$^4$; -(alkylene)$_m$-0-R$^5$, -(alkylene)$_m$-S(0)$_n$-R$^5$, or -(alkylene)$_m$-S(0)$_n$-NR$^3$R$^4$ any of which may be optionally independently substituted with one or more R$^x$ groups as allowed by valance, and wherein two R$^x$ groups bound to the same or adjacent atoms may optionally combine to form a ring; and R$^{10}$ is (i) NHR$^A$, wherein R$^A$ is unsubstituted or substituted C$_1$-C$_8$ alkyl, cycloalkylalkyl, or -TT-RR, C$_1$-C$_8$ cycloalkyl or cycloalkyl containing one or more heteroatoms selected from N, O, and S; TT is an unsubstituted or substituted C$_1$-C$_8$ alkyl or C$_3$-C$_8$ cycloalkyl linker; and RR is a hydroxyl, unsubstituted or substituted C$_1$-C$_6$ alkoxy, amino, unsubstituted or substituted C$_1$-C$_6$ alkylamino, unsubstituted or substituted di-C$_1$-C$_6$ alkylamino, unsubstituted or substituted C$_6$-C$_{10}$ aryl, unsubstituted or substituted heteroaryl comprising one or two 5- or 6-member rings and 1-4 heteroatoms selected from N, O and S, unsubstituted or substituted C$_3$-C$_{10}$ carbocycle, or unsubstituted or substituted heterocycle comprising one or two 5- or 6-member rings and 1-4 heteroatoms selected from N, O and S; or (ii) —C(O)—R$^{12}$ or —C(O)O—R$^{13}$, wherein R$^{12}$ is NHR$^A$ or R$^A$ and R$^{13}$ is R$^A$;
or a pharmaceutically acceptable salt, prodrug or isotopic variant, for example, partially or fully deuterated form thereof.

In some aspects, the compound is of Formula I or Formula II and R$^6$ is absent.

In some aspects, the compound is of Formula III:

and the variables are as defined for compounds of Formulae I and II and pharmaceutically acceptable salts thereof.

In some aspects, R$^x$ is not further substituted.

In some aspects, R$^2$ is -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valance, and wherein two R$^x$ groups bound to the same or adjacent atom may optionally combine to form a ring and wherein m is 0 or 1 and n is 0, 1 or 2.

In some aspects, R$^8$ is hydrogen or C$_1$-C$_3$ alkyl.

In some aspects, R is hydrogen or C$_1$-C$_3$ alkyl.

In some aspects, R$^2$ is -(alkylene)$_m$-heterocyclo, -(alkylene)$_m$-NR$^3$R$^4$, -(alkylene)$_m$-C(O)—NR$^3$R$^4$, -(alkylene)$_m$-C(O)—O-alkyl or -(alkylene)$_m$-OR$^5$ any of which may be optionally independently substituted with one or more R$^x$ groups as allowed by valance, and wherein two R$^x$ groups bound to the same or adjacent atom may optionally combine to form a ring.

In some aspects, R$^2$ is -(alkylene)$_m$-heterocyclo, -(alkylene)$_m$-NR$^3$R$^4$, -(alkylene)$_m$-C(O)—NR$^3$R$^4$, -(alkylene)$_m$-C(O)—O-alkyl or -(alkylene)$_m$-OR$^5$ without further substitution.

In some aspects, m in R$^2$ is 1. In a further aspect the alkylene in R$^2$ is methylene.

In some aspects, R$^2$ is $$—R^{2*}—\boxed{P}—(R^{x1})_t$$

wherein:
R$^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- and -(alkylene)$_m$-NH-(alkylene)$_m$- wherein each m is independently 0 or 1;
P is a 4- to 8-membered mono- or bicyclic saturated heterocyclyl group;
each R$^{x1}$ is independently -(alkylene)$_m$-(C(O))$_m$-(alkylene)$_m$-(N(R$^N$))$_m$-(alkyl)$_m$ wherein each m is independently 0 or 1 provided at least one m is 1, —(C(O))—O-alkyl, -(alkylene)$_m$-cycloalkyl wherein m is 0 or 1, —N(R$^N$)-cycloalkyl, —C(O)-cycloalkyl, -(alkylene)$_m$-heterocyclyl wherein m is 0 or 1, or —N(R$^N$)-heterocyclyl, —C(O)-heterocyclyl, —S(O)$_2$-(alkylene)$_m$ wherein m is 1 or 2, wherein:
R$^N$ is H, C$_1$ to C$_4$ alkyl or C$_1$ to C$_6$ heteroalkyl, and
wherein two R$^{x1}$ can, together with the atoms to which they attach on P, which may be the same atom, form a ring; and
t is 0, 1 or 2.

In some aspects, each R$^{x1}$ is only optionally substituted by unsubstituted alkyl, halogen or hydroxy.

In some aspects, R$^{x1}$ is hydrogen or unsubstituted C$_1$-C$_4$ alkyl.

In some aspects, at least one R$^{x1}$ is -(alkylene)$_m$-heterocyclyl wherein m is 0 or 1.

In some aspects, R$^2$ is $$—R^{2*}—N\boxed{P^*}—(R^{x1})_t$$

wherein P* is a 4- to 8-membered mono- or bicyclic saturated heterocyclyl group.

In some aspects, $R^2$ is

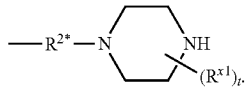

In some aspects, $R^2$ is

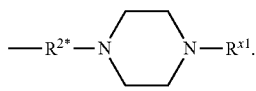

In some aspects, $R^2$ is

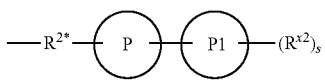

wherein:
$R^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- and -(alkylene)$_m$-NH-(alkylene)$_m$- wherein each m is independently 0 or 1;
P is a 4- to 8-membered mono- or bicyclic saturated heterocyclyl group;
P1 is a 4- to 6-membered monocyclic saturated heterocyclyl group;
each $R^{x2}$ is independently hydrogen or alkyl; and
s is 0, 1 or 2.

In some aspects, $R^2$ is

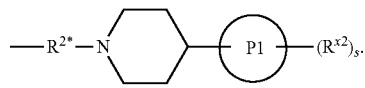

In some aspects, P1 includes at least one nitrogen.

In some aspects, any alkylene in $R^{2*}$ in any previous aspect is not further substituted.

Figure 13:
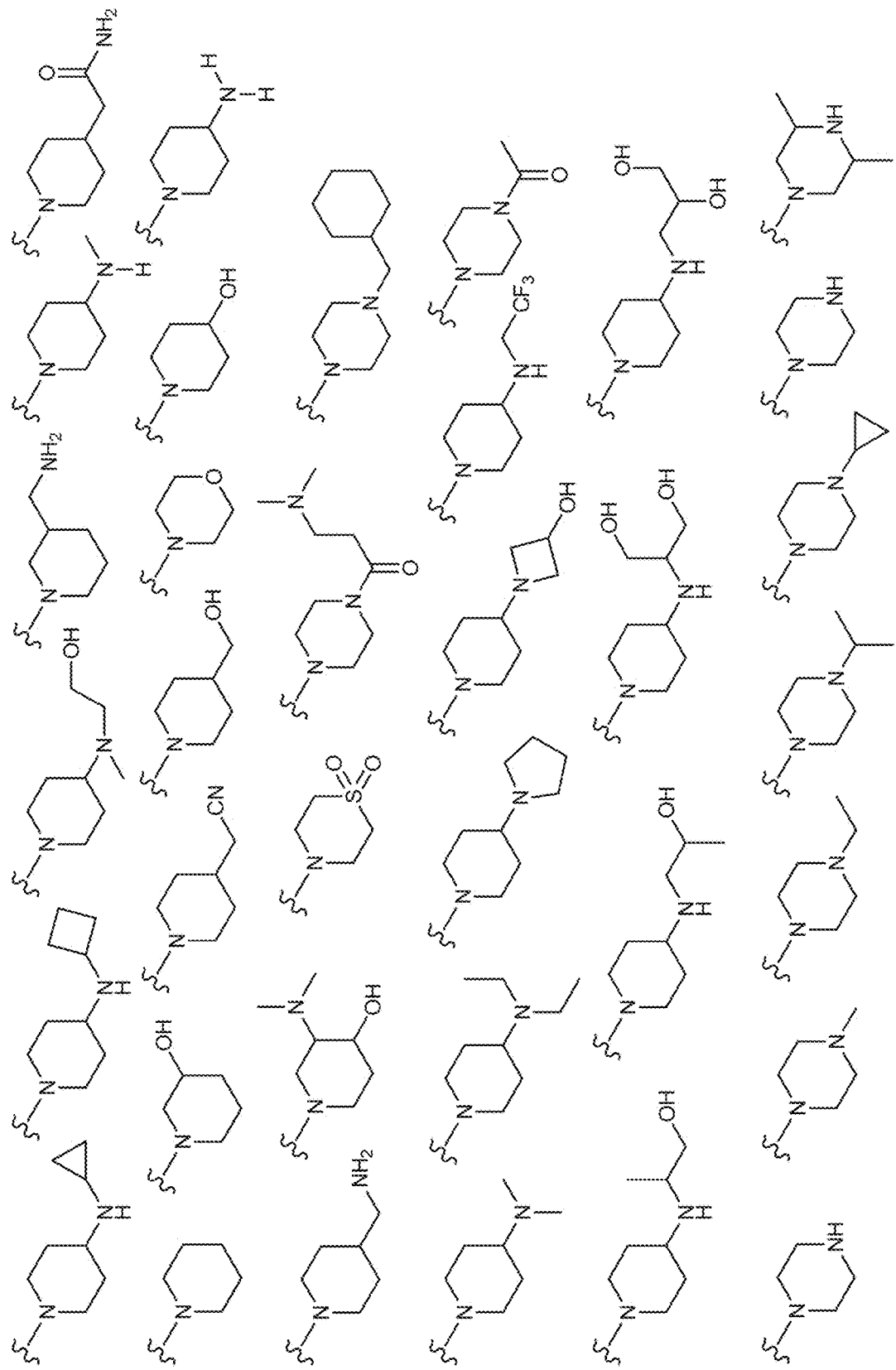
FIGS. 13-15 illustrate several exemplary embodiments of $R^2$ of the compounds of the invention.
Figure 14:
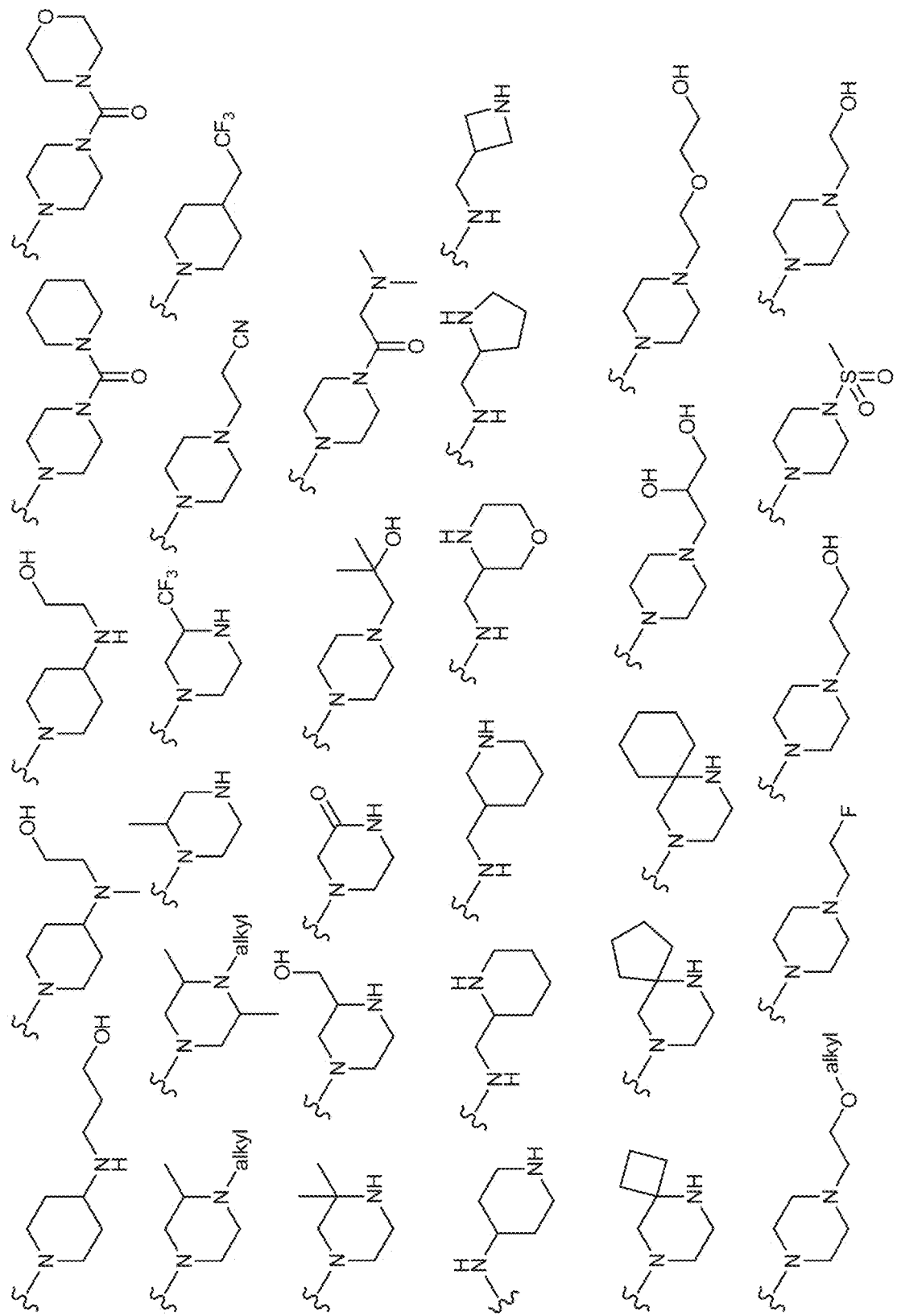
Figure 15:
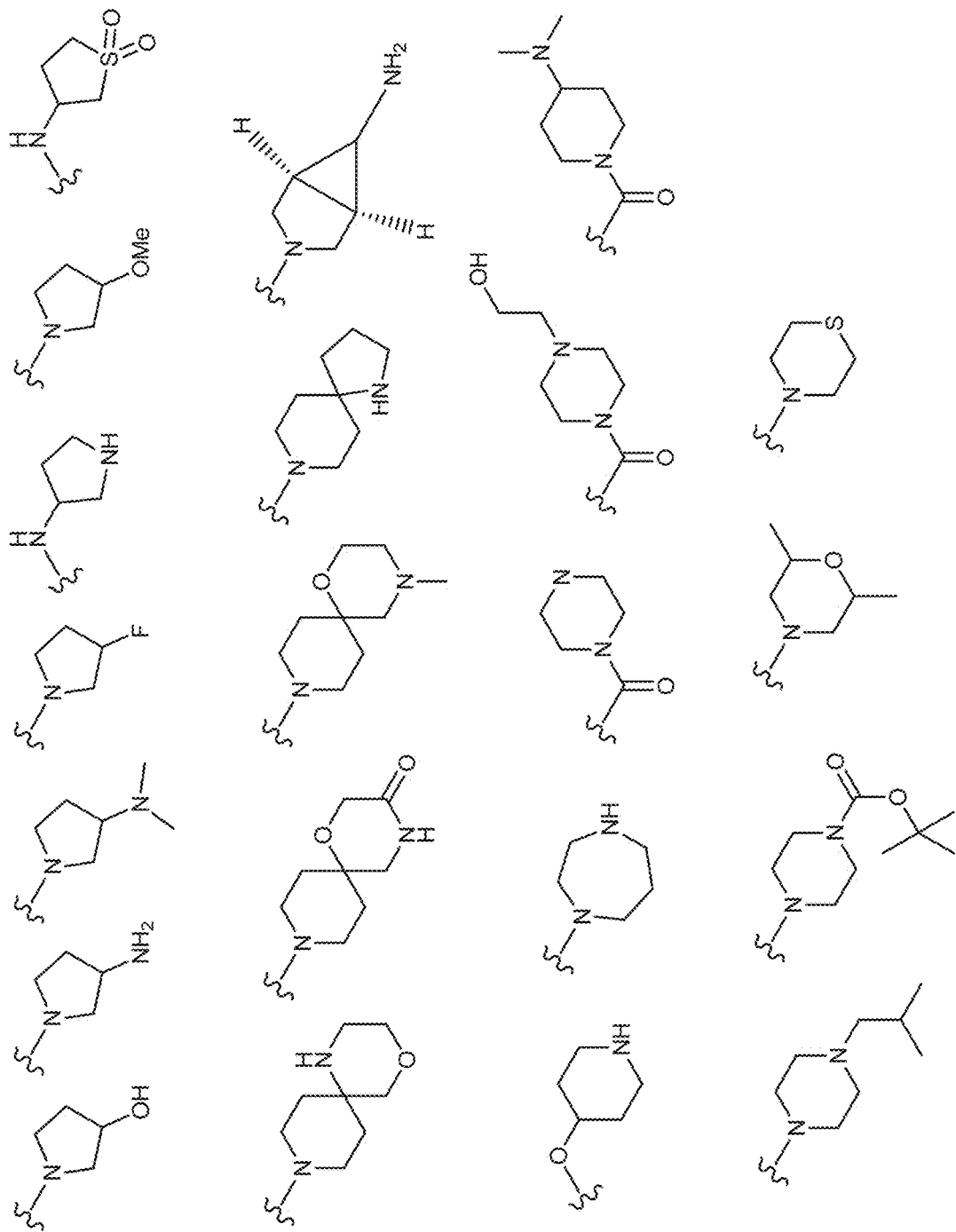
Figure 16A:
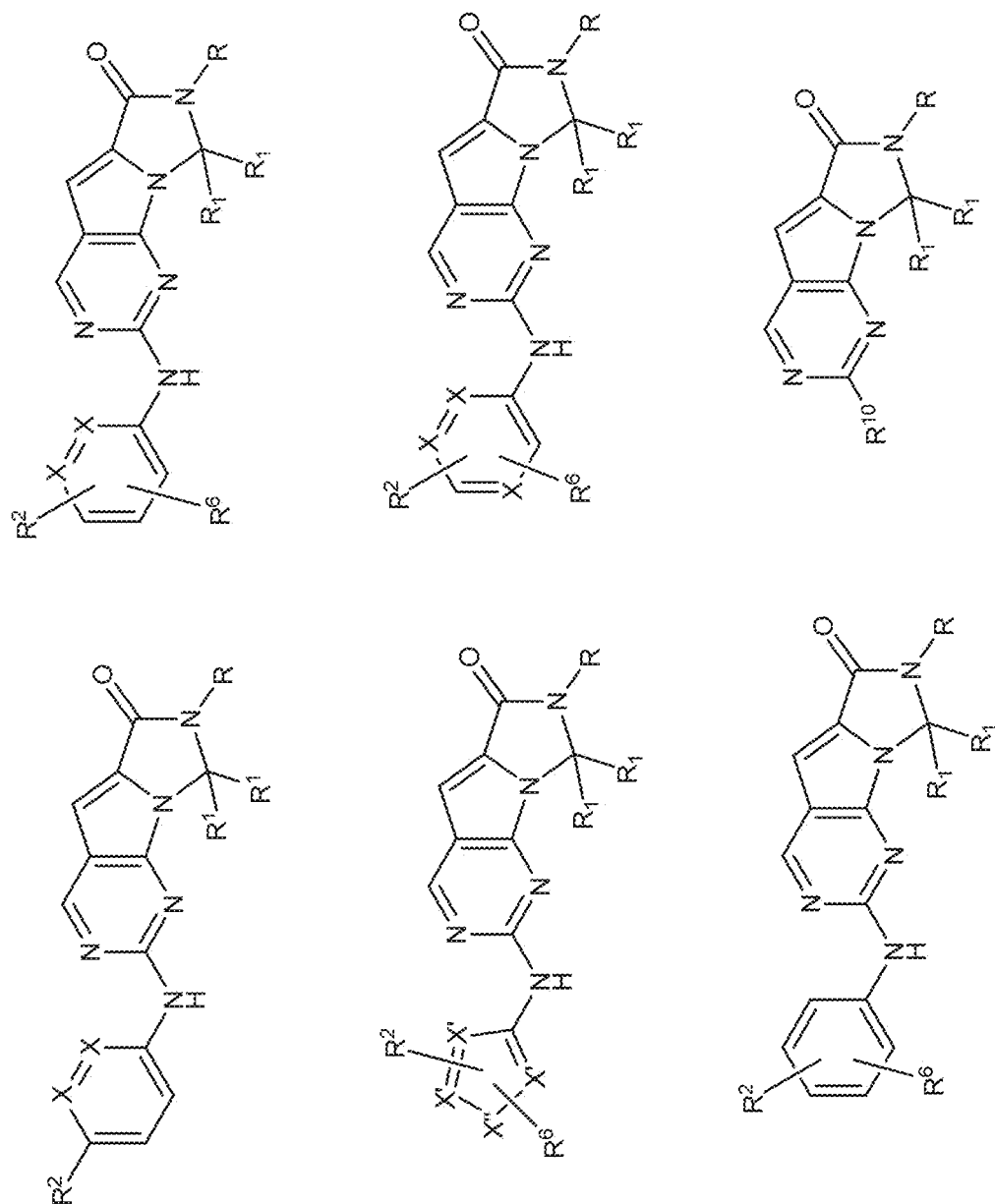
FIGS. 16A-16C, 17A-D, 18A-18C, 19A-19B, and 20A-20F illustrate several exemplary embodiments of the core structure of the compounds of the invention.
Figure 16B:
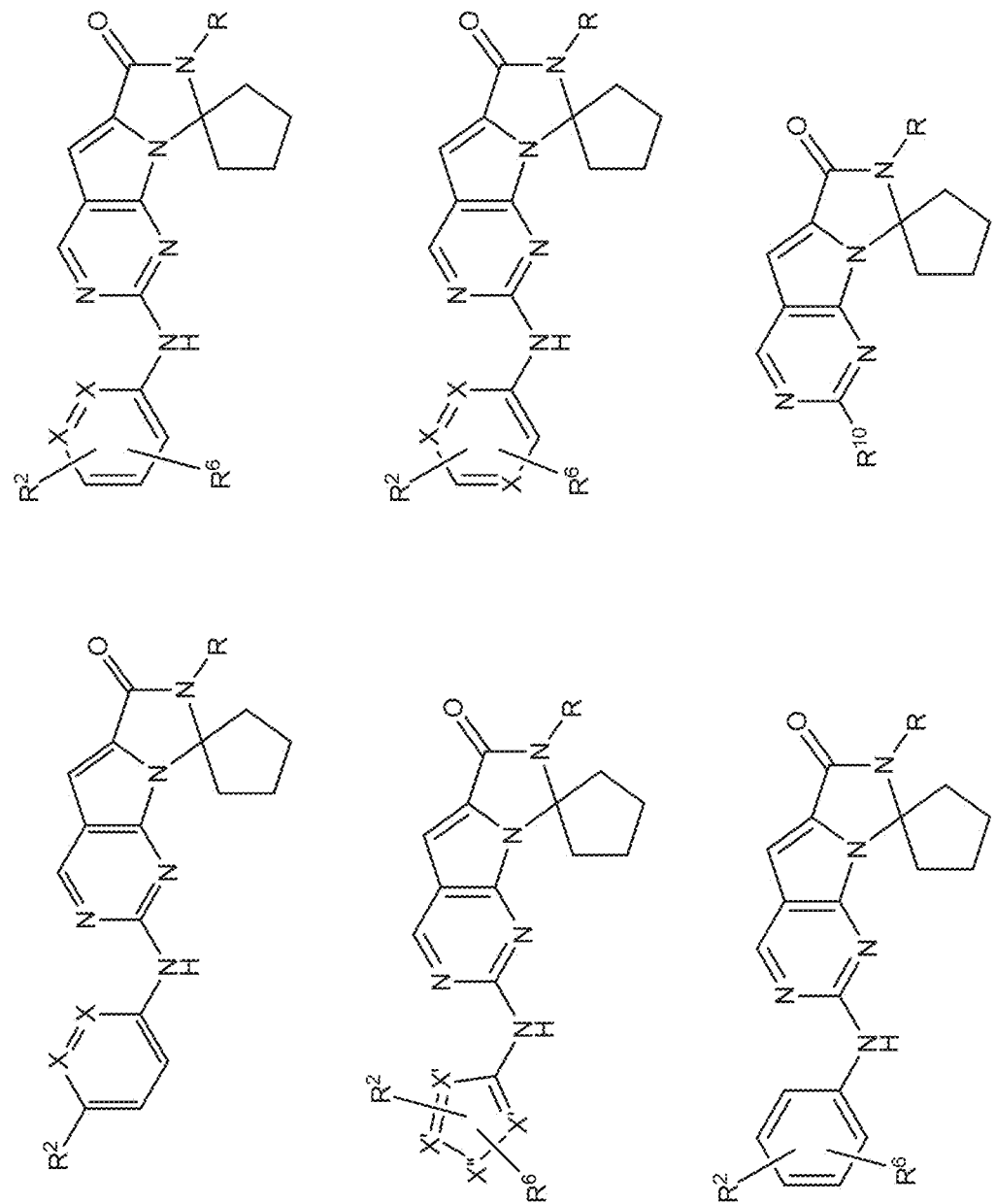
Figure 16C:
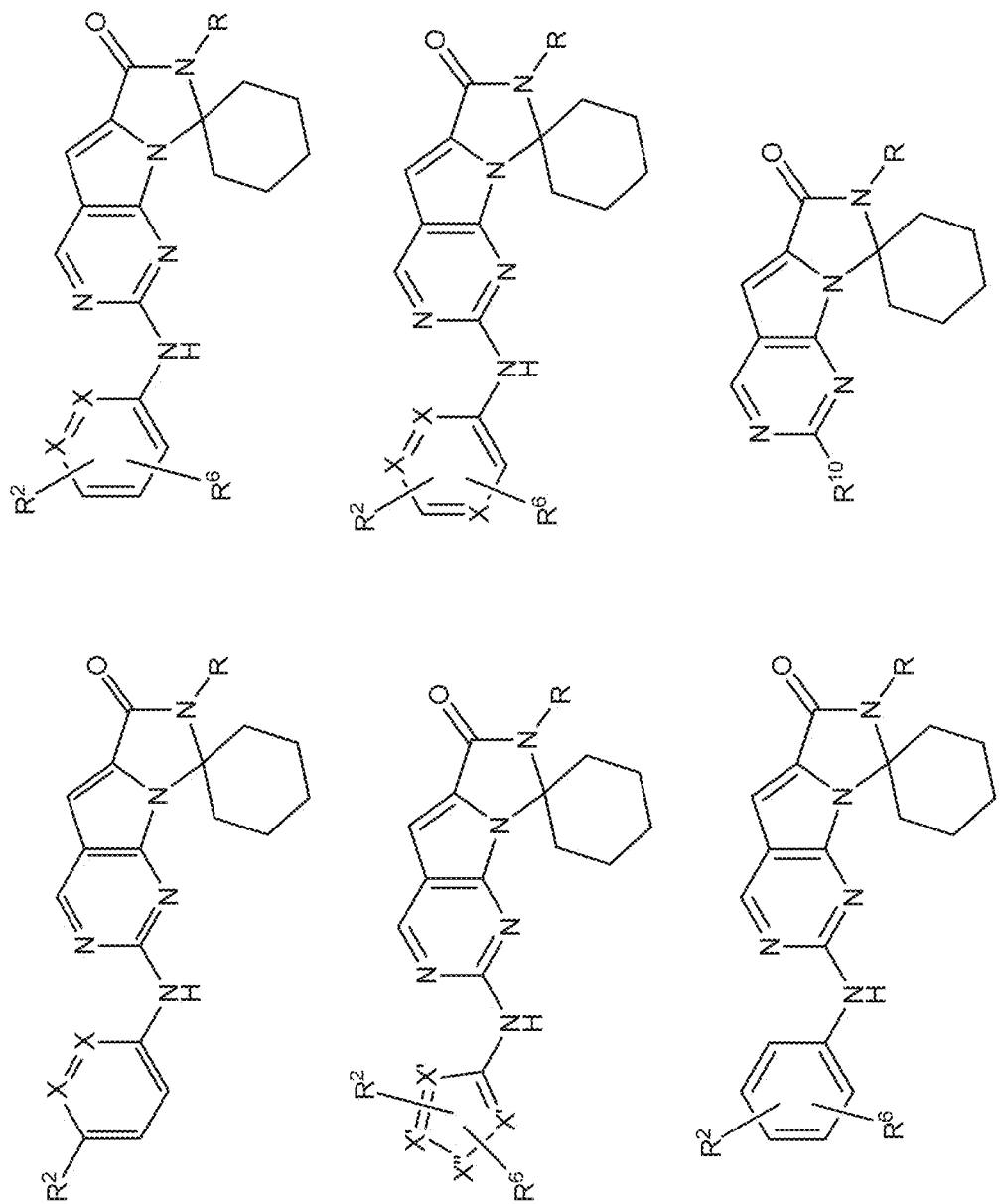
Figure 17A:
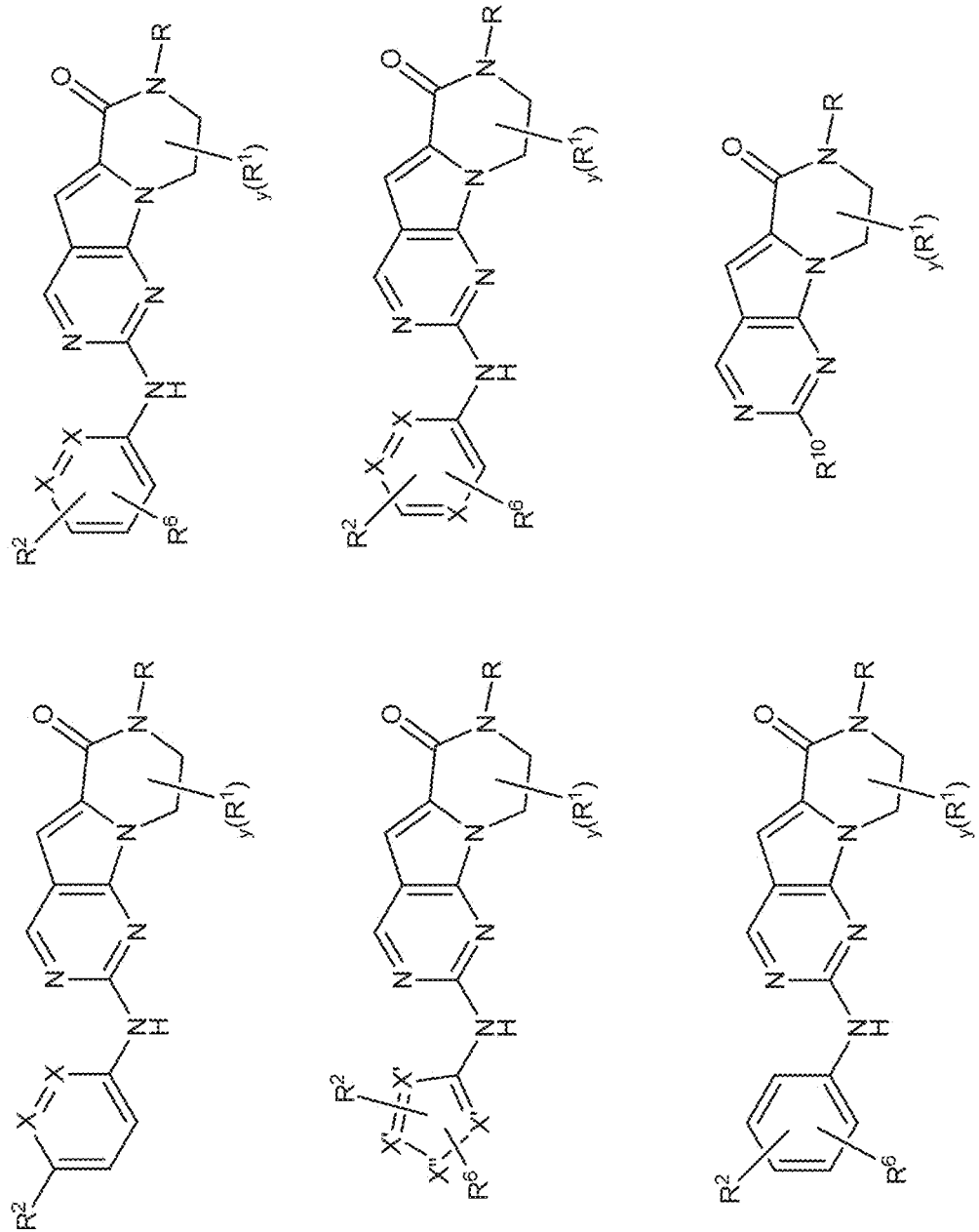
Figure 17B:
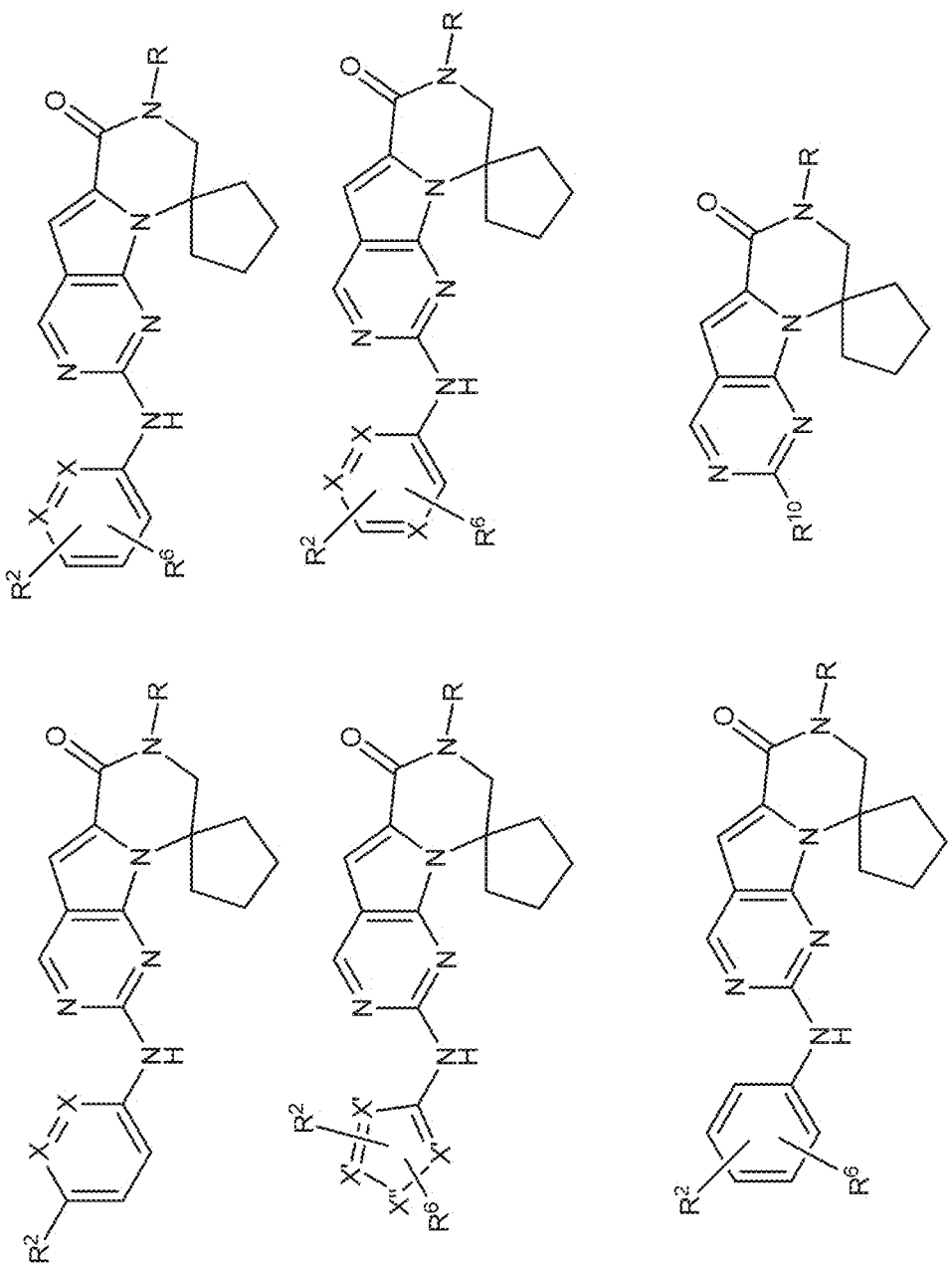
Figure 17C:
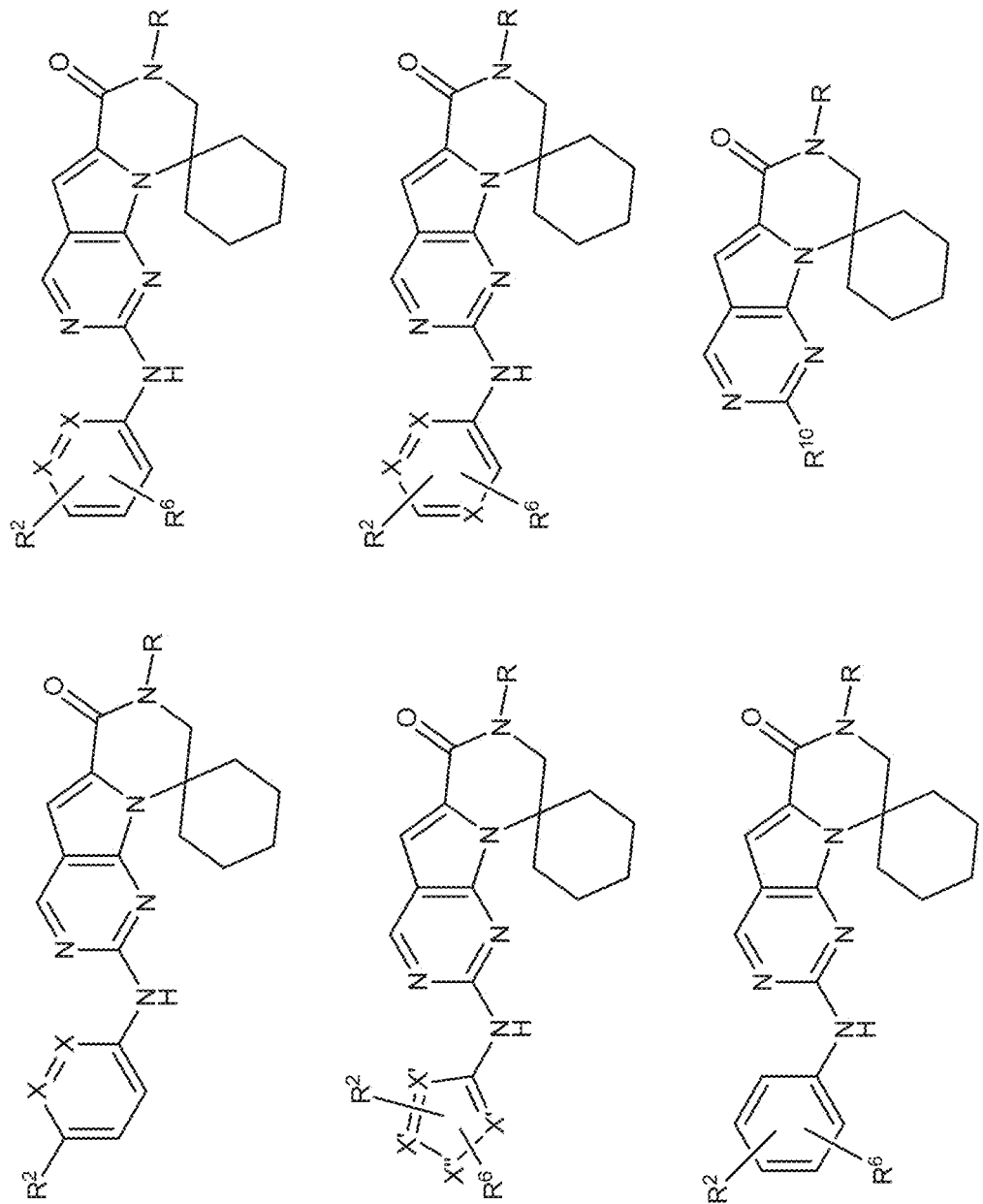
Figure 17D:
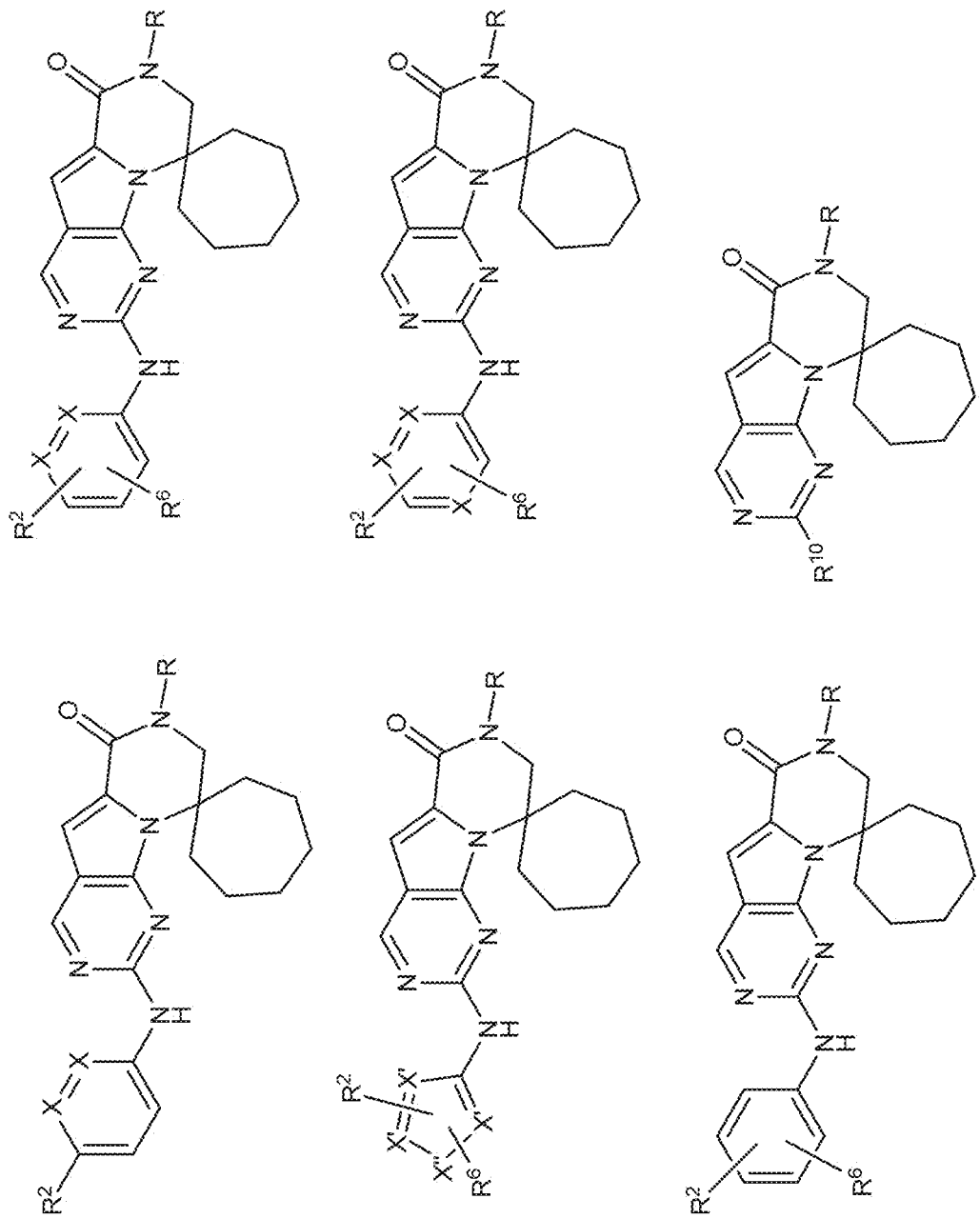
Figure 18A:
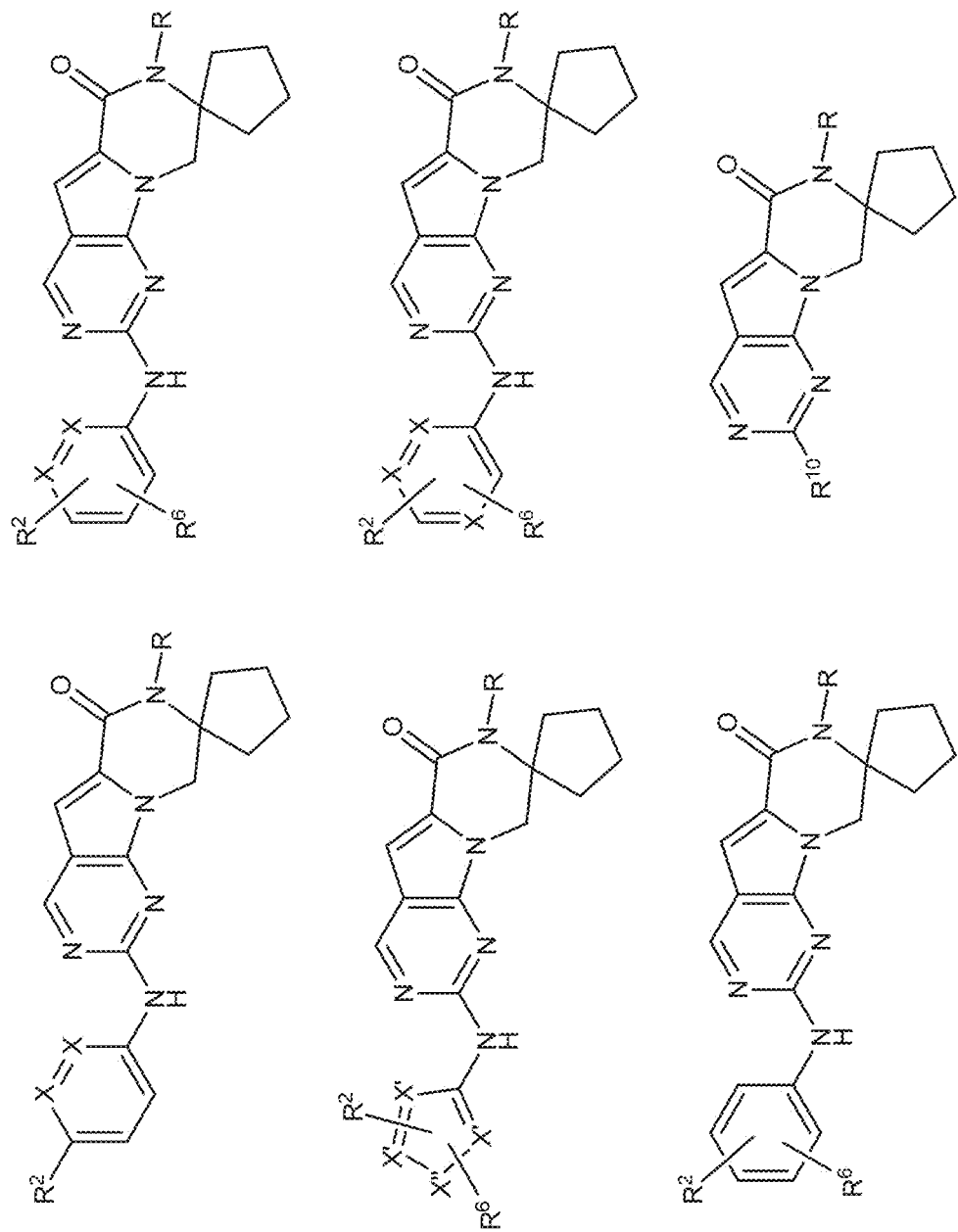
Figure 18B:
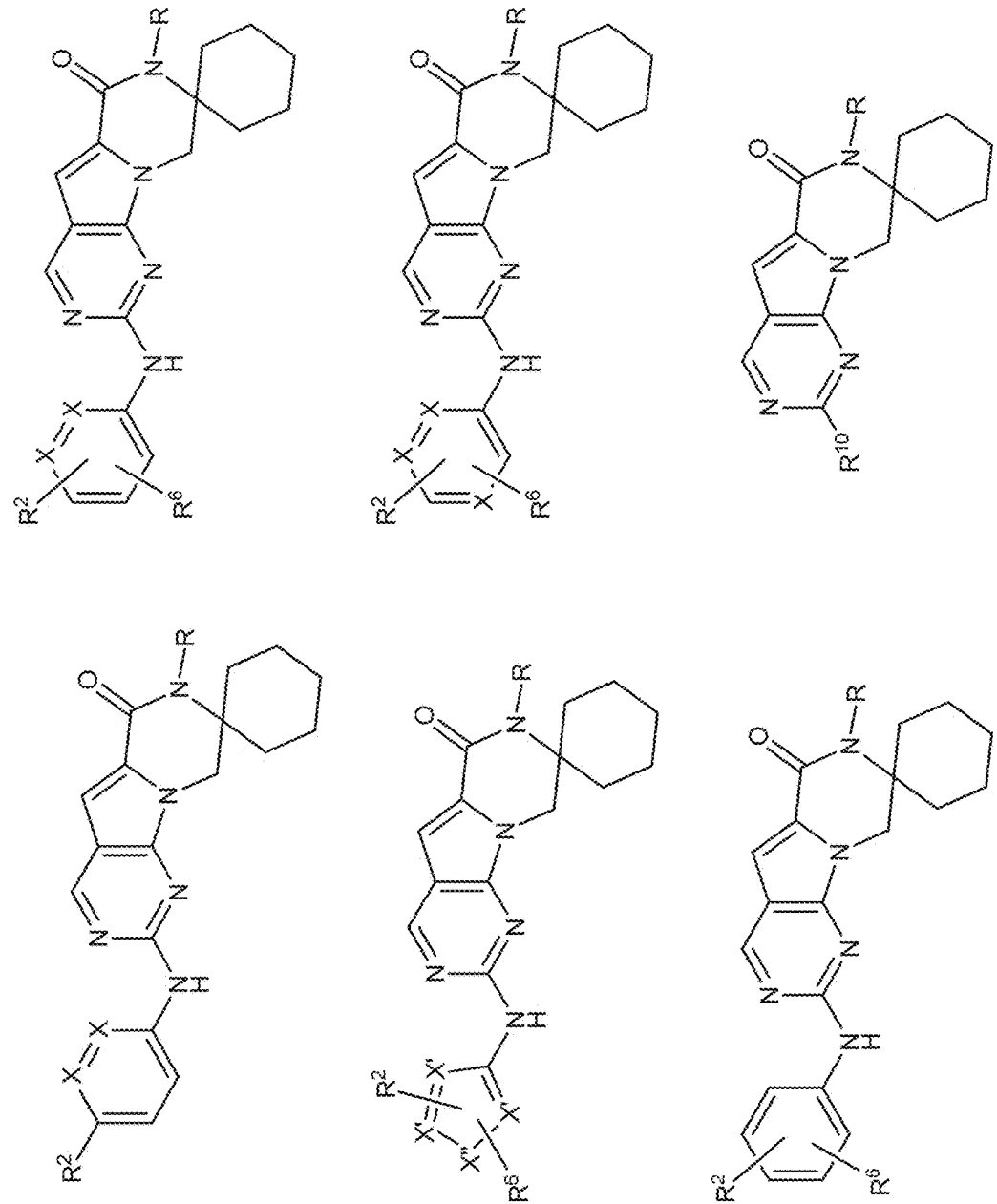
Figure 18C:
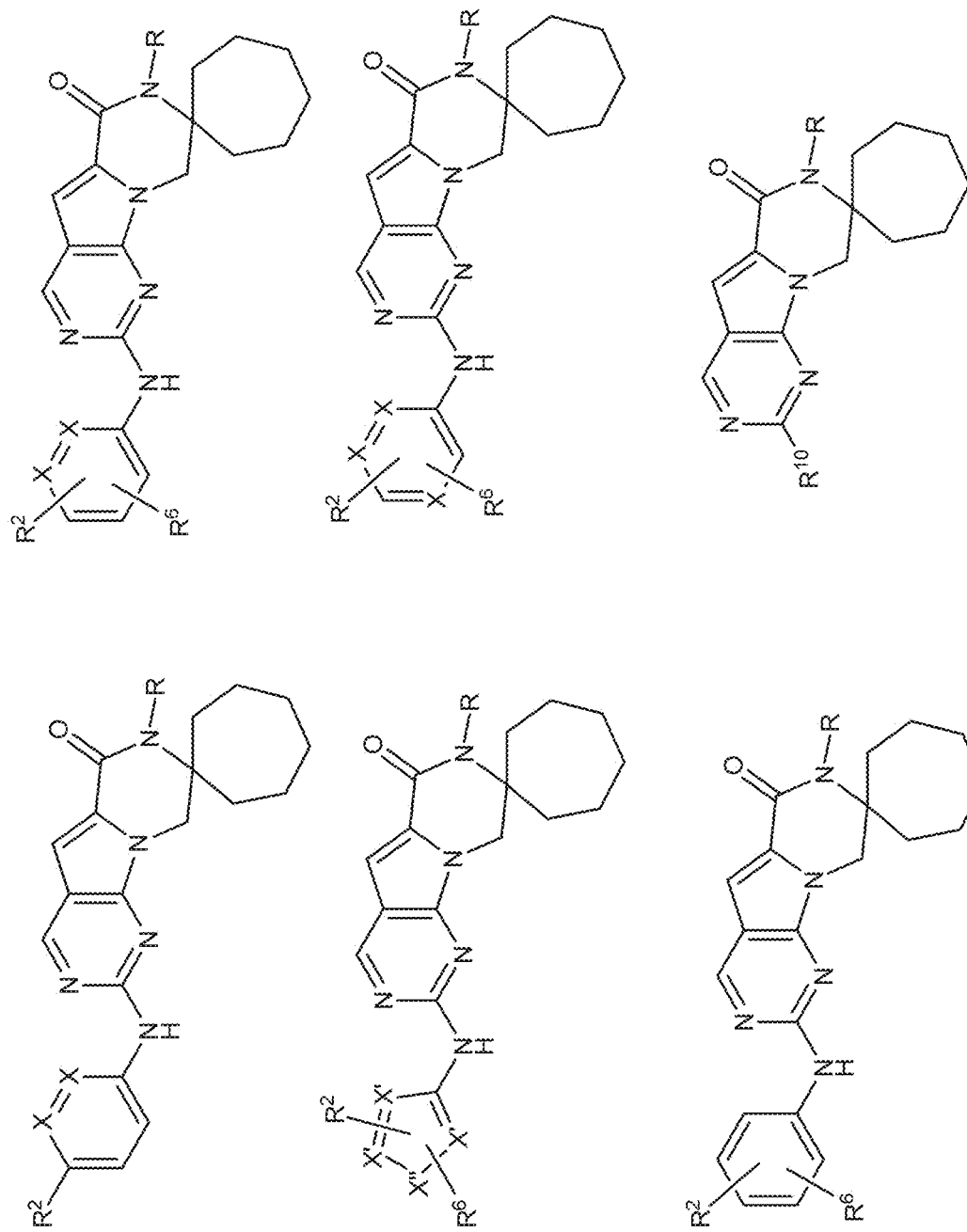
Figure 19A:
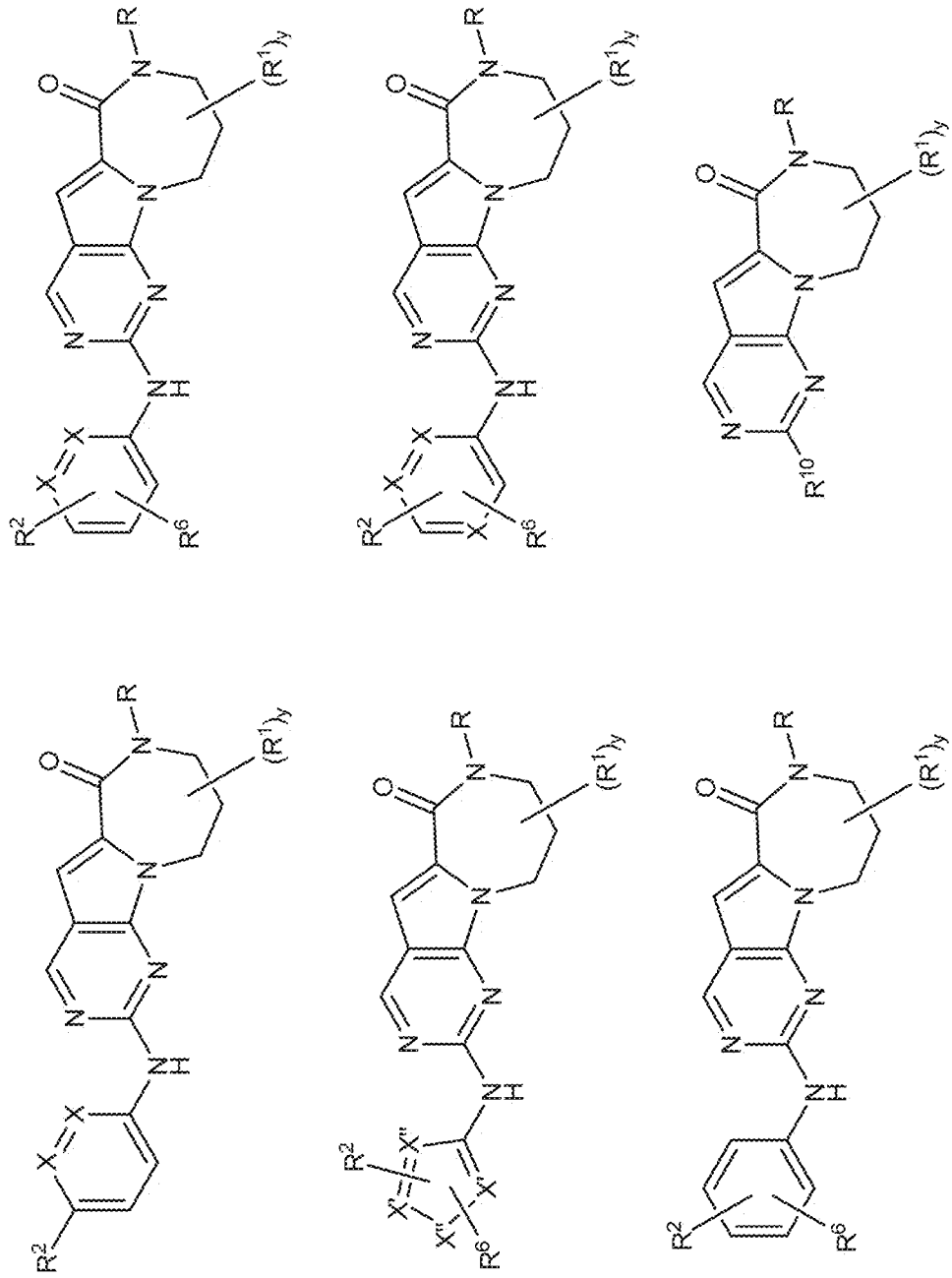
Figure 19B:
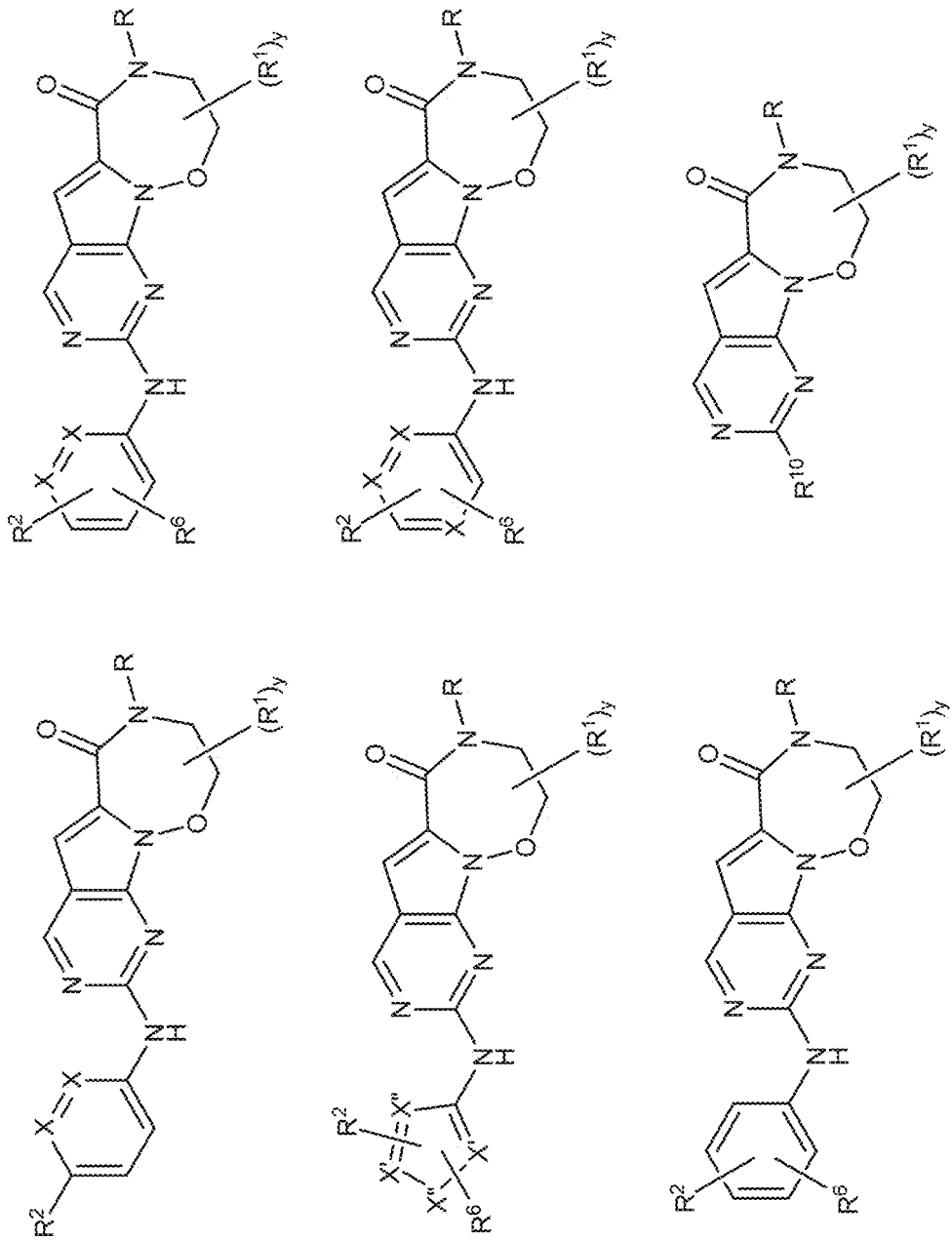
Figure 20A:
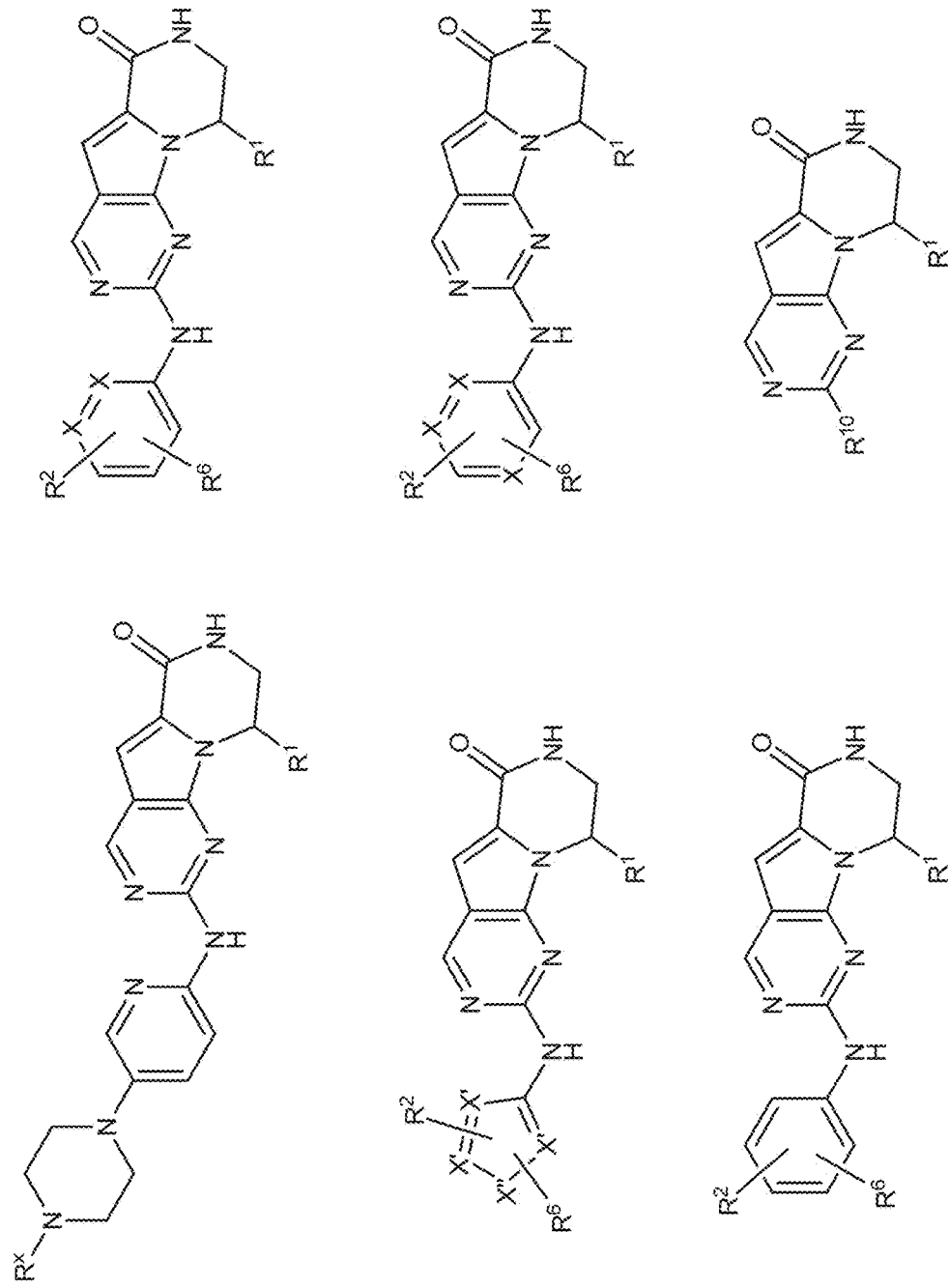
Figure 20B:
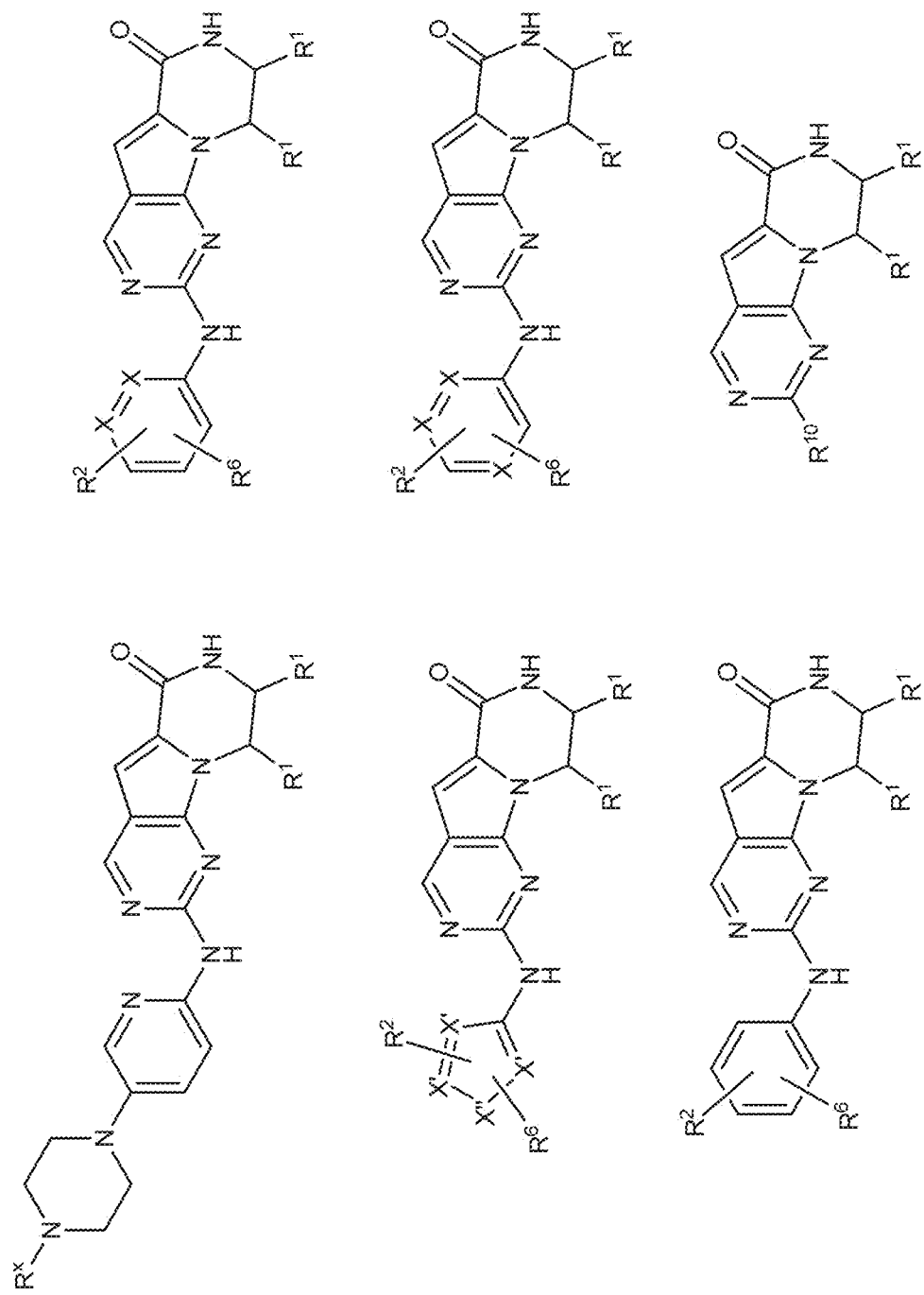
Figure 20C:
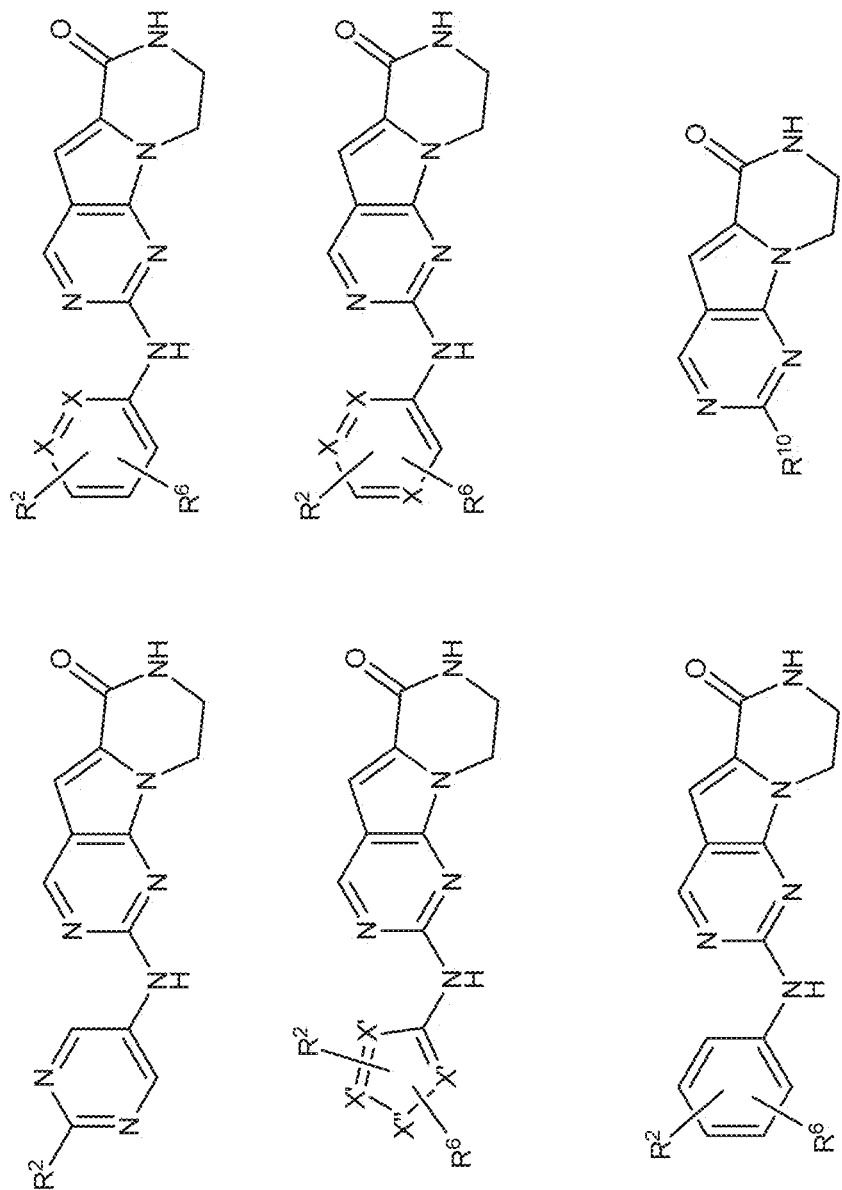
Figure 20D:
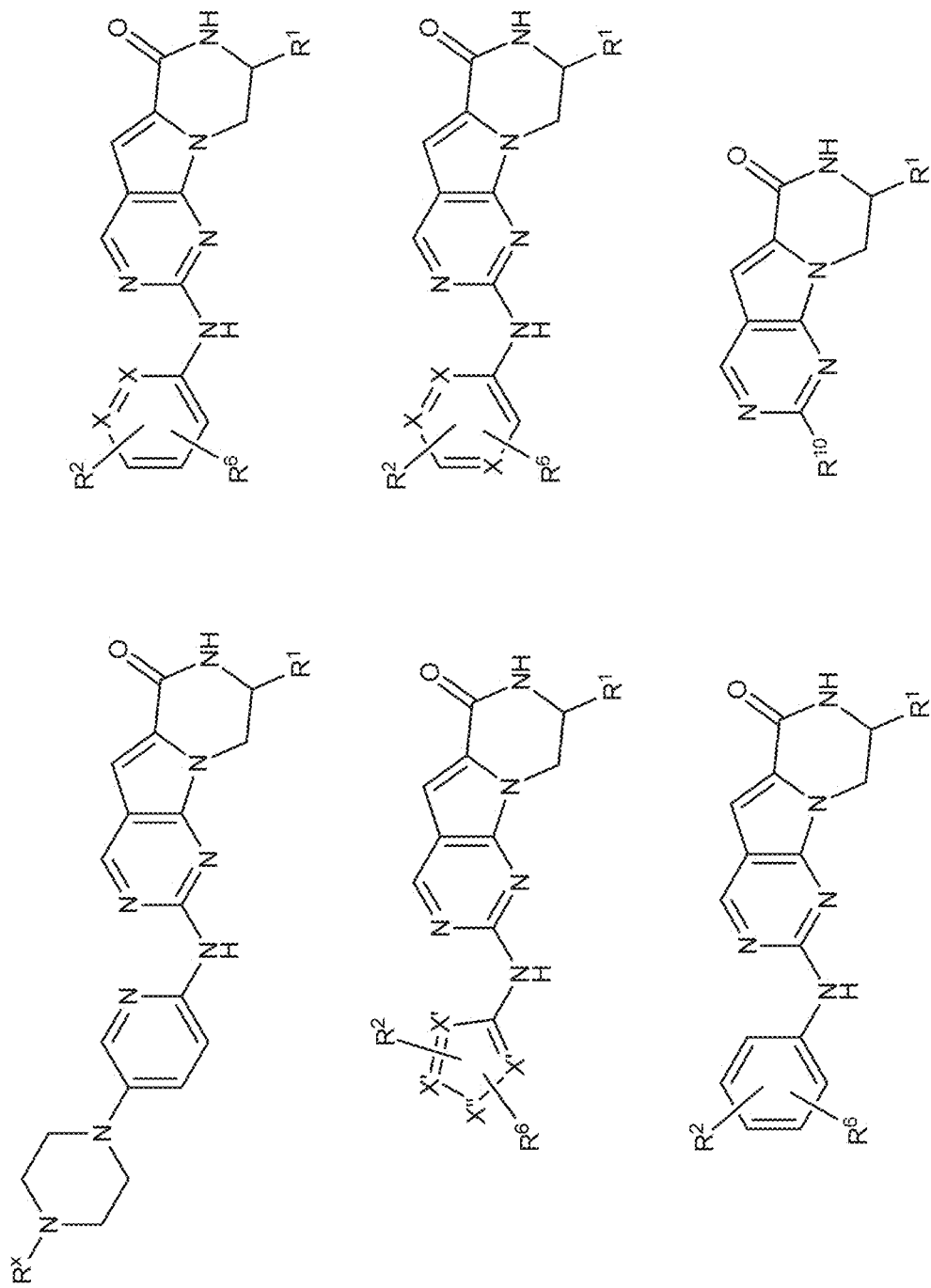
Figure 20E:
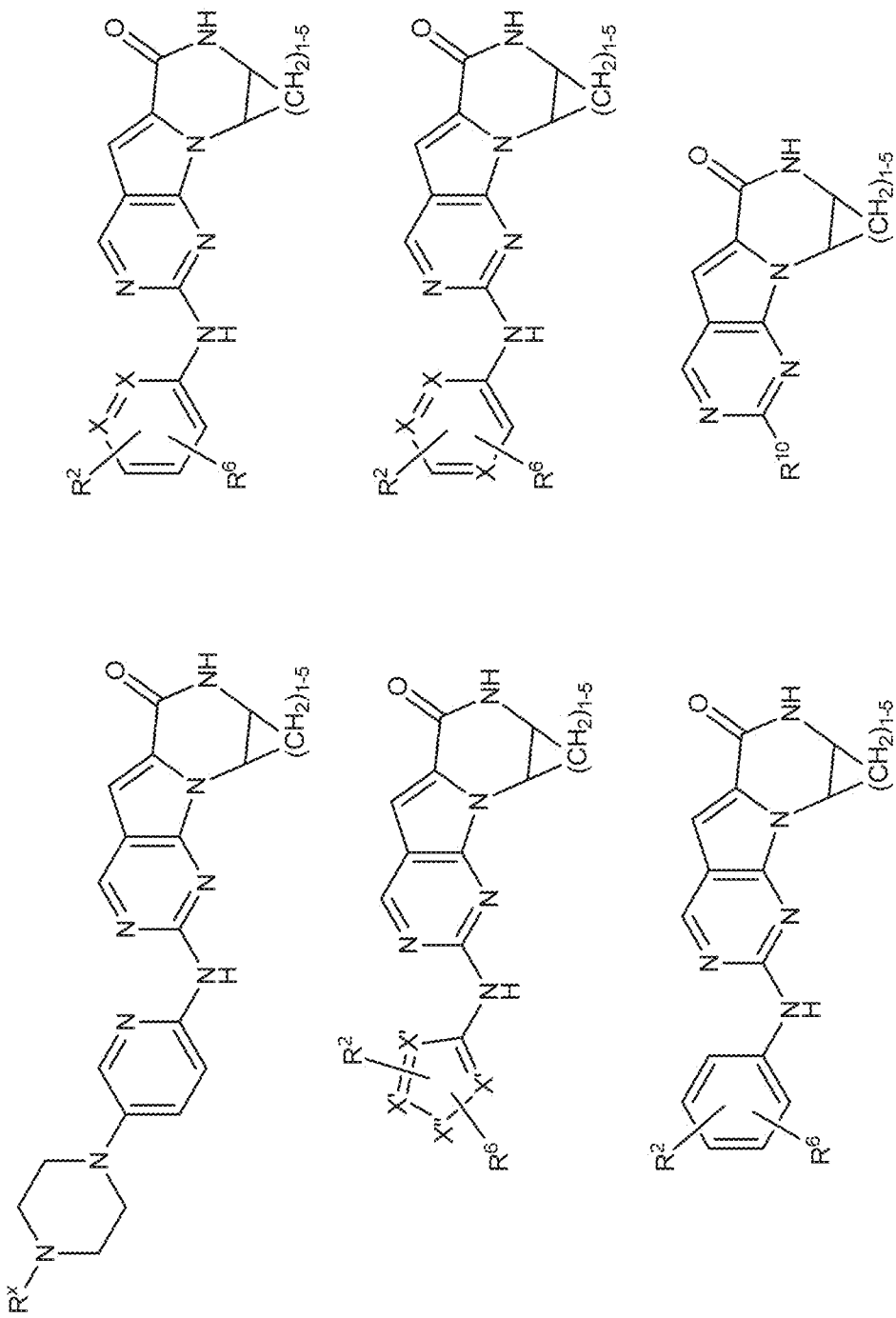
Figure 20F:
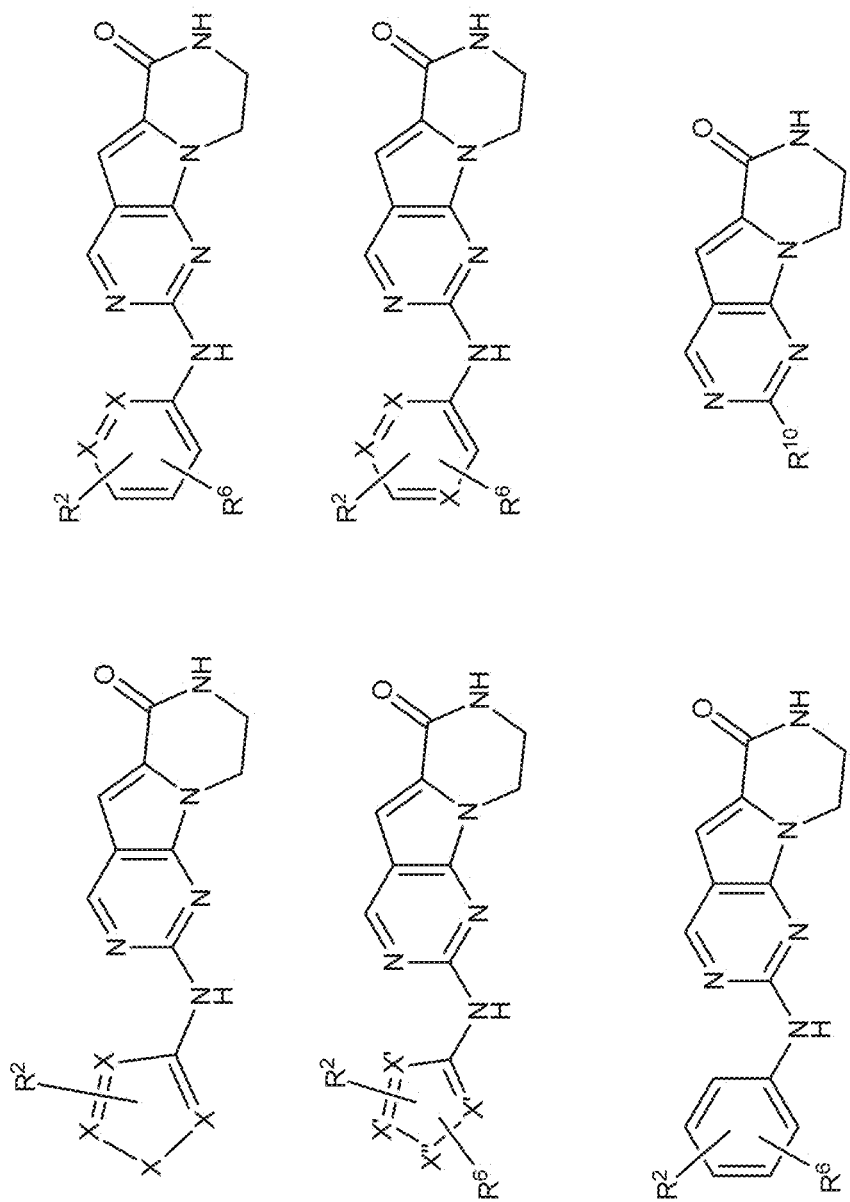

In some aspects, $R^2$ is selected from the structures depicted in FIGS. 13-15.

In some aspects, $R^2$ is

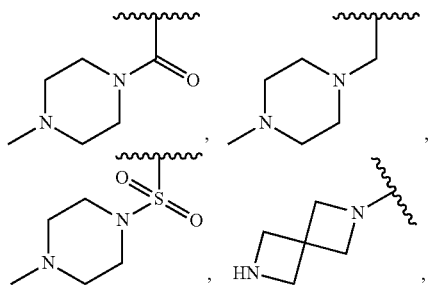

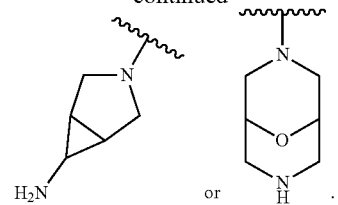

In some aspects, the compound has general Formula I and more specifically one of the general structures in FIGS. 16-20 wherein the variables are as previously defined.

In some aspects, the compound has general Formula Ia:

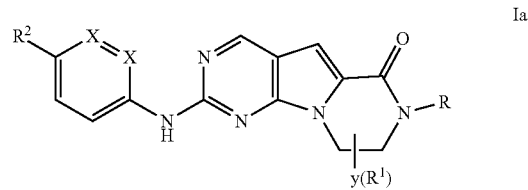

Ia wherein $R^1$, $R^2$, R and y are as previously defined.

In some embodiments, the compound has Formula Ia and R is alkyl.

In some embodiments, the compound has Formula Ia and R is H.

In some embodiments, the compound has Formula Ia and $R^2$ is

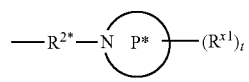

wherein P* is a 4- to 8-membered mono- or bicyclic saturated heterocyclyl group and $R^{2*}$, $R^{x1}$ and t are as previously defined.

In some embodiments, the compound has Formula Ia and $R^2$ is

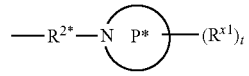

wherein P* is a 4- to 8-membered mono- or bicyclic saturated heterocyclyl group, $R^{x1}$ is hydrogen or unsubstituted $C_1$-$C_4$ alkyl and $R^{2*}$ is as previously defined.

In some embodiments, the compound has Formula Ib:

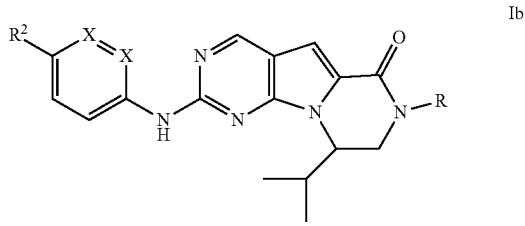

Ib wherein $R^2$ and R are as previously defined.

In some embodiments, the compound has Formula Ib and R is alkyl.

In some embodiments, the compound has Formula Ib and R is H.

In some embodiments, the compound has Formula Ib and $R^2$ is

wherein P* is a 4- to 8-membered mono- or bicyclic saturated heterocyclyl group and $R^{2*}$, $R^{x1}$ and t are as previously defined.

In some embodiments, the compound has Formula Ib and $R^2$ is

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ic:

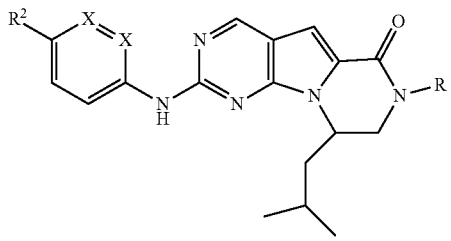

wherein $R^2$ and R are as previously defined.

In some embodiments, the compound has Formula Ic and R is alkyl.

In some embodiments, the compound has Formula Ic and R is H.

In some embodiments, the compound has Formula Ic and $R^2$ is

wherein P* is a 4- to 8-membered mono- or bicyclic saturated heterocyclyl group and $R^{2*}$, $R^{x1}$ and t are as previously defined.

In some embodiments, the compound has Formula Ic and $R^2$ is

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Id:

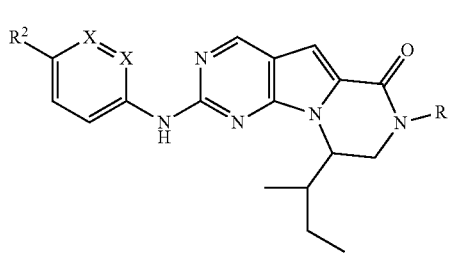

wherein $R^2$ and R are as previously defined.

In some embodiments, the compound has Formula Id and R is alkyl.

In some embodiments, the compound has Formula Id and R is H.

In some embodiments, the compound has Formula Id and $R^2$ is

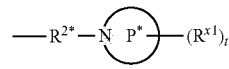

wherein P* is a 4- to 8-membered mono- or bicyclic saturated heterocyclyl group and $R^{2*}$, $R^{x1}$ and t are as previously defined.

In some embodiments, the compound has Formula Id and $R^2$ is

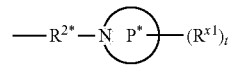

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ie:

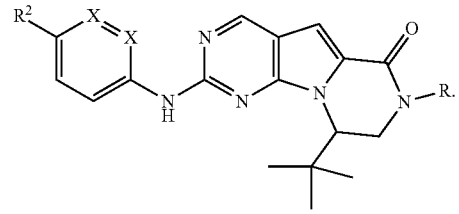

In some embodiments, the compound has Formula Ie and R is alkyl.

In some embodiments, the compound has Formula Ie and R is H.

In some embodiments, the compound has Formula Ie and $R^2$ is

wherein P* is a 4- to 8-membered mono- or bicyclic saturated heterocyclyl group and $R^{2*}$, $R^{x1}$ and t are as previously defined.

In some embodiments, the compound has Formula Ie and R² is

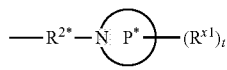

wherein P* is a 4- to 8-membered mono- or bicyclic saturated heterocyclyl group, R^{x1} is hydrogen or $C_1$-$C_4$ alkyl and R²* is as previously defined.

In some embodiments, the compound has Formula If:

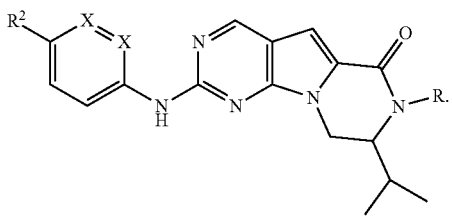

In some embodiments, the compound has Formula If and R is alkyl.

In some embodiments, the compound has Formula If and R is H.

In some embodiments, the compound has Formula If and R² is

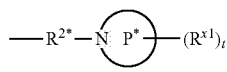

wherein P* is a 4- to 8-membered mono- or bicyclic saturated heterocyclyl group and R²*, R^{x1} and t are as previously defined.

In some embodiments, the compound has Formula If and R² is

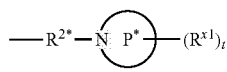

wherein P* is a 4- to 8-membered mono- or bicyclic saturated heterocyclyl group, R^{x1} is hydrogen or $C_1$-$C_4$ alkyl and R²* is as previously defined.

In some embodiments, the compound has Formula Ig:

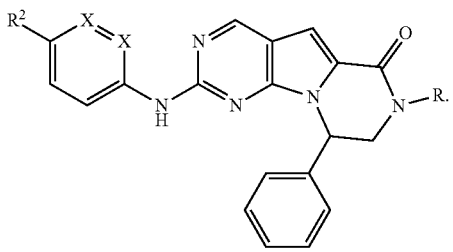

In some embodiments, the compound has Formula Ig and R is alkyl.

In some embodiments, the compound has Formula Ig and R is H.

In some embodiments, the compound has Formula Ig and R² is

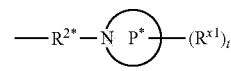

wherein P* is a 4- to 8-membered mono- or bicyclic saturated heterocyclyl group and R²*, R^{x1} and t are as previously defined.

In some embodiments, the compound has Formula Ig and R² is

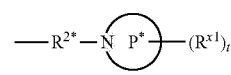

wherein P* is a 4- to 8-membered mono- or bicyclic saturated heterocyclyl group, R^{x1} is hydrogen or $C_1$-$C_4$ alkyl and R²* is as previously defined.

In some embodiments, the compound has Formula Ih:

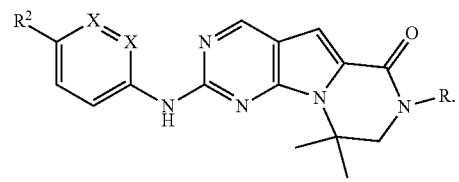

In some embodiments, the compound has Formula Ih and R is alkyl.

In some embodiments, the compound has Formula Ih and R is H.

In some embodiments, the compound has Formula Ih and R² is

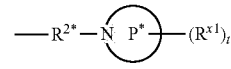

wherein P* is a 4- to 8-membered mono- or bicyclic saturated heterocyclyl group and R²*, R^{x1} and t are as previously defined.

In some embodiments, the compound has Formula Ih and R² is

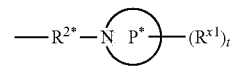

wherein P* is a 4- to 8-membered mono- or bicyclic saturated heterocyclyl group, R^{x1} is hydrogen or $C_1$-$C_4$ alkyl and R²* is as previously defined.

In some embodiments, the compound has Formula Ii:

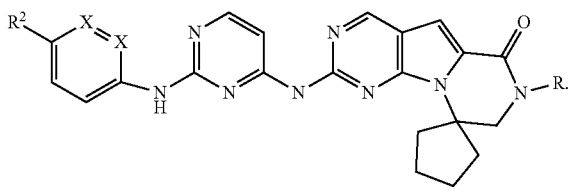

In some embodiments, the compound has Formula Ii and R is alkyl.

In some embodiments, the compound has Formula Ii and R is H.

In some embodiments, the compound has Formula Ii and $R^2$ is

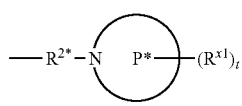

wherein P* is a 4- to 8-membered mono- or bicyclic saturated heterocyclyl group and $R^{2*}$, $R^{x1}$ and t are as previously defined.

In some embodiments, the compound has Formula Ii and $R^2$ is

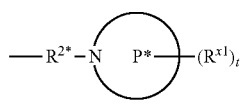

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ij:

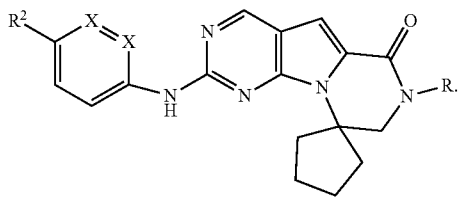

In some embodiments, the compound has Formula Ij and R is alkyl.

In some embodiments, the compound has Formula Ij and R is H.

In some embodiments, the compound has Formula Ij and $R^2$ is

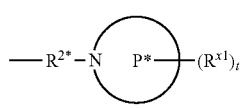

wherein P* is a 4- to 8-membered mono- or bicyclic saturated heterocyclyl group.

In some embodiments, the compound has Formula Ij and $R^2$ is

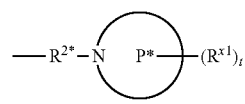

wherein P* is a 4- to 8-membered mono- or bicyclic saturated heterocyclyl group, $R^{x1}$ is hydrogen or $C_1$-$C_4$ alkyl.

In some embodiments, the compound has Formula Ij and R is H, and both X are N.

In some embodiments, the compound has the structure:

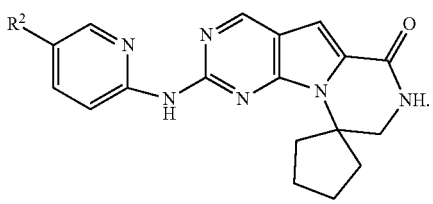

In some embodiments, the compound has Formula Ik and $R^2$ is

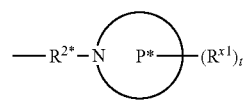

wherein P* is a 4- to 8-membered mono- or bicyclic saturated heterocyclyl group.

In some embodiments, the compound has Formula Ik and $R^2$ is

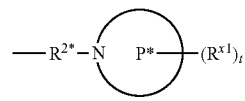

wherein P* is a 4- to 8-membered mono- or bicyclic saturated heterocyclyl group, $R^{x1}$ is hydrogen or $C_1$-$C_4$ alkyl.

In some embodiments, the compound has Formula Il:

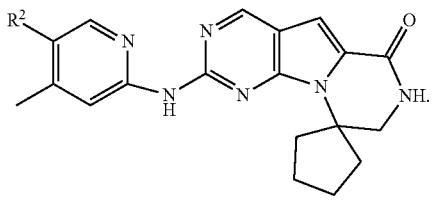

In some embodiments, the compound has Formula Il and $R^2$ is

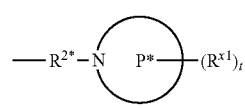

wherein P* is a 4- to 8-membered mono- or bicyclic saturated heterocyclyl group.

In some embodiments, the compound has Formula Il and $R^2$ is

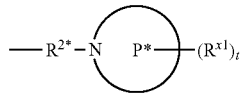

wherein P* is a 4- to 8-membered mono- or bicyclic saturated heterocyclyl group, $R^{x1}$ is hydrogen or $C_1$-$C_4$ alkyl.

In some embodiments, the compound has Formula Im:

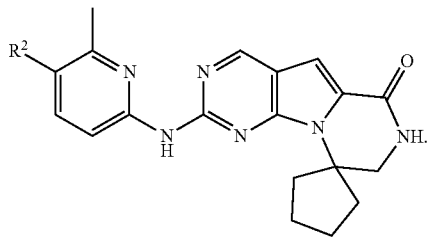

In some embodiments, the compound has Formula Im and $R^2$ is

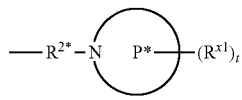

wherein P* is a 4- to 8-membered mono- or bicyclic saturated heterocyclyl group.

In some embodiments, the compound has Formula Im and $R^2$ is

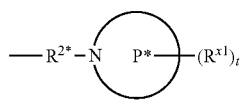

wherein P* is a 4- to 8-membered mono- or bicyclic saturated heterocyclyl group, $R^{x1}$ is hydrogen or $C_1$-$C_4$ alkyl.

In some embodiments, the compound has Formula IIa:

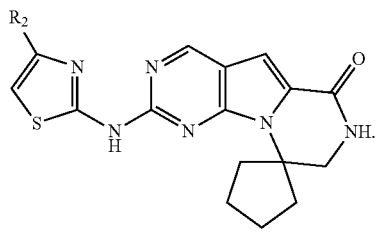

In some embodiments, the compound has Formula IIa and $R^2$ is

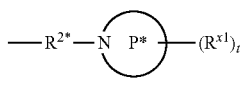

wherein P* is a 4- to 8-membered mono- or bicyclic saturated heterocyclyl group.

In some embodiments, the compound has Formula IIa and $R^2$ is

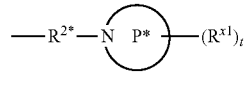

wherein P* is a 4- to 8-membered mono- or bicyclic saturated heterocyclyl group, $R^{x1}$ is hydrogen or $C_1$-$C_4$ alkyl.

In some embodiments, the compound has Formula IIb:

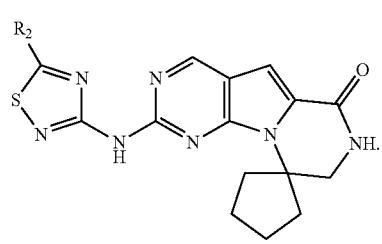

In some embodiments, the compound has Formula Im and $R^2$ is

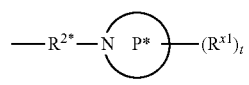

wherein P* is a 4- to 8-membered mono- or bicyclic saturated heterocyclyl group.

In some embodiments, the compound has Formula Im and $R^2$ is

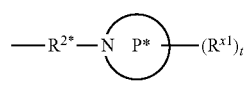

wherein P* is a 4- to 8-membered mono- or bicyclic saturated heterocyclyl group, $R^{x1}$ is hydrogen or $C_1$-$C_4$ alkyl.

In some aspects, the active compound is:

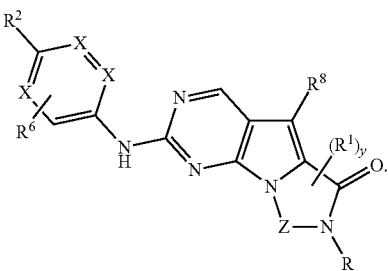

Further specific compounds that fall within the present invention and that can be used in the disclosed methods of treatment and compositions include the structures listed in Table 1 below.

TABLE 1
Structures of Anti-Neoplastic and Anti-Proliferative Agents
| Structure Reference | Structure |
|---|---|
| A | 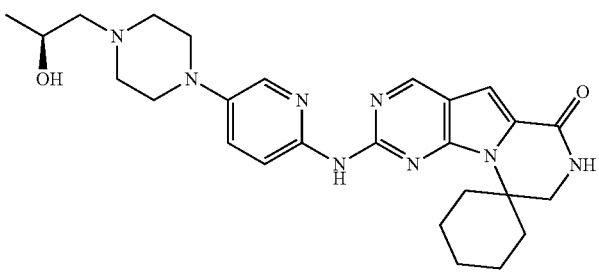 [SMILES: C[C@H](O)CN1CCN(c2ccc(Nc3ncc4cc5n(c4n3)C3(CCCCC3)CNC5=O)nc2)CC1] |
| B | 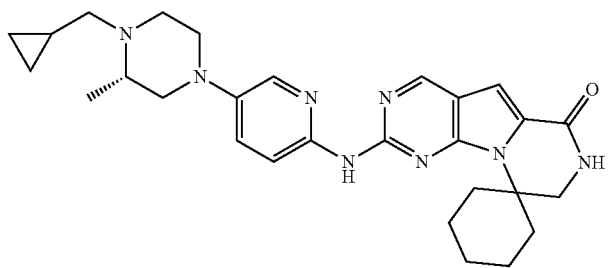 [SMILES: C[C@H]1CN(c2ccc(Nc3ncc4cc5n(c4n3)C3(CCCCC3)CNC5=O)nc2)CCN1CC1CC1] |
| C | 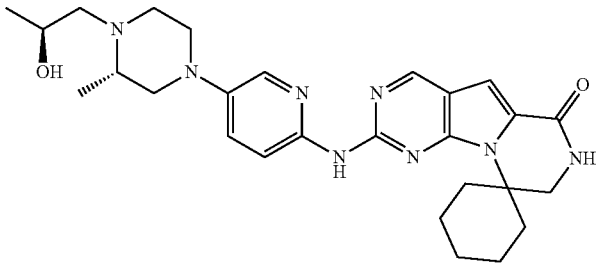 [SMILES: C[C@H](O)CN1CCN(c2ccc(Nc3ncc4cc5n(c4n3)C3(CCCCC3)CNC5=O)nc2)C[C@@H]1C] |
| D | 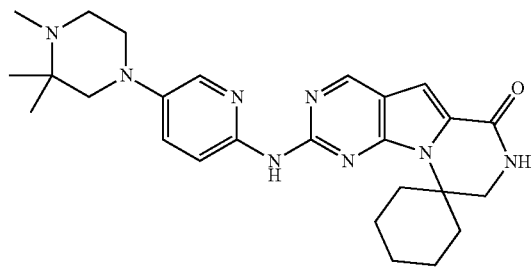 [SMILES: CN1CCN(c2ccc(Nc3ncc4cc5n(c4n3)C3(CCCCC3)CNC5=O)nc2)CC1(C)C] |
| E | 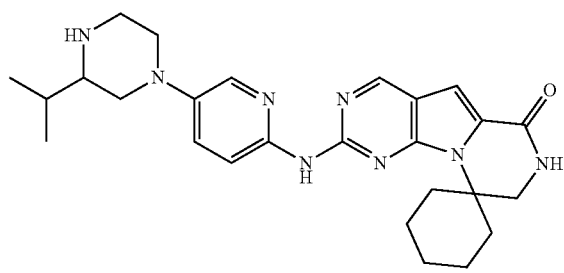 [SMILES: CC(C)C1CN(c2ccc(Nc3ncc4cc5n(c4n3)C3(CCCCC3)CNC5=O)nc2)CCN1] |

TABLE 1-continued
Structures of Anti-Neoplastic and Anti-Proliferative Agents
| Structure Reference | Structure |
|---|---|
| F | 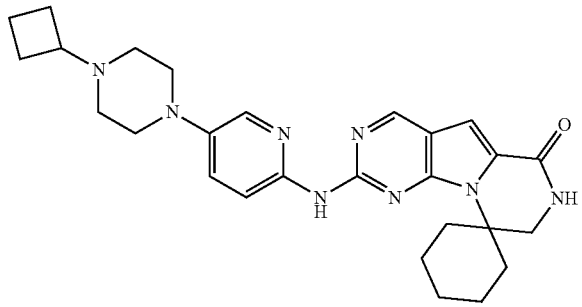 [SMILES: O=C1NCC2(CCCCC2)n2c1cc1cnc(Nc3ccc(N4CCN(C5CCC5)CC4)cn3)nc12] |
| G | 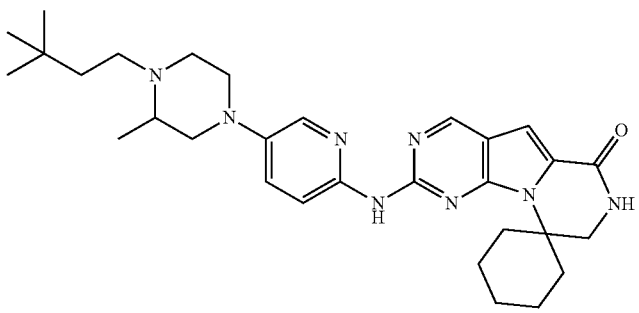 [SMILES: CC1CN(c2ccc(Nc3ncc4cc5n(c4n3)C3(CCCCC3)CNC5=O)nc2)CCN1CCC(C)(C)C] |
| H | 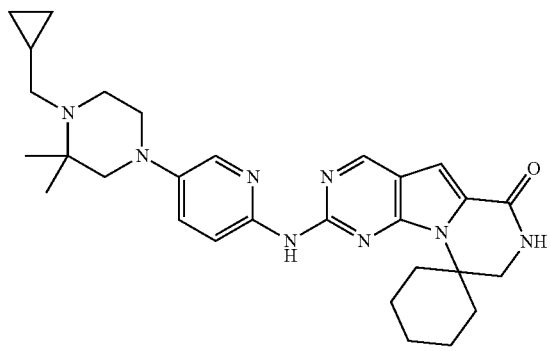 [SMILES: CC1(C)CN(c2ccc(Nc3ncc4cc5n(c4n3)C3(CCCCC3)CNC5=O)nc2)CCN1CC1CC1] |
| I | 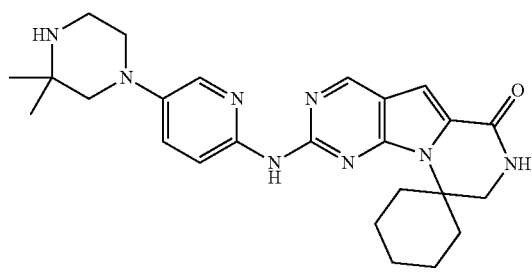 [SMILES: CC1(C)CN(c2ccc(Nc3ncc4cc5n(c4n3)C3(CCCCC3)CNC5=O)nc2)CCN1] |
| J | 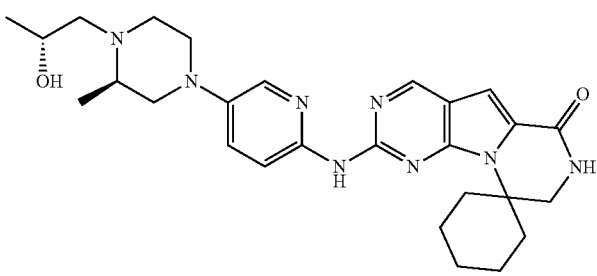 [SMILES: C[C@@H]1CN(c2ccc(Nc3ncc4cc5n(c4n3)C3(CCCCC3)CNC5=O)nc2)CCN1C[C@@H](C)O] |

TABLE 1-continued
Structures of Anti-Neoplastic and Anti-Proliferative Agents
| Structure Reference | Structure |
|---|---|
| K | 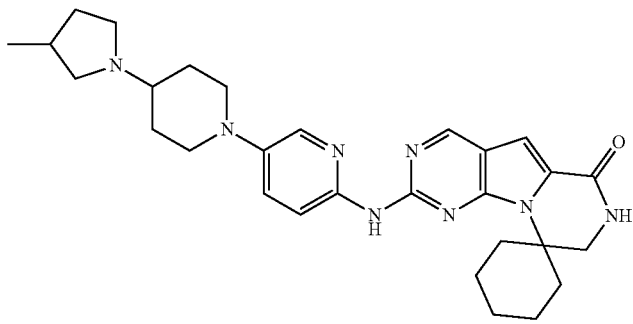 [SMILES: CC1CCN(C2CCN(c3ccc(Nc4ncc5cc6n(c5n4)C4(CCCCC4)CNC6=O)nc3)CC2)C1] |
| L | 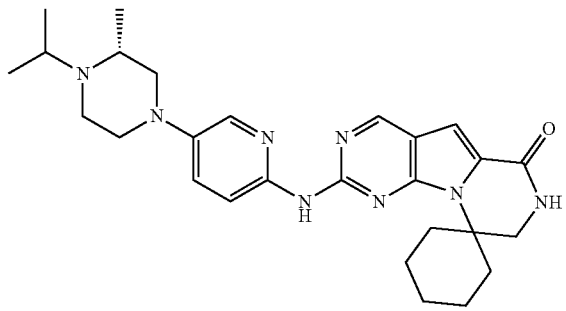 [SMILES: CC(C)N1CCN(c2ccc(Nc3ncc4cc5n(c4n3)C3(CCCCC3)CNC5=O)nc2)C[C@H]1C] |
| M | 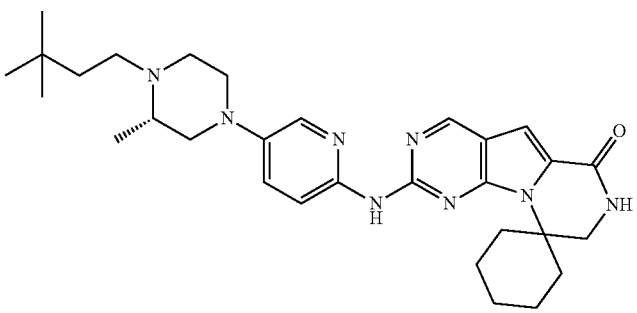 [SMILES: C[C@H]1CN(c2ccc(Nc3ncc4cc5n(c4n3)C3(CCCCC3)CNC5=O)nc2)CCN1CCC(C)(C)C] |
| N | 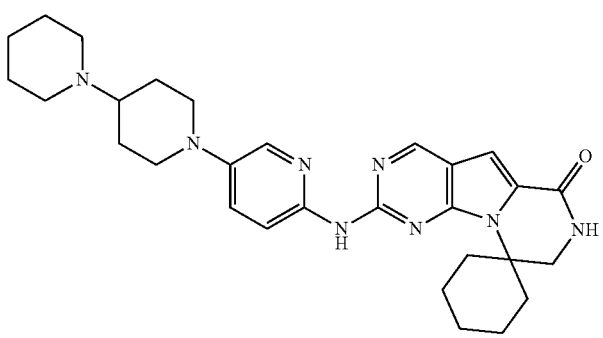 [SMILES: O=C1NCC2(CCCCC2)n2c1cc1cnc(Nc3ccc(N4CCC(N5CCCCC5)CC4)cn3)nc12] |

TABLE 1-continued
Structures of Anti-Neoplastic and Anti-Proliferative Agents
| Structure Reference | Structure |
|---|---|
| O | 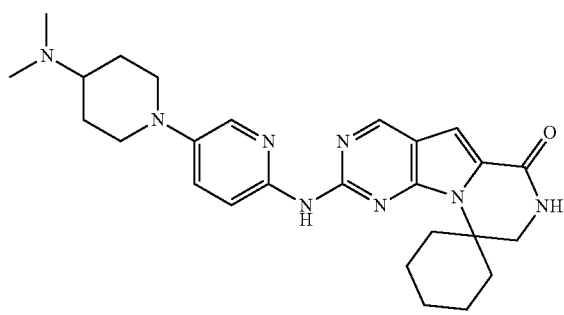 [SMILES: CN(C)C1CCN(c2ccc(Nc3ncc4cc5n(c4n3)C3(CCCCC3)CNC5=O)nc2)CC1] |
| P | 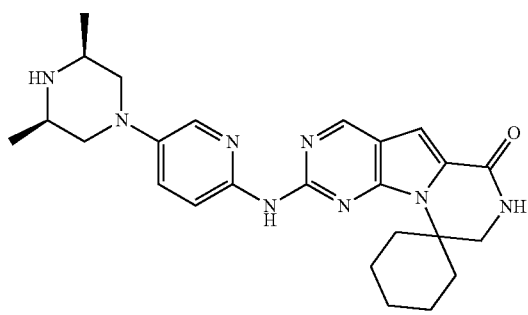 [SMILES: C[C@@H]1CN(c2ccc(Nc3ncc4cc5n(c4n3)C3(CCCCC3)CNC5=O)nc2)C[C@H](C)N1] |
| Q | 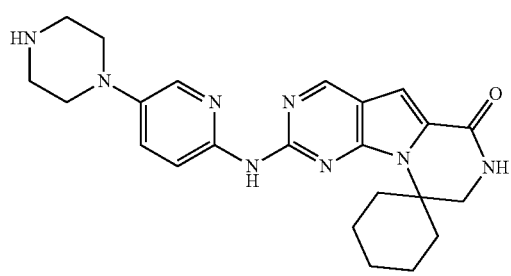 [SMILES: O=C1NCC2(CCCCC2)n2c1cc1cnc(Nc3ccc(N4CCNCC4)cn3)nc12] |
| R | 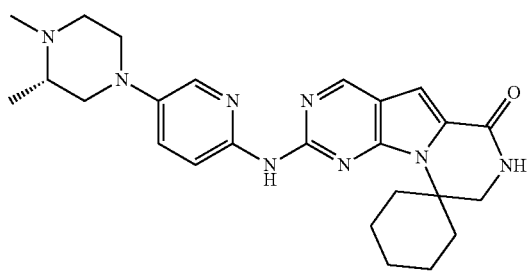 |
| S | 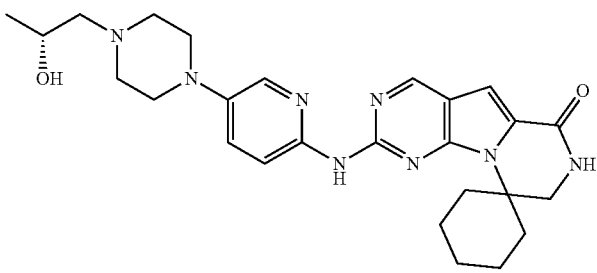 [SMILES: C[C@@H](O)CN1CCN(c2ccc(Nc3ncc4cc5n(c4n3)C3(CCCCC3)CNC5=O)nc2)CC1] |

TABLE 1-continued
Structures of Anti-Neoplastic and Anti-Proliferative Agents
| Structure Reference | Structure |
|---|---|
| T | 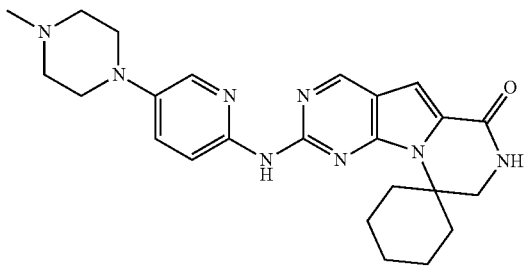 [SMILES: CN1CCN(c2ccc(Nc3ncc4cc5n(c4n3)C3(CCCCC3)CNC5=O)nc2)CC1] |
| U | 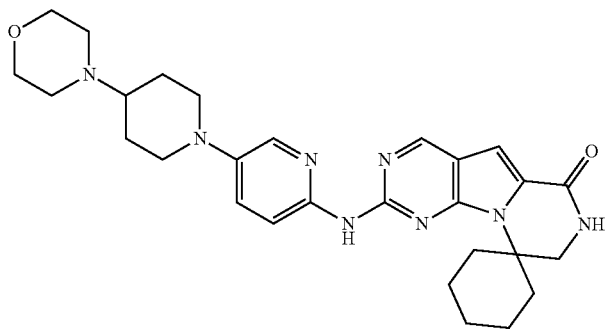 [SMILES: O=C1NCC2(CCCCC2)n2c1cc1cnc(Nc3ccc(N4CCC(N5CCOCC5)CC4)cn3)nc12] |
| V | 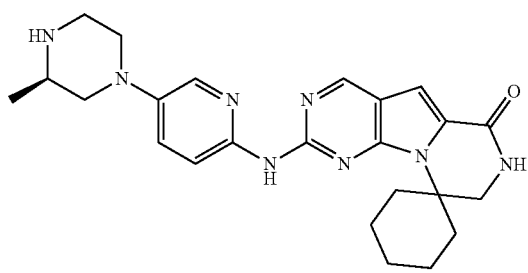 [SMILES: C[C@@H]1CN(c2ccc(Nc3ncc4cc5n(c4n3)C3(CCCCC3)CNC5=O)nc2)CCN1] |
| W | 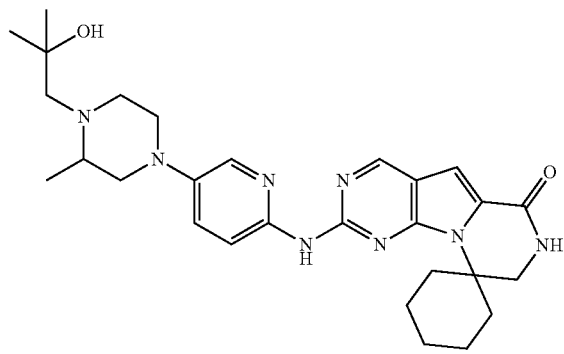 [SMILES: CC1CN(c2ccc(Nc3ncc4cc5n(c4n3)C3(CCCCC3)CNC5=O)nc2)CCN1CC(C)(C)O] |

TABLE 1-continued
Structures of Anti-Neoplastic and Anti-Proliferative Agents
| Structure Reference | Structure |
|---|---|
| X | 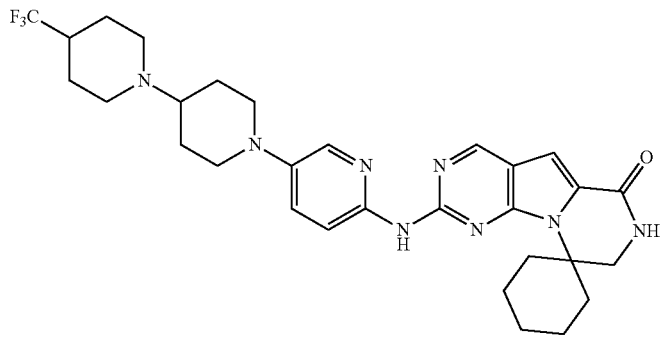 [SMILES: O=C1NCC2(CCCCC2)n2c1cc1cnc(Nc3ccc(N4CCC(N5CCC(C(F)(F)F)CC5)CC4)cn3)nc12] |
| Y | 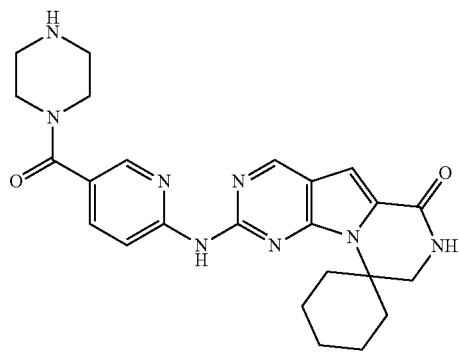 [SMILES: O=C1NCC2(CCCCC2)n2c1cc1cnc(Nc3ccc(C(=O)N4CCNCC4)cn3)nc12] |
| Z | 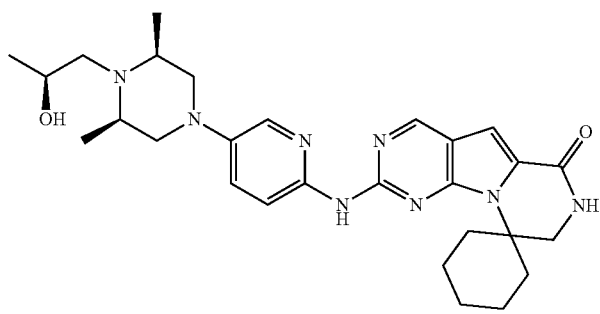 [SMILES: C[C@H](O)CN1[C@H](C)CN(c2ccc(Nc3ncc4cc5n(c4n3)C3(CCCCC3)CNC5=O)nc2)C[C@@H]1C] |
| AA | 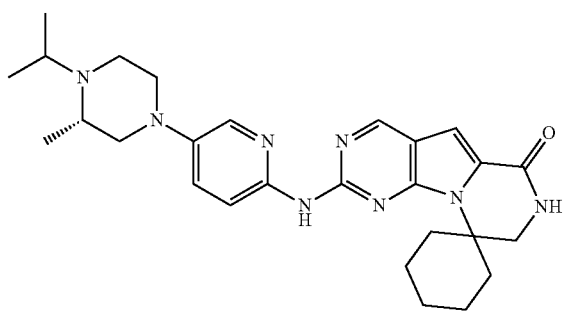 [SMILES: CC(C)N1CCN(c2ccc(Nc3ncc4cc5n(c4n3)C3(CCCCC3)CNC5=O)nc2)C[C@@H]1C] |

TABLE 1-continued
Structures of Anti-Neoplastic and Anti-Proliferative Agents
| Structure Reference | Structure |
|---|---|
| BB | 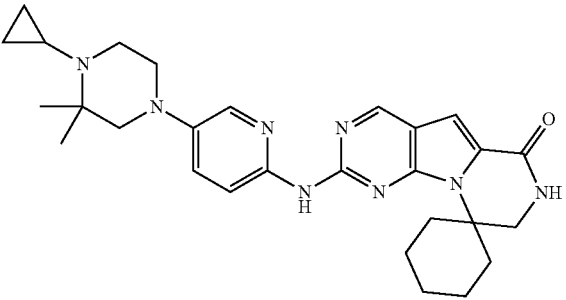 [SMILES: CC1(C)CN(c2ccc(Nc3ncc4cc5n(c4n3)C3(CCCCC3)CNC5=O)nc2)CCN1C1CC1] |
| CC | 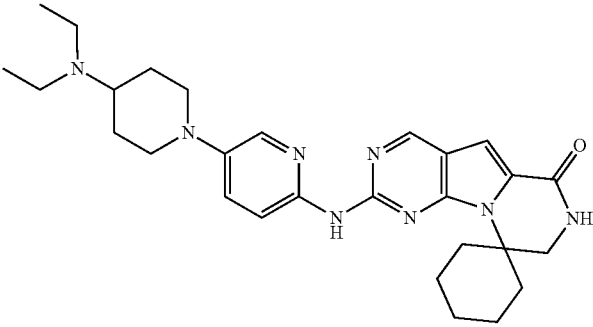 [SMILES: CCN(CC)C1CCN(c2ccc(Nc3ncc4cc5n(c4n3)C3(CCCCC3)CNC5=O)nc2)CC1] |
| DD | 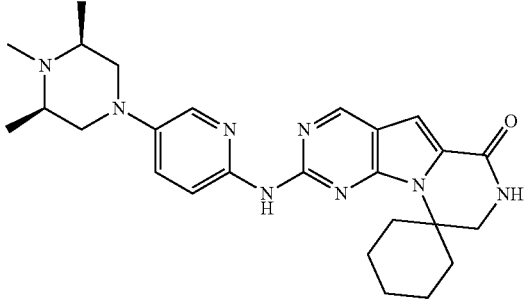 [SMILES: C[C@@H]1CN(c2ccc(Nc3ncc4cc5n(c4n3)C3(CCCCC3)CNC5=O)nc2)C[C@H](C)N1C] |
| EE | 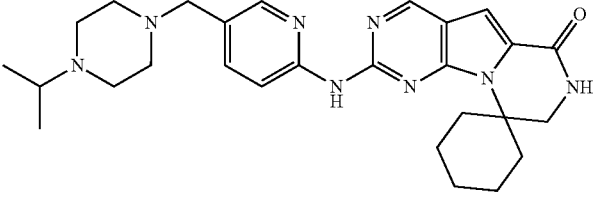 [SMILES: CC(C)N1CCN(Cc2ccc(Nc3ncc4cc5n(c4n3)C3(CCCCC3)CNC5=O)nc2)CC1] |
| FF | 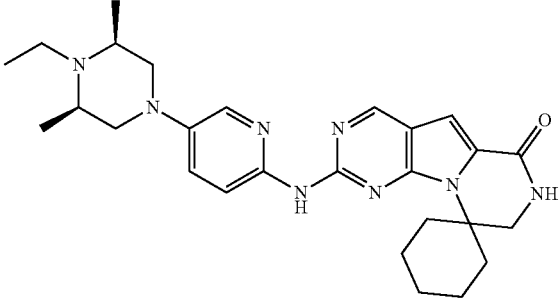 [SMILES: CCN1[C@H](C)CN(c2ccc(Nc3ncc4cc5n(c4n3)C3(CCCCC3)CNC5=O)nc2)C[C@@H]1C] |

TABLE 1-continued
Structures of Anti-Neoplastic and Anti-Proliferative Agents
| Structure Reference | Structure |
|---|---|
| GG | 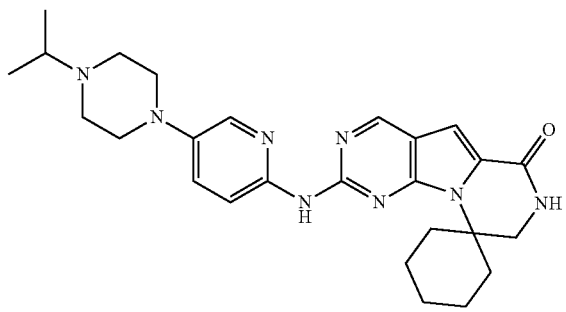 [SMILES: CC(C)N1CCN(c2ccc(Nc3ncc4cc5n(c4n3)C3(CCCCC3)CNC5=O)nc2)CC1] |
| HH | 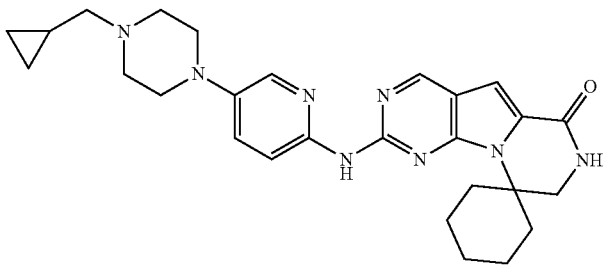 [SMILES: O=C1NCC2(CCCCC2)n2c1cc1cnc(Nc3ccc(N4CCN(CC5CC5)CC4)cn3)nc12] |
| II | 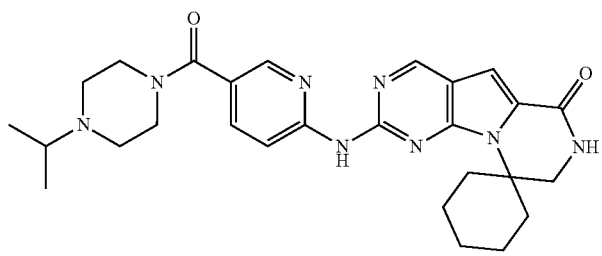 [SMILES: CC(C)N1CCN(C(=O)c2ccc(Nc3ncc4cc5n(c4n3)C3(CCCCC3)CNC5=O)nc2)CC1] |
| JJ | 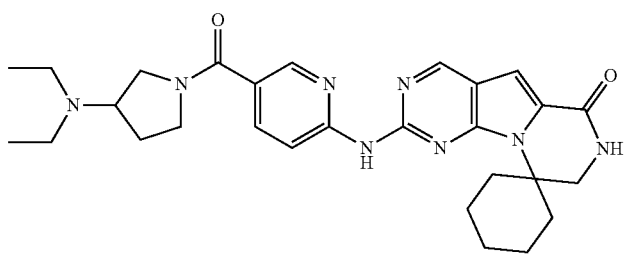 [SMILES: CCN(CC)C1CCN(C(=O)c2ccc(Nc3ncc4cc5n(c4n3)C3(CCCCC3)CNC5=O)nc2)C1] |
| KK | 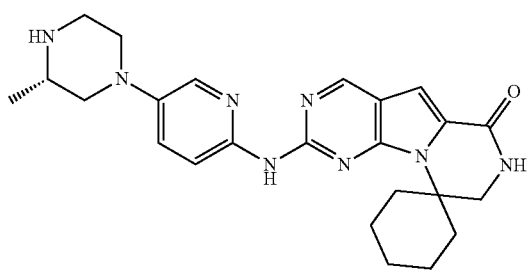 [SMILES: C[C@H]1CN(c2ccc(Nc3ncc4cc5n(c4n3)C3(CCCCC3)CNC5=O)nc2)CCN1] |

TABLE 1-continued
Structures of Anti-Neoplastic and Anti-Proliferative Agents
| Structure Reference | Structure |
|---|---|
| LL | 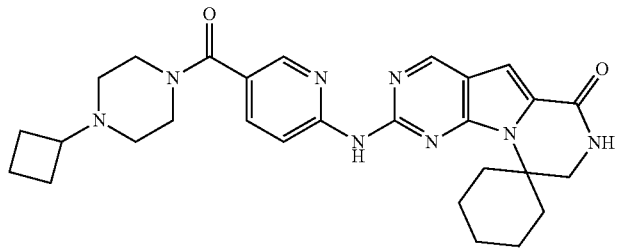 [SMILES: O=C1NCC2(CCCCC2)n2c1cc1cnc(Nc3ccc(C(=O)N4CCN(C5CCC5)CC4)cn3)nc12] |
| MM | 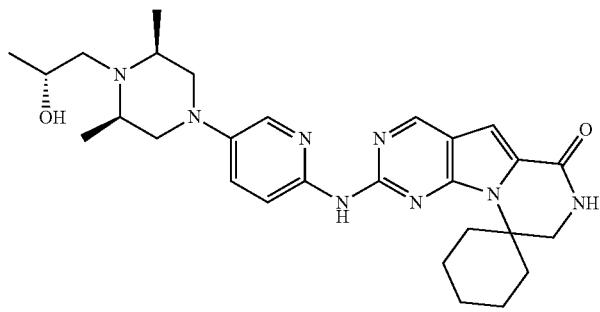 [SMILES: C[C@@H]1CN(c2ccc(Nc3ncc4cc5n(c4n3)C3(CCCCC3)CNC5=O)nc2)C[C@H](C)N1C[C@@H](C)O] |
| NN | 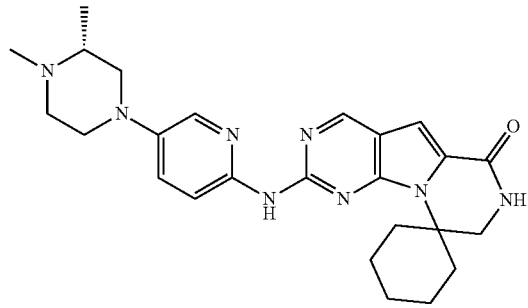 [SMILES: C[C@@H]1CN(c2ccc(Nc3ncc4cc5n(c4n3)C3(CCCCC3)CNC5=O)nc2)CCN1C] |
| OO | 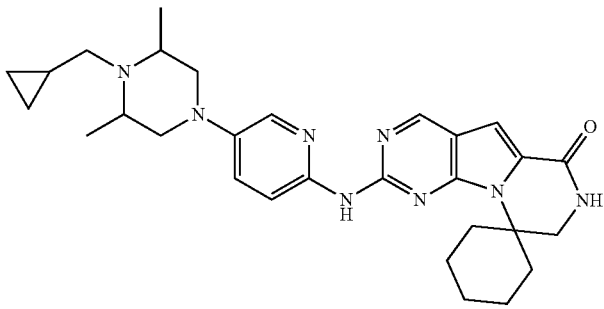 [SMILES: CC1CN(c2ccc(Nc3ncc4cc5n(c4n3)C3(CCCCC3)CNC5=O)nc2)CC(C)N1CC1CC1] |
| PP | 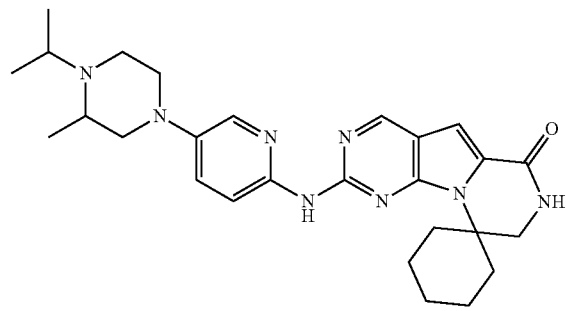 [SMILES: CC(C)N1CCN(c2ccc(Nc3ncc4cc5n(c4n3)C3(CCCCC3)CNC5=O)nc2)CC1C] |

TABLE 1-continued
Structures of Anti-Neoplastic and Anti-Proliferative Agents
| Structure Reference | Structure |
|---|---|
| QQ | 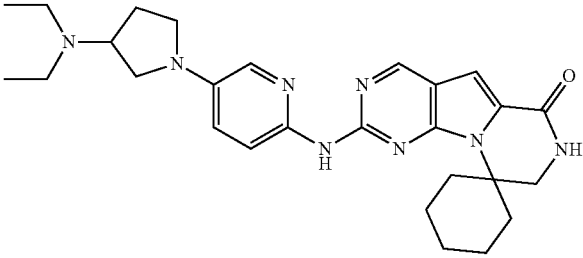 [SMILES: CCN(CC)C1CCN(c2ccc(Nc3ncc4cc5n(c4n3)C3(CCCCC3)CNC5=O)nc2)C1] |
| RR | 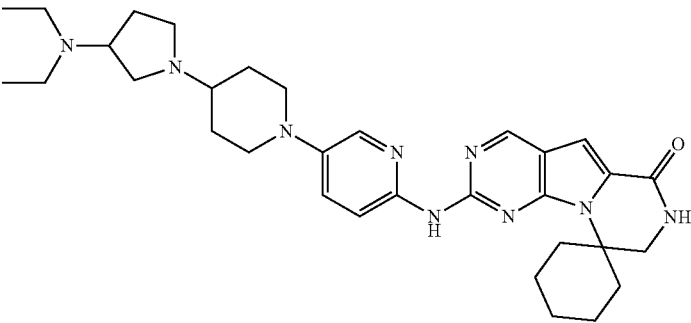 |
| SS | 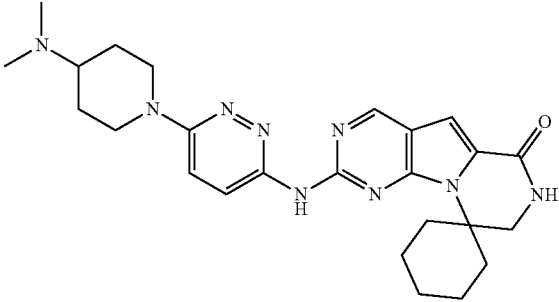 [SMILES: CN(C)C1CCN(c2ccc(Nc3ncc4cc5n(c4n3)C3(CCCCC3)CNC5=O)nn2)CC1] |
| TT | 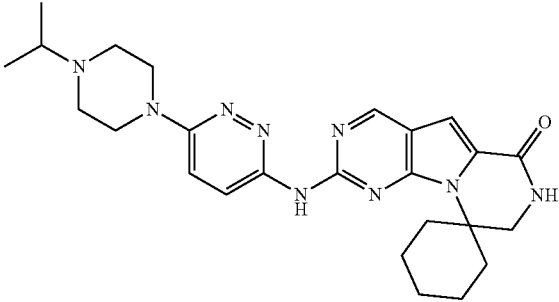 [SMILES: CC(C)N1CCN(c2ccc(Nc3ncc4cc5n(c4n3)C3(CCCCC3)CNC5=O)nn2)CC1] |
| UU | 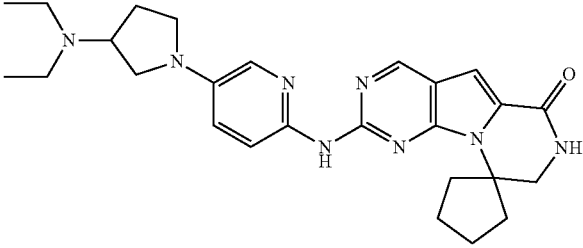 [SMILES: CCN(CC)C1CCN(c2ccc(Nc3ncc4cc5n(c4n3)C3(CCCC3)CNC5=O)nc2)C1] |

TABLE 1-continued
Structures of Anti-Neoplastic and Anti-Proliferative Agents
| Structure Reference | Structure |
|---|---|
| VV | 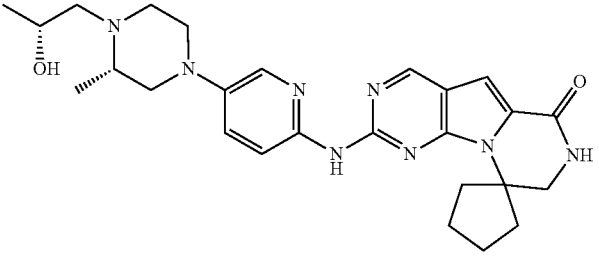 [SMILES: C[C@@H](O)CN1CCN(c2ccc(Nc3ncc4cc5n(c4n3)C3(CCCC3)CNC5=O)nc2)C[C@@H]1C] |
| WW | 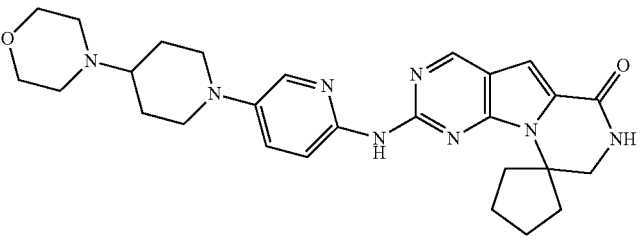 [SMILES: O=C1NCC2(CCCC2)n2c1cc1cnc(Nc3ccc(N4CCC(N5CCOCC5)CC4)cn3)nc12] |
| XX | 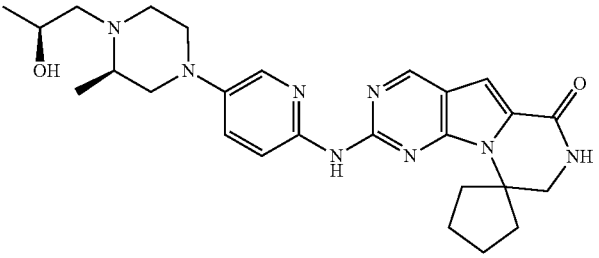 [SMILES: C[C@H](O)CN1CCN(c2ccc(Nc3ncc4cc5n(c4n3)C3(CCCC3)CNC5=O)nc2)C[C@H]1C] |
| YY | 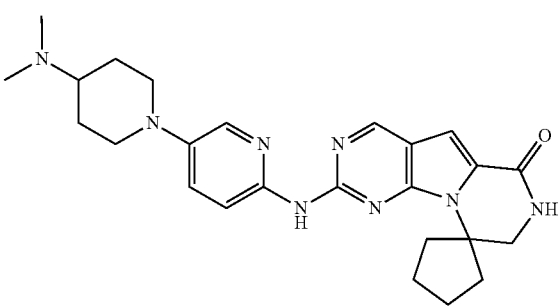 [SMILES: CN(C)C1CCN(c2ccc(Nc3ncc4cc5n(c4n3)C3(CCCC3)CNC5=O)nc2)CC1] |
| ZZ | 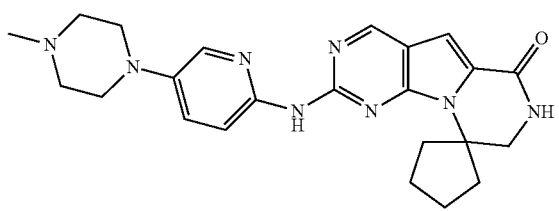 [SMILES: CN1CCN(c2ccc(Nc3ncc4cc5n(c4n3)C3(CCCC3)CNC5=O)nc2)CC1] |

TABLE 1-continued
Structures of Anti-Neoplastic and Anti-Proliferative Agents
| Structure Reference | Structure |
| --- | --- |
| AAA | 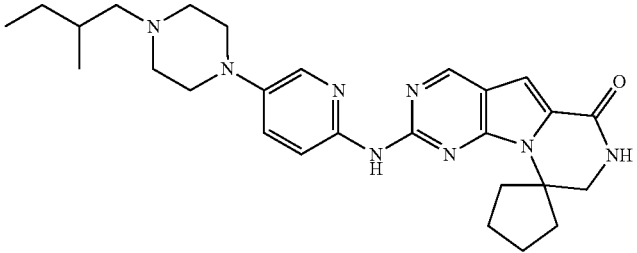 [SMILES: CCC(C)CN1CCN(c2ccc(Nc3ncc4cc5n(c4n3)C3(CCCC3)CNC5=O)nc2)CC1] |
| BBB | 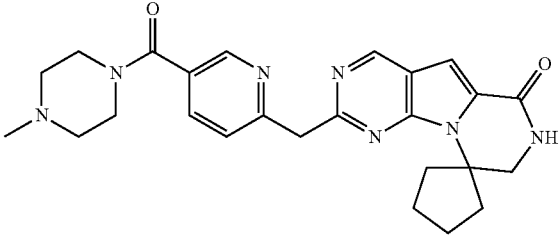 [SMILES: CN1CCN(C(=O)c2ccc(Cc3ncc4cc5n(c4n3)C3(CCCC3)CNC5=O)nc2)CC1] |
| CCC | 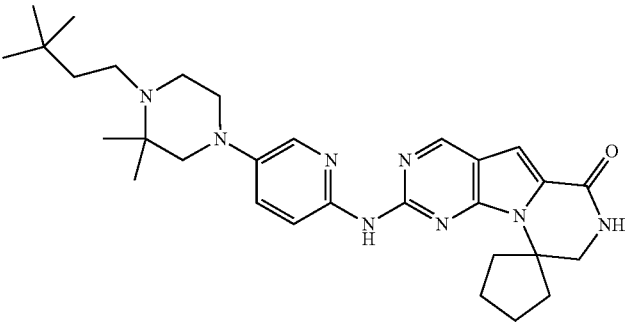 [SMILES: CC(C)(C)CCN1CCN(c2ccc(Nc3ncc4cc5n(c4n3)C3(CCCC3)CNC5=O)nc2)CC1(C)C] |
| DDD | 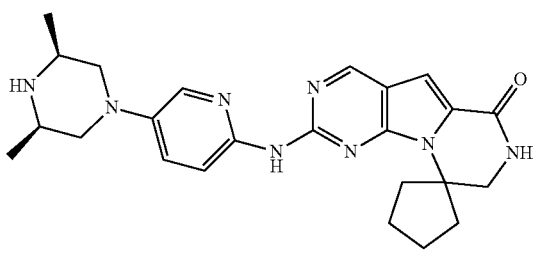 [SMILES: C[C@@H]1CN(c2ccc(Nc3ncc4cc5n(c4n3)C3(CCCC3)CNC5=O)nc2)C[C@H](C)N1] |
| EEE | 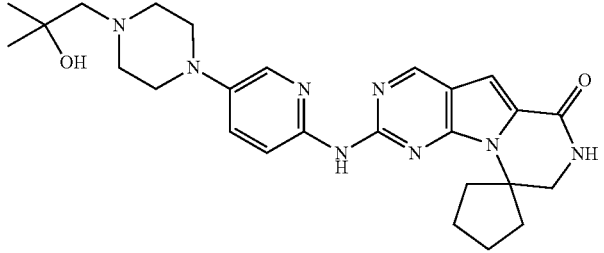 [SMILES: CC(C)(O)CN1CCN(c2ccc(Nc3ncc4cc5n(c4n3)C3(CCCC3)CNC5=O)nc2)CC1] |

TABLE 1-continued
Structures of Anti-Neoplastic and Anti-Proliferative Agents
| Structure Reference | Structure |
|---|---|
| FFF | 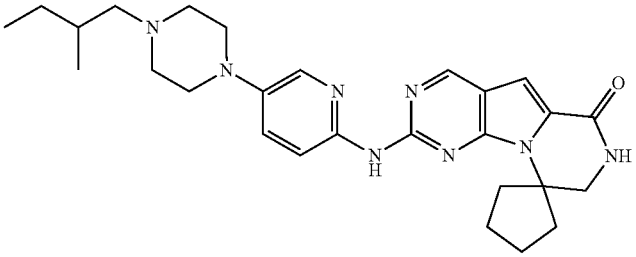 [SMILES: CCC(C)CN1CCN(c2ccc(Nc3ncc4cc5n(c4n3)C3(CCCC3)CNC5=O)nc2)CC1] |
| GGG | 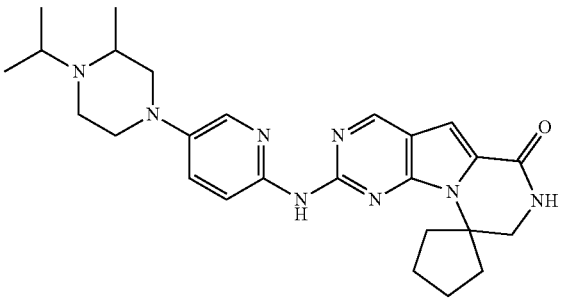 [SMILES: CC(C)N1CCN(c2ccc(Nc3ncc4cc5n(c4n3)C3(CCCC3)CNC5=O)nc2)CC1C] |
| HHH | 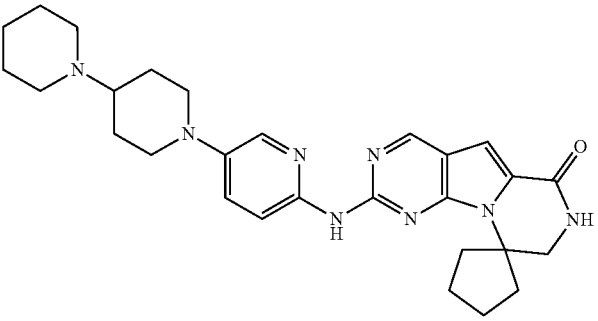 [SMILES: O=C1NCC2(CCCC2)n2c1cc1cnc(Nc3ccc(N4CCC(N5CCCCC5)CC4)cn3)nc12] |
| III | 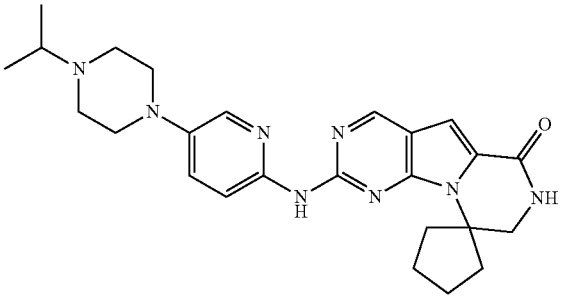 [SMILES: CC(C)N1CCN(c2ccc(Nc3ncc4cc5n(c4n3)C3(CCCC3)CNC5=O)nc2)CC1] |
| JJJ | 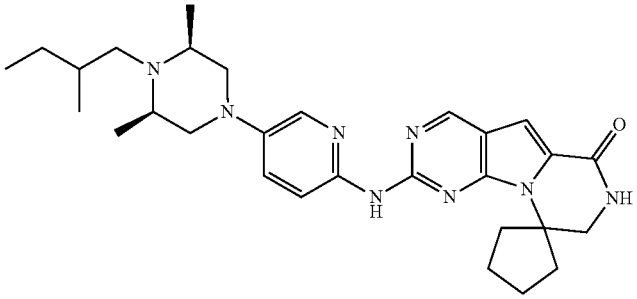 [SMILES: CCC(C)CN1[C@H](C)CN(c2ccc(Nc3ncc4cc5n(c4n3)C3(CCCC3)CNC5=O)nc2)C[C@@H]1C] |

TABLE 1-continued
Structures of Anti-Neoplastic and Anti-Proliferative Agents
| Structure Reference | Structure |
|---|---|
| KKK | 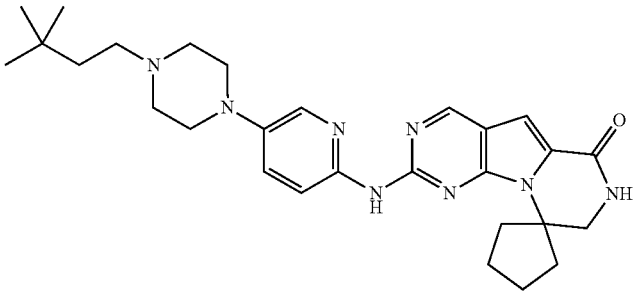 [SMILES: CC(C)(C)CCN1CCN(c2ccc(Nc3ncc4cc5n(c4n3)C3(CCCC3)CNC5=O)nc2)CC1] |
| LLL | 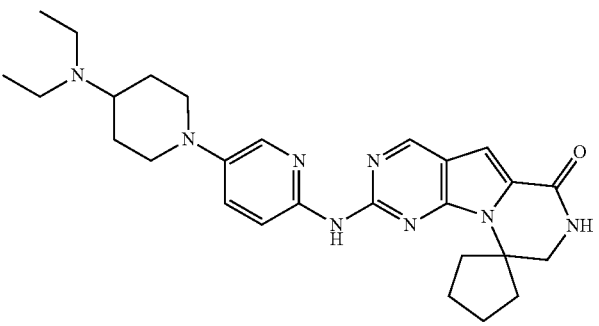 [SMILES: CCN(CC)C1CCN(c2ccc(Nc3ncc4cc5n(c4n3)C3(CCCC3)CNC5=O)nc2)CC1] |
| MMM | 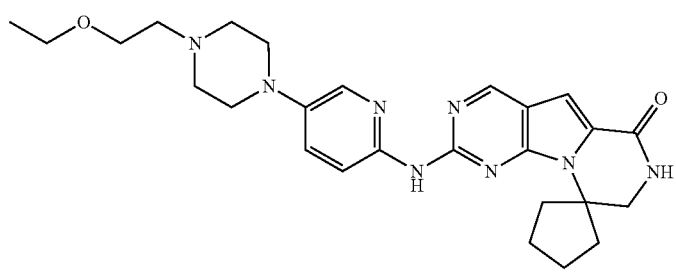 [SMILES: CCOCCN1CCN(c2ccc(Nc3ncc4cc5n(c4n3)C3(CCCC3)CNC5=O)nc2)CC1] |
| NNN | 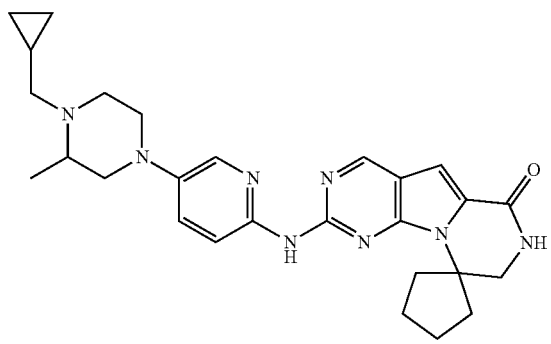 [SMILES: CC1CN(c2ccc(Nc3ncc4cc5n(c4n3)C3(CCCC3)CNC5=O)nc2)CCN1CC1CC1] |
| OOO | 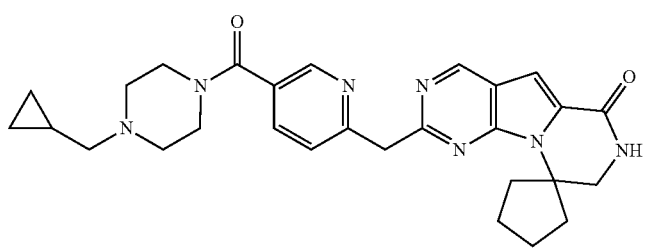 [SMILES: O=C1NCC2(CCCC2)n2c1cc1cnc(Cc3ccc(C(=O)N4CCN(CC5CC5)CC4)cn3)nc12] |

TABLE 1-continued

Structures of Anti-Neoplastic and Anti-Proliferative Agents

| Structure Reference | Structure |
|---|---|
| PPP | *(chemical structure)* |
| QQQ | *(chemical structure)* |
| RRR | *(chemical structure)* |
| SSS | *(chemical structure)* |
| TTT | *(chemical structure)* |
| UUU | *(chemical structure)* |

TABLE 1-continued

Structures of Anti-Neoplastic and Anti-Proliferative Agents

| Structure Reference | Structure |
|---|---|
| VVV | [chemical structure] |
| WWW | [chemical structure] |
| XXX | [chemical structure] |

Isotopic Substitution

The present invention includes compounds and the use of compounds with desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location.

Further specific compounds that fall within the present invention and that can be used in the disclosed methods of treatment and compositions include the structures of Formula I, II, III, IV, or V listed in Table 1 below.

Rb-Positive Cancers and Proliferative Disorders

In particular, the active compounds described herein can be used to treat a subject suffering from a Rb-positive cancer or other Rb-positive abnormal cellular proliferative disorder. In some embodiments, the cancer or cellular proliferation disorder is a CDK4/6-replication dependent cancer or cellular proliferation disorder, which refers to a cancer or cellular proliferation disorder that requires the activity of CDK4/6 for replication or proliferation, or which may be growth inhibited through the activity of a selective CDK4/6 inhibitor. Cancers and disorders of such type can be characterized by (e.g., that has cells that exhibit) the presence of a functional Retinoblastoma protein. Such cancers and disorders are classified as being Rb-positive. Rb-positive abnormal cellular proliferation disorders, and variations of this term as used herein, refer to disorders or diseases caused by uncontrolled or abnormal cellular division which are characterized by the presence of a functional Retinoblastoma protein, which can include cancers. In one aspect of the present invention, the compounds and methods described herein can be used to treat a non-cancerous Rb-positive abnormal cellular proliferation disorder. Examples of such disorders may include non-malignant lymphoproliferation, non-malignant breast neoplasms, psoriasis, arthritis, dermatitis, pre-cancerous colon lesions or pulps, angiogenesis disorders, immune mediated and non-immune mediated inflammatory diseases, arthritis, age-related macular degeneration, diabetes, and other non-cancerous or benign cellular proliferation disorders.

Targeted cancers suitable for administration of a compound described herein may include Rb-positive: estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, adenocarcinoma of the colon, adenocarcinoma of the rectum, central nervous system germ cell tumors, teratomas, estrogen receptor-negative breast cancer, estrogen receptor-positive breast cancer, familial testicular germ cell tumors, HER2-negative breast cancer, HER2-positive breast cancer, male breast cancer, ovarian immature teratomas, ovarian mature teratoma, ovarian monodermal and highly specialized teratomas, progesterone receptor-negative breast cancer, progesterone receptor-positive breast cancer, recurrent breast cancer, recurrent colon cancer, recurrent extragonadal germ cell tumors, recurrent extragonadal non-seminomatous germ cell tumor, recurrent extragonadal seminomas, recurrent malignant testicular germ cell tumors, recurrent melanomas, recurrent ovarian germ cell tumors, recurrent rectal cancer, stage III extragonadal non-seminomatous germ cell tumors, stage III extragonadal seminomas, stage III malignant testicular germ cell tumors, stage III ovarian germ cell tumors, stage IV breast cancers, stage IV colon cancers, stage IV extragonadal non-seminomatous germ cell tumors, stage IV extragonadal seminoma, stage IV melanomas, stage IV ovarian germ cell tumors, stage IV rectal cancers, testicular immature teratomas, testicular mature teratomas. In particular embodiments, the targeted cancers included estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, metastatic colorectal cancer, metastatic melanoma with CDK4 mutation or amplification, or cisplatin-refractory, unresectable germ cell tumors.

In one embodiment, the Rb-positive cancer is selected from an Rb-positive carcinoma, sarcoma, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

In one embodiment, the Rb-positive cancer is selected from the group consisting of Rb-positive: fibrosarcoma, myxosarcoma, chondrosarcoma, osteosarcoma, chordoma, malignant fibrous histiocytoma, hemangiosarcoma, angiosarcoma, lymphangiosarcoma. Mesothelioma, leiomyosarcoma, rhabdomyosarcoma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, bladder cancer, and Wilms tumor.

The presence or normal functioning of the retinoblastoma (Rb) tumor suppressor protein (Rb-positive) can be determined through any of the standard assays known to one of ordinary skill in the art, including but not limited to Western Blot, ELISA (enzyme linked immunoadsorbent assay), IHC (immunohistochemistry), and FACS (fluorescent activated cell sorting). The selection of the assay will depend upon the tissue, cell line or surrogate tissue sample that is utilized e.g., for example Western Blot and ELISA may be used with any or all types of tissues, cell lines or surrogate tissues, whereas the IHC method would be more appropriate wherein the tissue utilized in the methods of the present invention was a tumor biopsy. FACs analysis would be most applicable to samples that were single cell suspensions such as cell lines and isolated peripheral blood mononuclear cells. See for example, US 20070212736 "Functional Immunohistochemical Cell Cycle Analysis as a Prognostic Indicator for Cancer".

Alternatively, molecular genetic testing may be used for determination of retinoblastoma gene status. Molecular genetic testing for retinoblastoma includes the following as described in Lohmann D, Gallie B. Retinoblastoma. Gene Reviews. Funded by the NIH. Developed at the University of Washington, Seattle. Initial posting: 2000 Jul. 18 (available through NCBI Bookshelf website) or Parsam et al. "A comprehensive, sensitive and economical approach for the detection of mutations in the RB1 gene in retinoblastoma" Journal of Genetics, 88(4), 517-527 (2009).

In some embodiments, the cancer to be treated is selected from estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers.

CDK-Replication Dependent Cells and Cyclin-Dependent Kinase Inhibitors

Tissue-specific stem cells and subsets of other resident proliferating cells are capable of self-renewal, meaning that they are capable of replacing themselves throughout the adult mammalian lifespan through regulated replication. Additionally, stem cells divide asymmetrically to produce "progeny" or "progenitor" cells that in turn produce various components of a given organ. For example, in the hematopoietic system, the hematopoietic stem cells give rise to progenitor cells which in turn give rise to all the differentiated components of blood (e.g., white blood cells, red blood cells, and platelets) (see FIG. 1).

It has been found that certain proliferating cells, such as HSPCs, require the enzymatic activity of the proliferative kinases cyclin-dependent kinase 4 (CDK4) and/or cyclin-dependent kinase 6 (CDK6) for cellular replication. In contrast, the majority of proliferating cells in adult mammals (e.g., the more differentiated blood-forming cells in the bone marrow) do not require the activity of CDK4 and/or CDK6 (i.e., CDK4/6). These differentiated cells can proliferate in the absence of CDK4/6 activity by using other proliferative kinases, such as cyclin-dependent kinase 2 (CDK2) or cyclin-dependent kinase 1 (CDK1).

The present invention includes methods of treating certain cancers, in particular Rb-positive cancers, while minimizing the deleterious effects on CDK4/6-replication dependent healthy cells in a subject, and in particular, hematopoietic cells and/or progenitor cells (HSPCs), by the administration of a compound described herein to treat a specific Rb-positive cancer.

In one embodiment, the use of a compound described herein as a chemotherapeutic allows for an accelerated hematological recovery and reduced hematological deficiency risk due to HSPC replication delay compared to the use of other CDK4/6 inhibitors, for example, PD0332991. In one embodiment, the use of a compound described herein as a chemotherapeutic allows for a reduced or minimized off-cycle or drug holiday during the course of treatment compared to current treatment modalities using other CDK4/6 inhibitors, for example PD0332991. In one embodiment, the use of the compounds described herein as chemotherapeutics allows for the elimination of an off-cycle or drug holiday. In one embodiment, the use of the compounds described herein as chemotherapeutics allows for an extended period of administration with fewer off-cycle days or drug holidays compared to the use of current treatment modalities using other CDK4/6 inhibitors, for example PD0332991. In one embodiment, the use of the compounds described herein as chemotherapeutics allows for a faster blood count recovery during an off-cycle or drug holiday than the use of current modalities using other CDK4/6 inhibitors, for example PD0332991.

In certain embodiments, the compound administered is selected from the group consisting of a compound or composition comprising Formula I, Formula II, Formula III, Formula IV, or Formula V, or a combination thereof. In certain embodiments, the compound administered is selected from the group consisting of a compound selected from Table 1.

In certain aspects, compounds, methods, and compositions are provided as chemotherapeutics which reduce or limit the deleterious effect of CDK4/6 inhibition on CDK4/6-replication dependent healthy cells in a subject undergoing CDK4/6 inhibitory treatment for a Rb-positive cancer, the method comprising administering an effective amount of a compound described herein, wherein a substantial portion of the CDK4/6-replication dependent healthy cells return to pre-treatment baseline cell cycle activity (i.e., reenter the cell-cycle) within less than about 24, 30, 36, or 40 hours of administration of the compound. In certain embodiments wherein the compound has an $IC_{50}$ CDK4 inhibitory concentration that is at least 1500 times less than its $IC_{50}$ inhibitory concentration for CDK2. In certain embodiments, the compound administered is selected from the group consisting of the compound or a composition comprising Formula I, Formula II, Formula III, Formula IV, or Formula V, or a pharmaceutically acceptable composition, salt, isotopic analog, or prodrug thereof. In certain embodiments, the compound administered is selected from a compound contained in Table 1, or a pharmaceutically acceptable composition, salt, isotopic analog, or prodrug thereof. In one embodiment, the CDK4/6-replication dependent cells are hematopoietic stem cells and/or progenitor cells (HSPCs).

In certain aspects, compounds, methods, and composition are provided for use as chemotherapeutics which limit the deleterious effect of CDK4/6 inhibition on CDK4/6-replication dependent healthy cells in a subject undergoing treatment for a Rb-positive cancer, the method comprising administering an effective amount of a compound described herein, wherein a substantial portion of the CDK4/6-replication dependent healthy cells synchronously reenter the cell-cycle within less than about 24, 30, 36 or 40 hours following the dissipation of the compound's inhibitory effect. In certain embodiments wherein the compound has an $IC_{50}$ CDK4 inhibitory concentration that is at least 1500 times less than its $IC_{50}$ inhibitory concentration for CDK2. In certain embodiments, the compound administered is selected from the group consisting of the compound or a composition comprising Formula I, Formula II, Formula III, Formula IV, or Formula V, or a pharmaceutically acceptable composition, salt, isotopic analog, or prodrug thereof. In certain embodiments, the compound administered is selected from a compound contained in Table 1, or a pharmaceutically acceptable composition, salt, isotopic analog, or prodrug thereof. In one embodiment, the CDK4/6-replication dependent cells are hematopoietic stem cells and/or progenitor cells (HSPCs).

In certain aspects, compounds, methods, and composition are provided for use as chemotherapeutics which limit the deleterious effect of CDK4/6 inhibition on CDK4/6-replication dependent healthy cells in a subject, the method comprising administering an effective amount of a compound described herein to a subject with a Rb-positive cancer, wherein a substantial portion of the CDK4/6-replication dependent healthy cells reenter the cell-cycle synchronously within less than about 24, 30, 36, or 40 hours following the dissipation of the compound's CDK4/6 inhibitory effect. In one embodiment, the administered compound has an $IC_{50}$ CDK4 inhibitory concentration that is more than 500 times less than its $IC_{50}$ inhibitory concentration for CDK2. In certain embodiments, a substantial portion of the CDK4/6-replication dependent healthy cells reenter the cell-cycle synchronously within less than about 24, 30, 36, or 40 hours from the point in which the compound's concentration level in the subject's blood drops below a therapeutic effective concentration. In certain embodiments, the compound administered is selected from the group consisting of the compound or a composition comprising Formula I, Formula II, Formula III, Formula IV, or Formula V, or a pharmaceutically acceptable composition, salt, isotopic analog, or prodrug thereof. In certain embodiments, the compound administered is selected from a compound contained in Table 1, or a pharmaceutically acceptable composition, salt, isotopic analog, or prodrug thereof. In one embodiment, the CDK4/6-replication dependent cells are hematopoietic stem cells and/or progenitor cells (HSPCs). In one embodiment the CDK4/6-replication dependent healthy cells are renal epithelial cells.

In certain embodiments, the compound administered is selected from the group consisting of the compound or a composition comprising Formula I, Formula II, Formula III, Formula IV, or Formula V, or a pharmaceutically acceptable composition, salt, isotopic analog, or prodrug thereof, or compound contained in Table 1, or a pharmaceutically acceptable composition, salt, isotopic analog, or prodrug thereof, wherein the effect of the compound is short term and transient in nature, allowing a significant portion of the CDK4/6-replication dependent healthy cells to synchronously renter the cell-cycle quickly, for example within less than about 24, 30, 36, or 40 hours of the last administration of the compound.

The compounds for use in the described methods are highly selective, potent CDK4/6 inhibitors, with minimal CDK2 inhibitory activity. In one embodiment, a compound for use in the methods described herein has a CDK4/CycD1 $IC_{50}$ inhibitory concentration value that is >1500 times, >1800 times, >2000 times, >2200 times, >2500 times, >2700 times, >3000 times, >3200 times or greater lower than its respective $IC_{50}$ concentration value for CDK2/CycE inhibition. In one embodiment, a compound for use in the methods described herein has an $IC_{50}$ concentration value for CDK4/CycD1 inhibition that is about <1.50 nM, <1.25 nM, <1.0 nM, <0.90 nM, <0.85 nM, <0.80 nM, <0.75 nM, <0.70 nM, <0.65 nM, <0.60 nM, <0.55 nM, or less. In one embodiment, a CDK4/6 inhibitor for use in the methods described herein has an $IC_{50}$ concentration value for CDK2/CycE inhibition that is about >1.0 µM, >1.25 µM, >1.50 µM, >1.75 µM, >2.0 µM, >2.25 µM, >2.50 µM, >2.75 µM, >3.0 µM, >3.25 µM, >3.5 µM or greater. In one embodiment, a compound for use in the methods described herein has an $IC_{50}$ concentration value for CDK2/CycA $IC_{50}$ that is >0.80 µM, >0.85 µM, >0.90 µM, >0.95 µM, >0.1.0 µM, >1.25 µM, >1.50 µM, >1.75 µM, >2.0 µM, >2.25 µM, >2.50 µM, >2.75 uM, >3.0 µM or greater.

In certain embodiments, the compounds useful in the described methods may provide for a transient and quickly reversible G1-arrest of CDK4/6-replication dependent healthy cells while providing for growth inhibition of CDK4/6-replication dependent cancers. By having a limited-term transient effect, the use of such compounds as chemotherapeutics allows for the faster reentry of the CDK4/6-replication dependent healthy cells into the cell cycle following cessation of the treatment compared to, for example, longer acting CDK4/6 inhibitors such as PD0332991. The quicker dissipation of the G1 arresting effect on CDK4/6-replication dependent healthy cells makes such compounds preferable over longer acting CDK4/6 inhibitors in situations where: 1) the subject will be exposed to closely spaced treatments, wherein the use of a longer acting CDK4/6 inhibitor would prohibit the cycling of the CDK4/6-replication dependent healthy cells between exposures; 2) continuous or long-term treatment regimens wherein the long-term G1 arrest of CDK4/6-replication dependent healthy cells is a side effect of growth inhibition of the targeted cancer, and the subject would benefit from the CDK4/6-replication dependent healthy cells quickly reentering the cell-cycle following cessation of the treatment regime, between dosing of the inhibitor in a continuous regime, or between breaks in treatment in order to limit replication delay, thus reducing, limiting, or ameliorating further healthy cell damage, for example bone marrow suppression, upon cessation of the treatment. According to the present invention, chemotherapeutic regimens with the selective compounds described herein can be achieved by a number of different dosing schedules, including on-cycle/off-cycle regimes and continuous treatment regimes.

In one embodiment, the compounds described herein are used in CDK4/6-replication dependent healthy cell cycling strategies wherein a subject is exposed to regular, repeated chemotherapeutic treatments for an Rb-positive cancer. Such cycling allows CDK4/6-replication dependent cells to regenerate damaged blood cell lineages between regular, repeated treatments, and reduces the risk associated with long term CDK4/6 inhibition. This cycling between a state of G1-arrest and a state of replication is not feasible in limited time-spaced, repeated agent exposures using longer acting CDK4/6 inhibitors such as PD0332991, as the lingering G1-arresting effect of the compound prohibit significant and meaningful reentry into the cell-cycle by the CDK4/6-replication dependent cells before the next exposure to the CDK4/6 inhibitor, or delay the healthy cells from entering the cell cycle and reconstituting damaged tissues or cells following treatment cessation.

In one embodiment, the use of a compound described herein provides for a rapid, reentry into the cell cycle by CDK4/6-replication dependent healthy cells, for example HSPCs, so that the cells return to pre-treatment baseline cell cycle activity within less than about 40 hours, 36 hours, 30 hours, 28 hours, 24 hours or less. In one embodiment, the use of a compound described herein provides for a rapid, reentry into the cell cycle by CDK4/6-replication dependent healthy cells, for example HSPCs, so that the cells approach pre-treatment baseline cell cycle activity within less than about 40 hours, 36 hours, 30 hours, 28 hours, 24 hours, 18 hours, 16 hours, 14 hours, 12 hours or less. In one embodiment, the use of a compound described herein provides for a rapid, reentry into the cell cycle by CDK4/6-replication dependent cells so that the cells return to pre-treatment baseline cell cycle activity within less than about 40 hours, 36 hours, 30 hours, 28 hours, 24 hours, 18 hours, 16 hours, 14 hours, 12 hours or less from the last administration of a compound described herein. In one embodiment, the use of a compound described herein provides for a rapid, reentry into the cell cycle by CDK4/6-replication dependent healthy cells so that the cells approach pre-treatment baseline cell cycle activity within less than about 40 hours, 36 hours, 30 hours, 28 hours, 24 hours, 18 hours, 16 hours, 14 hours, 12 hours or less from the last administration of the compound. In one embodiment, the use of a compound described herein provides for a rapid, reentry into the cell cycle by CDK4/6-replication dependent healthy cells so that the cells approach pre-treatment baseline cell cycle activity within less than about 40 hours, 36 hours, 30 hours, 28 hours, 24 hours, 18 hours, 16 hours, 14 hours, 12 hours or less from the point in which the compound's concentration level in the subject's blood drops below a therapeutic effective concentration. In one embodiment, the CDK4/6-replication dependent healthy cells are HSPCs. In one embodiment, the CDK4/6-replication dependent healthy cells are renal epithelial cells. In one embodiment, the rapid reentry into the cell-cycle is synchronous.

In one embodiment, the use of a compound described herein provides for a rapid, reentry into the cell cycle by CDK4/6-replication dependent healthy cells, for example HSPCs, so that a portion of the cells exhibit a level of cell cycle activity or are capable of entering the cell cycle and proliferate during a continuous treatment regime, for example, a treatment regime wherein the compound is administered for an extended period, for example, 5 continuous days, 7 continuous days, 10 continuous days, 14 continuous days, 18 continuous days, 21 continuous days, 24 continuous days, 28 continuous days, 35 continuous days or more. In one embodiment, a compound useful in a described method is administered for a continuous period, for example, 21, 28, 35 days or more, without the requirement for an off-cycle period or drug holiday. In one embodiment, the use of a compound described herein eliminates the need for an off-cycle period, drug holiday, or reduction in co-administered anti-neoplastic compound concentration during treatment.

According to the present invention, a compound described herein can be administered as a chemotherapeutic to a subject having an Rb-positive proliferation disorder on any treatment schedule and in any dose consistent with the prescribed course of treatment. For instance the compound can be administered once a day, twice a day or three times a day. The compound can be administered on alternating days, or every third day, or every fourth day, or every fifth day, or every sixth day or once a week. The compound can be administered every other week or monthly.

Combination Therapy

In one aspect of the invention, the compounds disclosed herein can be beneficially administered in combination with another therapeutic regimen for beneficial, additive or synergistic effect.

In one embodiment, a compound/method of the present invention is used in combination with another therapy to treat the Rb-positive cancer. The second therapy can be an immunotherapy. As discussed in more detail below, the compound can be conjugated to an antibody, radioactive agent, or other targeting agent that directs the compound to the diseased or abnormally proliferating cell. In another embodiment, the compound is used in combination with another pharmaceutical or a biologic agent (for example an antibody) to increase the efficacy of treatment with a combined or a synergistic approach. In an embodiment, the compound can be used with T-cell vaccination, which typically involves immunization with inactivated autoreactive T cells to eliminate an Rb-positive cancer cell population as described herein. In another embodiment, the compound is used in combination with a bispecific T-cell Engager (BiTE), which is an antibody designed to simultaneously bind to specific antigens on endogenous T cells and Rb-positive cancer cells as described herein, linking the two types of cells.

In one embodiment, the additional therapy is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

Another group of cancer therapeutic MAbs are the immunoconjugates. These MAbs, which are sometimes called immunotoxins or antibody-drug conjugates, consist of an antibody attached to a cell-killing substance, such as a plant or bacterial toxin, a chemotherapy drug, or a radioactive molecule. The antibody latches onto its specific antigen on the surface of a cancer cell, and the cell-killing substance is taken up by the cell. FDA-approved conjugated MAbs that work this way include ado-trastuzumab emtansine, which targets the HER-2 molecule to deliver the drug DM1, which inhibits cell proliferation, to HER-2 expressing metastatic breast cancer cells.

Immunotherapies with T cells engineered to recognize cancer cells via bispecific antibodies (bsAbs) or chimeric antigen receptors (CARs) are approaches with potential to ablate both dividing and non/slow-dividing subpopulations of cancer cells.

Bispecific antibodies, by simultaneously recognizing target antigen and an activating receptor on the surface of an immune effector cell, offer an opportunity to redirect immune effector cells to kill cancer cells. The other approach is the generation of chimeric antigen receptors by fusing extracellular antibodies to intracellular signaling domains. Chimeric antigen receptor-engineered T cells are able to specifically kill tumor cells in a MHC-independent way.

In some embodiments, the compound can be administered to the subject in combination with other chemotherapeutic agents. If convenient, the compounds described herein can be administered at the same time as another chemotherapeutic agent, in order to simplify the treatment regimen. In some embodiments, the compound and the other chemotherapeutic can be provided in a single formulation. In one embodiment, the use of the compounds described herein is combined in a therapeutic regime with other agents. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apopototic inducing compounds, AKT inhibitors, including but not limited to, MK-2206, GSK690693, Perifosine, (KRX-0401), GDC-0068, Triciribine, AZD5363, Honokiol, PF-04691502, and Miltefosine, PD-1 inhibitors including but not limited to, Nivolumab, CT-011, MK-3475, BMS936558, and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of mTOR inhibitors include but are not limited to rapamycin and its analogs, everolimus (Afinitor), temsirolimus, ridaforolimus, sirolimus, and deforolimus. Examples of PI3 kinase inhibitors include but are not limited to Wortmannin, demethoxyviridin, perifosine, idelalisib, PX-866, IPI-145, BAY 80-6946, BEZ235, RP6503, TGR 1202 (RP5264), MLN1117 (INK1117), Pictilisib, Buparlisib, SAR245408 (XL147), SAR245409 (XL765), Palomid 529, ZSTK474, PWT33597, RP6530, CUDC-907, and AEZS-136. Examples of MEK inhibitors include but are not limited to Tametinib, Selumetinib, MEK162, GDC-0973 (XL518), and PD0325901. Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol. In a particular embodiment, a compound described herein is administered in combination with letrozole and/or tamoxifen. Other chemotherapeutic agents that can be used in combination with the compounds described herein include, but are not limited to, chemotherapeutic agents that do not require cell cycle activity for their anti-neoplastic effect.

In one embodiment, a CDK4/6 inhibitor described herein can be combined with a chemotherapeutic selected from, but are not limited to, Imatinib mesylate (Gleevac®), Dasatinib (Sprycel®), Nilotinib (Tasigna®), Bosutinib (Bosulif®), Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the additional therapeutic agent is an anti-inflammatory agent, a chemotherapeutic agent, a radiotherapeutic, additional therapeutic agents, or immunosuppressive agents.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™) Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, and celecoxib.

In one aspect of the present invention, a compound described herein can be combined with at least one immunosuppressive agent. The immunosuppressive agent is preferably selected from the group consisting of a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, anti-thymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In certain embodiments, a compound described herein is administered to the subject prior to treatment with another chemotherapeutic agent, during treatment with another chemotherapeutic agent, after administration of another chemotherapeutic agent, or a combination thereof.

In some embodiments, the selective compound can be administered to the subject such that the other chemotherapeutic agent can be administered either at higher doses (increased chemotherapeutic dose intensity) or more frequently (increased chemotherapeutic dose density). Dose-dense chemotherapy is a chemotherapy treatment plan in which drugs are given with less time between treatments than in a standard chemotherapy treatment plan. Chemotherapy dose intensity represents unit dose of chemotherapy administered per unit time. Dose intensity can be increased or decreased through altering dose administered, time interval of administration, or both.

In one embodiment of the invention, the compounds described herein can be administered in a concerted regimen with another agent such as a non-DNA-damaging, targeted anti-neoplastic agent or a hematopoietic growth factor agent. It has been recently been reported that the untimely administration of hematopoietic growth factors can have serious side effects. For example, the use of the EPO family of growth factors has been associated with arterial hypertension, cerebral convulsions, hypertensive encephalopathy, thromboembolism, iron deficiency, influenza like syndromes and venous thrombosis. The G-CSF family of growth factors has been associated with spleen enlargement and rupture, respiratory distress syndrome, allergic reactions and sickle cell complications. By combining the administration of the short-lived selective compounds described herein and methods of the present invention with the timely administration of hematopoietic growth factors, for example, at the time point wherein the affected cells are no longer under growth arrest, it is possible for the health care practitioner to decrease the amount of the growth factor to minimize the unwanted adverse effects while achieving the desired therapeutic benefit. In one embodiment, the growth factor is administered upon cessation of the effect of the compound on the CDK4/6 replication dependent healthy cells, for example HSPCs. Thus, in this embodiment, the use of a selective compound described herein in an anti-neoplastic therapeutic regime may allow the subject to receive a reduced amount of growth factor because the targeted hematopoietic cells will have reentered the cell cycle quicker than when other CDK4/6 inhibitors, for example PD0332991. In addition, rapid cell-cycle reentry following G1 arrest using a compound described herein provides for the ability to time the administration of hematopoietic growth factors to assist in the reconstitution of hematopoietic cell lines to maximize the growth factor effect, that is, when the growth factors will be most effective. As such, in one embodiment, the use of the compounds or methods described herein is combined with the use of hematopoietic growth factors including, but not limited to, granulocyte colony stimulating factor (G-CSF, for example, sold as Neupogen (filgrastin), Neulasta (pegfilgrastin), or lenograstin), granulocyte-macrophage colony stimulating factor (GM-CSF, for example sold as molgramostim and sargramostim (Leukine)), M-CSF (macrophage colony stimulating factor), thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbopoetin, Epocept, Nanokine, Epofit, Epogin, Eprex and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Reacrit) as well as for example Epocept, EPOTrust, Erypro Safe, Repoeitin, Vintor, Epofit, Erykine, Wepox, Espogen, Relipoeitin, Shanpoietin, Zyrop and EPIAO). In one embodiment, the CDK4/6 inhibitor is administered prior to administration of the hematopoietic growth factor. In one embodiment, the hematopoietic growth factor administration is timed so that the compound's effect on HSPCs has dissipated. In one embodiment, the growth factor is administered at least 20 hours after the administration of a compound described herein.

If desired, multiple doses of a compound described herein can be administered to the subject. Alternatively, the subject can be given a single dose of a compound described herein. For example, a compound can be administered so that CDK4/6-replication dependent healthy cells are G1 arrested wherein, due to the rapid dissipation of the G1-arresting effect of the compounds, a significant number of healthy cells reenter the cell-cycle and are capable of replicating shortly after exposure, for example, within about 24-48 hours or less, and continue to replicate until a following administration of the compound. In one embodiment, the compound is administered to allow for the cycling of the CDK4/6-replication dependent healthy cells between G1-arrest and reentry into the cell-cycle to accommodate a repeated-dosing treatment regimen, for example a long term repeated-dosing treatment regime.

In some embodiments, the CDK4/6-replication dependent healthy cells can be arrested for longer periods, for example, over a period of hours, days, weeks and/or months, through multiple, limited-time separated administrations of a compound described herein. Because of the rapid reentry into the cell cycle by CDK4/6-replication dependent healthy cells, for example HSPCs, upon dissipation of the compounds inhibitory intra-cellular effects, the cells are capable of reconstituting the cell lineages faster than CDK4/6 inhibitors with longer G1 arresting profiles, for example PD0332991.

The reduction in side effects, in particular myelosuppression, afforded by the compounds described herein can allow for dose intensification (e.g., more therapy can be given in a fixed period of time), which will translate to better efficacy. Therefore, the presently disclosed methods can result in regimens that are less toxic and more effective. When appropriate, the small molecules can be formulated for oral, topical, intranasal, inhalation, intravenous or any other desired form of administration.

A compound useful in the methods described herein is a selective CDK4/6 inhibitor compound that selectively inhibit at least one of CDK4 and CDK6 or through the inhibition of cellular replication of an Rb-positive cancer. In one embodiment, the compounds described herein have an $IC_{50}$ for CDK4 as measured in a CDK4/CycD1 $IC_{50}$ phosphorylation assay that is at least 1500 times or greater lower than the compound's $IC_{50}$s for CDK2 as measured in a CDK2/CycE $IC_{50}$ phosphorylation assay. In one embodiment, the CDK4/6 inhibitors are at least about 10 times or greater more potent (i.e., have an $IC_{50}$ in a CDK4/CycD1 phosphorylation assay that is at least 10 times or more lower) than PD0332991.

The use of a compound as described herein can induce selective G1 arrest in CDK4/6-dependent cells (e.g., as measured in a cell-based in vitro assay). In one embodiment, the CDK4/6 inhibitor is capable of increasing the percentage of CDK4/6-dependent cells in the G1 phase, while decreasing the percentage of CDK4/6-dependent cells in the G2/M phase and S phase. In one embodiment, the compound induces substantially pure (i.e., "clean") G1 cell cycle arrest in the CDK4/6-dependent cells, e.g., wherein treatment with the compound induces cell cycle arrest such that the majority of cells are arrested in G1 as defined by standard methods (e.g. propidium iodide (PI) staining or others) with the population of cells in the G2/M and S phases combined being less than about 30%, about 25%, about 20%, about 15%, about 10%, about 5%, about 3% or less of the total cell population. Methods of assessing the cell phase of a population of cells are known in the art (see, for example, in U.S. Patent Application Publication No. 2002/0224522) and include cytometric analysis, microscopic analysis, gradient centrifugation, elutriation, fluorescence techniques including immunofluorescence, and combinations thereof. Cytometric techniques include exposing the cell to a labeling agent or stain, such as DNA-binding dyes, e.g., PI, and analyzing cellular DNA content by flow cytometry. Immunofluorescence techniques include detection of specific cell cycle indicators such as, for example, thymidine analogs (e.g., 5-bromo-2-deoxyuridine (BrdU) or an iododeoxyuridine), with fluorescent antibodies.

In some embodiments, the use of a compound described herein result in reduced or substantially free of off-target effects, particularly related to inhibition of kinases other than CDK4 and or CDK6 such as CDK2, as the compounds described herein are poor inhibitors (e.g., >1 uM $IC_{50}$) of CDK2. Furthermore, because of the high selectivity for CDK4/6, the use of the compounds described herein should not induce cell cycle arrest in CDK4/6-independent cells. In addition, because of the short transient nature of the G1-arrest effect, the CDK4/6-replication dependent healthy cells more quickly reenter the cell-cycle than, comparatively, use of PD0332991 provides, resulting in the reduced risk of, in one embodiment, hematological deficiency during long term treatment regimens due to the ability of HSPCs to replicate between treatments.

In one aspect of the invention, a compound disclosed herein can be beneficially administered in combination with any therapeutic regimen entailing radiotherapy, chemotherapy, or other therapeutic agents. In additional embodiments the compounds disclosed herein can be beneficially administered in combination with therapeutic agents targeting auto-immune disorders.

Drug Conjugates

In one embodiment, the activity of an active compound for a purpose described herein can be augmented through conjugation to an agent that targets the diseased or abnormally proliferating cell or otherwise enhances activity, delivery, pharmacokinetics or other beneficial property.

For example, the compound can be administered as an antibody-drug conjugates (ADC). In certain embodiments, a selected compound described herein can be administered in conjugation or combination with an antibody or antibody fragment. Fragments of an antibody can be produced through chemical or genetic mechanisms. The antibody fragment can be an antigen binding fragment. For example, the antigen binding fragment can be selected from an Fab, Fab', (Fab')2, or Fv. The antibody fragment can be a Fab. Monovalent F(ab) fragments have one antigen binding site. The antibody can be a divalent (Fab')2 fragment, which has two antigen binding regions that are linked by disulfide bonds. In one embodiment, the antigen fragment is a (Fab'). Reduction of F(ab')2 fragments produces two monovalent Fab' fragments, which have a free sulfhydryl group that is useful for conjugation to other molecules.

A selected compound described herein can be administered in conjugation or combination with a Fv fragment. Fv fragments are the smallest fragment made from enzymatic cleavage of IgG and IgM class antibodies. Fv fragments have the antigen-binding site made of the VH and VC regions, but they lack the CH1 and CL regions. The VH and VL chains are held together in Fv fragments by non-covalent interactions.

In one embodiment, a selected compound as described herein can be administered in combination with an antibody fragment selected from the group consisting of an ScFv, domain antibody, diabody, triabody, tetrabody, Bis-scFv, minibody, Fab2, or Fab3 antibody fragment. In one embodiment, the antibody fragment is a ScFv. Genetic engineering methods allow the production of single chain variable fragments (ScFv), which are Fv type fragments that include the VH and VL domains linked with a flexible peptide When the linker is at least 12 residues long, the ScFv fragments are primarily monomeric. Manipulation of the orientation of the V-domains and the linker length creates different forms of Fv molecules Linkers that are 3-11 residues long yield scFv molecules that are unable to fold into a functional Fv domain. These molecules can associate with a second scFv molecule, to create a bivalent diabody. In one embodiment, the antibody fragment administered in combination with a selected compound described herein is a bivalent diabody. If the linker length is less than three residues, scFv molecules associate into triabodies or tetrabodies. In one embodiment, the antibody fragment is a triabody. In one embodiment, the antibody fragment is a tetrabody. Multivalent scFvs possess greater functional binding affinity to their target antigens than their monovalent counterparts by having binding to two more target antigens, which reduces the off-rate of the antibody fragment. In one embodiment, the antibody fragment is a minibody. Minibodies are scFv-CH3 fusion proteins that assemble into bivalent dimers. In one embodiment, the antibody fragment is a Bis-scFv fragment. Bis-scFv fragments are bispecific. Miniaturized ScFv fragments can be generated that have two different variable domains, allowing these Bis-scFv molecules to concurrently bind to two different epitopes.

In one embodiment, a selected compound described herein is administered in conjugation or combination with a bispecific dimer (Fab2) or trispecific dimer (Fab3). Genetic methods are also used to create bispecific Fab dimers (Fab2) and trispecific Fab trimers (Fab3). These antibody fragments are able to bind 2 (Fab2) or 3 (Fab3) different antigens at once.

In one embodiment, a selected compound described herein is administered in conjugation or combination with an rIgG antibody fragment. rIgG antibody fragments refers to reduced IgG (75,000 daltons) or half-IgG. It is the product of selectively reducing just the hinge-region disulfide bonds. Although several disulfide bonds occur in IgG, those in the hinge-region are most accessible and easiest to reduce, especially with mild reducing agents like 2-mercaptoethylamine (2-MEA). Half-IgG are frequently prepared for the purpose of targeting the exposing hinge-region sulfhydryl groups that can be targeted for conjugation, either antibody immobilization or enzyme labeling.

In other embodiments, a selected active compound described herein can be linked to a radioisotope to increase efficacy, using methods well known in the art. Any radioisotope that is useful against Rb-positive cancer cells can be incorporated into the conjugate, for example, but not limited to, $^{131}I$, $^{123}I$, $^{192}Ir$, $^{32}P$, $^{90}Sr$, $^{198}Au$, $^{226}Ra$, $^{90}Y$, $^{241}Am$, $^{252}Cf$, $^{60}Co$, or $^{137}Cs$.

Of note, the linker chemistry can be important to efficacy and tolerability of the drug conjugates. The thio-ether linked T-DM1 increases the serum stability relative to a disulfide linker version and appears to undergo endosomal degradation, resulting in intra-cellular release of the cytotoxic agent, thereby improving efficacy and tolerability, See, Barginear, M. F. and Budman, D. R., Trastuzumab-DM1: A review of the novel immune-conjugate for HER2-overexpressing breast cancer, The Open Breast Cancer Journal, 1:25-30, 2009.

Examples of early and recent antibody-drug conjugates, discussing drugs, linker chemistries and classes of targets for product development that may be used in the present invention can be found in the reviews by Casi, G. and Neri, D., Antibody-drug conjugates: basic concepts, examples and future perspectives, J. Control Release 161(2):422-428, 2012, Chari, R. V., Targeted cancer therapy: conferring specificity to cytotoxic drugs, Acc. Chem. Rev., 41(1):98-107, 2008, Sapra, P. and Shor, B., Monoclonal antibody-based therapies in cancer: advances and challenges, Pharmacol. Ther., 138(3):452-69, 2013, Schliemann, C. and Neri, D., Antibody-based targeting of the tumor vasculature, Biochim. Biophys. Acta., 1776(2):175-92, 2007, Sun, Y., Yu, F., and Sun, B. W., Antibody-drug conjugates as targeted cancer therapeutics, Yao Xue Xue Bao, 44(9):943-52, 2009, Teicher, B. A., and Chari, R. V., Antibody conjugate therapeutics: challenges and potential, Clin. Cancer Res., 17(20): 6389-97, 2011, Firer, M. A., and Gellerman, G. J., Targeted drug delivery for cancer therapy: the other side of antibodies, J. Hematol. Oncol., 5:70, 2012, Vlachakis, D. and Kossida, S., Antibody Drug Conjugate bioinformatics: drug delivery through the letterbox, Comput. Math. Methods Med., 2013; 2013:282398, Epub 2013 Jun. 19, Lambert, J. M., Drug-conjugated antibodies for the treatment of cancer, Br. J. Clin. Pharmacol., 76(2):248-62, 2013, Concalves, A., Tredan, O., Villanueva, C. and Dumontet, C., Antibody-drug conjugates in oncology: from the concept to trastuzumab emtansine (T-DM1), Bull. Cancer, 99(12):1183-1191, 2012, Newland, A. M., Brentuximab vedotin: a CD-30-directed antibody-cytotoxic drug conjugate, Pharmacotherapy, 33(1): 93-104, 2013, Lopus, M., Antibody-DM1 conjugates as cancer therapeutics, Cancer Lett., 307(2):113-118, 2011, Chu, Y. W. and Poison, A., Antibody-drug conjugates for the treatment of B-cell non-Hodgkin's lymphoma and leukemia, Future Oncol., 9(3):355-368, 2013, Bertholjotti, I., Antibody-drug conjugate—a new age for personalized cancer treatment, Chimia, 65(9): 746-748, 2011, Vincent, K. J., and Zurini, M., Current strategies in antibody engineering: Fc engineering and pH—dependent antigen binding, bispecific antibodies and antibody drug conjugates, Biotechnol. J., 7(12):1444-1450, 2012, Haeuw, J. F., Caussanel, V., and Beck, A., Immunoconjugates, drug-armed antibodies to fight against cancer, Med. Sci., 25(12):1046-1052, 2009 and Govindan, S. V., and Goldenberg, D. M., Designing immunoconjugates for cancer therapy, Expert Opin. Biol. Ther., 12(7):873-890, 2012.

Pharmaceutical Compositions and Dosage Forms

An active compound described herein, or its salt, isotopic analog, or prodrug can be administered in an effective amount to the host using any suitable approach which achieves the desired therapeutic result. The amount and timing of active compound administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases. Pharmaceutical formulations can be prepared for any desired route of administration including, but not limited to, oral, intravenous, or aerosol administration, as discussed in greater detail below.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In some embodiments, the dosage can be the amount of compound needed to provide a serum concentration of the active compound of up to between about 1 and 5, 10, 20, 30, or 40 µM. In some embodiments, a dosage from about 10 mg/kg to about 50 mg/kg can be employed for oral administration. Typically, a dosage from about 0.5 mg/kg to 5 mg/kg can be employed for intramuscular injection. In some embodiments, dosages can be from about 1 µmol/kg to about 50 µmol/kg, or, optionally, between about 22 µmol/kg and about 33 µmol/kg of the compound for intravenous or oral administration. An oral dosage form can include any appropriate amount of active material, including for example from 5 mg to, 50, 100, 200, or 500 mg per tablet or other solid dosage form.

In accordance with the presently disclosed methods, pharmaceutically active compounds as described herein can be administered orally as a solid or as a liquid, or can be administered intramuscularly, intravenously, or by inhalation as a solution, suspension, or emulsion. In some embodiments, the compounds or salts also can be administered by inhalation, intravenously, or intramuscularly as a liposomal suspension. When administered through inhalation the active compound or salt can be in the form of a plurality of solid particles or droplets having any desired particle size, and for example, from about 0.01, 0.1 or 0.5 to about 5, 10, 20 or more microns, and optionally from about 1 to about 2 microns. Compounds as disclosed in the present invention have demonstrated good pharmacokinetic and pharmacodynamics properties, for instance when administered by the oral or intravenous routes.

The pharmaceutical formulations can comprise an active compound described herein or a pharmaceutically acceptable salt thereof, in any pharmaceutically acceptable carrier. If a solution is desired, water may be the carrier of choice for water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration a pharmaceutical composition can take the form of solutions, suspensions, tablets, pills, capsules, powders, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed host matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the host matter described herein, there are provided injectable, stable, sterile formulations comprising an active compound as described herein, or a salt thereof, in a unit dosage form in a sealed container. The compound or salt is provided in the form of a lyophilizate, which is capable of being reconstituted with a suitable pharmaceutically acceptable carrier to form liquid formulation suitable for injection thereof into a host. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which suitable for administration as an aerosol by inhalation. These formulations comprise a solution or suspension of a desired compound described herein or a salt thereof, or a plurality of solid particles of the compound or salt. The desired formulations can be placed in a small chamber and nebulized. Nebulization can be accomplished by compressed air or by ultrasonic energy to form a plurality of liquid droplets or solid particles comprising the compounds or salts. The liquid droplets or solid particles may for example have a particle size in the range of about 0.5 to about 10 microns, and optionally from about 0.5 to about 5 microns. In one embodiment, the solid particles provide for controlled release through the use of a degradable polymer. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

Pharmaceutical formulations also are provided which provide a controlled release of a compound described herein, including through the use of a degradable polymer, as known in the art.

When the pharmaceutical formulations suitable for administration as an aerosol is in the form of a liquid, the formulations can comprise a water-soluble active compound in a carrier that comprises water. A surfactant can be present, which lowers the surface tension of the formulations sufficiently to result in the formation of droplets within the desired size range when hosted to nebulization.

The term "pharmaceutically acceptable salts" as used herein refers to those salts which are, within the scope of sound medical judgment, suitable for use in contact with hosts (e.g., human hosts) without undue toxicity, irritation, allergic response, and the like, commensurate with a reasonable benefit/risk ratio, and effective for their intended use, as well as the zwitterionic forms, where possible, of the compounds of the presently disclosed host matter.

Thus, the term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Preparation of Active Compounds

Syntheses

The disclosed compounds can be made by the following general schemes:

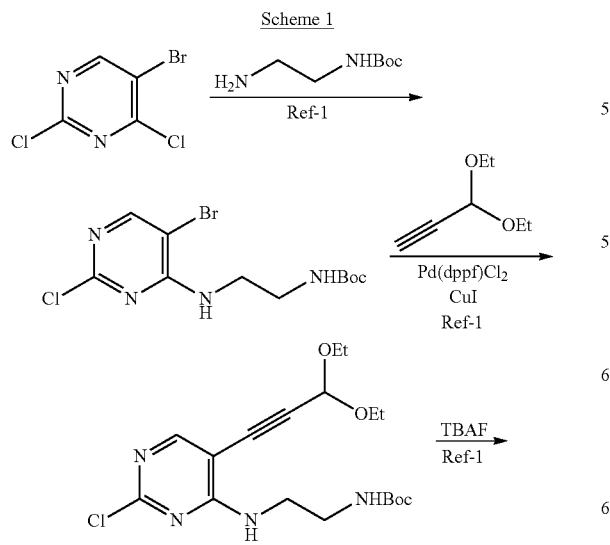

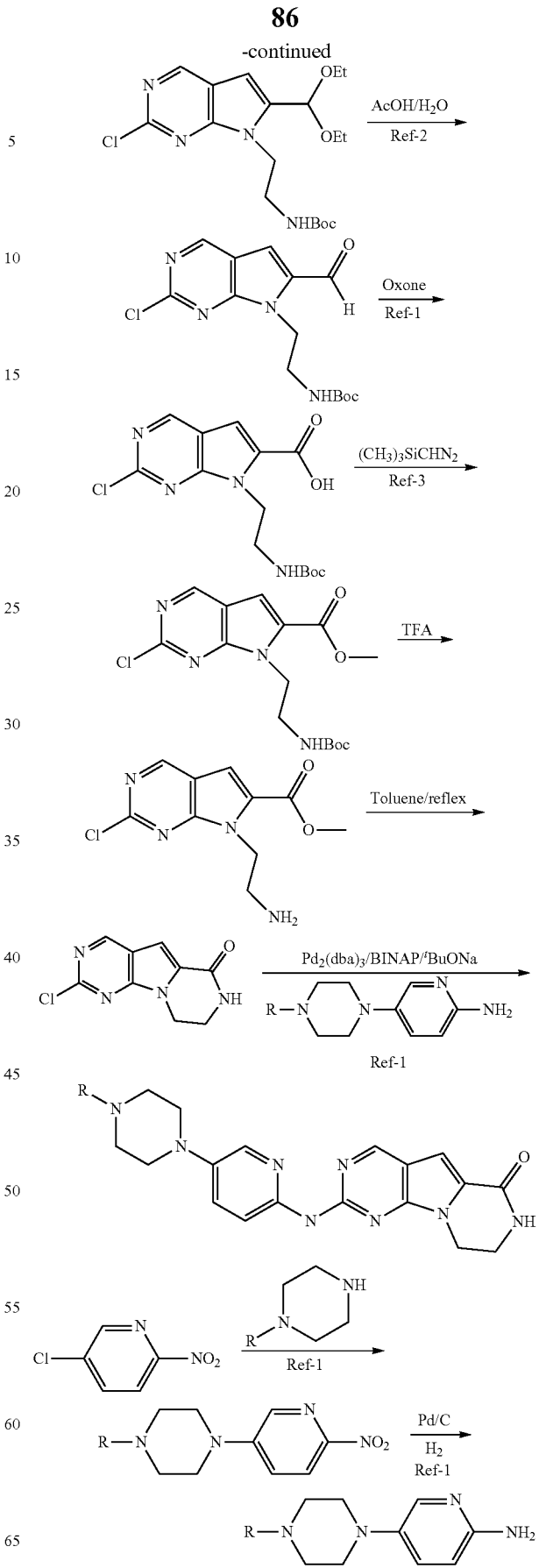

87
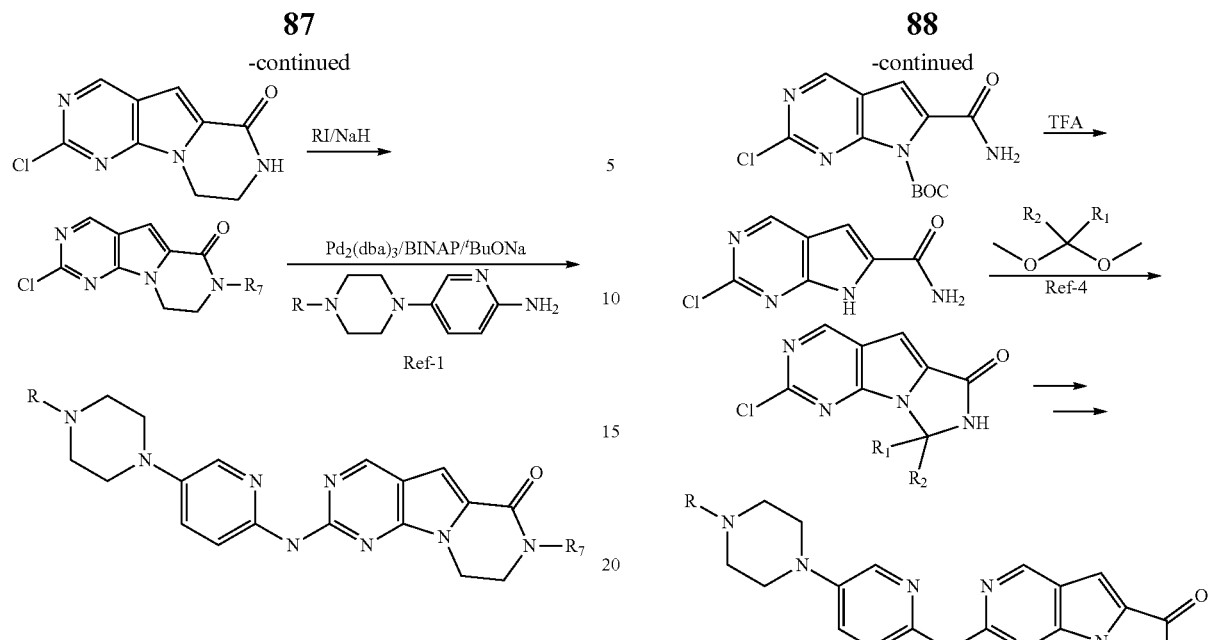
In Scheme 1, Ref-1 is WO 2010/020675 A1; Ref-2 is White, J. D.; et al. *J. Org. Chem.* 1995, 60, 3600; and Ref-3 Presser, A. and Hufner, A. *Monatshefte für Chemie* 2004, 135, 1015.
88
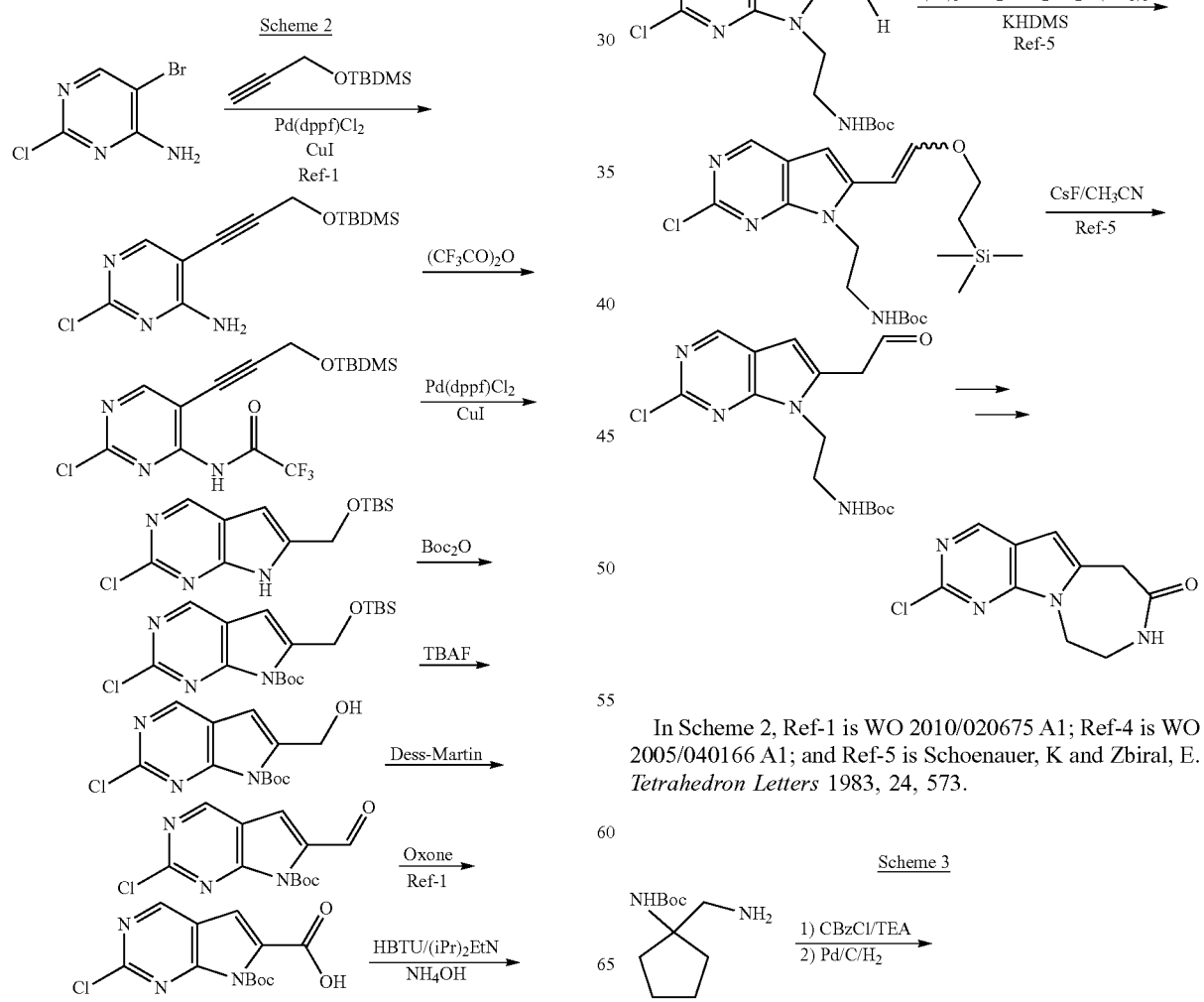
In Scheme 2, Ref-1 is WO 2010/020675 A1; Ref-4 is WO 2005/040166 A1; and Ref-5 is Schoenauer, K and Zbiral, E. *Tetrahedron Letters* 1983, 24, 573.

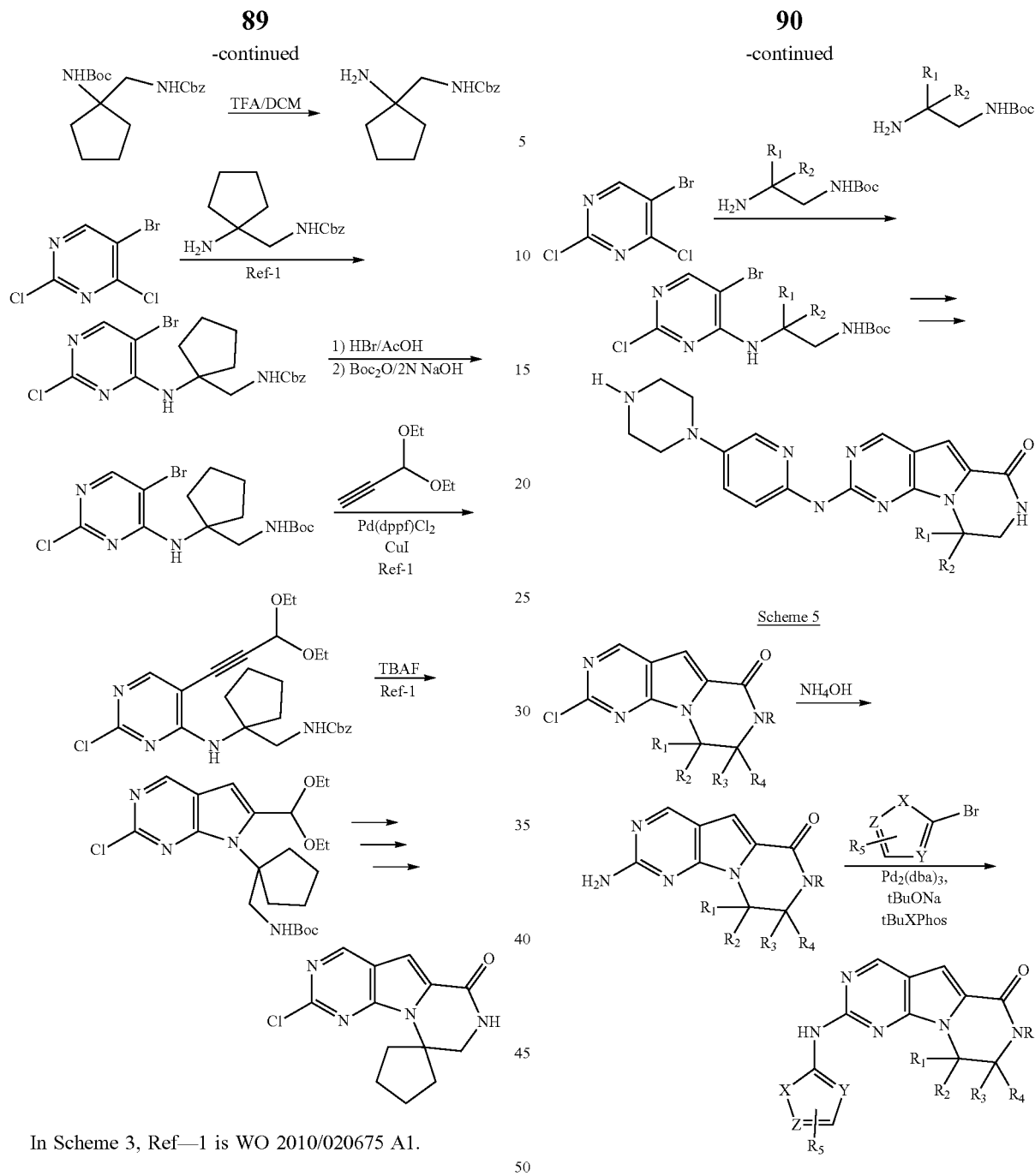
In Scheme 3, Ref—1 is WO 2010/020675 A1.
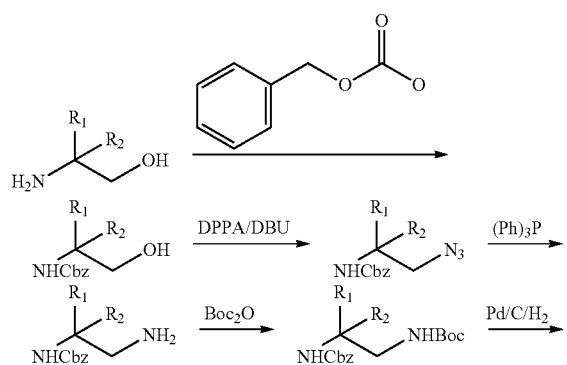
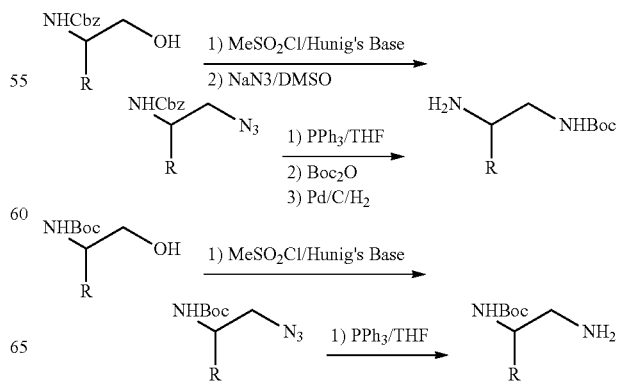

Scheme 7
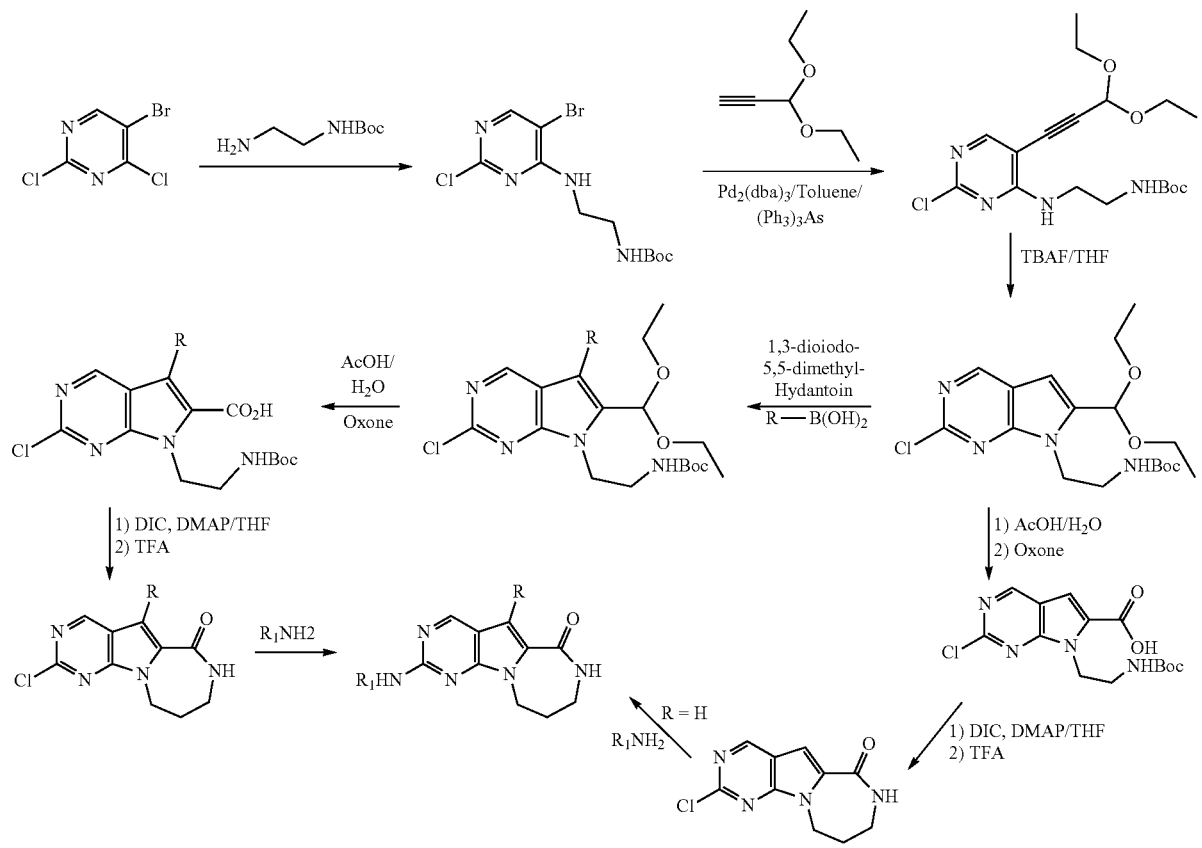
Scheme 8
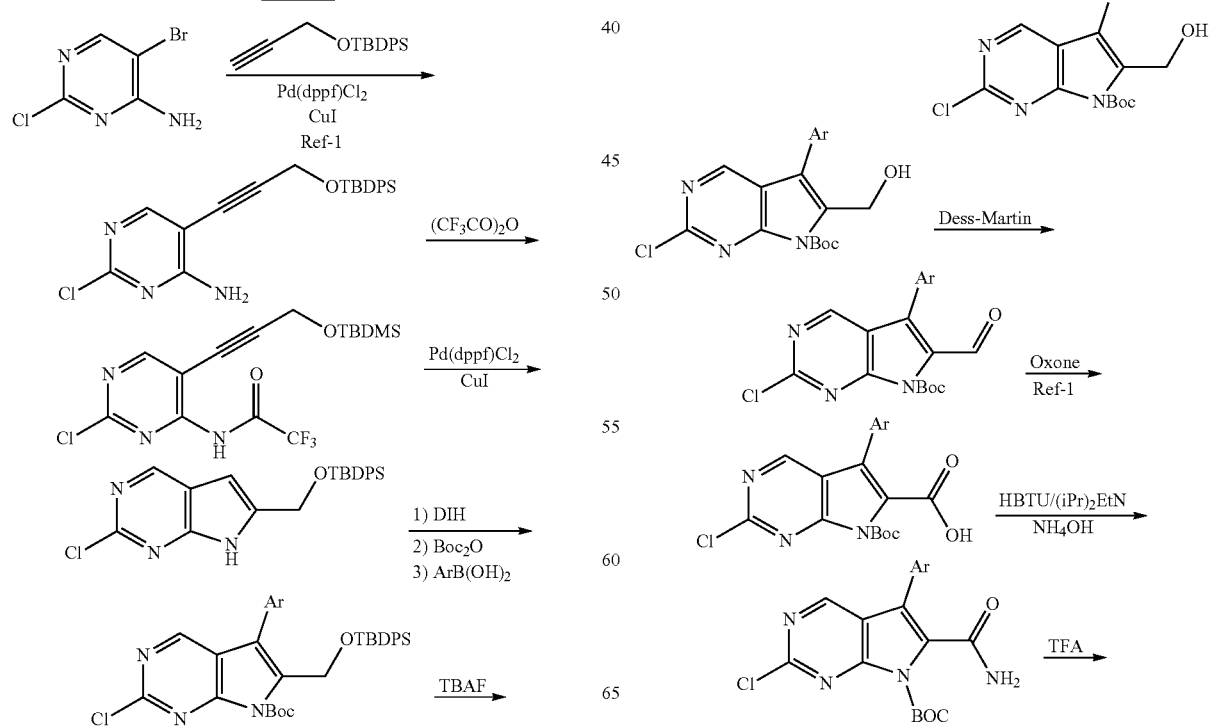

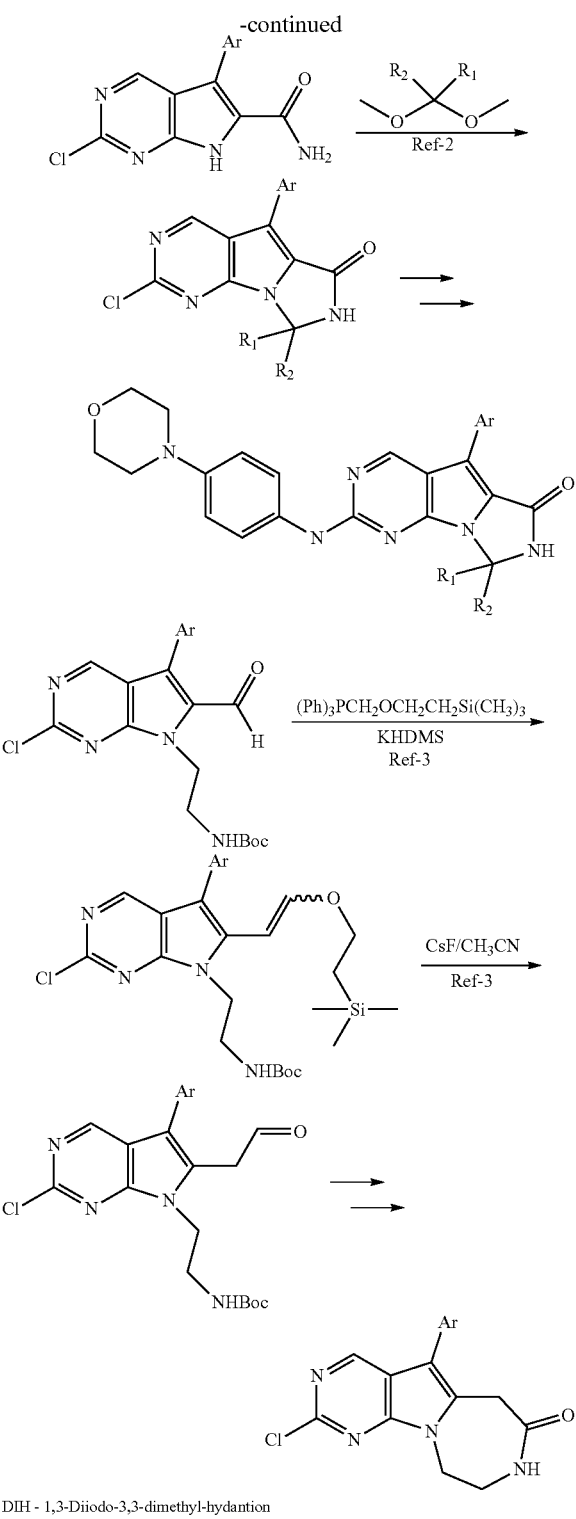

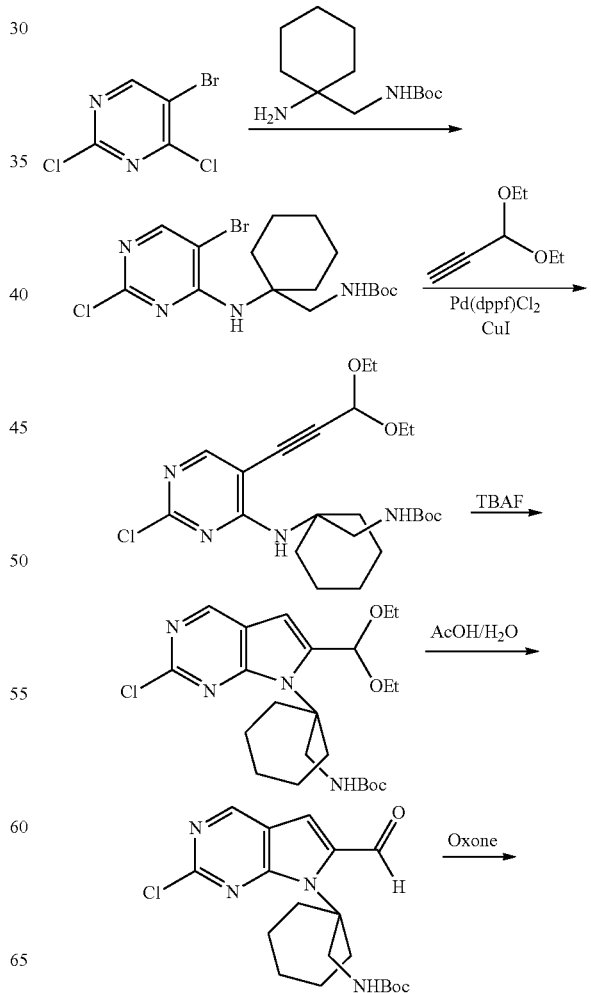

Scheme 9 acetic acid anhydride, tribromoacetic acid anhydride, trichloroacetic acid anhydride, or mixed anhydrides. The dehydrating agent can be a carbodiimide based compound such as but not limited to DCC (N,N-dicyclohexylcarbodiimide), EDC (1-ethyl-3-(3-dimethylaminopropyl)carbodiimide or DIC (N,N-diisopropylcarbodiimide). An additional step may be necessary to take off the N-protecting group and the methodologies are known to those skilled in the art.

Alternatively, the halogen moiety bonded to the pyrimidine ring can be substituted with any leaving group that can be displaced by a primary amine, for example to create an intermediate for a final product such as Br, I, F, SMe, $SO_2Me$, SOalkyl, $SO_2$ alkyl. See, for Example PCT/US2013/037878 to Tavares.

Other amine intermediates and final amine compounds can be synthesized by those skilled in the art. It will be appreciated that the chemistry can employ reagents that comprise reactive functionalities that can be protected and de-protected and will be known to those skilled in the art at the time of the invention. See for example, Greene, T. W. and Wuts, P. G. M., Greene's Protective Groups in Organic Synthesis, $4^{th}$ edition, John Wiley and Sons.

DIH - 1,3-Diiodo-3,3-dimethyl-hydantion

In Scheme 8, Ref-1 is WO 2010/020675 A1; Ref-2 is WO 2005/040166 A1; and Ref-3 is Schoenauer, K and Zbiral, E. *Tetrahedron Letters* 1983, 24, 573.

Alternatively, the lactam can be generated by reacting the carboxylic acid with a protected amine in the presence of a strong acid and a dehydrating agent, which can be together in one moiety as a strong acid anhydride. Examples of strong acid anhydrides include, but are not limited to, trifluoro-

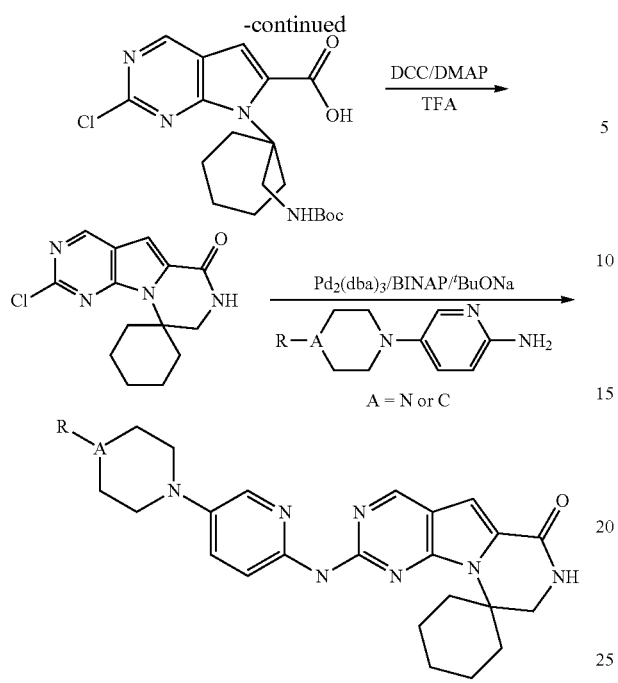

CDK4/6 Inhibitors of the present invention can be synthesized according to the generalized Scheme 9. Specific synthesis and characterization of the Substituted 2-amino-pyrimidines can be found in, for instance, WO2012/061156.

Compounds T, Q, GG, and U were prepared as above and were characterized by mass spectrometry and NMR as shown below:

Compound T
$^1$H NMR (600 MHz, DMSO-$d_6$) δ ppm 1.47 (br. s., 6H) 1.72 (br. s., 2H) 1.92 (br. s., 2H) 2.77 (br. s., 3H) 3.18 (br. s., 2H) 3.46 (br. s., 2H) 3.63 (br. s., 2H) 3.66 (d, J=6.15 Hz, 2H) 3.80 (br. s., 2H) 7.25 (s, 1H) 7.63 (br. s., 2H) 7.94 (br. s., 1H) 8.10 (br. s., 1H) 8.39 (br. s., 1H) 9.08 (br. s., 1H) 11.59 (br. s., 1H). LCMS ESI (M+H) 447.

Compound Q
$^1$H NMR (600 MHz, DMSO-$d_6$) δ ppm 0.82 (d, J=7.32 Hz, 2H) 1.08-1.37 (m, 3H) 1.38-1.64 (m, 2H) 1.71 (br. s., 1H) 1.91 (br. s., 1H) 2.80 (br. s., 1H) 3.12 (s, 1H) 3.41 (br. s., 4H) 3.65 (br. s., 4H) 4.09 (br. s., 1H) 7.26 (s, 1H) 7.52-7.74 (m, 2H) 7.94 (br. s., 1H) 8.13 (br. s., 1H) 8.40 (br. s., 1H) 9.09 (br. s., 1H) 9.62 (br. s., 1H) 11.71 (br. s., 1H). LCMS ESI (M+H) 433.

Compound GG
$^1$H NMR (600 MHz, DMSO-$d_6$) δ ppm 0.85 (br. s., 1H) 1.17-1.39 (m, 7H) 1.42-1.58 (m, 2H) 1.67-1.84 (m, 3H) 1.88-2.02 (m, 1H) 2.76-2.93 (m, 1H) 3.07-3.22 (m, 1H) 3.29-3.39 (m, 1H) 3.41-3.61 (m, 4H) 3.62-3.76 (m, 4H) 3.78-3.88 (m, 1H) 4.12 (br. s., 1H) 7.28 (s, 1H) 7.60-7.76 (m, 2H) 7.98 (s, 1H) 8.13 (br. s., 1H) 8.41 (s, 1H) 9.10 (br. s., 1H) 11.21 (br. s., 1H) 11.54 (s, 1H). LCMS ESI (M+H) 475.

Compound U
$^1$H NMR (600 MHz, DMSO-$d_6$) δ ppm 0.84 (t, J=7.61 Hz, 2H) 1.13-1.39 (m, 4H) 1.46 (d, J=14.05 Hz, 2H) 1.64-1.99 (m, 6H) 2.21 (br. s., 1H) 2.66-2.89 (m, 2H) 3.06 (br. s., 1H) 3.24-3.36 (m, 1H) 3.37-3.50 (m, 3H) 3.56-3.72 (m, 2H) 3.77-4.00 (m, 4H) 4.02-4.19 (m, 4H) 7.25 (s, 1H) 7.50-7.75 (m, 2H) 7.89 (d, J=2.93 Hz, 1H) 8.14 (d, J=7.32 Hz, 1H) 8.38 (br. s., 1 H) 9.06 (s, 1H) 11.53 (br. s., 1H). LCMS ESI (M+H) 517.

EXAMPLES

Intermediates B, E, K, L, 1A, 1F and 1CA were synthesized according to U.S. Pat. No. 8,598,186 entitled CDK Inhibitors to Tavares, F. X. and Strum, J. C.

The patents WO 2013/148748 entitled Lactam Kinase Inhibitors to Tavares, F. X., WO 2013/163239 entitled Synthesis of Lactams to Tavares, F. X., and U.S. Pat. No. 8,598,186 entitled CDK Inhibitors to Tavares, F. X. and Strum, J. C. are incorporated by reference herein in their entirety.

Example 1

Synthesis of tert-butyl N-[2-[(5-bromo-2-chloro-pyrimidin-4-yl)amino]ethyl]carbamate, Compound 1

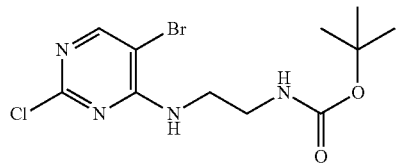 [SMILES: CC(C)(C)OC(=O)NCCNc1nc(Cl)ncc1Br]

To a solution of 5-bromo-2,4-dichloropyrimidine (3.2 g, 0.0135 mol) in ethanol (80 mL) was added Hunig's base (3.0 mL) followed by the addition of a solution of N-(tert-butoxycarbonyl)-1,2-diaminoethane (2.5 g, 0.0156 mole) in ethanol (20 mL). The contents were stirred overnight for 20 hrs. The solvent was evaporated under vacuum. Ethyl acetate (200 mL) and water (100 mL) were added and the layers separated. The organic layer was dried with magnesium sulfate and then concentrated under vacuum. Column chromatography on silica gel using hexane/ethyl acetate (0-60%) afforded tert-butyl N-[2-[(5-bromo-2-chloro-pyrimidin-4-yl)amino]ethyl]carbamate. $^1$HNMR ($d_6$-DMSO) δ ppm 8.21 (s, 1H), 7.62 (brs, 1H), 7.27 (brs, 1H), 3.39 (m, 2H), 3.12 (m, 2H), 1.34 (s, 9H). LCMS (ESI) 351 (M+H).

Example 2

Synthesis of tert-butyl N-[2-[[2-chloro-5-(3,3-diethoxyprop-1-ynyl)pyrimidin-4-yl]amino]ethyl]carbamate, Compound 2

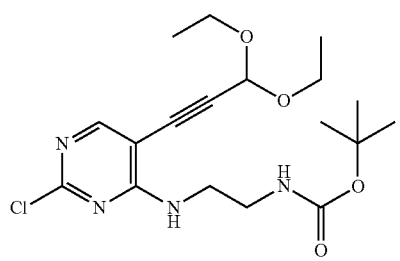 [SMILES: CCOC(C#Cc1cnc(Cl)nc1NCCNC(=O)OC(C)(C)C)OCC]

To tert-butyl N-[2-[(5-bromo-2-chloro-pyrimidin-4-yl) amino]ethyl]carbamate (1.265 g, 3.6 mmol) in THF (10 mL) was added the acetal (0.778 mL, 5.43 mmol), Pd(dppf) $CH_2Cl_2$ (148 mg), and triethylamine (0.757 mL, 5.43 mmol). The contents were degassed and then purged with nitrogen. To this was then added CuI (29 mg). The reaction mixture was heated at reflux for 48 hrs. After cooling, the contents were filtered over CELITE™ and concentrated. Column chromatography of the resulting residue using hexane/ethyl acetate (0-30%) afforded tert-butyl N-[2-[[2-chloro-5-(3,3-diethoxyprop-1-ynyl)pyrimidin-4-yl]amino]ethyl]carbamate. ¹HNMR (d6-DMSO) δ ppm 8.18 (s, 1H), 7.63 (brs, 1H), 7.40 (brs, 1H), 5.55 (s, 1H), 3.70 (m, 2H), 3.60 (m, 2H), 3.42 (m, 2H), 3.15 (m, 2H), 1.19-1.16 (m, 15H). LCMS (ESI) 399 (M+H).

Example 3

Synthesis of tert-butyl N-[2-[2-chloro-6-(diethoxymethyl)pyrrolo[2,3-d]pyrimidin-7-yl]ethyl]carbamate, Compound 3

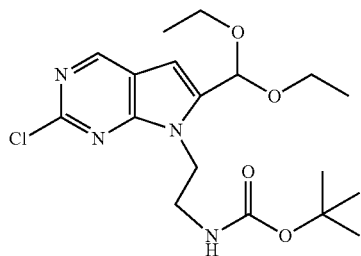 [SMILES: CCOC(OCC)c1cc2cnc(Cl)nc2n1CCNC(=O)OC(C)(C)C]

To a solution of the coupled product (2.1 g, 0.00526 mole) in THF (30 mL) was added TBAF solid (7.0 g). The contents were heated to and maintained at 65 degrees for 2 hrs. Concentration followed by column chromatography using ethyl acetate/hexane (0-50%) afforded tert-butyl N-[2-[2-chloro-6-(diethoxymethyl)pyrrolo[2,3-d]pyrimidin-7-yl]ethyl]carbamate as a pale brown liquid (1.1 g). ¹HNMR (d6-DMSO) δ ppm 8.88 (s, 1H), 6.95 (brs, 1H), 6.69 (s, 1H), 5.79 (s, 1H), 4.29 (m, 2H), 3.59 (m, 4H), 3.34 (m, 1H), 3.18 (m, 1H), 1.19 (m, 9H), 1.17 (m, 6H). LCMS (ESI) 399 (M+H).

Example 4

Synthesis of tert-butyl N-[2-(2-chloro-6-formyl-pyrrolo[2,3-d]pyrimidin-7-yl)ethyl]carbamate, Compound 4

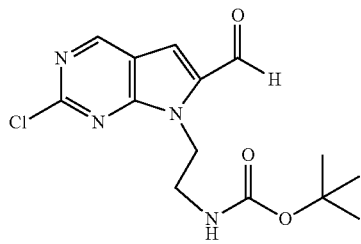 [SMILES: CC(C)(C)OC(=O)NCCn1c(C=O)cc2cnc(Cl)nc21]

To the acetal (900 mg) from the preceeding step was added AcOH (8.0 mL) and water (1.0 mL). The reaction was stirred at room temperature for 16 hrs. Conc. and column chromatography over silica gel using ethyl acetate/hexanes (0-60%) afforded tert-butyl N-[2-(2-chloro-6-formyl-pyrrolo[2,3-d]pyrimidin-7-yl)ethyl]carbamate as a foam (0.510 g). ¹HNMR (d6-DMSO) δ ppm 9.98 (s, 1H), 9.18 (s, 1H), 7.66 (s, 1H), 6.80 (brs, 1H), 4.52 (m, 2H), 4.36 (m, 2H), 1.14 (s, 9H). LCMS (ESI) 325 (M+H).

Example 5

Synthesis of 7-[2-(tert-butoxycarbonylamino)ethyl]-2-chloro-pyrrolo[2,3-d]pyrimidine-6-carboxylic acid, Compound 5

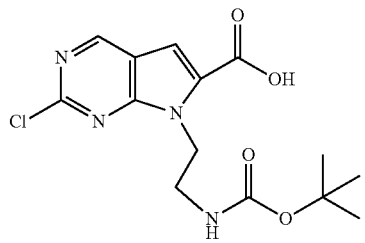 [SMILES: CC(C)(C)OC(=O)NCCn1c(C(=O)O)cc2cnc(Cl)nc21]

To the aldehyde (0.940 g) from the preceeding step in DMF (4 mL) was added oxone (1.95 g, 1.1 eq). The contents were stirred at room temp for 7 hrs. Silica gel column chromatography using hexane/ethyl acetate (0-100%) afforded 7-[2-(tert-butoxycarbonylamino)ethyl]-2-chloro-pyrrolo[2,3-d]pyrimidine-6-carboxylic acid (0.545 g). ¹HNMR (d6-DMSO) δ ppm 9.11 (s, 1H), 7.39 (s, 1H), 4.38 (m, 2H), 4.15 (m, 2H), 1.48 (m, 9H). LCMS (ESI) 341 (M+H).

Example 6

Synthesis of methyl 7-[2-(tert-butoxycarbonylamino)ethyl]-2-chloro-pyrrolo[2,3-d]pyrimidine-6-carboxylate, Compound 6

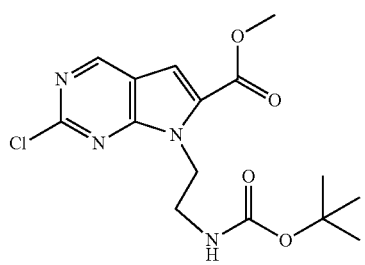 [SMILES: COC(=O)c1cc2cnc(Cl)nc2n1CCNC(=O)OC(C)(C)C]

To a solution of 2-chloro-7-propyl-pyrrolo[2,3-d]pyrimidine-6-carboxylic acid (0.545 g, 0.00156 mole) from the preceeding step in toluene (3.5 mL) and MeOH (1 mL) was added TMS-diazomethane (1.2 mL). After stirring overnight at room temperature, the excess of TMS-diazomethane was quenched with acetic acid (3 mL) and the reaction was concentrated under vacuum. The residue was purified by silica gel column chromatography with hexane/ethyl acetate (0-70%) to afford methyl 7-[2-(tert-butoxycarbonylamino)ethyl]-2-chloro-pyrrolo[2,3-d]pyrimidine-6-carboxylate as an off white solid (0.52 g). ¹HNMR (d6-DMSO) δ ppm 9.10 (s, 1H), 7.45 (s, 1H), 6.81 (brs, 1H) 4.60 (m, 2H), 3.91 (s, 3H), 3.29 (m, 2H), 1.18 (m, 9H) LCMS (ESI) 355 (M+H).

Example 7

Synthesis of Chloro Tricyclic Amide, Compound 7

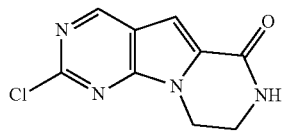 [SMILES: O=C1NCCn2c1cc1cnc(Cl)nc12]

To methyl 7-[2-(tert-butoxycarbonylamino)ethyl]-2-chloro-pyrrolo[2,3-d]pyrimidine-6-carboxylate (0.50 g, 0.0014 mole) from the preceeding step in dichloromethane (2.0 mL) was added TFA (0.830 mL). The contents were stirred at room temperature for 1 hr. Concentration under vacuum afforded the crude amino ester which was suspended in toluene (5 mL) and Hunig's base (0.5 mL). The contents were heated at reflux for 2 hrs. Concentration followed by silica gel column chromatography using hexane/ethyl acetate (0-50%) afforded the desired chloro tricyclic amide (0.260 g). $^1$HNMR (d6-DMSO) δ ppm 9.08 (s, 1H), 8.48 (brs, 1H), 7.21 (s, 1H) 4.33 (m, 2H), 3.64 (m, 2H). LCMS (ESI) 223 (M+H).

Example 8

Synthesis of Chloro-N-Methyltricyclic Amide, Compound 8

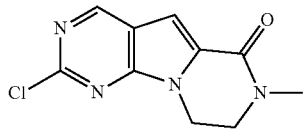

To a solution of the chloro tricycliclactam, Compound 7, (185 mg, 0.00083 mole) in DMF (2.0 mL) was added sodium hydride (55% dispersion in oil, 52 mg). After stirring for 15 mins, methyl iodide (62 μL, 1.2 eq). The contents were stirred at room temperature for 30 mins. After the addition of methanol (5 mL), sat NaHCO$_3$ was added followed by the addition of ethyl acetate. Separation of the organic layer followed by drying with magnesium sulfate and concentration under vacuum afforded the N-methylated amide in quantitative yield. $^1$HNMR (d6-DMSO) δ ppm 9.05 (s, 1H), 7.17 (s, 1H) 4.38 (m, 2H), 3.80 (m, 2H), 3.05 (s, 3H). LCMS (ESI) 237 (M+H).

Example 9

Synthesis of 1-Methyl-4-(6-Nitro-3-Pyridyl)Piperazine, Compound 9

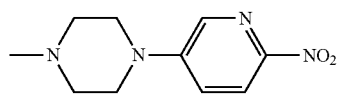

To 5-bromo-2-nitropyridine (4.93 g, 24.3 mmole) in DMF (20 mL) was added N-methylpiperazine (2.96 g, 1.1 eq) followed by the addition of DIPEA (4.65 mL, 26.7 mmole). The contents were heated at 90 degrees for 24 hrs. After addition of ethyl acetate (200 mL), water (100 mL) was added and the layers separated. Drying followed by concentration afforded the crude product which was purified by silica gel column chromatography using (0-10%) DCM/Methanol. $^1$HNMR (d6-DMSO) δ ppm 8.26 (s, 1H), 8.15 (1H, d, J=9.3 Hz), 7.49 (1H, d, J=9.4 Hz), 3.50 (m, 4H), 2.49 (m, 4H), 2.22 (s, 3H).

Example 10

Synthesis of 5-(4-methylpiperazin-1-yl)pyridin-2-amine, Compound 10

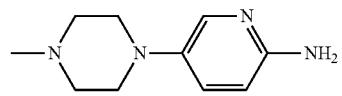

To 1-methyl-4-(6-nitro-3-pyridyl)piperazine (3.4 g) in ethyl acetate (100 mL) and ethanol (100 mL) was added 10% Pd/C (400 mg) and then the reaction was stirred under hydrogen (10 psi) overnight. After filtration through CELITE™, the solvents were evaporated and the crude product was purified by silica gel column chromatography using DCM/7N ammonia in MeOH (0-5%) to afford 5-(4-methylpiperazin-1-yl)pyridin-2-amine (2.2 g). $^1$HNMR (d6-DMSO) δ ppm 7.56 (1H, d, J=3 Hz), 7.13 (1H, m), 6.36 (1H, d, J=8.8 Hz), 5.33 (brs, 2H), 2.88 (m, 4H), 2.47 (m, 4H), 2.16 (s, 3H).

Example 11

Synthesis of tert-butyl 4-(6-amino-3-pyridyl)piperazine-1-carboxylate, Compound 11

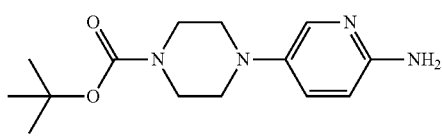

This compound was prepared as described in WO 2010/020675 A1.

Example 12

Synthesis of tert-butyl N-[2-(benzyloxycarbonylamino)-3-methyl-butyl] carbamate, Compound 12

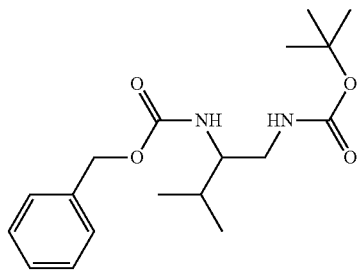 [SMILES: CC(C)C(CNC(=O)OC(C)(C)C)NC(=O)OCc1ccccc1]

To benzyl N-[1-(hydroxymethyl)-2-methyl-propyl]carbamate (11.0 g, 0.0464 mole) in dioxane (100 mL) cooled to 0° C. was added diphenylphosphoryl azide (10.99 mL, 1.1 eq) followed by the addition of DBU (8.32 mL, 1.2 eq). The contents were allowed to warm to room temperature and stirred for 16 hrs. After the addition of ethyl acetate (300 mL) and water (100 mL), the organic layer was separated and washed with satd. NaHCO$_3$ (100 mL). The organic layer was then dried (magnesium sulfate) and concentrated under vacuum. To this intermediate in DMSO (100 mL) was added sodium azide (7.54 g) and the contents then heated to 90 degrees for 2 hrs. After addition of ethyl acetate and water the layers were separated. The organic layer was dried with magnesium sulfate followed by concentration under vacuum to afford an oil that was purified by silica gel column chromatography using hexane/ethyl acetate (0-70%) to afford benzyl N-[1-(azidomethyl)-2-methyl-propyl] carbamate 6.9 g as a colorless oil.

To benzyl N-[1-(azidomethyl)-2-methyl-propyl] carbamate (6.9 g, 0.0263 mole) in THF (100 mL) was added triphenyl phosphine (7.59 g, 1.1 eq). The contents were stirred for 20 hrs. After addition of water (10 mL), and stirring for an additional 6 hrs, ethyl acetate was added and the layers separated. After drying with magnesium sulfate and concentration under vacuum, the crude product was purified by silica gel column chromatography using DCM/MeOH (0-10%) to afford benzyl N-[1-(aminomethyl)-2-methyl-propyl] carbamate as a yellow oil.

To benzyl N-[1-(aminomethyl)-2-methyl-propyl] carbamate (4.65 g, 0.019 mole) in THF (70 mL) was added 2N NaOH (20 mL) followed by the addition of di-tert-butyl dicarbonate (5.15 g, 1.2 eq). After stirring for 16 hrs, ethyl acetate was added and the layers separated. After drying with magnesium sulfate and concentration under vacuum, the crude product was purified using hexane/ethyl acetate (0-40%) over a silica gel column to afford intermediate A, tert-butyl N-[2-(benzyloxycarbonylamino)-3-methyl-butyl] carbamate, (6.1 g). $^1$HNMR (600 MHz, CHLOROFORM-d) δ ppm 0.89 (d, J=6.73 Hz, 3H) 0.92 (d, J=6.73 Hz, 3H) 1.38 (s, 9H) 1.70-1.81 (m, 1H) 3.18 (d, J=5.56 Hz, 2H) 3.47-3.60 (m, 1H) 4.76 (s, 1H) 4.89 (d, J=7.90 Hz, 1H) 5.07 (s, 2H) 7.25-7.36 (m, 5H). LCMS (ESI) 337 (M+H).

Example 13

Synthesis of tert-butyl N-[2-(benzyloxycarbonylamino)-4-methyl-pentyl] carbamate, Compound 13

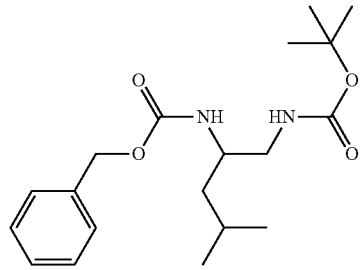 [SMILES: CC(C)CC(CNC(=O)OC(C)(C)C)NC(=O)OCc1ccccc1]

To a solution of benzyl N-[1-(hydroxymethyl)-3-methyl-butyl]carbamate (6.3 g, 0.025 mole) in DCM (100 mL) was added diisopropylethyl amine (5.25 mL, 1.2 eq) followed by the addition of methane sulfonylchloride (2.13 mL, 1.1 eq) at 0 degrees. After stirring for 3 hrs, water (100 mL) was added and the organic layer separated. After drying with magnesium sulfate and concentration under vacuum, the crude [2-(benzyloxycarbonylamino)-4-methyl-pentyl] methanesulfonate which was taken directly to the next step.

To the crude [2-(benzyloxycarbonylamino)-4-methyl-pentyl] methanesulfonate from the above reaction in DMF (50 mL), was added sodium azide 2.43 g. The reaction mixture was then heated to 85 degrees for 3 hrs. After cooling, ethyl acetate (300 mL) and water was added. The organic layer was separated, dried with magnesium sulfate and then concentrated under vacuum to afford the crude benzyl N-[1-(azidomethyl)-3-methyl-butyl] carbamate. To this crude intermediate was added THF (100 mL) followed by triphenylphosphine 7.21 g and stirred under nitrogen for 16 hrs. After addition of water (10 mL), and stirring for an additional 6 hrs, ethyl acetate was added and the layers separated. After drying with magnesium sulfate and concentration under vacuum, the crude product was columned using DCM/MeOH (0-10%) to afford benzyl N-[1-(aminomethyl)-3-methyl-butyl] carbamate (4.5 g).

To benzyl N-[1-(aminomethyl)-3-methyl-butyl] carbamate (4.5 g, 0.018 mole) in THF (60 mL) was added 2N NaOH (18 mL) followed by the addition of di-tert-butyl dicarbonate (4.19 g, 1.07 eq). After stirring for 16 hrs, ethyl acetate was added and the layers separated. After drying with magnesium sulfate and concentration under vacuum, the crude product was taken to the next step. $^1$HNMR (600 MHz, CHLOROFORM-d) δ ppm 0.89 (d, J=6.73 Hz, 6H) 1.25-1.34 (m, 1H) 1.39 (s, 9H) 1.57-1.71 (m, 2H) 3.04-3.26 (m, 2H) 3.68-3.80 (m, 1H) 4.72-4.89 (m, 2H) 5.06 (s, 2H) 7.25-7.38 (m, 5H). LCMS (ESI) 351 (M+H).

Example 14

Synthesis of tert-butyl N-[(2R)-2-(benzyloxycarbonylamino)-3-methyl-butyl] carbamate, Compound 14

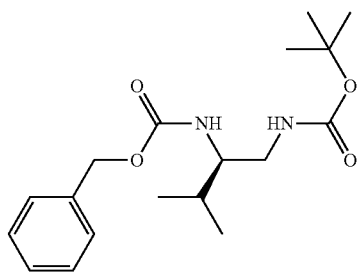 [SMILES: CC(C)[C@H](CNC(=O)OC(C)(C)C)NC(=O)OCc1ccccc1]

Compound 14 was synthesized from benzyl N-[(1R)-1-(hydroxymethyl)-2-methyl-propyl] carbamate using similar synthetic steps as that described for Compound 13. The analytical data (NMR and mass spec) was consistent with that for Compound 12.

Example 15

Synthesis of tert-butyl N-[(2S)-2-(benzyloxycarbonylamino)-3-methyl-butyl]carbamate, Compound 15

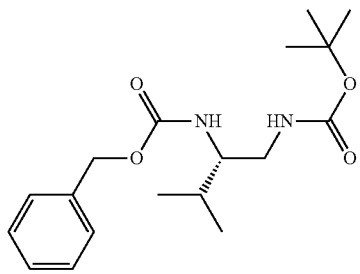 [SMILES: CC(C)[C@@H](CNC(=O)OC(C)(C)C)NC(=O)OCc1ccccc1]

Compound 15 was synthesized from benzyl N-[(1S)-1-(hydroxymethyl)-2-methyl-propyl] carbamate using similar synthetic steps as that described for Compound 13. The analytical data (NMR and mass spec) was consistent with that for Compound 12.

Example 16

Synthesis of tert-butyl N-[(1S)-1-(aminomethyl)-2-methyl-propyl]carbamate, Compound 16

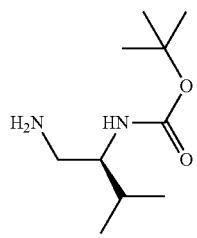

To a solution of tert-butyl N-[(1S)-1-(hydroxymethyl)-2-methyl-propyl]carbamate carbamate (6.3 g, 0.025 mole) in THF (100 mL) was added diisopropylethyl amine (5.25 mL, 1.2 eq) followed by the addition of methane sulfonylchloride (2.13 mL, 1.1 eq) at 0 degrees. After stirring for 3 hrs, water (100 mL) was added and the organic layer separated. After drying with magnesium sulfate and concentration under vacuum, the crude [(2S)-2-(tert-butoxycarbonylamino)-3-methyl-butyl] methanesulfonate was taken directly to the next step.

To the crude [(2S)-2-(tert-butoxycarbonylamino)-3-methyl-butyl] methanesulfonate from the above reaction in DMSO (50 mL), was added sodium azide (2.43 g). The reaction mixture was then heated to 85 degrees for 3 hrs. After cooling, ethyl acetate (300 mL) and water were added. The organic layer was separated, dried with magnesium sulfate and then concentrated under vacuum to afford the crude benzyl N-[1-(azidomethyl)-3-methyl-butyl] carbamate. To this crude intermediate was added THF (100 mL) followed by triphenylphosphine (7.21 g) and the reaction was stirred under nitrogen for 16 hrs. After addition of water (10 mL), and stirring for an additional 6 hrs, ethyl acetate was added and the layers separated. After drying with magnesium sulfate and concentration under vacuum, the crude product was purified by silica gel column chromatography using DCM/MeOH (0-10%) to afford benzyl N-[1-(aminomethyl)-3-methyl-butyl] carbamate (4.5 g). LCMS (ESI) 203 (M+H).

Example 17

Synthesis of tert-butyl N-[(1R)-1-(aminomethyl)-2-methyl-propyl]carbamate, Compound 17

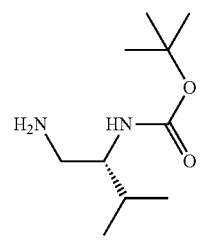

Compound 17 was synthesized from tert-butyl N-[(1R)-1-(hydroxymethyl)-2-methyl-propyl] carbamate using a similar synthetic sequence as described for Compound 16. The analytical data (NMR and mass spec) was consistent with Compound 16.

Example 18

Synthesis of tert-butyl N-[(2S)-2-(benzyloxycarbonylamino)-4-methyl-pentyl] carbamate, Compound 18

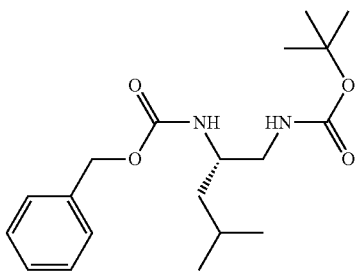 [SMILES: CC(C)C[C@@H](CNC(=O)OC(C)(C)C)NC(=O)OCc1ccccc1]

Compound 18 was synthesized from benzyl N-[(1S)-1-(hydroxymethyl)-3-methyl-butyl]carbamate using a similar synthetic sequence as described for Compound 13. The analytical data (NMR and mass spec) was consistent with Compound 13.

Example 19

Synthesis of tert-butyl N-[(2S)-2-(benzyloxycarbonylamino)-2-phenyl-ethyl] carbamate, Compound 19

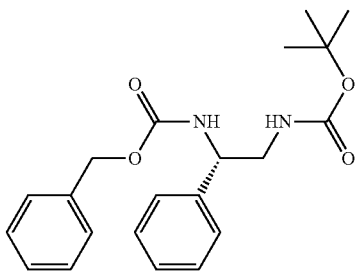 [SMILES: CC(C)(C)OC(=O)NC[C@@H](NC(=O)OCc1ccccc1)c1ccccc1]

Compound 19 was synthesized from benzyl N-[(1S)-2-hydroxy-1-phenyl-ethyl] carbamate using a similar synthetic sequence as described for Compound 13. ¹HNMR (600 MHz, DMSO-d₆) δ ppm 1.20-1.33 (m, 9H) 3.11 (t, J=6.29 Hz, 2H) 4.59-4.68 (m, 1H) 4.88-5.01 (m, 2H) 6.81 (t, J=5.42 Hz, 1H) 7.14-7.35 (m, 10H) 7.69 (d, J=8.49 Hz, 1H). LCMS (ESI) 371 (M+H).

Example 20

Synthesis of tert-butyl N-[(2S)-2-(benzyloxycarbonylamino)-3-methyl-pentyl] carbamate, Compound 20

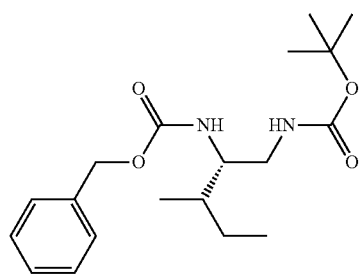 [SMILES: CCC(C)[C@@H](CNC(=O)OC(C)(C)C)NC(=O)OCc1ccccc1]

Compound 20 was synthesized from benzyl N-[(1S)-1-(hydroxymethyl)-2-methyl-butyl] carbamate using a similar synthetic sequence as described for Compound 13. ¹HNMR (600 MHz, CHLOROFORM-d) δ ppm 0.85-0.92 (m, 6H) 1.05-1.15 (m, 1H) 1.35-1.41 (m, 9H) 1.45-1.56 (m, 2H) 3.14-3.24 (m, 2H) 3.54-3.64 (m, 1H) 4.78 (s, 1H) 4.96 (d, J=7.91 Hz, 1H) 5.06 (s, 2H) 7.27-7.37 (m, 5H). LCMS (ESI) 351 (M+H).

Example 21

Synthesis of tert-butyl N-[(2S)-2-(benzyloxycarbonylamino)-3,3-dimethyl-butyl] carbamate, Compound 21

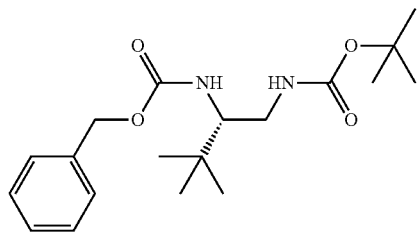 [SMILES: CC(C)(C)OC(=O)NC[C@@H](NC(=O)OCc1ccccc1)C(C)(C)C]

Compound 21 was synthesized from benzyl N-[(1S)-1-(hydroxymethyl)-2,2-dimethyl-propyl]carbamate using a similar synthetic sequence as described for Compound 13. LCMS (ESI) 351.

Example 22

Synthesis of tert-butyl N-[[1-(benzyloxycarbonylamino)cyclohexyl]methyl]carbamate, Compound 22

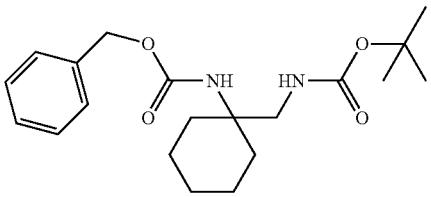 [SMILES: CC(C)(C)OC(=O)NCC1(NC(=O)OCc2ccccc2)CCCCC1]

To a solution of benzyl N-[1-(aminomethyl)cyclohexyl] carbamate (10.0 g, 0.0381 mole) in THF (150 mL) was added di-tert-butyl dicarbonate (9.15 g, 1.1 eq) and the contents were stirred at room temperature for 16 hrs. Ethyl acetate and water were then added. The organic layer was separated, dried over magnesium sulfate and then concentrated under vacuum to afford tert-butyl N-[[1-(benzyloxycarbonylamino)cyclohexyl]methyl] carbamate (13.1 g). ¹HNMR (600 MHz, DMSO-d₆) δ ppm 0.92-1.54 (m, 17H) 1.76-2.06 (m, 2H) 3.09 (d, J=6.15 Hz, 2H) 4.92 (s, 2H) 6.63 (d, J=17.27 Hz, 1H) 7.16-7.49 (m, 6H). LCMS (ESI) 363 (M+H).

Example 23

Synthesis of tert-butyl N-[[1-(benzyloxycarbonylamino)cyclopentyl]methyl] carbamate, Compound 23

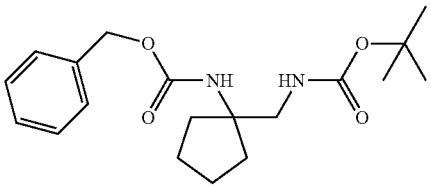 [SMILES: CC(C)(C)OC(=O)NCC1(NC(=O)OCc2ccccc2)CCCC1]

tert-butyl N-[[1-(benzyloxycarbonylamino)cyclopentyl]methyl]carbamate was synthesized in an analogous manner to tert-butyl N-[[1-(benzyloxycarbonylamino) cyclohexyl] methyl] carbamate. LCMS (ESI) 349 (M+H).

Example 24

Synthesis of 2-nitro-5-[4-(1-piperidyl)-1-piperidyl] pyridine, Compound 24

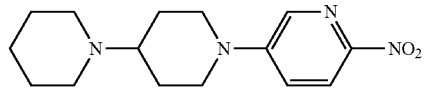

To 5-bromo-2-nitropyridine (1.2 g, 5.9 mmol) in DMSO (4 mL) was added 1-(4-piperidyl)piperidine (1.0 g, 5.9 mmole) and triethylamine (0.99 mL, 7.1 mmole). The contents were heated to 120° C. in a CEM Discovery microwave system for 3 hours. The crude reaction was then purified by silica gel column chromatography with DCM/methanol (0-20%) to afford 2-nitro-5-[4-(1-piperidyl)-1-piperidyl] pyridine as an oil (457 mg). ¹HNMR (600 MHz, DMSO-d₆) δ ppm 1.26-1.36 (m, 2H) 1.43 (m, 6H) 1.76 (m, 2H) 2.37 (m, 5H) 2.94 (t, J=12.74 Hz, 2H) 4.06 (d, J=13.47 Hz, 2H) 7.41 (dd, J=9.37, 2.64 Hz, 1H) 8.08 (d, J=9.37 Hz, 1H) 8.20 (d, J=2.64 Hz, 1H).

Example 25

Synthesis of 5-[4-(1-piperidyl)-1-piperidyl]pyridin-2-amine, Compound 25

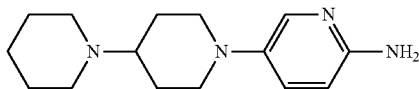

5-[4-(1-piperidyl)-1-piperidyl]pyridin-2-amine was prepared in a manner similar to that used in the synthesis of 5-(4-methylpiperazin-1-yl)pyridin-2-amine. ¹HNMR (600 MHz, DMSO-d₆) δ ppm 1.13-1.37 (m, 6H) 1.40-1.63 (m, 6H) 1.71 (m, 2H), 2.24 (m, 1H) 2.43 (m, 2H) 3.33 (d, J=12.30 Hz, 2H) 5.31 (s, 2H) 6.33 (d, J=8.78 Hz, 1H) 7.10 (dd, J=8.78, 2.93 Hz, 1H) 7.55 (d, J=2.64 Hz, 1H). LCMS (ESI) 261 (M+H).

Example 26

Synthesis of 4-[1-(6-nitro-3-pyridyl)-4-piperidyl] morpholine, Compound 26

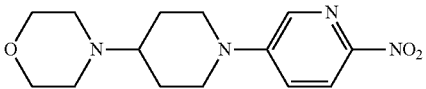 [SMILES: O=[N+]([O-])c1ccc(N2CCC(N3CCOCC3)CC2)cn1]

4-[1-(6-nitro-3-pyridyl)-4-piperidyl]morpholine was synthesized in a manner similar to that used in the synthesis of 2-nitro-5-[4-(1-piperidyl)-1-piperidyl]pyridine. ¹HNMR (600 MHz, DMSO-d₆) δ ppm 1.41 (m, 2H) 1.82 (m, 2H) 2.42 (m, 5H) 2.98 (t, J=12.44 Hz, 2H) 3.52 (s, 4H) 4.04 (d, J=12.88 Hz, 2H) 7.42 (d, J=9.37 Hz, 1H) 8.08 (d, J=9.08 Hz, 1H) 8.21 (s, 1H).

Example 27

Synthesis of 5-(4-morpholino-1-piperidyl) pyridin-2-amine, Compound 27

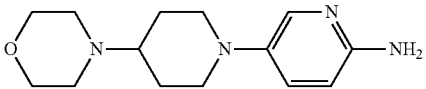

5-(4-morpholino-1-piperidyl)pyridin-2-amine was prepared in a manner similar to that used in the synthesis of 5-(4-methylpiperazin-1-yl)pyridin-2-amine. ¹HNMR (600 MHz, DMSO-d₆) δ ppm 1.34-1.52 (m, 2H) 1.78 (m, 2H) 2.14 (m, 1H) 2.43 (m, 4H) 3.32 (d, J=12.30 Hz, 4H) 3.47-3.59 (m, 4H) 5.32 (s, 2H) 6.34 (d, J=8.78 Hz, 1H) 7.11 (dd, J=8.93, 2.78 Hz, 1H) 7.47-7.62 (m, 1H). LCMS (ESI) 263 (M+H).

Example 28

Synthesis of 4-[1-(6-nitro-3-pyridyl)-4-piperidyl] thiomorpholine, Compound 28

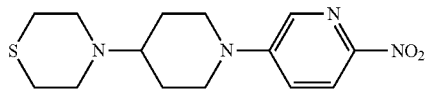 [SMILES: O=[N+]([O-])c1ccc(N2CCC(N3CCSCC3)CC2)cn1]

4-[1-(6-nitro-3-pyridyl)-4-piperidyl] thiomorpholine was synthesized in a manner similar to that used in the synthesis of 2-nitro-5-[4-(1-piperidyl)-1-piperidyl]pyridine. ¹HNMR (600 MHz, DMSO-d₆) δ ppm 1.40-1.52 (m, 2H) 1.71 (m, 2H) 2.49-2.55 (m, 4H) 2.56-2.63 (m, 1H) 2.68-2.75 (m, 4H) 2.88-2.98 (m, 2H) 4.09 (d, J=13.18 Hz, 2H) 7.42 (dd, J=9.22, 3.07 Hz, 1H) 8.08 (d, J=9.37 Hz, 1H) 8.20 (d, J=3.22 Hz, 1H).

Example 29

Synthesis of 5-(4-thiomorpholino-1-piperidyl) pyridin-2-amine, Compound 29

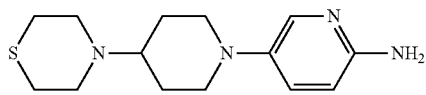

5-(4-thiomorpholino-1-piperidyl) pyridin-2-amine was prepared in a manner similar to that used in the synthesis of 5-(4-methylpiperazin-1-yl)pyridin-2-amine. ¹HNMR (600 MHz, DMSO-d₆) δ ppm 1.47-1.59 (m, 2H) 1.65 (m, 2H) 2.22-2.38 (m, 1H) 2.50-2.59 (m, 6H) 2.68-2.82 (m, 4H) 3.33 (d, J=12.00 Hz, 2H) 5.31 (s, 2H) 6.33 (d, J=9.08 Hz, 1H) 7.10 (dd, J=8.78, 2.93 Hz, 1H) 7.55 (d, J=2.64 Hz, 1H). LCMS (ESI) 279 (M+H).

Example 30

Synthesis of 2-nitro-5-(1-piperidyl)pyridine, Compound 30

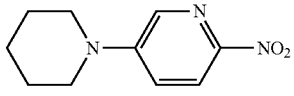

2-nitro-5-(1-piperidyl) pyridine was synthesized in a manner similar to that used in the synthesis of 2-nitro-5-[4-(1-piperidyl)-1-piperidyl]pyridine. ¹HNMR (600 MHz, DMSO-d₆) δ ppm 1.56 (m, 6H) 3.49 (d, J=4.39 Hz, 4H) 7.30-7.47 (m, 1H) 8.02-8.12 (m, 1H) 8.15-8.26 (m, 1H).

Example 31

Synthesis of 5-(1-piperidyl)pyridin-2-amine, Compound 31

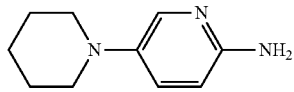

5-(1-piperidyl) pyridin-2-amine was prepared in a manner similar to that used in the synthesis of 5-(4-methylpiperazin-1-yl)pyridin-2-amine. $^1$HNMR (600 MHz, DMSO-d$_6$) δ ppm 1.39-1.46 (m, 2H) 1.51-1.62 (m, 4H) 2.75-2.92 (m, 4H) 5.30 (s, 2H) 6.34 (d, J=8.78 Hz, 1H) 7.09 (dd, J=8.78, 2.93 Hz, 1H) 7.54 (d, J=2.93 Hz, 1H). LCMS (ESI) 178 (M+H).

Example 32

Synthesis of 4-(6-nitro-3-pyridyl) thiomorpholine, Compound 32

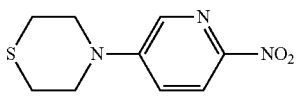

4-(6-nitro-3-pyridyl) thiomorpholine was synthesized in a manner similar to that used in the synthesis of 2-nitro-5-[4-(1-piperidyl)-1-piperidyl]pyridine. $^1$HNMR (600 MHz, DMSO-d$_6$) δ ppm 2.56-2.69 (m, 4H) 3.79-3.92 (m, 4H) 7.43 (dd, J=9.22, 3.07 Hz, 1H) 8.10 (d, J=9.37 Hz, 1H) 8.20 (d, J=2.93 Hz, 1H).

Example 33

Synthesis of 5-thiomorpholinopyridin-2-amine, Compound 33

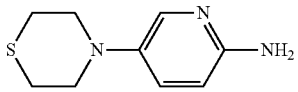

5-thiomorpholinopyridin-2-amine was prepared in a manner similar to that used in the synthesis of 5-(4-methylpiperazin-1-yl) pyridin-2-amine. $^1$HNMR (600 MHz, DMSO-d$_6$) δ ppm 2.59-2.73 (m, 4H) 3.04-3.20 (m, 4H) 5.41 (s, 2H) 6.35 (d, J=8.78 Hz, 1H) 7.10 (dd, J=8.78, 2.93 Hz, 1H) 7.57 (d, J=2.64 Hz, 1H). LCMS (ESI) 196 (M+H).

Example 34

Synthesis of tert-butyl (4R)-5-(6-nitro-3-pyridyl)-2,5-diazabicyclo[2.2.1]heptane-2-carboxylate, Compound 34

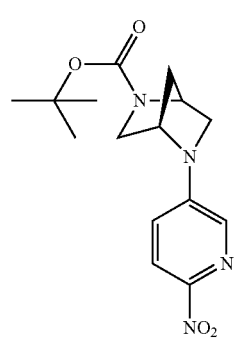

tert-butyl (4R)-5-(6-nitro-3-pyridyl)-2,5-diazabicyclo[2.2.1]heptane-2-carboxylate was synthesized in a manner similar to that used in the synthesis of 2-nitro-5-[4-(1-piperidyl)-1-piperidyl]pyridine. $^1$HNMR (600 MHz, DMSO-d$_6$) δ ppm 1.33 (d, J=32.21 Hz, 11H) 1.91 (m, 2H) 3.15 (d, J=10.25 Hz, 1H) 3.58 (m, 1H) 4.46 (m, 1H) 4.83 (s, 1H) 7.16 (s, 1H) 7.94 (s, 1H) 8.05-8.16 (m, 1H).

Example 35

Synthesis of tert-butyl (4R)-5-(6-amino-3-pyridyl)-2,5-diazabicyclo[2.2.1]heptane-2-carboxylate, Compound 35

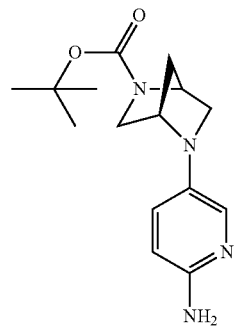 [SMILES: CC(C)(C)OC(=O)N1C[C@H]2CC1CN2c1ccc([N+](=O)[O-])nc1]

tert-butyl (4R)-5-(6-amino-3-pyridyl)-2,5-diazabicyclo[2.2.1]heptane-2-carboxylate was prepared in a manner similar to that used in the synthesis of 5-(4-methylpiperazin-1-yl)pyridin-2-amine. $^1$HNMR (600 MHz, DMSO-d$_6$) δ ppm 1.31 (d, J=31.91 Hz, 11H) 1.83 (m, 2H) 2.71-2.82 (m, 1H) 3.44 (m, 1H) 4.30 (d, 2H) 5.08 (s, 2H) 6.35 (d, J=8.78 Hz, 1H) 6.77-6.91 (m, 1H) 7.33 (s, 1H). LCMS (ESI) 291 (M+H).

Example 36

Synthesis of N,N-dimethyl-1-(6-nitro-3-pyridyl) piperidin-4-amine, Compound 36

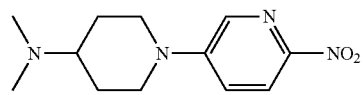

N,N-dimethyl-1-(6-nitro-3-pyridyl)piperidin-4-amine was synthesized in a manner similar to that used in the synthesis of 2-nitro-5-[4-(1-piperidyl)-1-piperidyl]pyridine. $^1$HNMR (600 MHz, DMSO-$d_6$) δ ppm 1.30-1.45 (m, 2H) 1.79 (m, 2H) 2.14 (s, 6H) 2.33 (m, 1H) 2.92-3.04 (m, 2H) 4.03 (d, J=13.76 Hz, 2H) 7.42 (dd, J=9.22, 3.07 Hz, 1H) 8.04-8.11 (m, 1H) 8.21 (d, J=2.93 Hz, 1H).

Example 37

Synthesis of 5-[4-(dimethylamino)-1-piperidyl] pyridin-2-amine, Compound 37

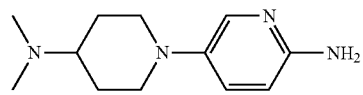 [SMILES: CN(C)C1CCN(c2ccc([N+](=O)[O-])nc2)CC1]

5-[4-(dimethylamino)-1-piperidyl]pyridin-2-amine was prepared in a manner similar to that used in the synthesis of 5-(4-methylpiperazin-1-yl)pyridin-2-amine. $^1$HNMR (600 MHz, DMSO-$d_6$) δ ppm 1.35-1.50 (m, 2H) 1.69-1.81 (m, 2H) 2.00-2.10 (m, 1H) 2.11-2.22 (s, 6H) 3.17-3.36 (m, 4H) 5.19-5.38 (s, 2H) 6.34 (d, J=8.78 Hz, 1H) 7.10 (dd, J=8.78, 2.93 Hz, 1H) 7.55 (d, J=2.63 Hz, 1H). LCMS (ESI) 221 (M+H).

Example 38

Synthesis of 4-(6-nitro-3-pyridyl) morpholine, Compound 38

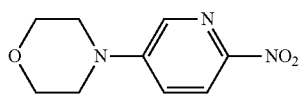

4-(6-nitro-3-pyridyl) morpholine was synthesized in a manner similar to that used in the synthesis of 2-nitro-5-[4-(1-piperidyl)-1-piperidyl] pyridine.

Example 39

Synthesis of 5-morpholinopyridin-2-amine, Compound 39

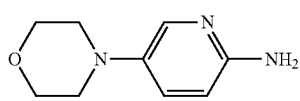

5-morpholinopyridin-2-amine was prepared in a manner similar to that used in the synthesis of 5-(4-methylpiperazin-1-yl) pyridin-2-amine. $^1$HNMR (600 MHz, CHLOROFORM-d) δ ppm 2.91-3.00 (m, 4H) 3.76-3.84 (m, 4H) 4.19 (br. s., 2H) 6.45 (d, J=8.78 Hz, 1H) 7.12 (dd, J=8.78, 2.93 Hz, 1H) 7.72 (d, J=2.93 Hz, 1H).

Example 40

Synthesis of 5-(4-isobutylpiperazin-1-yl) pyridin-2-amine, Compound 40

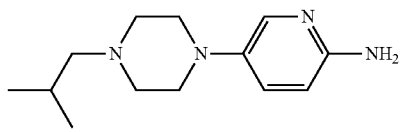 [SMILES: CC(C)CN1CCN(c2ccc(N)nc2)CC1]

1-isobutyl-4-(6-nitro-3-pyridyl)piperazine was synthesized in a manner similar to that used in the synthesis of 2-nitro-5-[4-(1-piperidyl)-1-piperidyl]pyridine which was then converted 5-(4-isobutylpiperazin-1-yl)pyridin-2-amine in a manner similar to that used in the synthesis of 5-(4-methylpiperazin-1-yl)pyridin-2-amine. $^1$HNMR (600 MHz, CHLOROFORM-d) δ ppm 0.88 (d, J=6.73 Hz, 6H) 1.71-1.84 (m, 1H) 2.10 (d, J=7.32 Hz, 2H) 2.46-2.58 (m, 4H) 2.97-3.07 (m, 4H) 4.12 (s, 2H) 6.45 (d, J=8.78 Hz, 1H) 7.14 (dd, J=8.78, 2.93 Hz, 1H) 7.75 (d, J=2.93 Hz, 1H). LCMS (ESI) 235 (M+H).

Example 41

Synthesis of 5-(4-isopropylpiperazin-1-yl) pyridin-2-amine, Compound 41

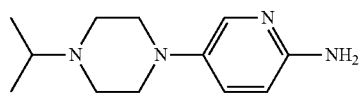

1-isopropyl-4-(6-nitro-3-pyridyl)piperazine was synthesized in a manner similar to that used in the synthesis of 2-nitro-5-[4-(1-piperidyl)-1-piperidyl]pyridine which was then converted to 5-(4-isopropylpiperazin-1-yl)pyridin-2-amine in a manner similar to that used in the synthesis of 5-(4-methylpiperazin-1-yl)pyridin-2-amine. $^1$HNMR (600 MHz, CHLOROFORM-d) δ ppm 1.06 (d, J=6.44 Hz, 6H) 2.59-2.75 (m, 5H) 2.97-3.10 (m, 4H) 4.13 (s, 2H) 6.45 (d, J=8.78 Hz, 1H) 7.15 (dd, J=9.08, 2.93 Hz, 1H) 7.76 (d, J=2.93 Hz, 1H). LCMS (ESI) 221 (M+H).

Example 42

Synthesis of 5-[(2R,6S)-2,6-dimethylmorpholin-4-yl]pyridin-2-amine, Compound 42

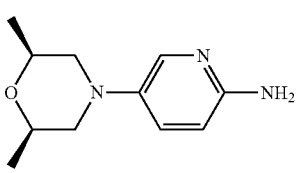

(2S,6R)-2,6-dimethyl-4-(6-nitro-3-pyridyl)morpholine was synthesized in a manner similar to that used in the synthesis of 2-nitro-5-[4-(1-piperidyl)-1-piperidyl]pyridine which was then converted to 5-[(2R,6S)-2,6-dimethylmorpholin-4-yl]pyridin-2-amine in a manner similar to that used in the synthesis of 5-(4-methylpiperazin-1-yl)pyridin-2-amine. ¹HNMR (600 MHz, CHLOROFORM-d) δ ppm 1.20 (d, J=6.44 Hz, 6H) 2.27-2.39 (m, 2H) 3.11-3.21 (m, 2H) 3.70-3.84 (m, 2H) 4.15 (s, 2H) 6.45 (d, J=8.78 Hz, 1H) 7.12 (dd, J=8.78, 2.93 Hz, 1H) 7.72 (d, J=2.63 Hz, 1H). LCMS (ESI) 208 (M+H).

Example 43

Synthesis of 5-[(3R,5S)-3,5-dimethylpiperazin-1-yl]pyridin-2-amine, Compound 43

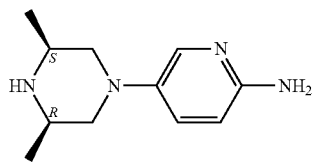

(3S,5R)-3,5-dimethyl-1-(6-nitro-3-pyridyl)piperazine was synthesized in a manner similar to that used in the synthesis of 2-nitro-5-[4-(1-piperidyl)-1-piperidyl]pyridine which was then converted to 5-[(3R,5S)-3,5-dimethylpiperazin-1-yl]pyridin-2-amine in a manner similar to that used in the synthesis of 5-(4-methylpiperazin-1-yl)pyridin-2-amine. ¹HNMR (600 MHz, CHLOROFORM-d) δ ppm 1.09 (d, J=6.44 Hz, 6H) 2.20 (t, J=10.83 Hz, 2H) 2.95-3.08 (m, 2H) 3.23 (dd, J=11.71, 2.05 Hz, 2H) 4.13 (s, 2H) 6.45 (d, J=8.78 Hz, 1H) 7.14 (dd, J=8.78, 2.93 Hz, 1H) 7.73 (d, J=2.63 Hz, 1H). LCMS (ESI) 207 (M+H).

Example 44

Synthesis of Compound 44

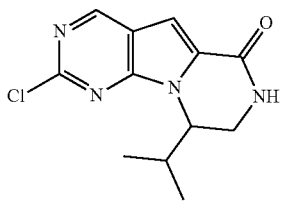 [SMILES: CC(C)C1CNC(=O)c2cc3cnc(Cl)nc3n21]

tert-butyl N-[2-[(5-bromo-2-chloro-pyrimidin-4-yl)amino]-3-methyl-butyl] carbamate

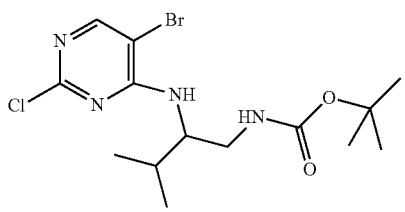 [SMILES: CC(C)C(CNC(=O)OC(C)(C)C)Nc1nc(Cl)ncc1Br]

A solution of intermediate A in ethanol (100 mL) was hydrogenated under 30 psi of hydrogen using 10% Pd/C (0.7 g) in a pressure bomb for 7 hrs. After filtration of the reaction mixture through CELITE™, the organic layer was concentrated under vacuum to afford tert-butyl N-(2-amino-3-methyl-butyl) carbamate (3.8 g).

To a solution of 5-bromo-2,4-dichloro-pyrimidine (7.11 g, 0.0312 mole) in ethanol (100 mL) was added diisopropylethyl amine (5.45 mL, 1.0 eq) and tert-butyl N-(2-amino-3-methyl-butyl) carbamate (6.31 g, 0.0312 mole). The reaction mixture was stirred at room temperature for 20 hrs. After concentration under vacuum, ethyl acetate and water were added. The organic layer was separated, dried with magnesium sulfate and then concentrated under vacuum. The crude product was purified by silica gel column chromatography using hexane/ethyl acetate (0-30%) to afford tert-butyl N-[2-[(5-bromo-2-chloro-pyrimidin-4-yl)amino]-3-methyl-butyl] carbamate. ¹HNMR (600 MHz, DMSO-d₆) δ ppm 0.77-0.85 (d, J=6.5 Hz, 3H) 0.87 (d, J=6.73 Hz, 3H) 1.31-1.39 (m, 9H) 1.82-1.93 (m, 1H) 2.94 (d, J=5.56 Hz, 1H) 3.08-3.22 (m, 2H) 3.98 (d, J=8.20 Hz, 1H) 6.96 (d, J=8.78 Hz, 1H) 8.21 (s, 1H). LCMS (ESI) 393 (M+H).

tert-butyl N-[2-[2-chloro-6-(diethoxymethyl)pyrrolo[2,3-d]pyrimidin-7-yl]-3-methyl-butyl]carbamate

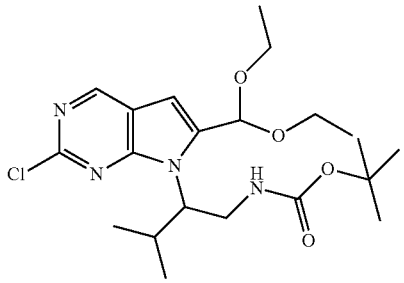 [SMILES: CCOC(OCC)c1cc2cnc(Cl)nc2n1C(CNC(=O)OC(C)(C)C)C(C)C]

tert-butyl N-[2-[2-chloro-6-(diethoxymethyl)pyrrolo[2,3-d]pyrimidin-7-yl]-3-methyl-butyl] carbamate was synthesized by hosting tert-butyl N-[2-[(5-bromo-2-chloro-pyrimidin-4-yl)amino]-3-methyl-butyl]carbamate to Sonogoshira conditions as described for tert-butyl N-[2-[[2-chloro-5-(3,3-diethoxyprop-1-ynyl)pyrimidin-4-yl]amino]ethyl]carbamate followed by subsequent treatment with TBAF as described in the synthesis of tert-butyl N-[2-[2-chloro-6-(diethoxymethyl)pyrrolo[2,3-d]pyrimidin-7-yl]ethyl]carbamate. ¹HNMR (600 MHz, DMSO-d₆) δ ppm 1.11 (d, J=6.44 Hz, 3H) 1.18 (t, J=7.03 Hz, 6H) 1.21-1.26 (m, 12H) 2.88 (br. s., 1H) 3.43-3.78 (m, 6H) 3.97-4.08 (m, 1H) 5.61 (s, 1H) 6.65 (s, 1H) 6.71-6.78 (m, 1H) 8.87 (s, 1H). LCMS (ESI) 441 (M+H).

7-[1-[(tert-butoxycarbonylamino)methyl]-2-methylpropyl]-2-chloro-pyrrolo[2,3-d]pyrimidine-6-carboxylic acid

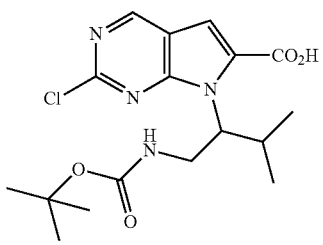 [SMILES: CC(C)C(CNC(=O)OC(C)(C)C)n1c(C(=O)O)cc2cnc(Cl)nc21]

To a solution tert-butyl N-[2-[[2-chloro-5-(3,3-diethoxy-prop-1-ynyl)pyrimidin-4-yl]amino]ethyl]carbamate in THF was added TBAF and the contents were heated at reflux for 3 hrs. Ethyl acetate and water were then added and the organic layer separated, dried with magnesium sulfate and then concentrated under vacuum. To this crude reaction was added acetic acid/water (9:1) and the contents were stirred for 12 hrs at room temperature. After concentration under vacuum, sat NaHCO$_3$ and ethyl acetate were added. The organic layer was separated, dried and then concentrated under vacuum. The crude reaction product thus obtained was dissolved in DMF, oxone was then added and the contents stirred for 3 hrs. After addition of ethyl acetate, the reaction mixture was filtered through CELITE' and concentrated under vacuum. Column chromatography of the crude product over silica gel using hexane/ethyl acetate (0-100%) afforded 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-d$_6$) δ ppm 0.85 (d, J=7.03 Hz, 3H) 0.97 (d, J=6.73 Hz, 3H) 1.52 (s, 9H) 1.99-2.23 (m, 1H) 3.98 (dd, J=14.05, 3.51 Hz, 1H) 4.47-4.71 (m, 2H) 7.47 (s, 1H) 9.17 (s, 1H). LCMS (ESI) 383 (M+H).

Compound 44

To 7-[1-[(tert-butoxycarbonylamino)methyl]-2-methyl-propyl]-2-chloro-pyrrolo[2,3-d]pyrimidine-6-carboxylic acid (0.050 g, 0.00013 mole) in DCM (1.5 mL) was added DIC (32.7 mg) and DMAP (10 mg). The contents were stirred for 2 hrs. Trifluoroacetic acid (0.4 mL) was then added and stirring continued for an additional 30 minutes. After addition of satd NaHCO$_3$ to neutralize the excess acid, ethyl acetate was added and the organic layer separated, dried using magnesium sulfate and then concentrated under vacuum. The crude product was purified by silica gel column chromatography using hexane/ethyl acetate (0-100%) to afford the product. $^1$HNMR (600 MHz, DMSO-d$_6$) δ ppm 0.72 (d, J=6.73 Hz, 3H) 0.97 (d, J=6.73 Hz, 3H) 2.09-2.22 (m, 1H) 3.57 (dd, J=13.18, 4.98 Hz, 1H) 3.72 (dd, J=13.61, 4.25 Hz, 1H) 4.53 (dd, J=8.05, 3.95 Hz, 1H) 7.20 (s, 1H) 8.34 (d, J=4.98 Hz, 1H) 9.08 (s, 1H). LCMS (ESI) 265 (M+H).

Example 45

Synthesis of Compound 45

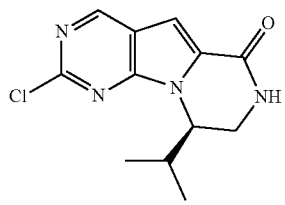 [SMILES: CC(C)[C@@H]1CNC(=O)c2cc3cnc(Cl)nc3n21]

Compound 14 was hydrogenated with 10% Pd/C to afford the intermediate tert-butyl N-[(2R)-2-amino-3-methyl-butyl] carbamate, which was then treated with 5-bromo-2,4-dichloro-pyrimidine using analogous reaction conditions as described for Compound 44 to afford Compound 45 The analytical data is consistent with that reported for the racemate (Intermediate 1A).

Example 46

Synthesis of Compound 46

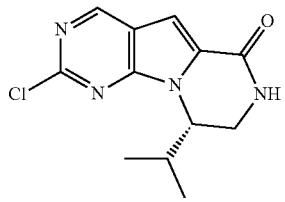 [SMILES: CC(C)[C@H]1CNC(=O)c2cc3cnc(Cl)nc3n21]

Compound 15 was hydrogenated with 10% Pd/C to afford the intermediate tert-butyl N-[(2S)-2-amino-3-methyl-butyl] carbamate, which was then treated with 5-bromo-2,4-dichloro-pyrimidine using analogous reaction conditions as described for Compound 44 to afford Compound 46. The analytical data (NMR and LCMS) was consistent with that reported for the racemate Compound 44.

Example 47

Synthesis of Compound 47

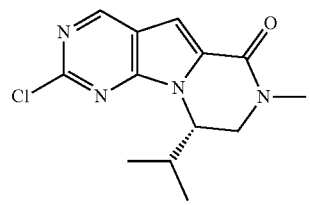 [SMILES: CC(C)[C@H]1CN(C)C(=O)c2cc3cnc(Cl)nc3n21]

To a solution of Compound 44 (80 mg, 0.00030 mole) in DMF (3 mL) was added a 60% dispersion of sodium hydride in oil (40 mg). After stirring for 15 minutes, methyl iodide (37 µL, 2 eq) was added. The contents were stirred at room temperature for 30 minutes. Saturated NaHCO$_3$ was then added followed by ethyl acetate. The organic layer was dried with magnesium sulfate and then concentrated under vacuum to afford the product. $^1$HNMR (600 MHz, DMSO-d$_6$) δ ppm 0.74 (d, J=6.73 Hz, 3H) 0.91 (d, J=6.73 Hz, 3H) 2.04-2.20 (m, 1H) 3.04 (s, 3H) 3.69 (dd, J=13.76, 1.17 Hz, 1H) 3.96 (dd, J=13.76, 4.68 Hz, 1H) 4.58 (dd, J=7.32, 3.51 Hz, 1H) 7.16 (s, 1H) 9.05 (s, 1H). LCMS (ESI) 279 (M+H).

Example 48

Synthesis of Compound 48

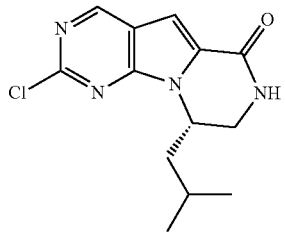 [SMILES: CC(C)C[C@H]1CNC(=O)c2cc3cnc(Cl)nc3n21]

tert-butyl N-[(2S)-2-[(5-bromo-2-chloro-pyrimidin-4-yl)amino]-4-methyl-pentyl]carbamate

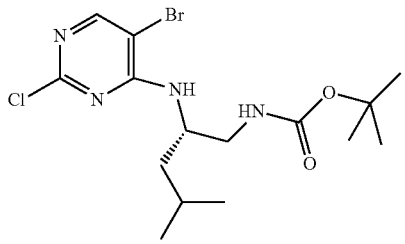 [SMILES: CC(C)C[C@@H](CNC(=O)OC(C)(C)C)Nc1nc(Cl)ncc1Br]

Compound 18 was hydrogenated with 10% Pd/C in ethanol under a blanket of hydrogen at 50 psi in a pressure bomb to afford tert-butyl N-[(2S)-2-amino-4-methyl-pentyl]carbamate which was then reacted with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-4-methyl-pentyl]carbamate. $^1$HNMR (600 MHz, CHLOROFORM-d) δ ppm 0.91 (d, J=6.44 Hz, 3H) 0.94 (d, J=6.44 Hz, 3H) 1.32-1.51 (m, 11H) 1.55-1.67 (m, 1H) 3.28 (t, J=5.86 Hz, 2H) 4.21-4.42 (m, 1H) 4.84 (s, 1H) 5.84 (d, J=7.32 Hz, 1H) 8.07 (s, 1H). LCMS (ESI) 407 (M+H).

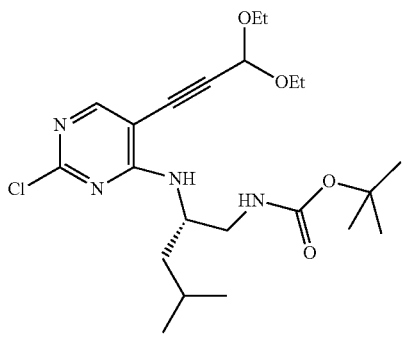 [SMILES: CCOC(C#Cc1cnc(Cl)nc1N[C@H](CNC(=O)OC(C)(C)C)CC(C)C)OCC]

To a solution of tert-butyl N-[(2S)-2-[(5-bromo-2-chloro-pyrimidin-4-yl)amino]-4-methyl-pentyl]carbamate (5.0 g, 12.3 mmole) in tolune (36 mL) and triethylamine (7.2 mL) was added under nitrogen, 3,3-diethoxyprop-1-yne (2.8 mL, 19.7 mmole), Pd$_2$(dba)$_3$ (1.1 g, 1.23 mmole), and triphenylarsine (3.8 g, 12.3 mmole). The contents were heated to 70 degrees for 24 hrs. After cooling to room temperature, the reaction mixture was filtered through CELITE™ and then concentrated under vacuum. The crude product was purified by silica gel column chromatography using hexane/ethyl acetate (0-30%) to afford (2S)—N2-[2-chloro-5-(3,3-diethoxyprop-1-ynyl)pyrimidin-4-yl]-4-methyl-pentane-1,2-diamine. LCMS (ESI) 455 (M+H).

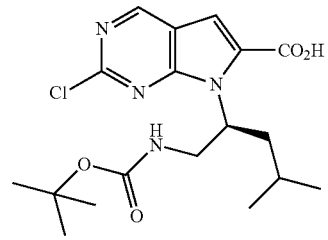 [SMILES: CC(C)C[C@@H](CNC(=O)OC(C)(C)C)n1c(C(=O)O)cc2cnc(Cl)nc21]

7-[(1S)-1-[(tert-butoxycarbonylamino)methyl]-3-methyl-butyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-d$_6$) δ ppm 0.88 (d, J=6.44 Hz, 3H) 0.97 (d, J=6.44 Hz, 3H) 1.47 (s, 9H) 1.49-1.54 (m, 1H) 1.56 (t, J=7.17 Hz, 2H) 3.98 (dd, J=13.91, 3.07 Hz, 1H) 3.76 (dd, J=13.31, 4.13 Hz, 1H) 4.38 (d, J=14.05 Hz, 1H) 4.90 (t, J=7.17 Hz, 1H) 7.41 (s, 1H) 9.11 (s, 1H). LCMS (M+H) 397.

Compound 48 was synthesized using an analogous synthetic sequence as that described for Compound 44. $^1$HNMR (600 MHz, DMSO-d$_6$) δ ppm 0.82 (d, J=6.73 Hz, 3H) 0.97 (d, J=6.44 Hz, 3H) 1.34-1.46 (m, 1H) 1.48-1.65 (m, 2H) 3.40 (dd, J=13.32, 5.42 Hz, 1H) 3.76 (dd, J=13.47, 4.10 Hz, 1H) 4.76-4.92 (m, 1H) 7.17 (s, 1H) 8.34 (d, J=5.27 Hz, 1H) 9.04 (s, 1H). LCMS (ESI) 279 (M+H).

Example 49

Synthesis of Compound 49

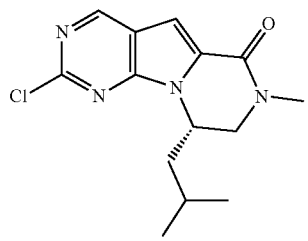 [SMILES: CC(C)C[C@H]1CN(C)C(=O)c2cc3cnc(Cl)nc3n21]

Compound 49 was synthesized in a manner similar to that described for Compound 47. $^1$HNMR (600 MHz, DMSO-d$_6$) δ ppm 0.82 (d, J=6.44 Hz, 3H) 0.97 (d, J=6.44 Hz, 3H) 1.37-1.68 (m, 3H) 3.04 (s, 3H) 3.56 (d, J=13.47 Hz, 1H) 4.00 (dd, J=13.32, 4.25 Hz, 1H) 4.82-4.94 (m, 1H) 7.16 (s, 1H) 9.03 (s, 1H). LCMS (ESI) 293 (M+H).

Example 50

Synthesis of Compound 50

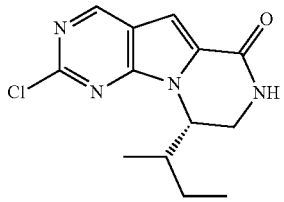 [SMILES: CCC(C)[C@H]1CNC(=O)c2cc3cnc(Cl)nc3n21]

tert-butyl N-[(2S)-2-[(5-bromo-2-chloro-pyrimidin-4-yl)amino]-3-methyl-pentyl]carbamate

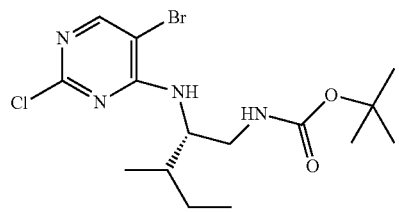 [SMILES: CCC(C)[C@@H](CNC(=O)OC(C)(C)C)Nc1nc(Cl)ncc1Br]

Compound 20 was hydrogenated using 10% Pd/C under hydrogen at 50 psi in a pressure vessel to afford tert-butyl N-[(2S)-2-amino-3-methyl-pentyl]carbamate which was reacted with 5-bromo-2,4-dichloro-pyrimidine using analogous reaction conditions as described for tert-butyl N-[2-[(5-bromo-2-chloro-pyrimidin-4-yl)amino]-3-methyl-butyl] carbamate to afford tert-butyl N-[2S)-2-[(5-bromo-2-chloro-pyrimidin-4-yl)amino]-3-methyl-pentyl]carbamate. ¹HNMR (600 MHz, CHLOROFORM-d) δ ppm 0.88-0.95 (m, 6H) 1.11-1.20 (m, 1H) 1.34 (s, 9H) 1.44-1.54 (m, 1H) 1.64-1.72 (m, 1H) 3.17-3.27 (m, 1H) 3.33-3.43 (m, 1H) 4.11-4.21 (m, 1H) 4.81 (s, 1H) 5.92 (d, J=8.20 Hz, 1H) 8.05 (s, 1H). LCMS (ESI) 407.

tert-butyl N-[(2S)-2-[[2-chloro-5-(3,3-diethoxyprop-1-ynyl)pyrimidin-4-yl]amino]-3-methyl-pentyl]carbamate

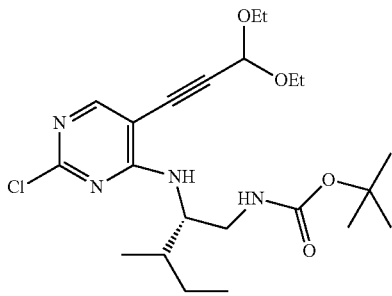 [SMILES: CCOC(C#Cc1cnc(Cl)nc1N[C@H](CNC(=O)OC(C)(C)C)C(C)CC)OCC]

tert-butyl N-[(2S)-2-[[2-chloro-5-(3,3-diethoxyprop-1-ynyl)pyrimidin-4-yl]amino]-3-methyl-pentyl]carbamate was synthesized using similar experimental conditions to that used in the synthesis of (2S)—N2-[2-chloro-5-(3,3-diethoxyprop-1-ynyl)pyrimidin-4-yl]-4-methyl-pentane-1,2-diamine. ¹HNMR (600 MHz, DMSO-d₆) δ ppm 0.76-0.89 (m, 6H) 1.03 (q, J=7.22 Hz, 3H) 1.10-1.17 (m, 3H) 1.25-1.42 (m, 11H) 1.59-1.73 (m, 1H) 3.35-3.47 (m, 4H) 3.51-3.73 (m, 2H) 3.99-4.11 (m, 1H) 5.52-5.56 (m, 1H) 6.76-7.03 (m, 2H) 8.12-8.23 (m, 1H). LCMS (ESI) 455 (M+H).

7-[(1S)-1-[(tert-butoxycarbonylamino)methyl]-2-methyl-butyl]-2-chloro-pyrrolo[2,3-d]pyrimidine-6-carboxylic acid

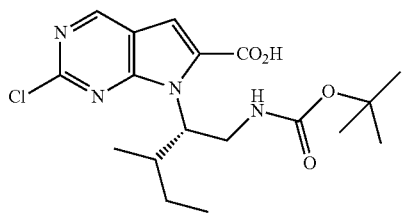 [SMILES: CCC(C)[C@@H](CNC(=O)OC(C)(C)C)n1c(C(=O)O)cc2cnc(Cl)nc21]

7-[(1 S)-1-[(tert-butoxycarbonylamino)methyl]-2-methyl-butyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. ¹HNMR (600 MHz, DMSO-d₆) δ ppm 0.80 (t, J=7.47 Hz, 3H) 0.86 (d, J=7.03 Hz, 3H) 1.06-1.30 (m, 2H) 1.48 (s, 9H) 1.79-1.96 (m, 1H) 3.95 (dd, J=14.05, 3.22 Hz, 1H) 4.52 (d, J=14.35 Hz, 1H) 4.61-4.73 (m, 1H) 7.43 (s, 1H) 9.13 (s, 1H). LCMS (ESI) 397 (M+H).

Compound 50 was synthesized using an analogous synthetic sequence as that described for Compound 44. ¹HNMR (600 MHz, DMSO-d₆) δ ppm 0.74 (t, J=7.32 Hz, 3H) 0.89 (d, J=6.73 Hz, 3H) 1.00-1.12 (m, 2H) 1.82-1.94 (m, 1H) 3.55 (dd, J=13.91, 4.83 Hz, 1H) 3.70 (dd, J=13.61, 4.25 Hz, 1H) 4.57 (dd, J=7.91, 4.10 Hz, 1H) 7.17 (s, 1H) 8.31 (d, J=5.27 Hz, 1H) 9.05 (s, 1H). LCMS (ESI) 279 (M+H).

Example 51

Synthesis of Compound 51

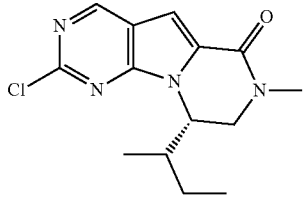 [SMILES: CCC(C)[C@H]1CN(C)C(=O)c2cc3cnc(Cl)nc3n21]

Compound 51 was synthesized in a manner similar to Compound 47. ¹HNMR (600 MHz, DMSO-d₆) δ ppm 0.77 (t, J=7.47 Hz, 3H) 0.84 (d, J=6.73 Hz, 3H) 1.07-1.16 (m, 2H) 1.82-1.95 (m, 1H) 3.03 (s, 3H) 3.68 (d, J=13.76 Hz, 1H) 3.96 (dd, J=13.76, 4.39 Hz, 1H) 4.59-4.70 (m, 1H) 7.16 (s, 1H) 9.04 (s, 1H). LCMS (ESI) 293 (M+H).

Example 52

Synthesis of Compound 52

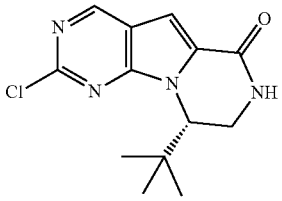 [SMILES: CC(C)(C)[C@H]1CNC(=O)c2cc3cnc(Cl)nc3n21]

tert-butyl N-[(2S)-2-[(5-bromo-2-chloro-pyrimidin-4-yl)amino]-3,3-dimethyl-butyl] carbamate

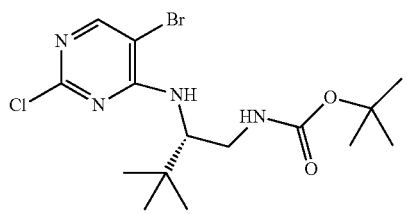 [SMILES: CC(C)(C)OC(=O)NC[C@@H](Nc1nc(Cl)ncc1Br)C(C)(C)C]

Compound 21 was hydrogenated using 10% Pd/C under hydrogen at 50 psi in a pressure vessel to afford tert-butyl N-[(2S)-2-amino-3,3-dimethyl-butyl]carbamate which was then reacted with 5-bromo-2,4-dichloro-pyrimidine using analogous reaction conditions as described using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-3,3-dimethyl-butyl]carbamate. LCMS (ESI) 407 (M+H).

tert-butyl N-[(2S)-2-[[2-chloro-5-(3,3-diethoxyprop-1-ynyl)pyrimidin-4-yl]amino]-3,3-dimethyl-butyl] carbamate

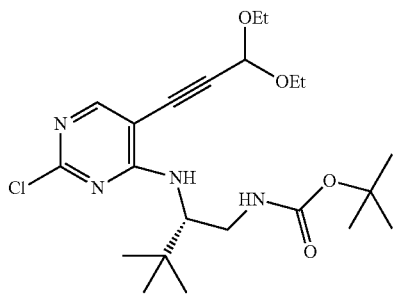 [SMILES: CCOC(C#Cc1cnc(Cl)nc1N[C@H](CNC(=O)OC(C)(C)C)C(C)(C)C)OCC]

tert-butyl N-[(2S)-2-[[2-chloro-5-(3,3-diethoxyprop-1-ynyl)pyrimidin-4-yl]amino]-3,3-dimethyl-butyl]carbamate was synthesized using similar experimental conditions to that used in the synthesis of (2S)—N2-[2-chloro-5-(3,3-diethoxyprop-1-ynyl)pyrimidin-4-yl]-4-methyl-pentane-1,2-diamine. LCMS (ESI) 455 (M+H).

7-[(1S)-1-[(tert-butoxycarbonylamino)methyl]-2,2-dimethyl-propyl]-2-chloro-pyrrolo[2,3-d]pyrimidine-6-carboxylic acid

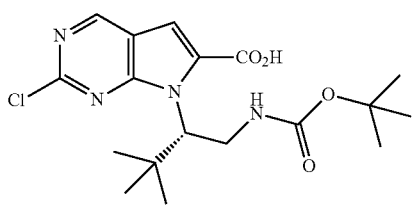 [SMILES: CC(C)(C)OC(=O)NC[C@@H](n1c(C(=O)O)cc2cnc(Cl)nc21)C(C)(C)C]

7-[(1 S)-1-[(tert-butoxycarbonylamino)methyl]-2,2-dimethyl -propyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. LCMS (ESI) 397 (M+H).

Intermediate 1F was synthesized using an analogous synthetic sequence as that described for intermediate 1A. LCMS (ESI) 279 (M+H).

Example 53

Synthesis of Compound 53

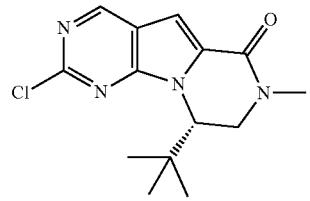 [SMILES: CN1C[C@H](C(C)(C)C)n2c(cc3cnc(Cl)nc32)C1=O]

Compound 53 was synthesized in a manner similar to that described for Intermediate 1CA. LCMS (ESI) 293 (M+H).

Example 54

Synthesis of Compound 54

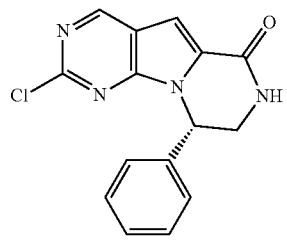 [SMILES: O=C1NC[C@H](c2ccccc2)n2c1cc1cnc(Cl)nc12]

tert-butyl N-[2S)-2-[(5-bromo-2-chloro-pyrimidin-4-yl)amino]-2-phenyl-ethyl] carbamate

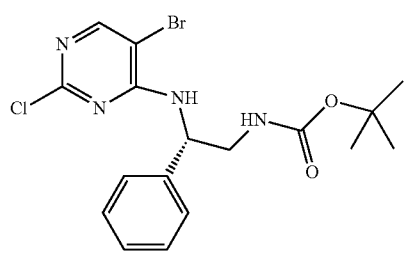 [SMILES: CC(C)(C)OC(=O)NC[C@@H](Nc1nc(Cl)ncc1Br)c1ccccc1]

Compound 21 was hydrogenated using 10% Pd/C under hydrogen at 50 psi in a pressure vessel to afford tert-butyl N-[(2S)-2-amino-2-phenyl-ethyl]carbamate which was then reacted with 5-bromo-2,4-dichloro-pyrimidine using analogous reaction conditions as described for tert-butyl N-[2-[(5-bromo-2-chloro-pyrimidin-4-yl)amino]-3-methyl -butyl]carbamate to afford tert-butyl N-[(2S)-2-[(5-bromo-2-chloro-pyrimidin-4-yl)amino]-2-phenyl-ethyl]carbamate. $^1$HNMR (600 MHz, DMSO-$d_6$) δ ppm 1.32 (s, 9H) 3.29-3.50 (m, 2H) 5.12-5.24 (m, 1H) 7.10 (t, J=5.27 Hz, 1H) 7.21 (t, J=6.88 Hz, 1H) 7.26-7.34 (m, 4H) 7.89 (d, J=7.32 Hz, 1H) 8.24 (s, 1H). LCMS (ESI) 427 (M+H).

123 tert-butyl N-[(2S)-2-[[2-chloro-5-(3,3-diethoxyprop-1-ynyl)pyrimidin-4-yl]amino]-2-phenyl-ethyl]carbamate

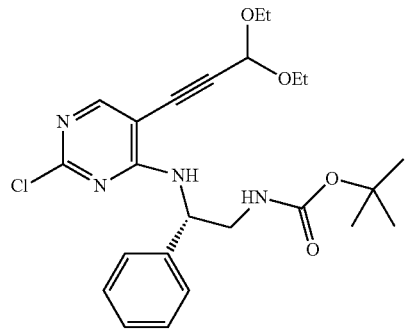 [SMILES: CCOC(C#Cc1cnc(Cl)nc1N[C@H](CNC(=O)OC(C)(C)C)c1ccccc1)OCC]

tert-butyl N-[(2S)-2-[[2-chloro-5-(3,3-diethoxyprop-1-ynyl)pyrimidin-4-yl]amino]-2-phenyl-ethyl]carbamate was synthesized using similar experimental conditions to those used in the synthesis of (2S)—N2-[2-chloro-5-(3,3-diethoxyprop-1-ynyl)pyrimidin-4-yl]-4-methyl-pentane-1,2-diamine. $^1$HNMR (600 MHz, DMSO-$d_6$) δ ppm 1.14 (t, J=7.03 Hz, 6H) 1.32 (s, 9H) 3.39 (s, 2H) 3.52-3.61 (m, 2H) 3.64-3.73 (m, 2H) 5.17-5.26 (m, 1H) 5.57 (s, 1H) 7.07-7.14 (m, 1H) 7.20-7.25 (m, 1H) 7.26-7.33 (m, 4H) 7.90 (d, J=7.61 Hz, 1H) 8.19 (s, 1H). LCMS (ESI) 475 (M+H).

7-[(1S)-2-(tert-butoxycarbonylamino)-1-phenyl-ethyl]-2-chloro-pyrrolo[2,3-d]pyrimidine-6-carboxylic acid

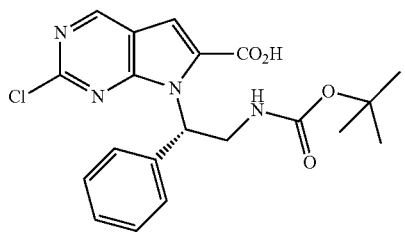 [SMILES: CC(C)(C)OC(=O)NC[C@H](c1ccccc1)n1c(C(=O)O)cc2cnc(Cl)nc21]

7-[(1S)-2-(tert-butoxycarbonylamino)-1-phenyl-ethyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. LCMS (ESI) 417 (M+H).

Compound 54

Compound 54 was synthesized using an analogous synthetic sequence as that described for Compound 44. $^1$HNMR (600 MHz, DMSO-$d_6$) δ ppm 3.58-3.69 (m, 1H) 4.13 (dd, J=13.47, 4.39 Hz, 1H) 6.07 (d, J=3.81 Hz, 1H) 6.85 (d, J=7.32 Hz, 2H) 7.19-7.31 (m, 3H) 7.34 (s, 1H) 8.27 (d, J=5.27 Hz, 1H) 9.13 (s, 1H). LCMS (ESI) 299 (M+H).

124

Example 55

Synthesis of Compound 55

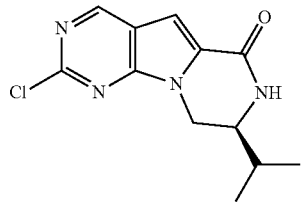 [SMILES: CC(C)[C@H]1Cn2c(cc3cnc(Cl)nc32)C(=O)N1]

tert-butyl N-[(1S)-1-[[(5-bromo-2-chloro-pyrimidin-4-yl)amino]methyl]-2-methyl-propyl] carbamate

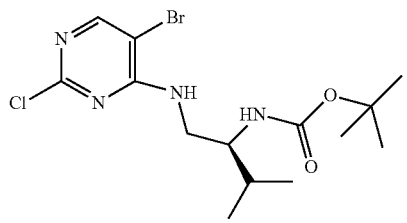 [SMILES: CC(C)[C@@H](CNc1nc(Cl)ncc1Br)NC(=O)OC(C)(C)C]

tert-butyl N-[(1S)-1-[[(5-bromo-2-chloro-pyrimidin-4-yl)amino]methyl]-2-methyl-propyl]carbamate was synthesized using 5-bromo-2,4-dichloro-pyrimidine and Intermediate E using analogous reaction conditions as described for tert-butyl N-[2-[(5-bromo-2-chloro-pyrimidin-4-yl)amino]-3-methyl-butyl]carbamate. $^1$HNMR (600 MHz, CHLOROFORM-d) δ ppm 0.95-1.02 (m, 6H) 1.35-1.45 (m, 9H) 1.75-1.90 (m, 1H) 3.35-3.48 (m, 1H) 3.52-3.61 (m, 1H) 3.64-3.76 (m, 1H) 4.56 (d, J=8.49 Hz, 1H) 6.47 (s, 1H) 8.07 (s, 1H). LCMS (ESI) 393 (M+H).

tert-butyl N-[(1S)-1-[[[2-chloro-5-(3,3-diethoxyprop-1-ynyl)pyrimidin-4-yl]amino]methyl]-2-methyl-propyl] carbamate

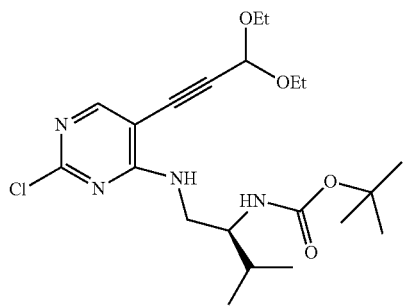 [SMILES: CCOC(C#Cc1cnc(Cl)nc1NC[C@@H](NC(=O)OC(C)(C)C)C(C)C)OCC]

tert-butyl N-[(1S)-1-[[[2-chloro-5-(3,3-diethoxyprop-1-ynyl)pyrimidin-4-yl]amino]methyl]-2-methyl-propyl]carbamate was synthesized using similar experimental conditions to those used in the synthesis (2S)—N2-[2-chloro-5-

(3,3-diethoxyprop-1-ynyl)pyrimidin-4-yl]-4-methyl-pentane-1,2-diamine. ¹HNMR (600 MHz, CHLOROFORM-d) δ ppm 0.90-1.00 (m, 6H) 1.18-1.25 (m, 6H) 1.34-1.36 (m, 9H) 1.69-1.90 (m, 1H) 3.34-3.82 (m, 6H) 4.53-4.77 (m, 1H) 5.45-5.55 (m, 1H) 6.37 (dd, J=15.37, 6.59 Hz, 1H) 6.56 (s, 1H) 8.05 (s, 1H). LCMS (ESI) 441 (M+H).

7-[(2S)-2-(tert-butoxycarbonylamino)-3-methyl-butyl]-2-chloro-pyrrolo[2,3-d]pyrimidine-6-carboxylic acid

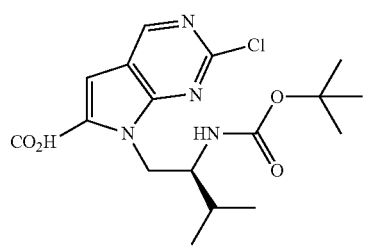 [SMILES: CC(C)[C@@H](Cn1c(C(=O)O)cc2cnc(Cl)nc21)NC(=O)OC(C)(C)C]

7-[(2 S)-2-(tert-butoxycarbonylamino)-3-methyl-butyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. ¹HNMR (600 MHz, CHLOROFORM-d) δ ppm 0.90 (d, J=6.73 Hz, 3H) 0.96 (d, J=7.03 Hz, 3H) 1.55-1.66 (m, 10H) 4.14 (dd, J=13.61, 3.95 Hz, 1H) 4.52-4.63 (m, 1H) 4.84 (dd, J=13.61, 1.32 Hz, 1H) 7.37 (s, 1H) 8.95 (s, 1H). LCMS (ESI) 383 (M+H).

Compound 55

Compound 55 was synthesized using an analogous synthetic sequence as that described for Compound 44. LCMS (ESI) 265 (M+H).

Example 56

Synthesis of Compound 56

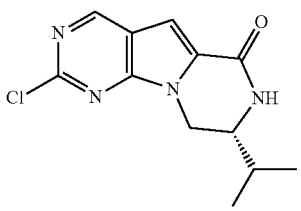 [SMILES: CC(C)[C@@H]1Cn2c(cc3cnc(Cl)nc32)C(=O)N1]

Compound 56 was synthesized using 5-bromo-2,4-dichloro-pyrimidine and Compound 17 as starting materials, and following a similar sequence of synthetic steps as for Compound 55. The analytical data was consistent with that described for its antipode (Compound 55). ¹HNMR (600 MHz, DMSO-d₆) δ ppm 0.88 (d, J=6.44 Hz, 6H) 1.73-1.86 (m, 1H) 3.67-3.76 (m, 2H) 4.11-4.21 (m, 1H) 7.13-7.19 (m, 1H) 8.56 (s, 1H) 9.05 (s, 1H). LCMS (ESI) 265 (M+H).

Example 57

Synthesis of Compound 57

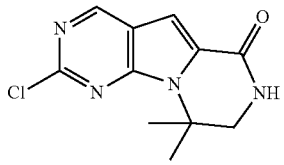 [SMILES: CC1(C)CNC(=O)c2cc3cnc(Cl)nc3n21]

tert-butyl N-[2-[5-bromo-2-chloro-pyrimidin-4-yl)amino]-2-methyl-propyl]carbamate

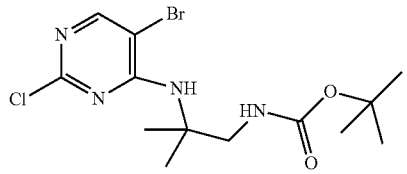 [SMILES: CC(C)(CNC(=O)OC(C)(C)C)Nc1nc(Cl)ncc1Br]

tert-butyl N-[2-[(5-bromo-2-chloro-pyrimidin-4-yl)amino]-2-methyl-propyl]carbamate was synthesized using 5-bromo-2,4-dichloro-pyrimidine and tert-butyl N-(2-amino-2-methyl-propyl)carbamate using analogous reaction conditions as described for tert-butyl N-[2-[(5-bromo-2-chloro-pyrimidin-4-yl)amino]-3-methyl-butyl]carbamate. LCMS (ESI) 379 (M+H).

tert-butyl N-[2-[[2-chloro-5-(3,3-diethoxyprop-1-ynyl)pyrimidin-4-yl]amino]-2-methyl-propyl]carbamate

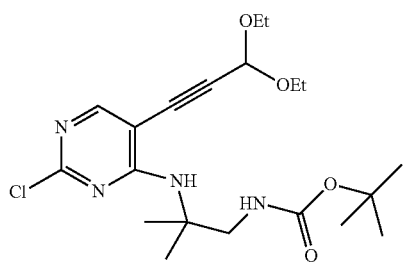 [SMILES: CCOC(C#Cc1cnc(Cl)nc1NC(C)(C)CNC(=O)OC(C)(C)C)OCC]

tert-butyl N-[2-[[2-chloro-5-(3,3-diethoxyprop-1-ynyl)pyrimidin-4-yl]amino]-2-methyl-propyl]carbamate was synthesized using similar experimental conditions to those used in the synthesis of (2S)—N2-[2-chloro-5-(3,3-diethoxyprop-1-ynyl)pyrimidin-4-yl]-4-methyl-pentane-1,2-diamine. ¹HNMR (600 MHz, DMSO-d₆) δ ppm 1.11-1.22 (m, 6H) 1.31-1.45 (m, 15H) 3.10-3.24 (m, 2H) 3.51-3.76 (m, 4H) 5.60 (s, 1H) 6.94 (s, 1H) 7.33 (t, J=6.44 Hz, 1H) 8.18 (s, 1H). LCMS (ESI) 427 (M+H).

7-[2-(tert-butoxycarbonylamino)-1,1-dimethyl-ethyl]-2-chloro-pyrrolo[2,3-d]pyrimidine-6-carboxylic acid

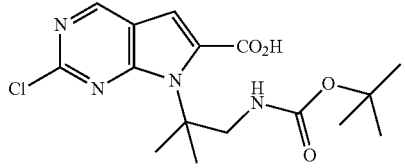 [SMILES: CC(C)(C)OC(=O)NCC(C)(C)n1c(C(=O)O)cc2cnc(Cl)nc21]

7-[2-(tert-butoxycarbonylamino)-1,1-dimethyl-ethyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-$d_6$) δ ppm 1.43 (s, 9H) 1.73 (s, 6H) 4.06 (s, 2H) 7.46 (s, 1H) 9.23 (s, 1H). LCMS (ESI) 369 (M+H).

Compound 57

Compound 57 was synthesized using an analogous synthetic sequence as that described for Compound 44. $^1$HNMR (600 MHz, DMSO-$d_6$) δ ppm 1.73 (s, 6H) 3.50 (d, J=2.93 Hz, 2H) 7.25 (s, 1H) 8.46-8.55 (m, 1H) 9.07 (s, 1H). LCMS (ESI) 251 (M+H).

Example 58

Synthesis of Compound 58

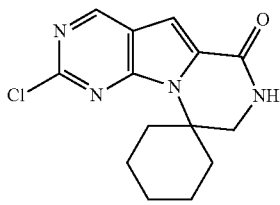 [SMILES: O=C1NCC2(CCCCC2)n2c1cc1cnc(Cl)nc12]

tert-butyl N-[[1-[(5-bromo-2-chloro-pyrimidin-4-yl)amino]cyclohexyl]methyl]carbamate

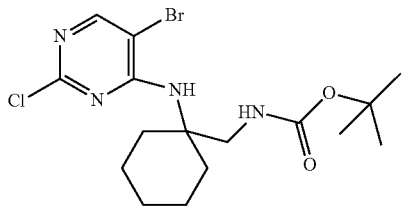 [SMILES: CC(C)(C)OC(=O)NCC1(Nc2nc(Cl)ncc2Br)CCCCC1]

tert-butyl N-[[1-[(5-bromo-2-chloro-pyrimidin-4-yl)amino]cyclohexyl]methyl] carbamate was synthesized using 5-bromo-2,4-dichloro-pyrimidine and Intermediate K using the analogous reaction conditions as described for tert-butyl N-[2-[(5-bromo-2-chloro-pyrimidin-4-yl)amino]-3-methyl-butyl] carbamate. $^1$HNMR (600 MHz, DMSO-$d_6$) δ ppm 1.18-1.54 (m, 17H) 2.23 (d, J=14.35 Hz, 2H) 3.36 (d, J=6.44 Hz, 2H) 5.82 (s, 1H) 6.93 (s, 1H) 8.22 (s, 1H). LCMS (ESI) 419 (M+H).

tert-butyl N-[[1-[[2-chloro-5-(3,3-diethoxyprop-1-ynyl)pyrimidin-4-yl]amino]cyclohexyl] methyl] carbamate

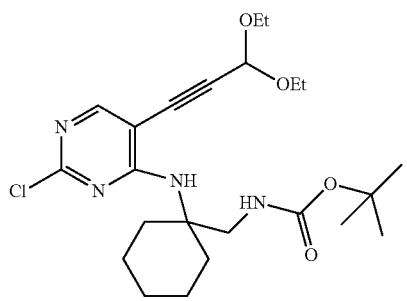 [SMILES: CCOC(C#Cc1cnc(Cl)nc1NC1(CNC(=O)OC(C)(C)C)CCCCC1)OCC]

tert-butyl N-[[1-[[2-chloro-5-(3,3-diethoxyprop-1-ynyl)pyrimidin-4-yl]amino]cyclohexyl]methyl] carbamate was synthesized using similar experimental conditions to those used in the synthesis of (2S)—N2-[2-chloro-5-(3,3-diethoxyprop-1-ynyl)pyrimidin-4-yl]-4-methyl-pentane-1,2-diamine. $^1$HNMR (600 MHz, DMSO-$d_6$) δ ppm 1.08-1.16 (m, 6H) 1.17-1.54 (m, 17H) 2.13 (br. s., 2H) 3.36 (d, J=6.73 Hz, 2H) 3.50-3.69 (m, 4H) 5.72 (s, 1H) 6.94 (s, 1H) 5.72 (br. s., 1H) 8.17 (s, 1H). LCMS (ESI) 467 (M+H).

7-[1-[(tert-butoxycarbonylamino)methyl]cyclohexyl]-2-chloro-pyrrolo[2,3-d]pyrimidine-6-carboxylic acid

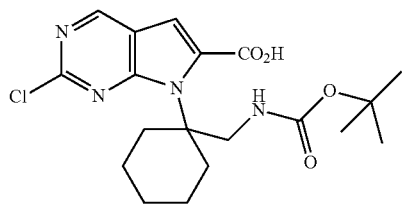 [SMILES: CC(C)(C)OC(=O)NCC1(n2c(C(=O)O)cc3cnc(Cl)nc32)CCCCC1]

7-[1-[(tert-butoxycarbonylamino)methyl] cyclohexyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d] pyrimidine-6-carboxylic acid. $^1$HNMR (600 MHz, DMSO-$d_6$) δ ppm 1.37-1.54 (m, 13H) 1.75 (br. s., 4H) 2.74 (br. s., 2H) 3.78-3.84 (m, 2H) 7.44-7.51 (m, 1H) 8.23 (s, 1H) 9.11 (s, 1H). LCMS (ESI) 409 (M+H).

Compound 58

Compound 58 was synthesized using an analogous synthetic sequence as that described for Compound 44. $^1$HNMR (600 MHz, DMSO-$d_6$) δ ppm 1.28 (br. s., 2H) 1.42 (br. s., 2H) 1.70 (br. s., 4H) 1.85-1.95 (m, 2H) 2.69 (m, 2H) 7.16-7.25 (m, 1H) 8.41 (br. s., 1H) 9.04 (s, 1H). LCMS 291 (M+H).

Example 59

Synthesis of Compound 59

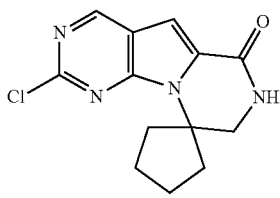 [SMILES: O=C1NCC2(CCCC2)n2c1cc1cnc(Cl)nc12]

tert-butyl N-[[1-[(5-bromo-2-chloro-pyrimidin-4-yl)amino]cyclopentyl]methyl] carbamate

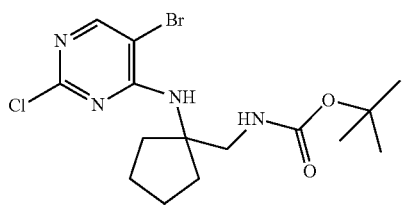 [SMILES: CC(C)(C)OC(=O)NCC1(Nc2nc(Cl)ncc2Br)CCCC1]

tert-butyl N-[[1-[(5-bromo-2-chloro-pyrimidin-4-yl)amino]cyclopentyl] methyl] carbamate was synthesized using 5-bromo-2,4-dichloro-pyrimidine and Intermediate L using analogous reaction conditions as described for tert-butyl N-[2-[(5-bromo-2-chloro-pyrimidin-4-yl)amino]-3-methyl-butyl]carbamate. $^1$HNMR (600 MHz, DMSO-$d_6$) δ ppm 1.34 (s, 9H) 1.50-1.58 (m, 2H) 1.63-1.78 (m, 4H) 1.96-2.06 (m, 2H) 3.25 (d, J=6.15 Hz, 2H) 6.71 (s, 1H) 7.18 (t, J=6.29 Hz, 1H) 8.20 (s, 1H). LCMS (ESI) 405 (M+H).

tert-butyl N-[[1-[[2-chloro-5-(3,3-diethoxyprop-1-ynyl)pyrimidin-4-yl]amino]cyclopentyl] methyl] carbamate

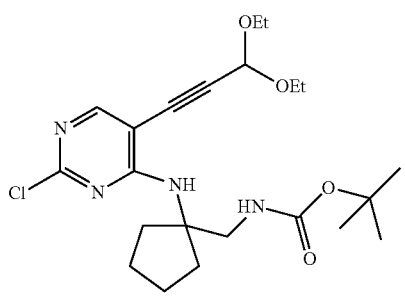 [SMILES: CCOC(C#Cc1cnc(Cl)nc1NC1(CNC(=O)OC(C)(C)C)CCCC1)OCC]

tert-butyl N-[[1-[[2-chloro-5-(3,3-diethoxyprop-1-ynyl)pyrimidin-4-yl]amino]cyclopentyl]methyl]carbamate was synthesized using similar experimental conditions to that used in the synthesis of (2S)—N2-[2-chloro-5-(3,3-diethoxyprop-1-ynyl)pyrimidin-4-yl]-4-methyl-pentane-1,2-diamine. LCMS (ESI) 453 (M+H).

7-[1-[(tert-butoxycarbonylamino)methyl]cyclopentyl]-2-chloro-pyrrolo[2,3-d]pyrimidine-6-carboxylic acid

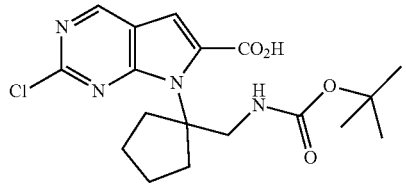 [SMILES: CC(C)(C)OC(=O)NCC1(n2c(C(=O)O)cc3cnc(Cl)nc32)CCCC1]

7-[1-[(tert-butoxycarbonylamino)methyl]cyclopentyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-$d_6$) δ ppm 1.47 (s, 9H) 1.74 (br. s., 2H) 1.88 (br. s., 2H) 2.04 (br. s., 2H) 2.41-2.45 (m, 2H) 4.06 (s, 2H) 7.45 (s, 1H) 9.11 (s, 1H). LCMS (ESI) 395 (M+H).

Compound 59

Compound 59 was synthesized using an analogous synthetic sequence as that described for Compound 44. $^1$HNMR (600 MHz, DMSO-$d_6$) δ ppm 1.72 (br. s., 2H) 1.86-1.93 (m, 2H) 1.99 (d, J=3.81 Hz, 2H) 2.40 (br. s., 2H) 3.48 (d, J=2.34 Hz, 2H) 7.22 (s, 1H) 8.53 (br. s., 1H) 9.05 (s, 1H). LCMS (ESI) 277 (M+H).

Example 60

Synthesis of Compound 60

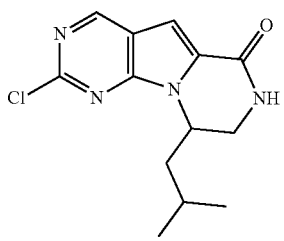 [SMILES: CC(C)CC1CNC(=O)c2cc3cnc(Cl)nc3n21]

tert-butyl N-[2-[(5-bromo-2-chloro-pyrimidin-4-yl)amino]-4-methyl-pentyl] carbamate

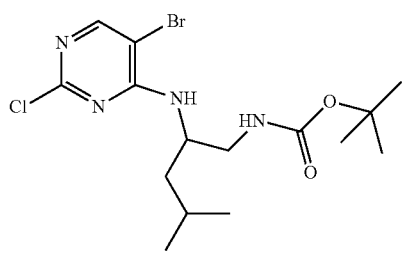 [SMILES: CC(C)CC(CNC(=O)OC(C)(C)C)Nc1nc(Cl)ncc1Br]

tert-butyl N-[2-[(5-bromo-2-chloro-pyrimidin-4-yl)amino]-4-methyl-pentyl]carbamate was synthesized using 5-bromo-2,4-dichloro-pyrimidine and Intermediate B using analogous reaction conditions as described for tert-butyl N-[2-[(5-bromo-2-chloro-pyrimidin-4-yl)amino]-3-methyl-butyl]carbamate. The analytical data is consistent with that described for the L-enantiomer.

tert-butyl N-[2-[[2-chloro-5-(3,3-diethoxyprop-1-ynyl)pyrimidin-4-yl]amino]-4-methyl-pentyl] carbamate

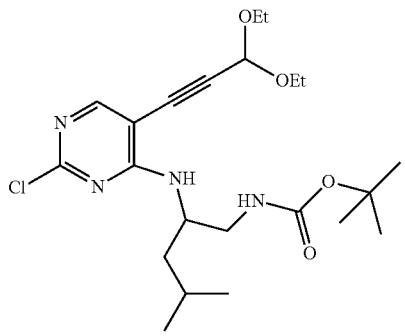 [SMILES: CCOC(C#Cc1cnc(Cl)nc1NC(CNC(=O)OC(C)(C)C)CC(C)C)OCC]

tert-butyl N-[2-[[2-chloro-5-(3,3-diethoxyprop-1-ynyl) pyrimidin-4-yl] amino]-4-methyl-pentyl]carbamate was synthesized using similar experimental conditions to that used in the synthesis of tert-butyl N-[2-[[2-chloro-5-(3,3-diethoxyprop-1-ynyl)pyrimidin-4-yl]amino]ethyl]carbamate. $^1$HNMR (600 MHz, CHLOROFORM-d) δ ppm 1.21-1.31 (m, 12H) 1.38-1.46 (m, 11H) 1.70 (m, 1H) 3.24 (m, 2H) 3.65-3.82 (m, 4H) 4.86 (br s., 1H), 5.65 (s, 1H) 5.85 (br s., 1H) 6.94 (s, 1H) 8.21 (s, 1H). LCMS (ESI) 455 (M+H).

7-[1-[(tert-butoxycarbonylamino)methyl]-3-methyl-butyl]-2-chloro-pyrrolo[2,3-d]pyrimidine-6-carboxylic acid

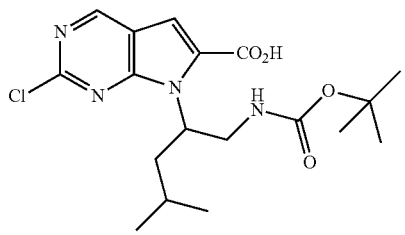 [SMILES: CC(C)CC(CNC(=O)OC(C)(C)C)n1c(C(=O)O)cc2cnc(Cl)nc21]

7-[1-[(tert-butoxycarbonylamino)methyl]-3-methyl-butyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. The analytical data was consistent with that described for the L-isomer.

Compound 60

Compound 60 was synthesized using an analogous synthetic sequence as that described for Compound 44. The analytical data was consistent with that described for the L-isomer.

Example 61

Synthesis of Compound 61

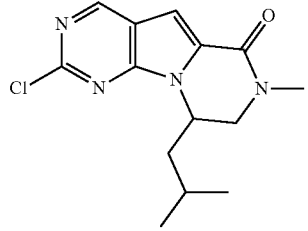 [SMILES: CC(C)CC1CN(C)C(=O)c2cc3cnc(Cl)nc3n21]

To a solution of Compound 60 (100 mg, 0.00024 mole) in DMF (3.0 mL) was added sodium hydride (60% dispersion in oil), (27.6 mg, 3 eq). After stirring for 15 mins, methyl iodide (30, 2 eq) was added. The contents were stirred at room temperature for 30 mins. After the addition of sat NaHCO$_3$, ethyl acetate was added. Separation of the organic layer followed by drying with magnesium sulfate and concentration under vacuum afforded the product. Analytical data was similar to the Compound 49.

Example 62

Synthesis of Compound 62

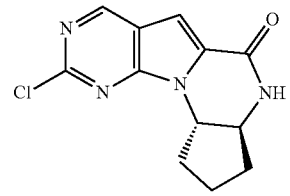 [SMILES: O=C1N[C@H]2CCC[C@@H]2n2c1cc1cnc(Cl)nc12]

tert-butyl N-[(1S,2S)-2-[(5-bromo-2-chloro-pyrimidin-4-yl)amino]cyclopentyl]carbamate

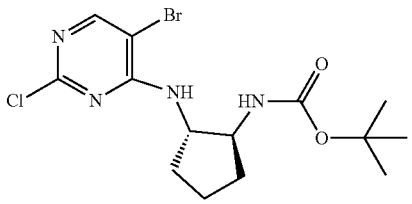 [SMILES: CC(C)(C)OC(=O)N[C@H]1CCC[C@@H]1Nc1nc(Cl)ncc1Br]

tert-butyl N-[(1S,2S)-2-[(5-bromo-2-chloro-pyrimidin-4-yl)amino]cyclopentyl]carbamate was synthesized by treating tert-butyl N-[(1S,2S)-2-aminocyclopentyl]carbamate with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate. $^1$HNMR (600 MHz, DMSO-d$_6$) δ ppm 1.27 (s, 9H) 1.42-1.54 (m, 2H) 1.56-1.65 (m, 2H) 1.80-1.88 (m, 1H) 1.96-2.01 (m, 1H) 3.88-3.96 (m, 1H) 4.03-4.09 (m, 1H) 6.91 (d, J=8.20 Hz, 1H) 7.41 (d, J=7.32 Hz, 1H) 8.18 (s, 1H). LCMS (ESI) 391 (M+H).

133 tert-butyl N-[(1S,2S)-2-[[2-chloro-5-(3,3-diethoxy-prop-1-ynyl)pyrimidin-4-yl]amino]cyclopentyl]carbamate

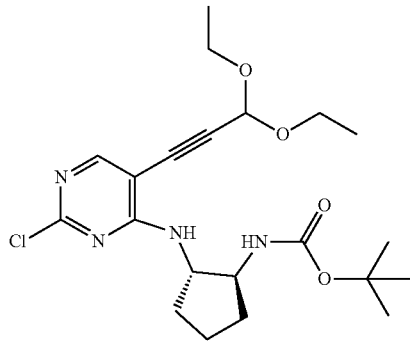 [SMILES: CCOC(C#Cc1cnc(Cl)nc1N[C@H]1CCC[C@@H]1NC(=O)OC(C)(C)C)OCC]

tert-butyl N-[(1S,2S)-2-[[2-chloro-5-(3,3-diethoxyprop-1-ynyl)pyrimidin-4-yl]amino]cyclopentyl]carbamate was synthesized using similar experimental conditions to that used in the synthesis of (2S)—N2-[2-chloro-5-(3,3-diethoxyprop-1-ynyl)pyrimidin-4-yl]-4-methyl-pentane-1,2-diamine. $^1$HNMR (600 MHz, DMSO-$d_6$) δ ppm 1.13 (t, 6H) 1.28 (s, 9H) 1.42-1.52 (m, 2H) 1.58-1.65 (m, 2H) 1.81-1.90 (m, 1H) 1.99-2.08 (m, 1H) 3.49-3.60 (m, 2H) 3.63-3.71 (m, 2H) 3.84-3.93 (m, 1H) 3.96-4.04 (m, 1H) 5.53 (s, 1H) 6.96 (d, J=7.90 Hz, 1H) 7.34 (d, J=7.03 Hz, 1H) 8.14 (s, 1H). LCMS (ESI) 439 (M+H).

7-[(1S,2S)-2-(tert-butoxycarbonylamino)cyclopentyl]-2-chloro-pyrrolo[2,3-d]pyrimidine-6-carboxylic acid

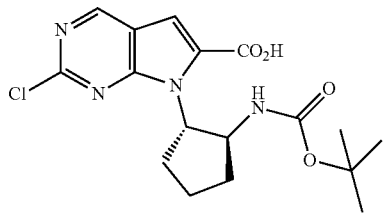 [SMILES: CC(C)(C)OC(=O)N[C@H]1CCC[C@@H]1n1c(C(=O)O)cc2cnc(Cl)nc21]

7-[(1 S,2 S)-2-(tert-butoxycarbonylamino)cyclopentyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-$d_6$) δ ppm 1.41-1.52 (m, 9H) 1.55-1.68 (m, 1H) 1.88-2.00 (m, 2H) 2.05-2.15 (m, 1H) 2.26-2.35 (m, 1H) 2.71-2.89 (m, 1H) 4.01-4.16 (m, 1H) 4.28-4.45 (m, 1H) 7.41 (s, 1H) 9.11 (s, 1H). LCMS (ESI) 381 (M+H).

Compound 62

Compound 62 was synthesized using an analogous synthetic sequence as that described for Compound 44. $^1$HNMR (600 MHz, DMSO-$d_6$) δ ppm 1.48-1.60 (m, 1H) 1.88-1.98 (m, 3H) 1.99-2.08 (m, 1H) 2.66-2.75 (m, 1H) 3.63-3.74 (m, 1H) 3.99-4.12 (m, 1H) 7.21 (s, 1H) 8.89 (s, 1H) 9.04 (s, 1H). LCMS (ESI) 263 (M+H).

134

Example 63

Synthesis of Compound 63

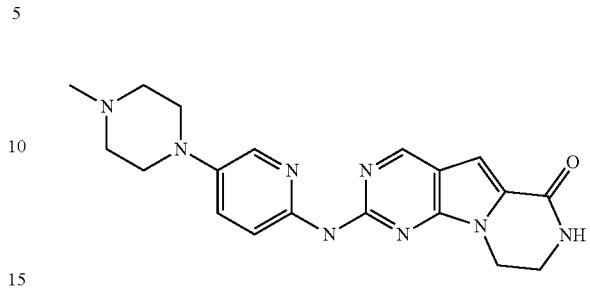

To chloro tricycliclactam (0.050 g, 0.225 mmole) in dioxane (2.0 mL) under nitrogen was added 5-(4-methylpiperazin-1-yl)pyridin-2-amine (0.052 g, 1.2 eq, 0.270 mmole) followed by the addition of Pd$_2$(dba)3 (18.5 mg), BINAP (25 mg) and sodium-tert-butoxide (31 mg, 0.324 mmole). The contents of the flask are degassed for 10 minutes and then heated to 100 degrees for 12 hours. The crude reaction was loaded on a silica gel column and eluted with DCM/MeOH (0-15%) to afford the desired product (26 mg). To this compound dissolved in DCM/MeOH (10%) was added 3N HCl in iso-propanol (2 eq) and the reaction was stirred overnight. Concentration under vacuum afforded the hydrochloride salt. $^1$HNMR ($d_6$-DMSO) δ ppm 11.13 (brs, 1H), 9.07 (s, 1H), 8.42 (s, 1H), 8.03 (br m 1H), 7.99 (s, 1H), 7.67 (brm, 1H), 7.18 (s, 1H), 4.33 (m, 2H), 3.79 (m, 2H), 3.64 (m, 2H), 3.50 (m, 2H), 3.16 (m, 4H), 2.79 (s, 3H). LCMS (ESI) 379 (M+H).

Example 64

Synthesis of Compound 64

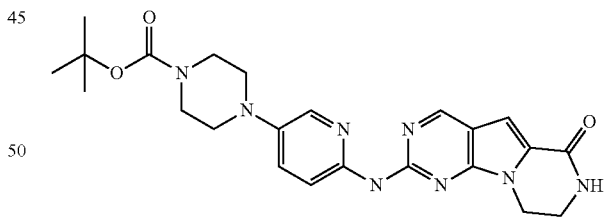

To chloro tricycliclactam (0.075 g, 0.338 mmole) in dioxane (3.5 mL) under nitrogen was added tert-butyl 4-(6-amino-3-pyridyl)piperazine-1-carboxylate (0.098 g, 1.05 eq) followed by the addition of Pd$_2$(dba)3 (27 mg), BINAP (36 mg) and sodium-tert-butoxide (45 mg). The contents were heated at reflux for 11 hrs. The crude reaction was loaded onto a silica gel column and eluted with DCM/MeOH (0-10%) to afford the desired product (32 mg). $^1$HNMR ($d_6$-DMSO) δ ppm 9.48 (s, 1H), 8.84 (s, 1H), 8.29 (s, 1H), 8.18 (s, 1H), 7.99 (s, 1H), 7.42 (m, 1H), 6.98 (s, 1H), 4.23 (m, 2H), 3.59 (m, 2H), 3.45 (m, 4H), 3.50 (m, 2H), 3.05 (m, 4H). LCMS (ESI) 465 (M+H).

Example 65

Synthesis of Compound 65

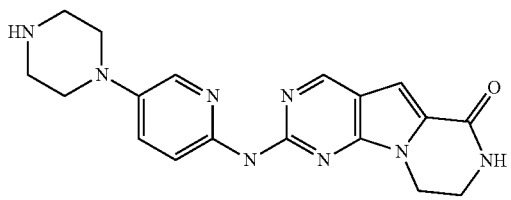 [SMILES: O=C1NCCn2c1cc1cnc(Nc3ccc(N4CCNCC4)cn3)nc12]

To a solution of Compound 64 (23 mg) in 10% DCM/MeOH was added 10 mL of a 3M solution of HCl in iso-propanol. The contents were stirred for 16 hrs. Concentration of the reaction mixture afforded the hydrochloride salt. $^1$HNMR (d$_6$-DMSO) δ ppm 9.01 (s, 1H), 7.94 (m, 1H), 7.86 (m, 1H), 7.23 (s, 1H), 4.30 (m, 2H), 3.64 (m, 2H), 3.36 (m, 4H), 3.25 (m, 4H). LCMS (ESI) 465 (M+H).

Example 66

Synthesis of Compound 66

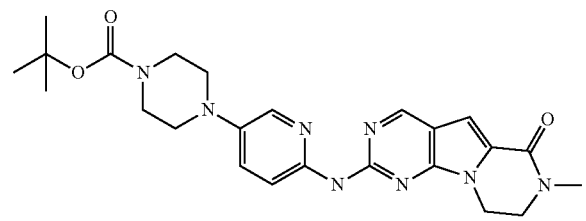 [SMILES: CN1CCn2c(cc3cnc(Nc4ccc(N5CCN(C(=O)OC(C)(C)C)CC5)cn4)nc32)C1=O]

To chloro-N-methyltricyclic amide (0.080 g, 0.338 mmole) in dioxane (3.5 mL) under nitrogen was added tert-butyl 4-(6-amino-3-pyridyl)piperazine-1-carboxylate 0.102 g (1.1 eq) followed by the addition of Pd$_2$(dba)3 (27 mg), BINAP (36 mg) and sodium-tert-butoxide (45 mg). The contents were heated at reflux for 11 hrs. The crude product was purified using silica gel column chromatography with an eluent of dichloromethane/methanol (0-5%) to afford the desired product (44 mg). $^1$HNMR (d$_6$-DMSO) δ ppm 9.49 (s, 1H), 8.85 (s, 1H), 8.32 (m, 1H), 8.02 (s, 1H), 7.44 (m, 1H), 7.00 (s, 1H), 4.33 (m, 2H), 3.80 (m, 2H), 3.48 (m, 4H), 3.07 (m, 4H), 3.05 (s, 3H), 1.42 (s, 9H). LCMS (ESI) 479 (M+H).

Example 67

Synthesis of Compound 67

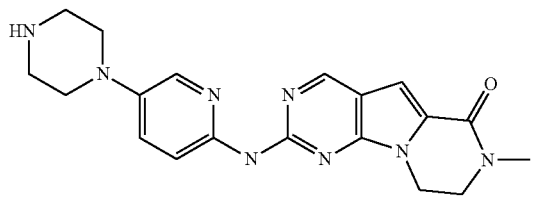 [SMILES: CN1CCn2c(cc3cnc(Nc4ccc(N5CCNCC5)cn4)nc32)C1=O]

To Compound 66 (32 mg) was added 3N HCL (10 mL) in isopropanol and the contents were stirred at room temperature overnight for 16 hrs. Concentration afforded the hydrochloride salt. $^1$HNMR (d$_6$-DMSO) δ ppm 9.13 (m, 2H), 8.11 (m, 1H), 8.10 (s, 1H), 7.62 (m, 1H), 7.21 (s, 1H), 4.43 (m, 2H), 3.85 (m, 2H), 3.41 (m, 4H), 3.28 (m, 4H), 3.08 (s, 3H). LCMS (ESI) 379 (M+H).

Example 68

Synthesis of Compound 68

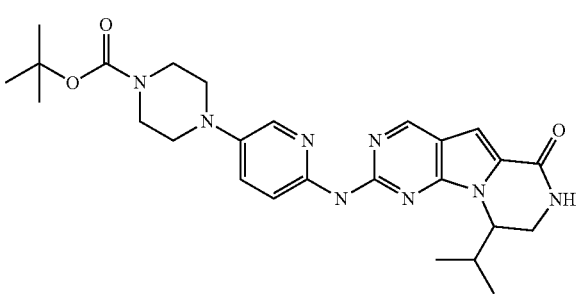 [SMILES: CC(C)C1CNC(=O)c2cc3cnc(Nc4ccc(N5CCN(C(=O)OC(C)(C)C)CC5)cn4)nc3n21]

Compound 68 was synthesized using similar experimental conditions to that described for compound 64. $^1$HNMR (600 MHz, DMSO-d$_6$) δ ppm 0.79 (d, J=7.03 Hz, 3H) 1.01 (d, J=6.73 Hz, 3H) 1.35-1.48 (m, 9H) 2.16 (dd, J=14.64, 6.73 Hz, 1H) 3.00-3.14 (m, 4H) 3.40-3.51 (m, 4H) 3.51-3.60 (m, 1H) 3.63-3.74 (m, 1H) 4.44 (dd, J=7.90, 3.81 Hz, 1H) 6.99 (s, 1H) 7.46 (dd, J=8.93, 2.78 Hz, 1H) 7.94-8.09 (m, 2H) 8.31 (dd, J=9.08, 1.46 Hz, 1H) 8.85 (s, 1H) 9.46 (s, 1H). LCMS (ESI) 507 (M+H).

Example 69

Synthesis of Compound 69

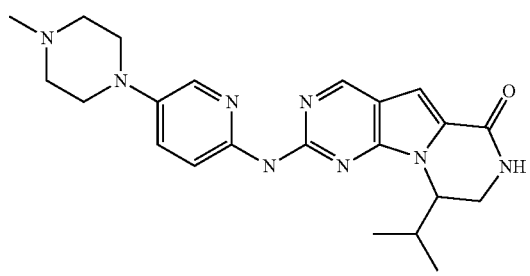 [SMILES: CC(C)C1CNC(=O)c2cc3cnc(Nc4ccc(N5CCN(C)CC5)cn4)nc3n21]

Compound 69 was synthesized using similar experimental conditions to those described for compound 63 and was recovered as an HCl salt. $^1$HNMR (600 MHz, DMSO-d$_6$) δ ppm 0.77-0.86 (m, 3H) 0.96 (d, J=7.03 Hz, 3H) 2.10-2.24 (m, 1H) 3.07 (s, 3H) 3.37-3.79 (m, 8H) 4.00 (dd, J=13.61, 4.54 Hz, 2H) 4.63-4.73 (m, 1H) 7.20 (s, 1H) 7.58-7.71 (m, 1H) 7.99 (d, J=2.34 Hz, 1H) 8.12 (d, J=9.37 Hz, 1H) 9.11 (s, 1H) 9.41 (br. s., 2H) 11.76 (br. s., 1H). LCMS (ESI) 421 (M+H).

Example 70

Synthesis of Compound 70

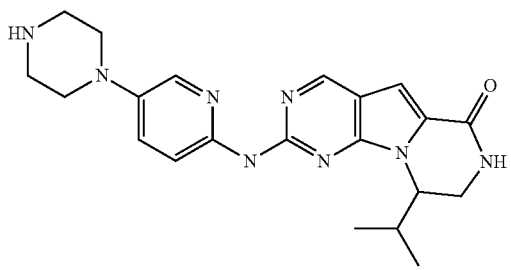 [SMILES: CC(C)C1CNC(=O)c2cc3cnc(Nc4ccc(N5CCNCC5)cn4)nc3n21]

Compound 70 was synthesized using similar experimental conditions to those described for compounds 64 and 65 and was recovered as an HCl salt. The characterization data (NMR and LCMS) was consistent with that reported for compound 71.

Example 71

Synthesis of Compound 71

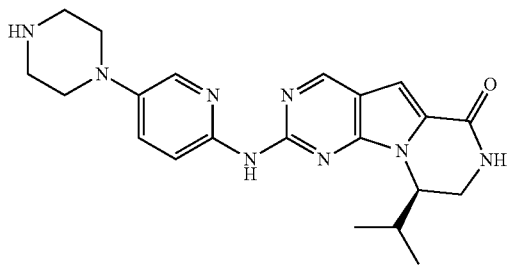 [SMILES: CC(C)[C@@H]1CNC(=O)c2cc3cnc(Nc4ccc(N5CCNCC5)cn4)nc3n21]

Compound 71 was synthesized using similar experimental conditions to those described for compounds 64 and 65 and was recovered as an HCl salt. $^1$HNMR (600 MHz, DMSO-$d_6$) δ ppm 0.79 (d, J=6.73 Hz, 3H) 1.01 (d, J=6.73 Hz, 3H) 2.18 (dd, J=14.49, 7.17 Hz, 1H) 3.18-3.84 (m, 10H) 4.53-4.71 (m, 1H) 7.24 (s, 1H) 7.65 (d, J=9.37 Hz, 1H) 8.01 (d, J=2.64 Hz, 1H) 8.14 (d, J=1.46 Hz, 1H) 8.35 (d, J=5.27 Hz, 1H) 9.14 (s, 1H) 9.46 (s, 2H) 11.80 (s, 1H) LCMS (ESI) 407 (M+H).

Example 72

Synthesis of Compound 72 (Compound UUU)

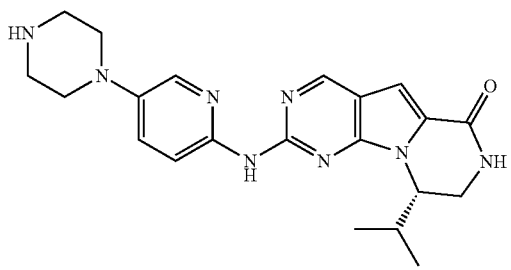 [SMILES: CC(C)[C@H]1CNC(=O)c2cc3cnc(Nc4ccc(N5CCNCC5)cn4)nc3n21]

Compound 72 was synthesized using similar experimental conditions to that described for compounds 64 and 65 and was recovered as an HCl salt. $^1$HNMR (600 MHz, DMSO-$d_6$) δ ppm 0.77 (d, J=7.03 Hz, 3H) 0.99 (d, J=6.73 Hz, 3H) 2.10-2.24 (m, 1H) 3.18-3.81 (m, 10H) 4.54-4.69 (m, 1H) 7.22 (s, 1H) 7.63 (d, J=9.08 Hz, 1H) 7.99 (d, J=2.63 Hz, 1H) 8.11 (s, 1H) 8.33 (d, J=5.27 Hz, 1H) 9.12 (s, 1H) 9.43 (s, 2H) 11.77 (s, 1H). LCMS (ESI) 407 (M+H).

Example 73

Synthesis of Compound 73

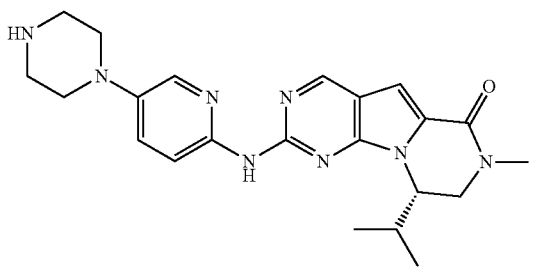 [SMILES: CC(C)[C@H]1CN(C)C(=O)c2cc3cnc(Nc4ccc(N5CCNCC5)cn4)nc3n21]

Compound 73 was synthesized using similar experimental conditions to those described for compounds 64 and 65 and was recovered as an HCl salt. $^1$H NMR (600 MHz, DMSO-$d_6$) δ ppm 0.84 (d, J=6.73 Hz, 3H) 0.98 (d, J=6.73 Hz, 3H) 2.12-2.26 (m, 1H) 3.09 (s, 3H) 3.22-3.81 (m, 8H) 4.01 (dd, J=13.61, 4.25 Hz, 2H) 4.59-4.72 (m, 1H) 7.19 (s, 1H) 7.74 (s, 1H) 7.96-8.10 (m, 2H) 9.08 (s, 1H) 9.22 (s, 2H). LCMS (ESI) 421 (M+H).

Example 74

Synthesis of Compound 74

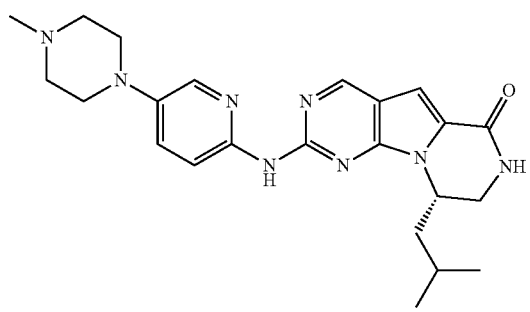 [SMILES: CC(C)C[C@H]1CNC(=O)c2cc3cnc(Nc4ccc(N5CCN(C)CC5)cn4)nc3n21]

Compound 74 was synthesized using similar experimental conditions to those described for compound 63 and was recovered as an HCl salt. $^1$HNMR (600 MHz, DMSO-$d_6$) δ ppm 0.85 (d, J=4.98 Hz, 3H) 0.95 (d, J=4.98 Hz, 3H) 1.42-1.70 (m, 3H) 2.77 (d, J=2.93 Hz, 3H) 3.07-4.14 (m, 10H) 4.95 (s, 1H) 7.20 (s, 1H) 7.66 (d, J=9.66 Hz, 1H) 7.94

(s, 1H) 8.08-8.16 (m, 1H) 8.33 (d, J=4.68 Hz, 1H) 9.09 (s, 1H) 11.38 (s, 1H) 11.71 (s, 1H). LCMS (ESI) 435 (+H).

Example 75

Synthesis of Compound 75

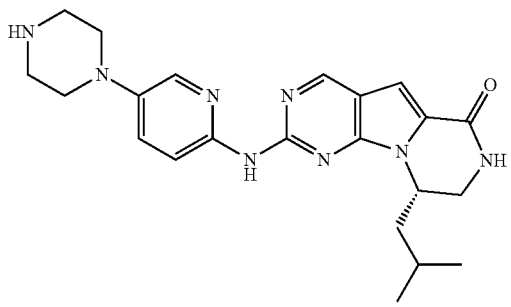 [SMILES: CC(C)C[C@H]1CNC(=O)c2cc3cnc(Nc4ccc(N5CCNCC5)cn4)nc3n21]

Compound 75 was synthesized using similar experimental conditions to those described for compounds 64 and 65 and was recovered as an HCl salt. $^1$H NMR (600 MHz, DMSO-$d_6$) δ ppm 0.87 (d, J=6.15 Hz, 3H) 0.94 (d, J=6.15 Hz, 3H) 1.57 (d, J=84.61 Hz, 3H) 3.05 (s, 3H) 3.13-3.55 (m, 8H) 3.69 (d, J=78.17 Hz, 2H) 4.90 (s, 1H) 7.15 (s, 1H) 7.63-7.85 (m, 1H) 7.93 (s, 1H) 8.26 (s, 1H) 9.03 (s, 1H) 9.20 (s, 2H). LCMS (ESI) 421 (M+H).

Example 76

Synthesis of Compound 76

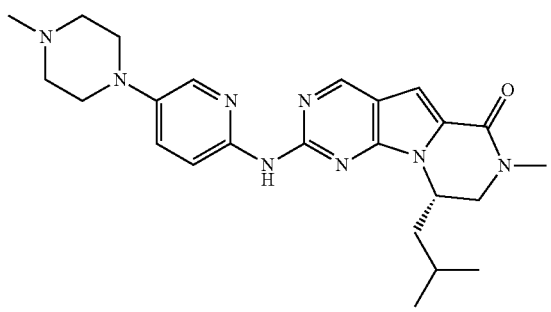

Compound 76 was synthesized using similar experimental conditions to those described for compound 63 and was recovered as an HCl salt. $^1$HNMR (600 MHz, DMSO-$d_6$) δ ppm 0.85 (d, J=6.44 Hz, 3H) 0.95 (d, J=6.44 Hz, 3H) 1.43-1.70 (m, 3H) 2.78 (d, J=2.93 Hz, 3H) 3.05 (s, 3H) 3.24-3.84 (m, 8H) 4.01 (d, J=9.66 Hz, 2H) 4.89-5.01 (m, 1H) 7.15 (s, 1H) 7.77 (s, 1H) 7.91-8.05 (m, 2H) 9.03 (s, 1H) 10.96-11.55 (m, 2H). LCMS (ESI) 449 (M+H).

Example 77

Synthesis of Compound 77

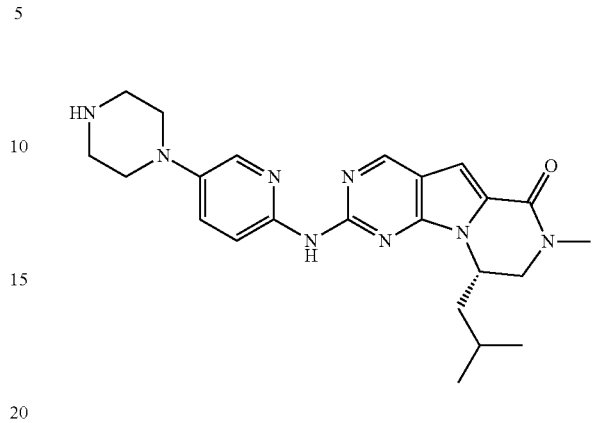

Compound 77 was synthesized using similar experimental conditions to those described for compounds 64 and 65 and was recovered as an HCl salt. $^1$H NMR (600 MHz, DMSO-$d_6$) δ ppm 0.83-0.88 (d, J=6.15 Hz, 3H) 0.95 (d, J=6.15 Hz, 3H) 1.40-1.71 (m, 3H) 3.28-3.83 (m, 8H) 4.00 (d, J=3.22 Hz, 2H) 4.91-5.08 (m, 1H) 7.17 (s, 1H) 7.68 (d, J=9.66 Hz, 1H) 7.93 (s, 1H) 8.07 (s, 1H) 9.06 (s, 1H) 9.40 (s, 2H) 11.59 (s, 1H). LCMS (ESI) 435 (M+H).

Example 78

Synthesis of Compound 78

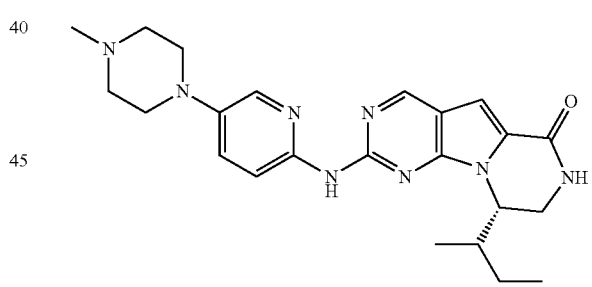

To Compound 50 0.060 g (0.205 mmole) was added 5-(4-methylpiperazin-1-yl)pyridin-2-amine (35.42 mg, 0.9 eq) followed by the addition of 1,4-dioxane (3 mL). After degassing with nitrogen, Pd$_2$dba$_3$ (12 mg), BINAP (16 mg) and sodium tert-butoxide (24 mg) were added. The contents were then heated at 90 degrees in a CEM Discovery microwave for 3 hrs. The reaction was then loaded onto a silica gel column and purified by eluting with DCM/MeOH (0-15%). $^1$HNMR (600 MHz, DMSO-$d_6$) δ ppm 0.75 (t, J=7.47 Hz, 3H) 0.91 (d, J=6.73 Hz, 3H) 1.04-1.20 (m, 2H) 1.80-1.98 (m, 1H) 2.77 (d, J=3.81 Hz, 3H) 2.94-3.90 (m, 10H) 4.54-4.68 (m, 1H) 7.06-7.23 (m, 2H) 7.56-7.75 (m, 1H) 7.90-8.12 (m, 2H) 8.29 (s, 1H) 9.07 (s, 1H) 10.98-11.74 (m, 2H). LCMS (ESI) 435 (M+H).

Example 79

Synthesis of Compound 79

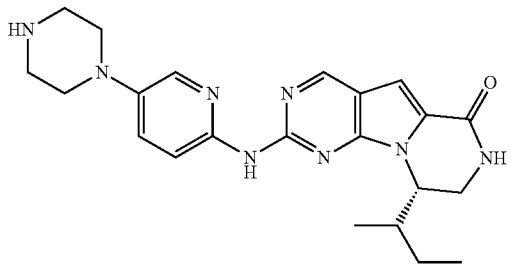 [SMILES: CCC(C)[C@H]1CNC(=O)c2cc3cnc(Nc4ccc(N5CCNCC5)cn4)nc3n21]

Compound 79 was synthesized in a similar manner to that described for compound 78 followed by the deblocking step described for compound 65 and was converted to an HCl salt. ¹HNMR (600 MHz, DMSO-$d_6$) δ ppm 0.75 (t, J=7.32 Hz, 3H) 0.90 (d, J=6.73 Hz, 3H) 1.07-1.15 (m, 2H) 1.85-1.94 (m, 1H) 3.17-3.75 (m, 10H) 4.58-4.67 (m, 1H) 7.17 (s, 1H) 7.71 (s, 1H) 7.96 (s, 1H) 7.98-8.05 (m, 1H) 8.28 (d, J=4.10 Hz, 1H) 9.06 (s, 1H) 9.39 (s, 2H). LCMS (ESI) 421 (M+H).

Example 80

Synthesis of Compound 80

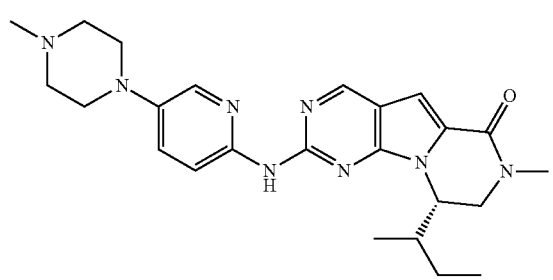

Compound 80 was synthesized in a similar manner to that described for compound 78. ¹HNMR (600 MHz, DMSO-$d_6$) δ ppm 0.78 (t, J=7.32 Hz, 3H) 0.86 (d, J=6.73 Hz, 3H) 1.13-1.21 (m, 2H) 1.84-1.96 (m, 1H) 2.77 (d, J=4.39 Hz, 3H) 3.04 (s, 3H) 3.11-3.84 (m, 8H) 3.98 (dd, J=13.61, 4.25 Hz, 2H) 4.66-4.74 (m, 1H) 7.17 (s, 1H) 7.64 (s, 1H) 7.96 (d, J=2.34 Hz, 1H) 8.03-8.13 (m, 1H) 9.08 (s, 1H) 11.26 (s, 1H) 11.66 (s, 1H). LCMS (ESI) 449 (M+H).

Example 81

Synthesis of Compound 81

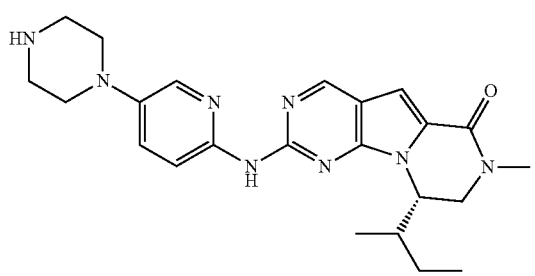 [SMILES: CCC(C)[C@H]1CN(C)C(=O)c2cc3cnc(Nc4ccc(N5CCNCC5)cn4)nc3n21]

The compound was synthesized in a similar manner to that described for compound 78 followed by the deblocking step described for compound 65 and was converted to an HCl salt. ¹HNMR (600 MHz, DMSO-$d_6$) δ ppm 0.78 (t, J=7.32 Hz, 3H) 0.85 (d, J=6.73 Hz, 3H) 1.10-1.27 (m, 2H) 1.82-1.99 (m, 1H) 3.04 (s, 3H) 3.28-3.77 (m, 8H) 3.97 (dd, J=13.91, 4.54 Hz, 2H) 4.62-4.75 (m, 1H) 7.07-7.24 (m, 1H) 7.62-7.75 (m, 1H) 7.94 (d, J=2.34 Hz, 1H) 7.97-8.08 (m, 1H) 9.05 (s, 1H) 9.29 (s, 2H). LCMS (ESI) 435 (M+H).

Example 82

Synthesis of Compound 82

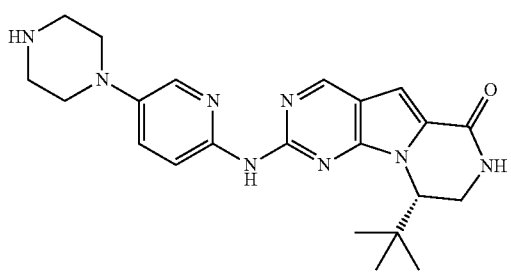 [SMILES: CC(C)(C)[C@H]1CNC(=O)c2cc3cnc(Nc4ccc(N5CCNCC5)cn4)nc3n21]

The compound was synthesized in a similar manner to that described for compound 78 followed by the deblocking step described for compound 65 and was converted to an HCl salt. ¹HNMR (600 MHz, DMSO-$d_6$) δ ppm 0.96 (s, 9H) 3.15-3.87 (m, 10H) 4.42-4.53 (m, 1H) 6.99 (s, 1H) 7.24 (s, 1H) 8.06 (s, 1H) 8.11-8.21 (m, 1H) 8.79-8.98 (m, 2H) 9.25 (s, 2H) 9.88 (s, 1H). LCMS (ESI) 421 (M+H).

Example 83

Synthesis of Compound 83

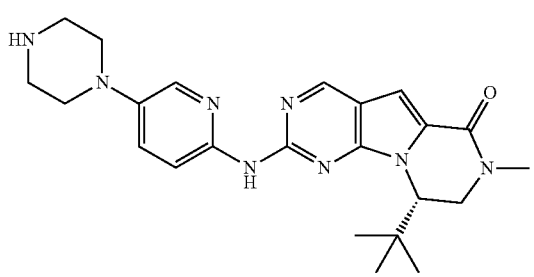 [SMILES: CN1C[C@H](C(C)(C)C)n2c(cc3cnc(Nc4ccc(N5CCNCC5)cn4)nc32)C1=O]

Compound 83 was synthesized in a similar manner to that described for compound 78 followed by the deblocking step described for compound 65 and was converted to an HCl salt. ¹HNMR (600 MHz, DMSO-$d_6$) δ ppm 0.95 (s, 9H) 2.79 (d, J=4.10 Hz, 3H) 3.06-3.86 (m, 10H) 4.56-4.67 (m, 1H) 7.17 (s, 1H) 7.70 (s, 1H) 7.96 (d, J=2.63 Hz, 1H) 7.99-8.08 (m, 1H) 8.26 (s, 1H) 9.06 (s, 1H) 10.80 (s, 1H). LCMS (ESI) 435 (M+H).

Example 84

Synthesis of Compound 84

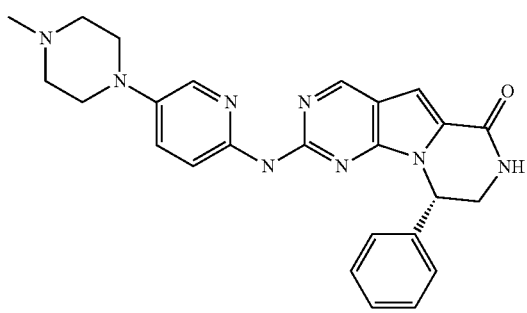 [SMILES: CN1CCN(c2ccc(Nc3ncc4cc5n(c4n3)[C@@H](c3ccccc3)CNC5=O)nc2)CC1]

Compound 84 was synthesized in a similar manner to that described for compound 78 and was converted to an HCl salt. $^1$HNMR (600 MHz, DMSO-d$_6$) δ ppm 2.75-2.81 (m, 3H) 3.12-3.16 (m, 2H) 3.46-3.54 (m, 4H) 3.60-3.69 (m, 2H) 3.72-3.79 (m, 1H) 4.07-4.18 (m, 2H) 6.06-6.09 (m, 1H) 6.90 (d, J=7.61 Hz, 2H) 7.20-7.31 (m, 3H) 7.33 (s, 1H) 7.49-7.55 (m, 1H) 7.62-7.70 (m, 1H) 7.92 (d, J=2.93 Hz, 1H) 8.22 (s, 1H) 9.14 (s, 1H). LCMS (ESI) 455 (M+H).

Example 85

Synthesis of Compound 85

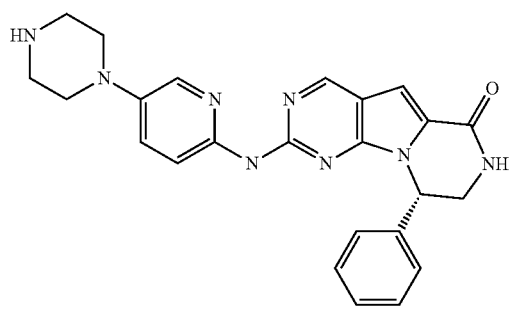 [SMILES: O=C1NC[C@H](c2ccccc2)n2c1cc1cnc(Nc3ccc(N4CCNCC4)cn3)nc12]

Compound 85 was synthesized in a similar manner to that described for compound 78 followed by the deblocking step described for compound 65 and was converted to an HCl salt. $^1$HNMR (600 MHz, DMSO-d$_6$) δ ppm 3.21 (s, 4H) 3.35-3.67 (m, 5H) 4.07-4.20 (m, 2H) 6.13 (s, 1H) 6.90 (d, J=7.32 Hz, 2H) 7.22-7.31 (m, 3H) 7.36 (s, 1H) 7.48 (d, J=9.37 Hz, 1H) 7.93 (d, J=2.34 Hz, 1H) 8.04-8.11 (m, 1H) 8.25 (d, J=4.98 Hz, 1H) 9.17 (s, 1H) 11.77 (br, s., 1H). LCMS (ESI) 441 (M+H).

Example 86

Synthesis of Compound 86

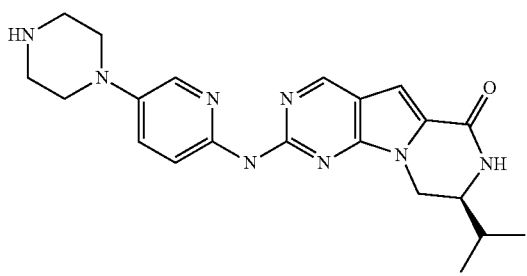 [SMILES: CC(C)[C@H]1Cn2c(cc3cnc(Nc4ccc(N5CCNCC5)cn4)nc32)C(=O)N1]

Compound 86 was synthesized in a similar manner to that described for compound 78 followed by the deblocking step described for compound 65 and was converted to an HCl salt. $^1$HNMR (600 MHz, DMSO-d$_6$) δ ppm 0.90 (d, J=6.15 Hz, 6H) 1.72-1.89 (m, 1H) 3.15-3.92 (m, 9H) 4.10-4.46 (m, 2H) 7.18 (s, 1H) 7.59 (d, J=8.78 Hz, 1H) 8.00 (s, 1H) 8.13 (d, J=9.37 Hz, 1H) 8.55 (s, 1H) 9.09 (s, 1H) 9.67 (s, 2H) 11.91 (s, 1H). LCMS (ESI) 407 (ESI).

Example 87

Synthesis of Compound 87

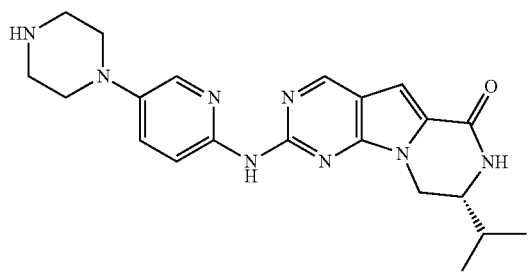 [SMILES: CC(C)[C@@H]1Cn2c(cc3cnc(Nc4ccc(N5CCNCC5)cn4)nc32)C(=O)N1]

Compound 87 was synthesized in a manner similar to compound 86 and was converted to an HCl salt. The characterization data (NMR and LCMS) was similar to that obtained for the antipode compound 86.

Example 88

Synthesis of Compound 88

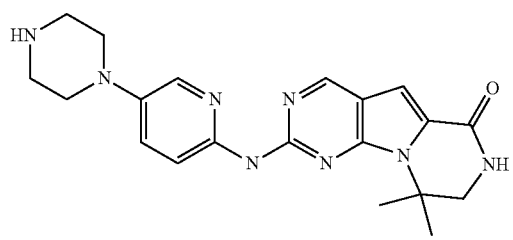 [SMILES: CC1(C)CNC(=O)c2cc3cnc(Nc4ccc(N5CCNCC5)cn4)nc3n21]

Compound 88 was synthesized in a similar manner to that described for compound 78 followed by the deblocking step described for compound 65 and was converted to an HCl salt. $^1$HNMR (600 MHz, DMSO-d$_6$) δ ppm 1.78 (s, 6H) 3.40-3.53 (m, 6H) 3.64-3.73 (m, 4H) 7.27 (s, 1H) 7.66 (d, J=9.37 Hz, 1H) 7.98 (d, J=2.34 Hz, 1H) 8.12 (br. s., 1H) 8.47 (br. s., 1H) 9.11 (s, 1H) 9.45 (br. s., 2H) 11.62 (br. s., 1H). LCMS (ESI) 393 (M+H).

Example 89

Synthesis of Compound 89 (Also Referred to as Compound T)

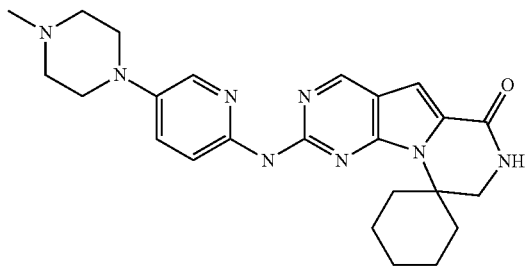 [SMILES: CN1CCN(c2ccc(Nc3ncc4cc5n(c4n3)C3(CCCCC3)CNC5=O)nc2)CC1]

Compound 89 was synthesized in a similar manner to that described for compound 78 and was converted to an HCl salt. $^1$HNMR (600 MHz, DMSO-d$_6$) δ ppm 1.47 (br. s., 6H) 1.72 (br. s., 2H) 1.92 (br. s., 2H) 2.77 (br. s., 3H) 3.18 (br. s., 2H) 3.46 (br. s., 2H) 3.63 (br. s., 2H) 3.66 (d, J=6.15 Hz, 2H) 3.80 (br. s., 2H) 7.25 (s, 1H) 7.63 (br. s., 2H) 7.94 (br. s., 1H) 8.10 (br. s., 1H) 8.39 (br. s., 1H) 9.08 (br. s., 1H) 11.59 (br. s., 1H). LCMS (ESI) 447 (M+H).

Example 90

Synthesis of Compound 90 (Also Referred to as Compound Q)

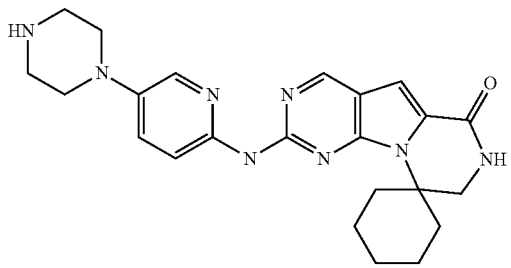 [SMILES: O=C1NCC2(CCCCC2)n2c1cc1cnc(Nc3ccc(N4CCNCC4)cn3)nc12]

Compound 90 was synthesized in a similar manner to that described for compound 78 followed by the deblocking step described for compound 65 and was converted to an HCl salt. $^1$HNMR (600 MHz, DMSO-d$_6$) δ ppm 1.27-1.64 (m, 6H) 1.71 (br. s., 2H) 1.91 (br. s., 2H) 2.80 (br. s., 1H) 3.17-3.24 (m, 2H) 3.41 (br. s., 4H) 3.65 (br. s., 4H) 7.26 (br. s., 1H) 7.63 (br. s., 1 H) 7.94 (br. s., 1H) 8.13 (br. s., 1H) 8.40 (br. s., 1H) 9.09 (br. s., 1H) 9.62 (br. s., 1H) 11.71 (br. s., 1H). LCMS (ESI) 433 (M+H).

Example 91

Synthesis of Compound 91 (Also Referred to as Compound ZZ)

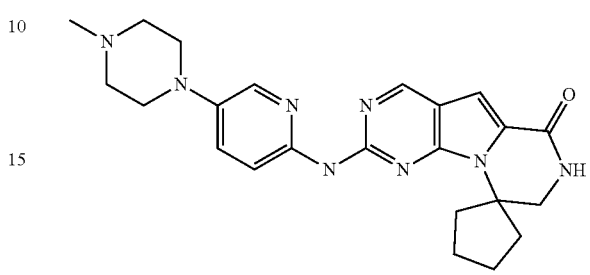

Compound 91 was synthesized using similar conditions to those described for compound 78 and was converted to an HCl salt. $^1$HNMR (600 MHz, DMSO-d$_6$) δ ppm 1.64-1.75 (m, 2H) 1.83-1.92 (m, 2H) 1.96-2.06 (m, 2H) 2.49-2.58 (m, 2H) 2.79 (d, J=3.81 Hz, 3H) 3.06-3.18 (m, 4H) 3.59-3.69 (m, 2H) 3.73-3.83 (m, 2H) 4.04-4.12 (m, 2H) 7.17 (br. s., 1H) 7.60-7.70 (m, 2H) 7.70-7.92 (m, 2H) 7.96 (br. s., 1H) 8.41 (br. s., 1H) 8.98 (br. s., 1H) 10.77 (br. s., 1H). LCMS (ESI) 433 (M+H).

Example 92

Synthesis of Compound 92

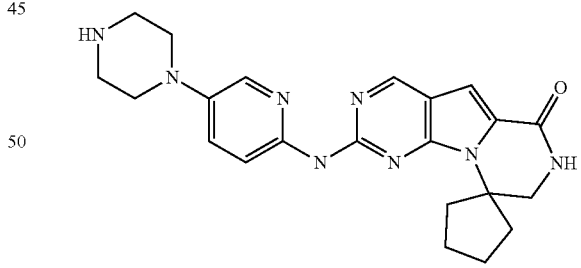

Compound 92 was synthesized in a similar manner to that described for compound 78 followed by the deblocking step described for compound 65 and was converted to an HCl salt. $^1$HNMR (600 MHz, DMSO-d$_6$) δ ppm 1.64-1.75 (m, 2H) 1.84-1.92 (m, 2H) 1.96-2.05 (m, 2H) 2.48-2.56 (m, 2H) 3.22 (br. s., 4H) 3.42-3.48 (m, 4H) 3.60-3.69 (m, 2H) 4.05-4.13 (m, 1H) 7.18 (s, 1H) 7.65 (d, J=13.47 Hz, 1H) 7.70-7.77 (m, 1H) 7.94 (d, J=1.76 Hz, 1H) 8.42 (br. s., 1H) 9.00 (s, 1H) 9.15 (br. s., 2H). LCMS (ESI) 419 (M+H).

Example 93

Synthesis of Compound 93

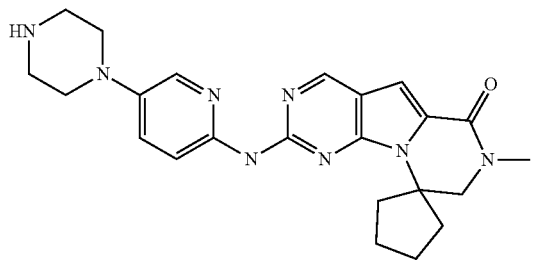 [SMILES: CN1CC2(CCCC2)n2c(cc3cnc(Nc4ccc(N5CCNCC5)cn4)nc32)C1=O]

Compound 93 was synthesized in a similar manner to that described for compound 78 followed by the deblocking step described for compound 65 and was converted to an HCl salt. $^1$HNMR (600 MHz, DMSO-$d_6$) δ ppm 1.76 (br. s., 2H) 1.89 (br. s., 2H) 2.03 (br. s., 2H) 2.47-2.58 (m, 2H) 3.04 (s, 3H) 3.22 (br. s., 4H) 3.39 (br. s., 4H) 3.66 (s, 2H) 7.21 (s, 1H) 7.67 (d, J=9.37 Hz, 1H) 7.93 (br. s., 1H) 7.98-8.09 (m, 1H) 9.04 (s, 1H) 9.34 (br. s., 2H) 11.31 (br. s., 1H). LCMS (ESI) 433 (M+H).

Example 94

Synthesis of Compound 94

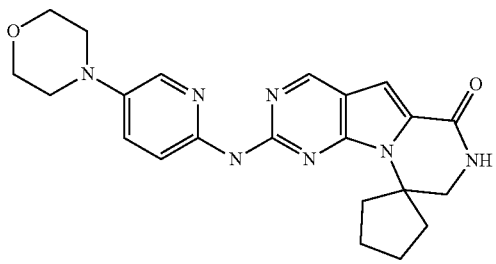 [SMILES: O=C1NCC2(CCCC2)n2c1cc1cnc(Nc3ccc(N4CCOCC4)cn3)nc12]

Compound 94 was synthesized using similar conditions to that described for compound 78 and was converted to an HCl salt. $^1$HNMR (600 MHz, DMSO-$d_6$) δ ppm 1.66-1.77 (m, 2H) 1.84-1.94 (m, 2H) 1.96-2.08 (m, 2H) 2.48-2.57 (m, 2H) 3.36-3.52 (m, 4H) 3.60-3.80 (m, 6H) 7.21 (s, 1H) 7.53-7.74 (m, 2H) 7.86 (s, 1H) 8.02 (s, 1H) 8.45 (s, 1H) 9.03 (s, 1H) 11.19 (br. s., 1H). LCMS (ESI) 420 (M+H).

Example 95

Synthesis of Compound 95

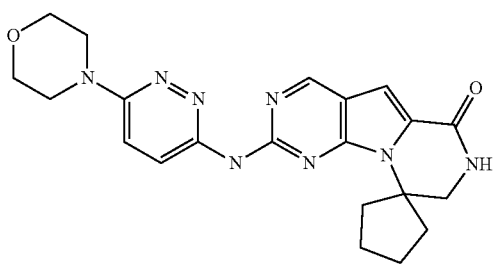 [SMILES: O=C1NCC2(CCCC2)n2c1cc1cnc(Nc3ccc(N4CCOCC4)nn3)nc12]

Compound 95 was synthesized using similar conditions to that described for compound 78 and was converted to an HCl salt. $^1$HNMR (600 MHz, DMSO-$d_6$) δ ppm 1.65-1.79 (m, 2H) 1.85-1.95 (m, 2H) 1.97-2.08 (m, 2H) 2.47-2.54 (m, 2H) 3.40-3.58 (m, 5H) 3.65 (dd, J=21.67, 5.56 Hz, 1H) 3.69-3.78 (m, 4H) 7.24 (s, 1H) 7.97-8.17 (m, 2H) 8.48 (s, 1H) 9.08 (s, 1H) 11.81 (s, 1H). LCMS (ESI) 421 (M+H).

Example 96

Synthesis of Compound 96

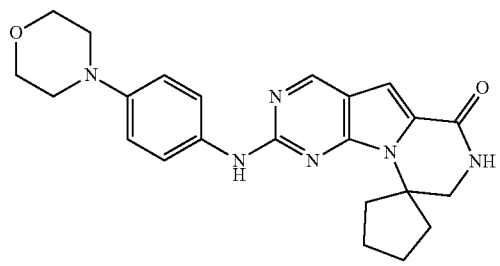 [SMILES: O=C1NCC2(CCCC2)n2c1cc1cnc(Nc3ccc(N4CCOCC4)cc3)nc12]

Compound 96 was synthesized using similar conditions to that described for compound 78 and was converted to an HCl salt. $^1$HNMR (600 MHz, DMSO-$d_6$) δ ppm 1.55-1.74 (m, 2H) 1.80-1.98 (m, 4H) 2.48-2.60 (m, 2H) 3.40-3.50 (m, 4H) 3.57-3.72 (m, 2H) 3.90-4.20 (m, 4H) 7.08 (s, 1H) 7.37-7.57 (m, 2H) 7.70 (m, 2H) 8.32 (s, 1H) 8.88 (s, 1H) 9.98 (s, 1H). LCMS (ESI) 419 (M+H).

Example 97

Synthesis of Compound 97 (Also Referred to as Compound III)

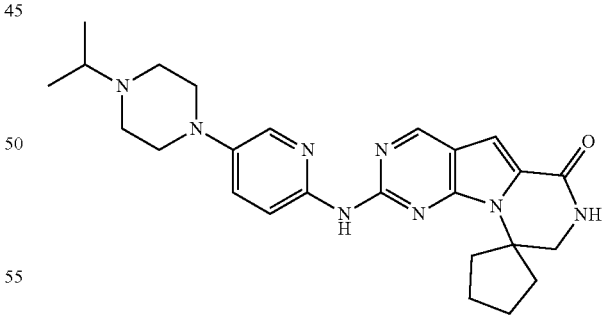

Compound 97 was synthesized using similar conditions to that described for compound 78 and was converted to an HCl salt. $^1$HNMR (600 MHz, DMSO-$d_6$) δ ppm 1.30 (d, J=5.27 Hz, 6H) 1.65-1.78 (m, 2H) 1.83-1.95 (m, 2H) 1.97-2.10 (m, 2H) 2.45-2.55 (m, 2H) 3.25-3.36 (m, 1H) 3.39-3.48 (m, 4H) 3.60-3.70 (m, 4H) 3.75-4.15 (m, 2H) 7.24 (s, 1H) 7.54-7.75 (m, 2H) 7.95 (s, 1H) 8.10 (s, 1H) 8.49 (s, 1H) 9.07 (s, 1H) 11.25 (s, 1H) 11.48 (s, 1H). LCMS (ESI) 461 (M+H).

Example 98

Synthesis of Compound 98

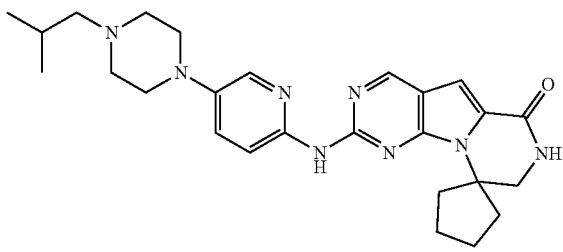 [SMILES: CC(C)CN1CCN(c2ccc(Nc3ncc4cc5n(c4n3)C3(CCCC3)CNC5=O)nc2)CC1]

Compound 98 was synthesized using similar conditions to that described for compound 78 and was converted to an HCl salt. $^1$H NMR (600 MHz, DMSO-d$_6$) δ ppm 0.99 (d, J=6.15 Hz, 6H) 1.65-1.78 (m, 2H) 1.90 (m, 2H) 1.97-2.08 (m, 2H) 2.08-2.17 (m, 1H) 2.45-2.55 (m, 2H) 2.88-3.02 (m, 2H) 3.33-3.48 (m, 4H) 3.50-3.90 (m, 6H) 7.24 (s, 1H) 7.67 (s, 2H) 7.94 (s, 1H) 8.12 (s, 1H) 8.49 (s, 1H) 9.07 (s, 1H) 10.77 (s, 1H) 11.51 (s, 1H). LCMS (ESI) 475 (M+H).

Example 99

Synthesis of Compound 99

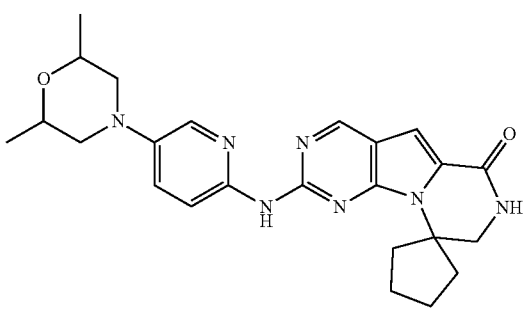 [SMILES: CC1CN(c2ccc(Nc3ncc4cc5n(c4n3)C3(CCCC3)CNC5=O)nc2)CC(C)O1]

Compound 99 was synthesized using similar conditions to those described for compound 78 and was converted to an HCl salt. $^1$HNMR (600 MHz, DMSO-d$_6$) δ ppm 1.13 (d, J=5.86 Hz, 6H) 1.66-1.77 (m, 2H) 1.84-1.94 (m, 2H) 1.97-2.09 (m, 2H) 2.40-2.53 (m, 2H) 3.37-3.49 (m, 2H) 3.50-3.59 (m, 2H) 3.59-3.73 (m, 4H) 7.23 (s, 1H) 7.64 (m, 3H) 7.85 (s, 1H) 8.11 (s, 1H) 8.47 (s, 1H) 9.05 (s, 1H). 11.35 (br s., 1H). LCMS (ESI) 448 (M+H).

Example 100

Synthesis of Compound 100

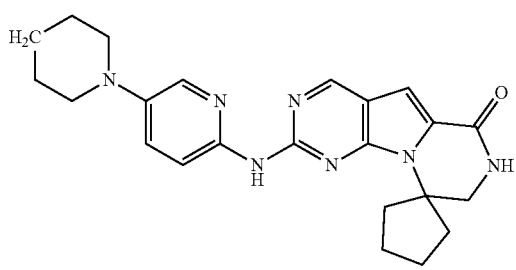 [SMILES: O=C1NCC2(CCCC2)n2c1cc1cnc(Nc3ccc(N4CCCCC4)cn3)nc12]

Compound 100 was synthesized using similar conditions to that described for compound 78 and was converted to an HCl salt. $^1$HNMR (600 MHz, DMSO-d$_6$) δ ppm 1.50-1.57 (m, 2H) 1.62-1.68 (m, 3H) 1.68-1.75 (m, 2H) 1.84-1.92 (m, 2H) 1.97-2.08 (m, 2H) 2.48-2.53 (m, 2H) 3.14-3.23 (m, 4H) 3.43-3.47 (m, 2H) 3.58-3.70 (m, 2H) 7.22 (s, 1H) 7.58-7.70 (m, 2H) 7.85-8.00 (m, 1H) 8.16 (d, 1H) 8.46 (s, 1H) 9.04 (s, 1H) 11.37 (br s., 1H). LCMS (ESI) 418 (M+H).

Example 101

Synthesis of Compound 101 (Also Referred to as Compound WW)

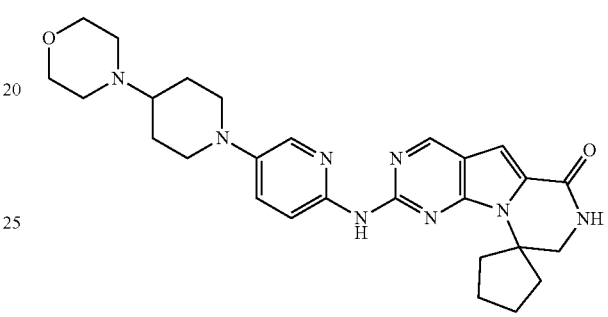

Compound 101 was synthesized using similar conditions to those described for compound 78 and was converted to an HCl salt. $^1$HNMR (600 MHz, DMSO-d$_6$) δ ppm 1.72 (s, 2H) 1.90 (s, 4H) 2.03 (s, 2H) 2.21 (s, 2H) 2.48-2.54 (m, 2H) 2.73 (s, 2H) 3.03 (s, 2H) 3.25-3.35 (m, 1H) 3.38-3.48 (m, 4H) 3.65-3.99 (m, 5H) 7.23 (s, 1H) 7.63 (d, J=9.66 Hz, 1H) 7.90 (s, 1H) 8.13 (s, 1H) 8.47 (s, 1H) 9.06 (s, 1H) 10.50 (br s., 1H). LCMS (ESI) 503 (M+H).

Example 102

Synthesis of Compound 102 (Also Referred to as Compound HHH)

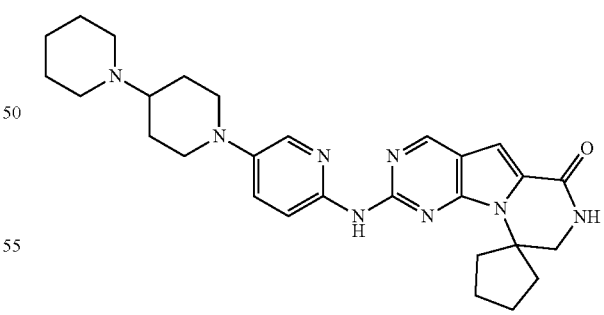

Compound 102 was synthesized using similar conditions to those described for compound 78 and was converted to an HCl salt. $^1$HNMR (600 MHz, DMSO-d$_6$) δ ppm 1.63-1.85 (m, 6H) 1.87-1.92 (m, 2H) 1.99-2.06 (m, 2H) 2.15-2.23 (m, 2H) 2.47-2.53 (m, 1H) 2.69-2.79 (m, 2H) 2.81-2.91 (m, 2H) 2.98-3.08 (m, 2H) 3.32-3.48 (m, 4H) 3.57-3.72 (m, 4H) 3.77-3.85 (m, 2H) 7.22 (s, 1H) 7.60-7.68 (m, 2H) 7.90 (s, 1H) 8.07 (s, 1H) 8.46 (s, 1H) 9.04 (s, 1H). 11.41 (br s., 1H). LCMS (ESI) 501 (M+H).

Example 103

Synthesis of Compound 103

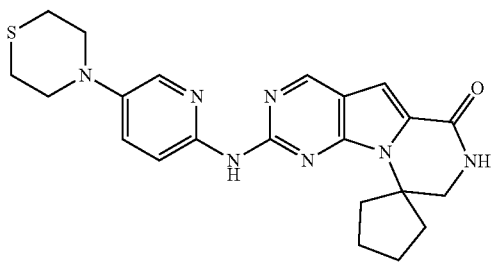 [SMILES: O=C1NCC2(CCCC2)n2c1cc1cnc(Nc3ccc(N4CCSCC4)cn3)nc12]

Compound 103 was synthesized using similar conditions to those described for compound 78 and was converted to an HCl salt. $^1$HNMR (600 MHz, DMSO-d$_6$) δ ppm 1.64-1.76 (m, 2H) 1.87-1.93 (m, 2H) 2.00-2.07 (m, 2H) 2.48-2.53 (m, 2H) 2.67-2.72 (m, 4H) 3.44-3.47 (m, 2H) 3.50-3.55 (m, 4H) 7.24 (s, 1H) 7.61 (d, J=9.37 Hz, 2H) 7.86 (d, J=2.63 Hz, 1H) 8.09 (d, J=12.88 Hz, 1H) 8.48 (s, 1H) 9.06 (s, 1H) 11.41 (br s., 1H). LCMS (ESI) 436 (M+H).

Example 104

Synthesis of Compound 104

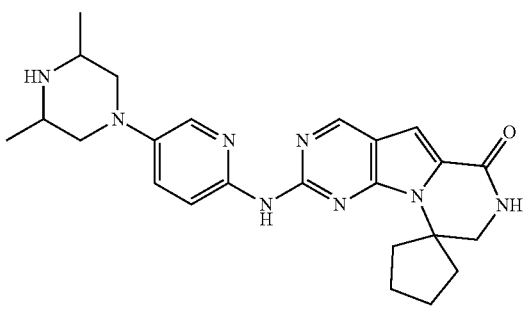 [SMILES: CC1CN(c2ccc(Nc3ncc4cc5n(c4n3)C3(CCCC3)CNC5=O)nc2)CC(C)N1]

Compound 104 was synthesized using similar conditions to those described for compound 78 and was converted to an HCl salt. $^1$HNMR (600 MHz, DMSO-d$_6$) δ ppm 1.29 (d, J=6.73 Hz, 6H) 1.66-1.79 (m, 2H) 1.84-1.95 (m, 2H) 1.98-2.09 (m, 2H) 2.46-2.55 (m, 2H) 3.29-3.39 (m, 2H) 3.58-3.70 (m, 4H) 3.77-3.86 (m, 4H) 7.24 (s, 1H) 7.66 (d, J=9.37 Hz, 1H) 7.96 (d, J=2.93 Hz, 1H) 8.08 (s, 1H) 8.48 (s, 1H) 9.06 (s, 1H) 9.28 (s, 1H) 9.67 (s, 1H) 11.36 (s, 1H). LCMS (ESI) 447 (M+H).

Example 105

Synthesis of Compound 105

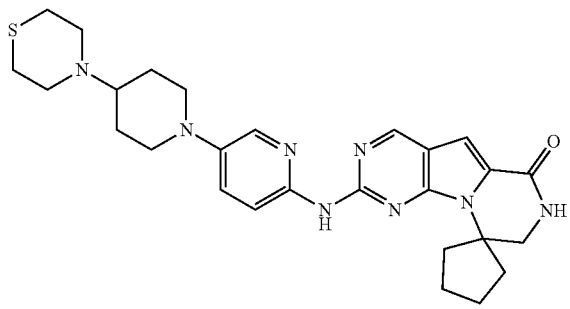 [SMILES: O=C1NCC2(CCCC2)n2c1cc1cnc(Nc3ccc(N4CCC(N5CCSCC5)CC4)cn3)nc12]

Compound 105 was synthesized using similar conditions to those described for compound 78 and was converted to an HCl salt. $^1$HNMR (600 MHz, DMSO-d$_6$) δ ppm 1.73 (s, 2H) 1.76-1.85 (m, 2H) 1.85-1.94 (m, 2H) 1.98-2.07 (m, 2H) 2.19-2.26 (m, 2H) 2.48-2.52 (m, 1H) 2.70-2.81 (m, 4H) 3.13-3.20 (m, 1H) 3.30-3.48 (m, 3H) 3.58-3.71 (m, 4H) 3.78-3.84 (m, 4H) 7.24 (s, 1H) 7.62 (d, J=9.37 Hz, 2H) 7.89 (d, J=1.17 Hz, 1H) 8.09-8.18 (m, 1H) 8.48 (s, 1H) 9.06 (s, 1H) 11.46 (br s., 1H). LCMS (ESI) 519 (M+H).

Example 106

Synthesis of Compound 106

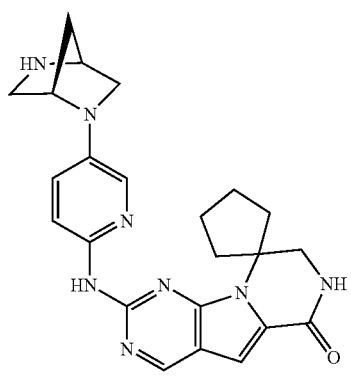 [SMILES: O=C1NCC2(CCCC2)n2c1cc1cnc(Nc3ccc(N4CC5C[C@@H]4CN5)cn3)nc12]

Compound 106 was synthesized using similar conditions to those described for compound 78 followed by the deblocking step described for compound 65 and was converted to an HCl salt. $^1$HNMR (600 MHz, DMSO-d$_6$) δ ppm 1.65-1.75 (m, 2H) 1.85-1.93 (m, 2H) 1.93-1.99 (m, 1H) 2.00-2.06 (m, 2H) 2.08-2.14 (m, 1H) 2.47-2.55 (m, 2H) 3.07-3.25 (m, 2H) 3.25-3.69 (m, 5H) 4.46 (s, 1H) 4.67 (s, 1H) 7.22 (s, 1H) 7.58-7.69 (m, 2H) 8.46 (s, 1H) 9.02 (s, 1H) 9.34 (s, 1H) 9.65 (s, 1H). LCMS (ESI) 431 (M+H).

Example 107

Synthesis of Compound 107 (also referred to as Compound YY)

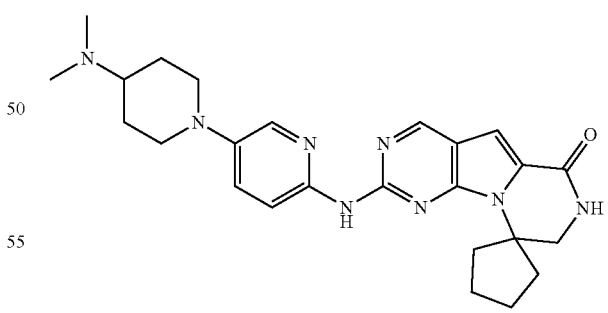

Compound 107 was synthesized using similar conditions to those described for compound 78 and was converted to an HCl salt. $^1$HNMR (600 MHz, DMSO-d$_6$) δ ppm 1.65-1.82 (m, 3H) 1.89 (br. s., 2H) 1.98-2.08 (m, 2H) 2.13 (br. s., 2H) 2.47-2.55 (m, 2H) 2.68 (d, J=4.98 Hz, 6H) 2.71-2.80 (m, 2H) 3.29-3.71 (m, 10H) 7.16-7.26 (m, 1H) 7.67 (d, J=9.66 Hz, 2H) 7.91 (d, J=2.05 Hz, 1H) 8.14 (br. s., 1H) 8.48 (br. s., 1H) 9.05 (s, 1H) 11.14 (br. s., 1H) 11.43 (br. s., 1H). LCMS (ESI) 461 (M+H).

Example 108

Synthesis of Compound 108

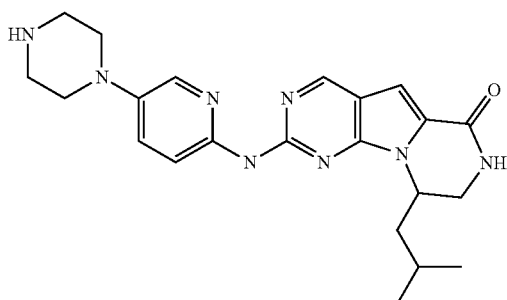

Compound 108 was synthesized in a manner similar to that described for compounds 64 and 65 and was recovered as an HCl salt. The analytical data was consistent with that described for the antipode compound 75.

Example 109

Synthesis of Compound 109

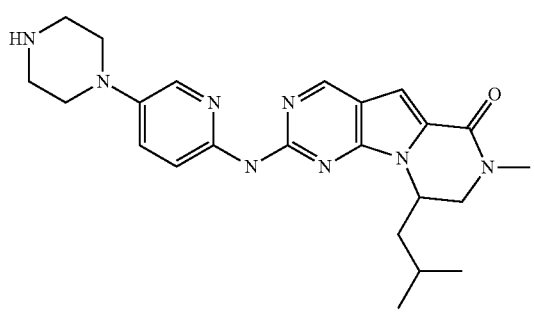 [SMILES: CC(C)CC1CN(C)C(=O)c2cc3cnc(Nc4ccc(N5CCNCC5)cn4)nc3n21]

Compound 109 was synthesized in a manner similar to that described for compounds 64 and 65 and was recovered as an HCl salt. The analytical data was consistent with that described for the antipode compound 75.

Example 110

Synthesis of Compound 110

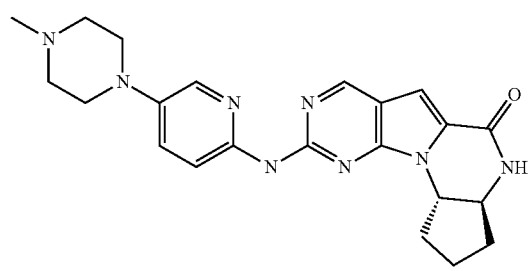 [SMILES: CN1CCN(c2ccc(Nc3ncc4cc5n(c4n3)[C@H]3CCC[C@@H]3NC5=O)nc2)CC1]

Compound 110 was synthesized in a similar manner to that described for compound 78 and then converted to its hydrochloride salt. $^1$HNMR (600 MHz, DMSO-$d_6$) δ ppm 1.50-1.65 (m, 1H) 1.92-2.02 (m, 3H) 2.06-2.15 (m, 1H) 2.78 (d, J=3.81 Hz, 4H) 3.10-3.20 (m, 4H) 3.47-3.51 (m, 2H) 3.64-3.71 (m, 1H) 3.76-3.83 (m, 2H) 3.98-4.14 (m, 1H) 7.20 (s, 2H) 7.77 (s, 1H) 7.97 (s, 2H) 8.81 (s, 1H) 9.03 (s, 1H) 10.97 (br s., 1H). LCMS (ESI) 419 (M+H).

Example 111

Synthesis of Compound 111

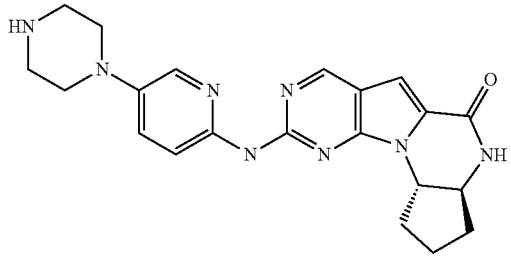 [SMILES: O=C1N[C@H]2CCC[C@@H]2n2c1cc1cnc(Nc3ccc(N4CCNCC4)cn3)nc12]

Compound 111 was synthesized in a similar manner to that described for compound 78 and then converted to its hydrochloride salt. $^1$HNMR (600 MHz, DMSO-$d_6$) δ ppm 1.54-1.59 (m, 1H) 1.92-2.01 (m, 3H) 2.06-2.15 (m, 1H) 2.76-2.84 (m, 1H) 3.17-3.24 (m, 6H) 3.64-3.71 (m, 2H) 4.02-4.11 (m, 2H) 7.22 (s, 2H) 7.64 (s, 1H) 7.97 (s, 2H) 8.75 (s, 1H) 8.97 (s, 1H) 9.21 (s, 1H). LCMS (ESI) 405 (M+H).

Example 112

Synthesis of Compound 112

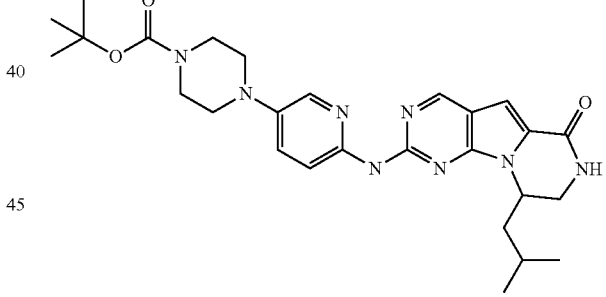

Compound 112 was synthesized using similar experimental conditions to that described for compound 64.

Example 113

Synthesis of tert-butyl N-[2-[(5-bromo-2-chloropyrimidin-4-yl)amino]ethyl]carbamate, Compound 113

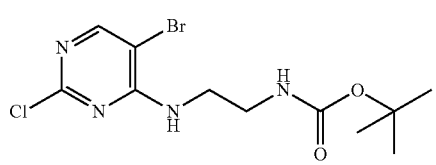 [SMILES: CC(C)(C)OC(=O)NCCNc1nc(Cl)ncc1Br]

To a solution of 5-bromo-2,4-dichloropyrimidine (12.80 g, 0.054 mole) in ethanol (250 mL) was added Hunig's base (12.0 mL) followed by the addition of a solution of N-(tert-butoxycarbonyl)-1,2-diaminoethane (10 g, 0.0624 mole) in ethanol (80 mL). The contents were stirred overnight for 20 hrs. The solvent was evaporated under vacuum. Ethyl acetate (800 mL) and water (300 mL) were added and the layers separated. The organic layer was dried with magnesium sulfate and then concentrated under vacuum. Column chromatography on silica gel using hexane/ethyl acetate (0-60%) afforded tert-butyl N-[2-[(5-bromo-2-chloro-pyrimidin-4-yl)amino]ethyl]carbamate. LCMS (ESI) 351 (M+H).

Example 114

Synthesis of tert-butyl N-[2-[[2-chloro-5-(3,3-diethoxyprop-1-ynyl)pyrimidin-4 yl]amino]ethyl]carbamate, Compound 114

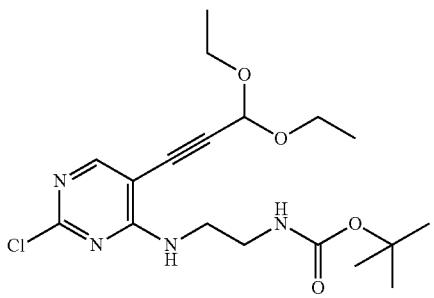 [SMILES: CCOC(C#Cc1cnc(Cl)nc1NCCNC(=O)OC(C)(C)C)OCC]

To tert-butyl N-[2-[(5-bromo-2-chloro-pyrimidin-4-yl)amino]ethyl]carbamate (5 g, 14.23 mmole) in toluene (42 mL) and triethylamine (8.33 mL) under nitrogen was added triphenyl arsine (4.39 g), 3,3-diethoxyprop-1-yne (3.24 mL) and Pddba (1.27 g). The contents were heated at 70 degrees for 24 hrs. After filtration through CELITE®, the crude reaction was columned using hexane/ethyl acetate (0-20%) to afford the desired product 3.9 g). Column chromatography of the resulting residue using hexane/ethyl acetate (0-30%) afforded tert-butyl N-[2-[[2-chloro-5-(3,3-diethoxyprop-1-ynyl)pyrimidin-4-yl]amino]ethyl]carbamate. LCMS (ESI) 399 (M+H).

Example 115

Synthesis of tert-butyl N-[2-[2-chloro-6-(diethoxymethyl)pyrrolo[2,3-d]pyrimidin-7-yl]ethyl]carbamate, Compound 115

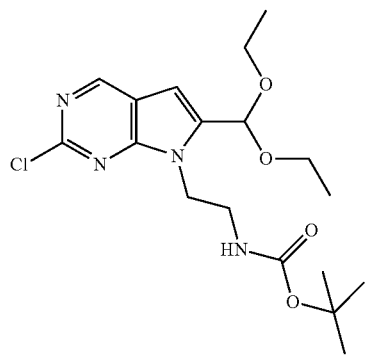 [SMILES: CCOC(OCC)c1cc2cnc(Cl)nc2n1CCNC(=O)OC(C)(C)C]

To a solution of Compound 114 (3.9 g, 0.00976 mole) in THF (60 mL) was added TBAF (68.3 mL, 7 eq). The contents were heated to 45 degrees for 2 hrs. Concentration followed by column chromatography using ethyl acetate/hexane (0-50%) afforded tert-butyl N-[2-[2-chloro-6-(diethoxymethyl)pyrrolo[2,3-d]pyrimidin-7-yl]ethyl]carbamate as a pale brown liquid (1.1 g). $^1$HNMR ($d_6$-DMSO) δ ppm 8.88 (s, 1H), 6.95 (brs, 1H), 6.69 (s, 1H), 5.79 (s, 1H), 4.29 (m, 2H), 3.59 (m, 4H), 3.34 (m, 1H), 3.18 (m, 1H), 1.19 (m, 9H), 1.17 (m, 6H). LCMS (ESI) 399 (M+H).

Example 116

Synthesis of tert-butyl N-[2-[2-chloro-6-(diethoxymethyl)-5-iodo-pyrrolo[2,3-d]pyrimidin-7-yl]ethyl]carbamate, Compound 116

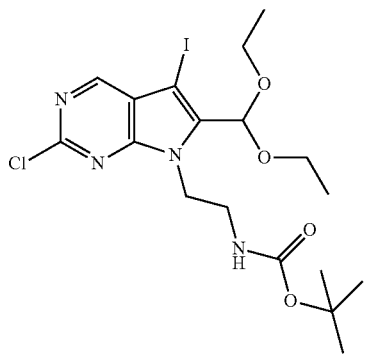 [SMILES: CCOC(OCC)c1c(I)c2cnc(Cl)nc2n1CCNC(=O)OC(C)(C)C]

To tert-butyl N-[2-[2-chloro-6-(diethoxymethyl)pyrrolo[2,3-d]pyrimidin-7-yl]ethyl]carbamate (0.1 g, 0.00025 mol) in acetonitrile (2 mL) was added 1,3-diiodo-5,5-dimethylhydantoin (95 mg, 1 eq), and solid NaHCO$_3$ (63 mg, 3 eq). The reacation was stirred at room tempreature for 16 hrs. The reaction was filtered and concentrated in vacuo. The product was purified by silica gel column chromatography using hexane/ethylacetate (0-50%) to afford tert-butyl N-[2-[2-chloro-6-(diethoxymethyl)-5-iodo-pyrrolo[2,3-d]pyrimidin-7-yl]ethyl]carbamate as a pale yellow solid (0.03 g). LCMS (ESI) 525 (M+H).

Example 117

Synthesis of tert-Butyl N-[2-[2-chloro-6-(diethoxymethyl)-5-(o-tolyl)pyrrolo[2,3-d]pyrimidin-7-yl]ethyl]carbamate, Compound 117

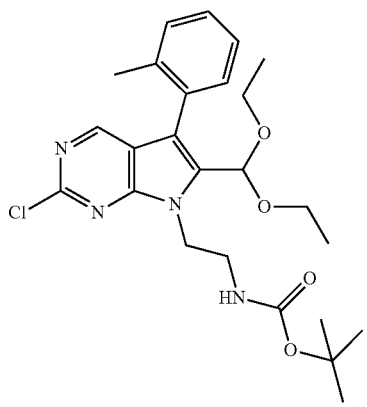 [SMILES: CCOC(OCC)c1c(-c2ccccc2C)c2cnc(Cl)nc2n1CCNC(=O)OC(C)(C)C]

To tert-butyl N-[2-[2-chloro-6-(diethoxymethyl)-5-iodo-pyrrolo[2,3-d]pyrimidin-7-yl]ethyl]carbamate (0.1 g, 0.19 mmole) in dioxane (3 mL) was added 2-methylphenylboronic acid (28 mg), tetrakis(triphenylphosphine)palladium (25 mg) and potassium phosphate (250 mg) in water (0.3 mL). The reaction was heated in a CEM Discovery microwave at 90° C. for 3 hrs. The crude reaction was loaded onto silica gel and columned using hexane/ethyl acetate (0-30%) to afford tert-butyl N-[2-[2-chloro-6-(diethoxymethyl)-5-(o-tolyl)pyrrolo[2,3-d]pyrimidin-7-yl]ethyl]carbamate (0.06 g). LCMS (ESI) 489 (M+H).

Example 118

Synthesis of 7-[2-(tert-butoxycarbonylamino)ethyl]-2-chloro-5-(o-tolyl)pyrrolo[2,3-d]pyrimidine-6-carboxylic acid, Compound 118

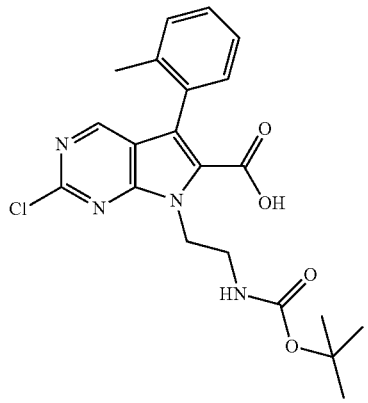 [SMILES: Cc1ccccc1-c1c(C(=O)O)n(CCNC(=O)OC(C)(C)C)c2nc(Cl)ncc12]

To tert-butyl N-[2-[2-chloro-6-(diethoxymethyl)-5-(o-tolyl)pyrrolo[2,3-d]pyrimidin-7-yl]ethyl]carbamate (0.85 g, 1.74 mmole) in AcOH (10 mL) was added water (1.5 mL). The reaction was stirred at room temperature for 16 hrs. The crude reaction was then concentrated under vacuum. After the addition of ethyl acetate (50 mL), the organic layer was washed with satd. NaHCO₃. The organic layer was dried with magnesium sulfate and then concentrated under vacuum to afford the crude intermediate, tert-butyl N-[2-[2-chloro-6-formyl-5-(o-tolyl)pyrrolo[2,3-d]pyrimidin-7-yl]ethyl]carbamate. To this crude intermediate in DMF (5 mL) was added oxone (1.3 g). After stirring for 2.5 hrs, water (20 mL) and ethyl acetate (100 mL) were added. The organic layer was separated, dried and then concentrated under vacuum to afford the crude product which was columned over silica gel using hexane/ethyl acetate (0-50%) to afford 7-[2-(tert-butoxycarbonylamino)ethyl]-2-chloro-5-(o-tolyl)pyrrolo[2,3-d]pyrimidine-6-carboxylic acid (0.112 g). LCMS (ESI) 431 (M+H).

Example 119

Synthesis of Compound 119

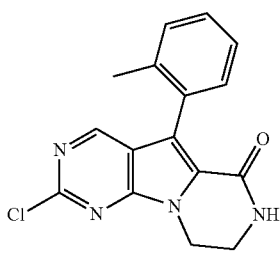 [SMILES: Cc1ccccc1-c1c2n(c3nc(Cl)ncc13)CCNC2=O]

To 7-[2-(tert-butoxycarbonylamino)ethyl]-2-chloro-5-(o-tolyl)pyrrolo[2,3-d]pyrimidine-6-carboxylic acid (0.1 g, 0.261 mmol) in DCM (4.1 mL) was added DMAP (20 mg) followed by the addition of N,N'-diisopropylcarbodiimide (0.081 mL, 2 eq). After stirring for 3 hrs, TFA (0.723 mL) was added. Stirring was then continued for another 30 minutes. The reaction mixture was neutralized with satd. NaHCO₃. DCM (20 mL) was then added and the organic layer separated, dried with magnesium sulfate and then concentrated under vacuum to afford the crude product which was columned using hexane/ethylacetate (0-100%) to afford chloro tricyclic amide Compound 119 (0.65 g). LCMS (ESI) 313 (M+H).

Example 120

Synthesis of Compound 120

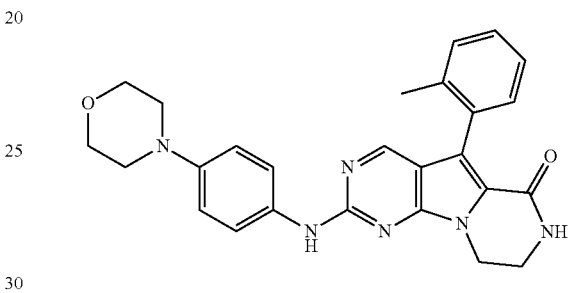

To the chloro tricyclic amide (0.040 g, 0.128 mmole) (Compound 119) in dioxane (2.5 mL) under nitrogen was added Pd₂(dba)₃ (12 mg), sodium tert-butoxide (16 mg), BINAP (16 mg) and 4-morpholinoaniline (22.7 mg, 1 eq). The reaction mixture was heated at 90° C. in a CEM Discovery microwave for 3.0 hrs. The crude reaction was loaded onto a silica gel column and the contents eluted with DCM/MeOH (0-6%) to afford the product (10 mg). LCMS (ESI) 455 (M+H). ¹HNMR (600 MHz, DMSO-d₆) δ ppm 2.14 (s, 3H) 3.23-3.50 (m, 2H) 3.57-3.73 (m, 2H), 3.81-3.92 (m, 8H), 7.11-7.31 (m, 4H) 7.31-7.48 (m, 1H) 7.58-7.73 (m, 1H) 7.77-7.95 (m, 2H) 8.05-8.21 (m, 1H) 8.44 (s, 1H) 9.85-10.01 (m, 1H).

Example 121

Synthesis of Compound 121

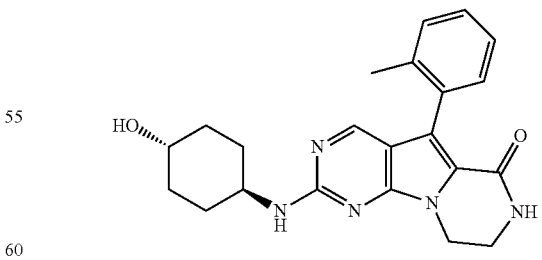

To the chloro tricyclic amide (0.024 g) (Compound 119) in N-methyl-2-pyrrolidone (NMP) (1.5 mL) was added trans-4-aminocyclohexanol (0.0768 mmol, 26.54 mg, 3 eq) and Hunig's base (0.4 mL). The reaction was heated in a CEM Discovery microwave vessel at 150° C. for 1.2 hrs. The crude reaction was loaded onto a silica gel column and the contents eluted with DCM/MeOH (0-10%) to afford the product (21 mg). LCMS (ESI) 392 (M+H). $^1$HNMR (600 MHz, DMSO-$d_6$) δ ppm 1.23 (d, J=8.78 Hz, 4H) 1.84 (br. s., 4H) 2.11 (s, 3H) 3.34-3.43 (m, 1H) 3.55 (br. s., 2H) 3.72 (br. s., 1H) 4.13 (br. s., 2H) 4.50 (br. s., 1H) 7.03 (br. s., 1H) 7.12-7.28 (m, 4H) 7.96 (br. s., 1H) 8.18 (br. s., 1H).

Example 122

Synthesis of 7-[2-(tert-butoxycarbonylamino)ethyl]-2-chloro-pyrrolo[2,3-d]pyrimidine-6-carboxylic acid, Compound 122

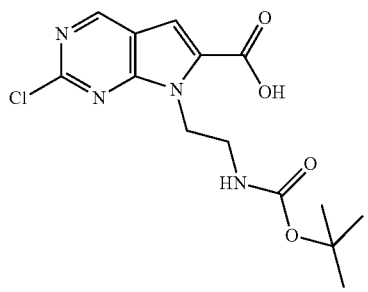 [SMILES: CC(C)(C)OC(=O)NCCn1c(C(=O)O)cc2cnc(Cl)nc21]

7-[2-(tert-butoxycarbonylamino)ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 341 (M+H).

Example 123

Synthesis of Compound 123

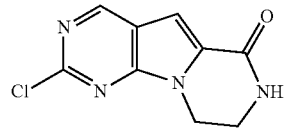 [SMILES: O=C1NCCn2c1cc1cnc(Cl)nc12]

Chloro tricyclic amide, Compound 123, was synthesized using a similar experimental procedure as that described for the synthesis of chloro tricyclic amide (Compound 119). LCMS (ESI) 223 (M+H).

Example 124

Synthesis of Compound 124

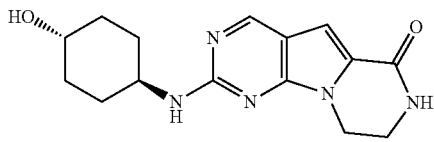 [SMILES: O=C1NCCn2c1cc1cnc(N[C@H]3CC[C@H](O)CC3)nc12]

To the chloro tricyclic amide, Compound 123 (0.035 g, 0.00157 mole) in NMP (1.5 mL) was added Hunig's base (0.3 mL) followed by the addition of the trans-4-aminocyclohexanol (54.2 mg). The reaction mixture was heated at 150° C. for 1.5 hrs. The crude reaction was loaded onto a silica gel column and the column was eluted with DCM/MeOH (0-10%) to afford the product (5 mg). LCMS (ESI) 302 (M+H).

Example 125

Synthesis of tert-butyl N-[2-[(5-bromo-2-chloro-pyrimidin-4-yl)amino]-2-methyl-propyl]carbamate, Compound 125

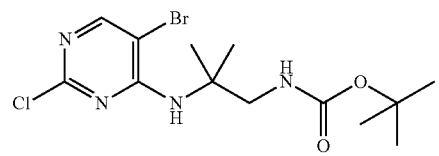 [SMILES: CC(C)(CNC(=O)OC(C)(C)C)Nc1nc(Cl)ncc1Br]

tert-butyl N-[2-[(5-bromo-2-chloro-pyrimidin-4-yl)amino]-2-methyl-propyl]carbamate was synthesized by treating 5-bromo-2,4-dichloropyrimidine with tert-butyl N-(2-amino-2-methyl-propyl)carbamate using similar experimental conditions as described for the synthesis of tert-butyl N-[2-[(5-bromo-2-chloro-pyrimidin-4-yl)amino]ethyl]carbamate. LCMS (ESI) (M+H) 379.

Example 126

Synthesis of tert-butyl N-[2-[[2-chloro-5-(3,3-diethoxyprop-1-ynyl)pyrimidin-4-yl]amino]-2-methyl-propyl]carbamate, Compound 126

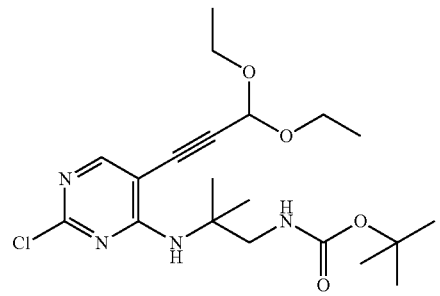 [SMILES: CCOC(C#Cc1cnc(Cl)nc1NC(C)(C)CNC(=O)OC(C)(C)C)OCC]

tert-butyl N-[2-[[2-chloro-5-(3,3-diethoxyprop-1-ynyl)pyrimidin-4-yl] amino]-2-methyl-propyl]carbamate was synthesized by treating tert-butyl N-[2-[(5-bromo-2-chloro-pyrimidin-4-yl)amino]-2-methyl-propyl]carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl] amino] ethyl]carbamate LCMS (ESI) (M+H) 427.

Example 127

Synthesis of tert-butyl N-[2-[2-chloro-6-(diethoxymethyl)pyrrolo[2,3-d]pyrimidin-7-yl]-2-methyl-propyl]carbamate, Compound 127

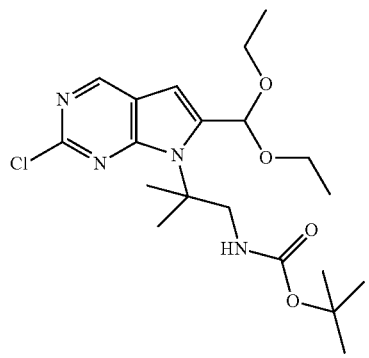 [SMILES: CCOC(OCC)c1cc2cnc(Cl)nc2n1C(C)(C)CNC(=O)OC(C)(C)C]

tert-butyl N-[2-[2-chloro-6-(diethoxymethyl)pyrrolo[2,3-d]pyrimidin-7-yl]-2-methyl-propyl]carbamate was synthesized by treating tert-butyl N-[2-[[2-chloro-5-(3,3-diethoxy-prop-1-ynyl)pyrimidin-4-yl]amino]-2-methyl-propyl]carbamate with TBAF using similar experimental conditions as described for the synthesis tert-butyl N-[2-[2-chloro-6-(diethoxymethyl)pyrrolo[2,3-d]pyrimidin-7-yl]ethyl]carbamate. LCMS (ESI) (M+H) 427.

Example 128

Synthesis of 7-[2-(tert-butoxycarbonylamino)-1,1-dimethyl-ethyl]-2-chloro-pyrrolo[2,3-d]pyrimidine-6-carboxylic acid, Compound 128

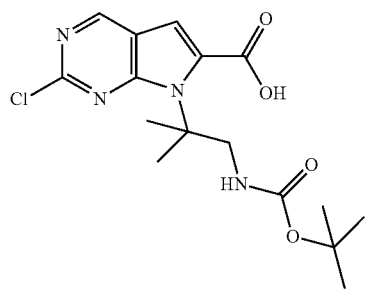 [SMILES: CC(C)(C)OC(=O)NCC(C)(C)n1c(C(=O)O)cc2cnc(Cl)nc21]

7-[2-(tert-butoxycarbonylamino)-1,1-dimethyl-ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 369 (M+H).

Example 129

Synthesis of Compound 129

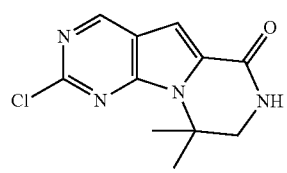 [SMILES: CC1(C)CNC(=O)c2cc3cnc(Cl)nc3n21]

Chloro tricyclic amide, Compound 129, was synthesized using a similar procedure as that described for the synthesis of chloro tricyclic amide, Compound 119. LCMS (ESI) 251 (M+H).

Example 130

Synthesis of Compound 130

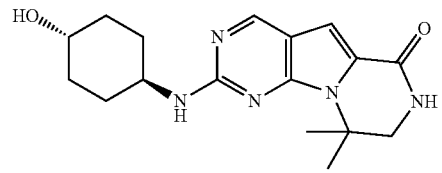 [SMILES: CC1(C)CNC(=O)c2cc3cnc(N[C@H]4CC[C@H](O)CC4)nc3n21]

Compound 130 was synthesized by treating chlorotricyclic amine Compound 129 with trans-4-aminocyclohexanol using similar experimental conditions as for compound 124. LCMS (ESI) 330 (M+H). $^1$HNMR (600 MHz, DMSO-$d_6$) δ ppm 1.07-1.34 (m, 4H) 1.47-2.05 (m, 10H) 3.09 (m, 1H) 3.51 (d, J=2.91 Hz, 2H) 3.57 (m, 1H) 4.50 (br. s., 1H) 6.89 (s, 1H) 6.94-7.05 (m, 1H) 8.04 (br. s., 1H) 8.60 (s, 1H) 9.00 (br. s., 1H).

Example 131

Synthesis of benzyl N-[1-[[(5-bromo-2-chloro-pyrimidin-4-yl)amino]methyl]propyl]carbamate, Compound 131

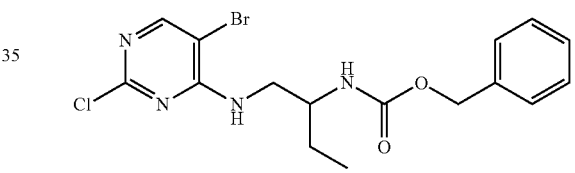

Benzyl N-[1-[[(5-bromo-2-chloro-pyrimidin-4-yl)amino]methyl]propyl]carbamate was synthesized by treating 5-bromo-2,4-dichloropyrimidine with benzyl N-[1-(aminomethyl)propyl]carbamate using similar experimental conditions as described for the synthesis of tert-butyl N-[2-[(5-bromo-2-chloro-pyrimidin-4-yl)amino]ethyl]carbamate. LCMS (ESI) (M+H) 413.

Example 132

Synthesis of benzyl N-[1-[[[2-chloro-5-(3,3-diethoxyprop-1-ynyl)pyrimidin-4-yl]amino]methyl]propyl]carbamate, Compound 132

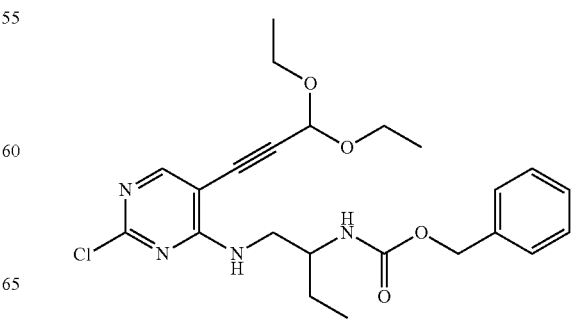

Benzyl N-[1-[[[2-chloro-5-(3,3-diethoxyprop-1-ynyl)pyrimidin-4-yl]amino]methyl]propyl]carbamate was prepared by treating benzyl N-[1-[[(5-bromo-2-chloro-pyrimidin-4-yl)amino]methyl]propyl]-carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4-yl]amino]ethyl]carbamate LCMS (ESI) (M+H) 461.

Example 133

Synthesis of benzyl N-[1-[[2-chloro-6-(diethoxymethyl)pyrrolo[2,3-d]pyrimidin-7-yl]methyl]propyl] carbamate, Compound 133

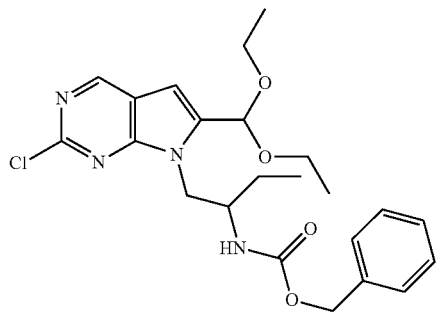 [SMILES: CCOC(OCC)c1cc2cnc(Cl)nc2n1CC(CC)NC(=O)OCc1ccccc1]

Benzyl N-[1-[[2-chloro-6-(diethoxymethyl)pyrrolo[2,3-d]pyrimidin-7-yl]methyl]propyl]carbamate was synthesized by treating benzyl N-[1-[[[2-chloro-5-(3,3-diethoxyprop-1-ynyl)pyrimidin-4-yl]amino]methyl]propyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) (M+H) 461.

Example 134

Synthesis of 7-[2-(benzyloxycarbonylamino)butyl]-2-chloro-pyrrolo[2,3-d]pyrimidine-6-carboxylic acid, Compound 134

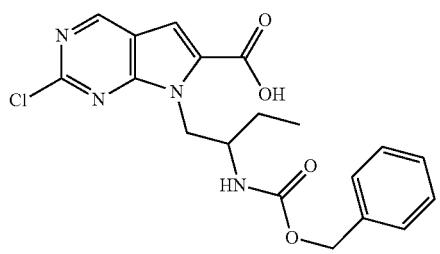 [SMILES: CCC(Cn1c(C(=O)O)cc2cnc(Cl)nc21)NC(=O)OCc1ccccc1]

7-[2-(benzyloxycarbonylamino)butyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 403 (M+H).

Example 135

Synthesis of Compound 135

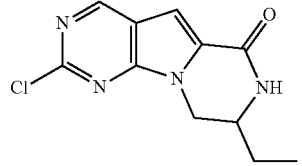 [SMILES: CCC1Cn2c(cc3cnc(Cl)nc32)C(=O)N1]

To a solution of 7-[2-(benzyloxycarbonylamino)butyl]-2-chloro-pyrrolo[2,3-d]pyrimidine-6-carboxylic acid in dichloromethane was added HBr, the reaction was stirred at 45 degrees for 3 hrs. After concentration, 2N NaOH was added to basify (pH=8.0) the reaction followed by the addition of THF (20 mL). Boc$_2$O was then added (1.2 eq) and the reaction was stirred for 16 hrs. To the crude reaction mixture was then added ethyl acetate (100 mL) and water (50 mL) and the organic phase was separated, dried (magnesium sulfate) and then concentrated under vacuum. To the crude product was added dichloromethane (30 mL) followed by DIC and DMAP. After stirring for 2 hrs, TFA was added and the contents stirred for an hour. The solvents were evaporated under vacuum and the residue basified with satd. NaHCO$_3$. Ethyl acetate was then added and the organic layer separated, dried (magnesium sulfate) and then concentrated under vacuum. Column chromatography with hexane/ethyl acetate (0-100%) afforded the desired chlorotricyclic core, Compound 135. LCMS (ESI) 251 (M+H).

Example 136

Synthesis of Compound 136

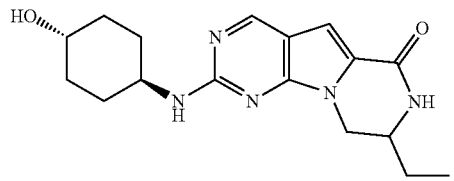 [SMILES: CCC1Cn2c(cc3cnc(N[C@H]4CC[C@H](O)CC4)nc32)C(=O)N1]

Compound 136 was synthesized by treating chlorotricyclic amine, Compound 135, with trans-4-aminocyclohexanol using similar experimental conditions as for compound 124. LCMS (ESI) 330 (M+H). $^1$HNMR (600 MHz, DMSO-d$_6$) δ ppm 0.80-0.95 (m, 3H) 1.35-1.92 (m, 10H) 3.66 (br. m., 3H) 4.17 (br. s., 2H) 4.47 (br. s., 1H) 6.85 (s, 1H) 6.96 (br. s., 1H) 8.15 (br. s., 1H) 8.62 (br. s., 1H).

Example 137

Synthesis of tert-butyl N-[1[[(5-bromo-2-chloro-pyrimidin-4-yl)amino]methyl]cyclopentyl]carbamate, Compound 137

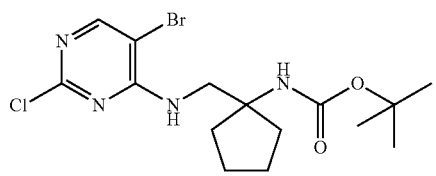 [SMILES: CC(C)(C)OC(=O)NC1(CNc2nc(Cl)ncc2Br)CCCC1]

tert-butyl N-[1-[[(5-bromo-2-chloro-pyrimidin-4-yl)amino]methyl]cyclopentyl]carbamate was synthesized by treating 5-bromo-2,4-dichloropyrimidine with tert-butyl N-[1-(aminomethyl)cyclopentyl]carbamate using similar experimental conditions as described for the synthesis of tert-butyl N-[2-[(5-bromo-2-chloro-pyrimidin-4-yl)amino]ethyl]carbamate. LCMS (ESI) 405 (M+H).

Example 138

Synthesis of tert-butyl N-[1-[[[2-chloro-5-(3,3-diethoxyprop-1-ynyl)pyrimidin-4-yl]amino]methyl]cyclopentyl]carbamate, Compound 138

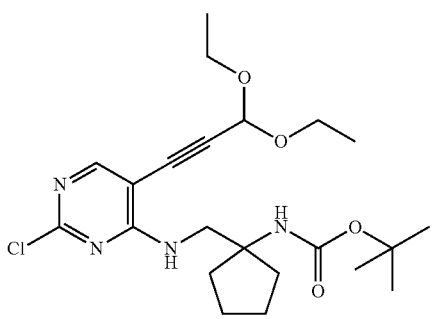 [SMILES: CCOC(C#Cc1cnc(Cl)nc1NCC1(NC(=O)OC(C)(C)C)CCCC1)OCC]

tert-butyl N-[1-[[[2-chloro-5-(3,3-diethoxyprop-1-ynyl)pyrimidin-4-yl]amino]methyl]cyclopentyl]carbamate was synthesized by treating tert-butyl N-[1-[[(5-bromo-2-chloro-pyrimidin-4-yl)amino]methyl]cyclopentyl]carbamate with with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate LCMS (ESI) 453 (M+H).

Example 139

Synthesis of tert-butyl N-[1-[[2-chloro-6-(diethoxymethyl)pyrrolo[2,3-d]pyrimidin-7-yl]methyl]cyclopentyl]carbamate, Compound 139

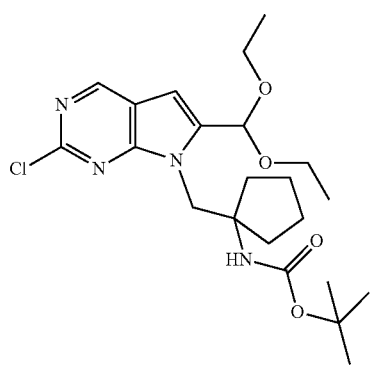 [SMILES: CCOC(OCC)c1cc2cnc(Cl)nc2n1CC1(NC(=O)OC(C)(C)C)CCCC1]

tert-butyl N-[1-[[2-chloro-6-(diethoxymethyl)pyrrolo[2,3-d]pyrimidin-7-yl]methyl]cyclopentyl]carbamate was synthesized by treating tert-butyl N-[2-[[2-chloro-5-(3,3-diethoxyprop-1-ynyl)pyrimidin-4-yl]amino]-2-methylpropyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) 453 (M+H).

Example 140

Synthesis of 7-[[1-(tert-butoxycarbonylamino)cyclopentyl]methyl]-2-chloro-pyrrolo[2,3-d]pyrimidine-6-carboxylic acid, Compound 140

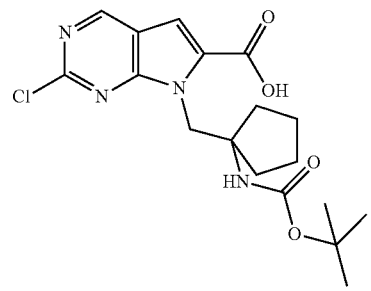 [SMILES: CC(C)(C)OC(=O)NC1(Cn2c(C(=O)O)cc3cnc(Cl)nc32)CCCC1]

7-[[1-(tert-butoxycarbonylamino)cyclopentyl]methyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 395 (M+H).

Example 141

Synthesis of Compound 141

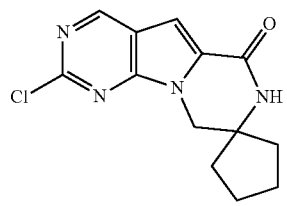 [SMILES: O=C1NC2(CCCC2)Cn2c1cc1cnc(Cl)nc12]

Chlorotricyclic core Compound 141 was synthesized using a similar experimental procedure as that described for the synthesis of chloro tricyclic amide Compound 119. LCMS (ESI) 277 (M+H).

Example 142

Synthesis of Compound 142

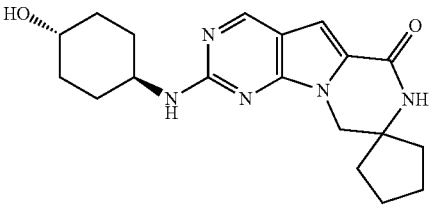 [SMILES: O=C1NC2(CCCC2)Cn2c1cc1cnc(N[C@H]3CC[C@H](O)CC3)nc12]

Compound 142 was synthesized by treating chlorotricyclic amine, Compound 141, with trans-4-aminocyclohexanol using similar experimental conditions as for Compound 124. LCMS (ESI) 356 (M+H). ¹HNMR (600 MHz, DMSO-d₆) δ ppm 1.08-1.32 (m, 8H) 1.60-2.09 (m, 8H) 3.03-3.17 (m, 1H) 3.35 (s, 2H) 3.54-3.62 (m, 1H) 4.51 (d, J=4.39 Hz, 1H) 6.88 (s, 1H) 6.96 (br. s., 1H) 8.07 (br. s., 1H) 8.58 (s, 1H).

Example 143

Synthesis of tert-butyl N-[[1-[(5-bromo-2-chloro-pyrimidin-4-yl)amino]cyclopentyl]methyl]carbamate, Compound 143

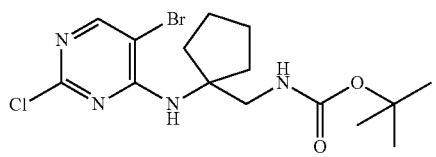 [SMILES: CC(C)(C)OC(=O)NCC1(Nc2nc(Cl)ncc2Br)CCCC1]

tert-butyl N-[[1-[(5-bromo-2-chloro-pyrimidin-4-yl)amino]cyclopentyl]methyl]carbamate was synthesized by treating 5-bromo-2,4-dichloropyrimidine with tert-butyl N-[(1-aminocyclopentyl)methyl]carbamate using similar experimental conditions as described for the synthesis of tert-butyl N-[2-[(5-bromo-2-chloro-pyrimidin-4-yl)amino]ethyl]carbamate. LCMS (ESI) 405 (M+H).

Example 144

Synthesis of tert-butyl N-[2-[[2-chloro-5-(3,3-diethoxyprop-1-ynyl)pyrimidin-4-yl]amino]-2-methyl-propyl]carbamate, Compound 144

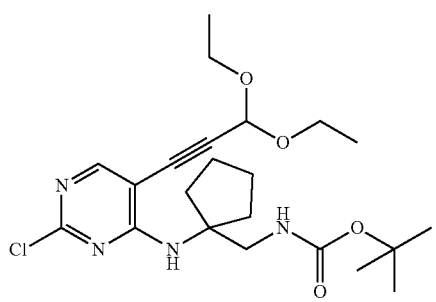 [SMILES: CCOC(C#Cc1cnc(Cl)nc1NC1(CNC(=O)OC(C)(C)C)CCCC1)OCC]

tert-butyl N-[[1-[[2-chloro-5-(3,3-diethoxyprop-1-ynyl)pyrimidin-4-yl]amino]cyclopentyl]methyl]carbamate was synthesized by treating tert-butyl N-[2-[(5-bromo-2-chloro-pyrimidin-4-yl)amino]-2-methyl-propyl]carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate. LCMS (ESI) 453 (M+H).

Example 145

Synthesis of tert-butyl N-[[1-[2-chloro-6-(diethoxymethyl)pyrrolo[2,3-d]pyrimidin-7-yl]cyclopentyl]methyl]carbamate, Compound 145

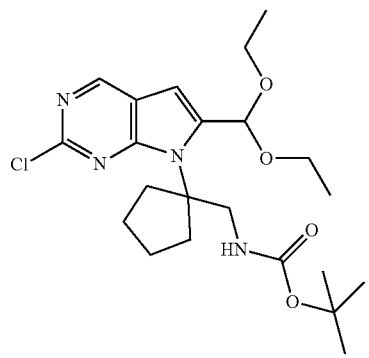 [SMILES: CCOC(OCC)c1cc2cnc(Cl)nc2n1C1(CNC(=O)OC(C)(C)C)CCCC1]

tert-Butyl N-[[1-[2-chloro-6-(diethoxymethyl)pyrrolo[2,3-d]pyrimidin-7-yl]cyclopentyl]methyl]carbamate was synthesized by treating tert-butyl N-[2-[[2-chloro-5-(3,3-diethoxyprop-1-ynyl)pyrimidin-4-yl]amino]-2-methyl-propyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) 4534 (M+H).

Example 146

Synthesis of 7-[2-(tert-butoxycarbonylamino)-1,1-dimethyl-ethyl]-2-chloro-pyrrolo[2,3-d]pyrimidine-6carboxylic acid, Compound 146

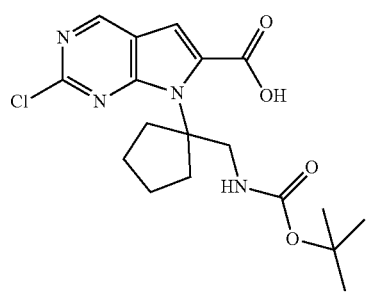 [SMILES: CC(C)(C)OC(=O)NCC1(n2c(C(=O)O)cc3cnc(Cl)nc32)CCCC1]

7-[2-(tert-Butoxycarbonylamino)-1,1-dimethyl-ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 395 (M+H).

Example 147

Synthesis of Compound 147

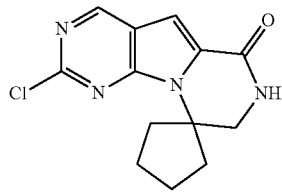 [SMILES: O=C1NCC2(CCCC2)n2c1cc1cnc(Cl)nc12]

Chloro tricyclic amide, Compound 147 was synthesized using a similar experimental procedure as that described for the chloro tricyclic amide, Compound 119. LCMS (ESI) 277 (M+H).

Example 148

Synthesis of Compound 148

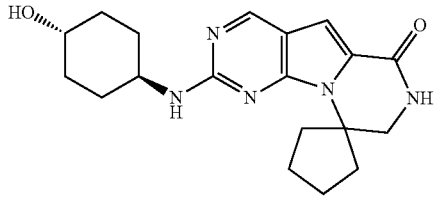 [SMILES: O=C1NCC2(CCCC2)n2c1cc1cnc(N[C@H]3CC[C@H](O)CC3)nc12]

Compound 148 was synthesized by treating chlorotricyclic amine, Compound 147, with trans-4-aminocyclohexanol using similar experimental conditions as for Compound 124. LCMS (ESI) 356 (M+H). $^1$HNMR (600 MHz, DMSO-$d_6$) δ ppm 1.06-1.35 (m, 8H) 1.45-1.95 (m, 8H) 3.10 (m, 1H) 3.58 (br. s., 2H) 3.95 (br. s., 1H) 4.49 (br. s., 1H) 6.84 (s, 1H) 6.85-6.93 (m, 1H) 8.29 (s, 1H) 8.61 (br. s., 1H).

Example 149

Synthesis of Compound 149

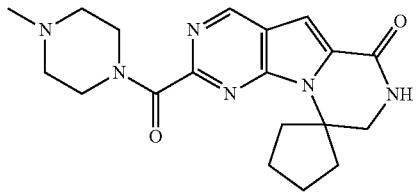 [SMILES: CN1CCN(C(=O)c2ncc3cc4n(c3n2)C2(CCCC2)CNC4=O)CC1]

Step 1: Compound 59 is Boc protected according to the method of A. Sarkar et al. (JOC, 2011, 76, 7132-7140).
Step 2: Boc-protected Compound 59 is treated with 5 mol % $NiCl_2(Ph_3)_2$, 0.1 eq triphenylphosphine, 3 eq Mn, 0.1 eq tetraethylammonium iodide, in DMI under $CO_2$ (1 atm) at 25° C. for 20 hours to convert the aryl halide derivative into the carboxylic acid.
Step 3: The carboxylic acid from Step 2 is converted to the corresponding acid chloride using standard conditions.
Step 4: The acid chloride from Step 3 is reacted with N-methyl piperazine to generate the corresponding amide.
Step 5: The amide from Step 4 is deprotected using trifluoroacetic acid in methylene chloride to generate the target compound. Compound 149 is purified by silica gel column chromatography eluting with a dichloromethane—methanol gradient to provide Compound 149.

Each of Compounds 119 through 147 and corresponding compounds with various $R^8$, $R^1$ and Z definitions may be reacted with sodium hydride and an alkyl halide or other halide to insert the desired R substitution prior to reaction with an amine, such as described above for the synthesis of Compound 120, to produce the desired product of Formulae I, II, III, IV, or V.

Example 150

CDK4/6 Inhibition In Vitro Assay

Selected compounds disclosed herein were tested in CDK4/cyclinD1, CDK2/CycA and CDK2/cyclinE kinase assays by Nanosyn (Santa Clara, Calif.) to determine their inhibitory effect on these CDKs. The assays were performed using microfluidic kinase detection technology (Caliper Assay Platform). The compounds were tested in 12-point dose-response format in singlicate at Km for ATP. Phosphoacceptor substrate peptide concentration used was 1 µM for all assays and Staurosporine was used as the reference compound for all assays. Specifics of each assay are as described below:

CDK2/CyclinA: Enzyme concentration: 0.2 nM; ATP concentration: 50 µM; Incubation time: 3 hr.

CDK2/CyclinE: Enzyme concentration: 0.28 nM; ATP concentration: 100 µM; Incubation time: 1 hr.

CDK4/CyclinD1: Enzyme concentration: 1 nM; ATP concentration: 200 µM; Incubation time: 10 hr.

The inhibitory $IC_{50}$ values for the compounds in Table 1 for CDK4/CycD1, CDK2/CycE, CDK2/CycA, as well as fold selectivity are presented in Table 2.

TABLE 2

Selective Inhibition of CDK4

| Structure | CDK4/CycD1 $IC_{50}$ [nM] | CDK2/CycE $IC_{50}$ [nM] | Fold Selectivity (CDK2/CycE/CDK4) | CDK2/CycA $IC_{50}$ [nM] | Fold Selectivity (CDK2/CycA/CDK4) |
|---|---|---|---|---|---|
| A | 4.2 | 6350 | 1516 | 3160 | 754 |
| B | 0.4 | 3040 | 6862 | 1890 | 4266 |
| C | 1.4 | 1920 | 1333 | 616 | 428 |
| D | 0.9 | 3480 | 3779 | 1500 | 1629 |
| E | 1 | 695 | 688 | 204 | 202 |
| F | 1.5 | 628 | 419 | 190 | 127 |
| G | 1.5 | 2580 | 1767 | 646 | 442 |
| H | 1.5 | 1520 | 1013 | 377 | 251 |
| I | 2 | 2120 | 1065 | 1130 | 568 |
| J | 0.7 | 5110 | 7707 | 4340 | 6546 |
| K | 1 | 1070 | 1019 | 738 | 703 |
| L | 5.7 | 4530 | 789 | 1490 | 260 |
| M | 2.3 | 2280 | 1004 | 1410 | 621 |
| N | 1 | 1500 | 1500 | ND | ND |
| O | 2.5 | 41410 | 1636 | 3150 | 1245 |
| P | 3.3 | 3560 | 1085 | 1010 | 308 |
| Q | 0.6 | 1080 | 1722 | 3030 | 4833 |
| R | 0.5 | 1920 | 3918 | 1360 | 2776 |
| S | 1.7 | 1250 | 718 | 342 | 197 |
| T | 0.8 | 1660 | 2022 | 1670 | 2034 |
| U | 0.7 | 1460 | 2229 | 857 | 1308 |
| V | 2.9 | 3500 | 1224 | 2130 | 745 |
| W | 2.7 | 3970 | 1481 | 539 | 201 |

TABLE 2-continued

Selective Inhibition of CDK4

| Structure | CDK4/ CycD1 IC$_{50}$ [nM] | CDK2/ CycE IC$_{50}$ [nM] | Fold Selectivity (CDK2/ CycE/ CDK4) | CDK2/ CycA IC$_{50}$ [nM] | Fold Selectivity (CDK2/ CycA/ CDK4) |
|---|---|---|---|---|---|
| X | 0.9 | 11600 | 12975 | 1840 | 2058 |
| Y | 2.5 | 124 | 50 | 61 | 25 |
| Z | 3.2 | 3710 | 1174 | 647 | 205 |
| AA | 0.5 | 6100 | 13319 | 4630 | 10109 |
| BB | 0.8 | 1680 | 2017 | 502 | 603 |
| CC | 1.6 | 1250 | 791 | 755 | 478 |
| DD | 1.9 | 9620 | 5200 | 8360 | 4519 |
| EE | 3.8 | 1660 | 432 | 1110 | 289 |
| FF | 1.2 | 4620 | 3949 | 1400 | 1197 |
| GG | 1 | 3580 | 3377 | 1510 | 1425 |
| HH | 1.7 | 1280 | 766 | 265 | 159 |
| II | 2 | 367 | 184 | 239 | 120 |
| JJ | 1.4 | 288 | 204 | ND | ND |
| KK | 2.3 | 1760 | 762 | 915 | 396 |
| LL | 2 | 202 | 103 | 108 | 55 |
| MM | 1.8 | 3390 | 1863 | 597 | 328 |
| NN | 3.7 | 4700 | 1274 | 1560 | 423 |
| OO | 9 | 3980 | 442 | 570 | 63 |
| PP | 3.1 | 3600 | 1146 | 3090 | 984 |
| QQ | 4.1 | 3060 | 746 | 2570 | 627 |
| RR | 1.2 | 1580 | 1374 | 693 | 603 |
| SS | 0.8 | 1460 | 1865 | 1390 | 1775 |
| TT | 0.8 | 1260 | 1550 | 596 | 733 |
| UU | 7.3 | 3960 | 542 | ND | ND |
| VV | 3.3 | 2630 | 809 | 789 | 243 |
| WW | 0.7 | 1350 | 204 | ND | ND |
| XX | 1.3 | 7300 | 5615 | 6290 | 4838 |
| YY | 4.6 | 6900 | 1490 | ND | ND |
| ZZ | 10.5 | 9960 | 949 | ND | ND |
| AAA | 2.3 | 6010 | 2591 | 2130 | 918 |
| BBB | 2.8 | 187 | 68 | 85 | 31 |
| CCC | 2 | 2170 | 1074 | 457 | 226 |
| DDD | 9.5 | 9350 | 986 | ND | ND |
| EEE | 0.2 | 2950 | 1266 | 943 | 405 |
| FFF | 4.7 | 4540 | 966 | 1370 | 291 |
| GGG | 13.7 | 7610 | 555 | ND | ND |
| HHH | 6.8 | 2840 | 419 | ND | ND |
| III | 6 | 3770 | 626 | ND | ND |
| JJJ | 3.2 | 5200 | 1620 | 2830 | 882 |
| KKK | 1.3 | 291 | 231 | 87.3 | 69 |
| LLL | 3.2 | 1620 | 509 | 4530 | 1425 |
| MMM | 3.2 | 1890 | 600 | 990 | 314 |
| NNN | 1.4 | 2930 | 2154 | 1010 | 743 |
| OOO | 2.4 | 393 | 164 | 203 | 85 |
| PPP | 0.8 | 16500 | 21263 | 2640 | 3402 |
| QQQ | 10.5 | 11100 | 1057 | ND | ND |
| RRR | 2.6 | 4500 | 1758 | ND | ND |
| SSS | 2 | 2280 | 1112 | 1880 | 917 |
| TTT | 3.4 | 3030 | 899 | ND | ND |
| UUU | 18 | 16460 | 914 | ND | ND |
| VVV | 7.4 | 4380 | 589 | ND | ND |
| WWW | 18.5 | 2500 | 135 | ND | ND |
| XXX | 11.4 | 6620 | 581 | ND | ND |

To further characterize its kinase activity, Compound T was screened against 456 (395 non-mutant) kinases using DiscoveRx's KINOMEscan™ profiling service. The compound was screened using a single concentration of 1000 nM (>1000 times the IC50 on CDK4). Results from this screen confirmed the high potency against CDK4 and high selectivity versus CDK2. Additionally, the kinome profiling showed that Compound T was relatively selective for CDK4 and CDK6 compared to the other kinases tested. Specifically, when using an inhibitory threshold of 65%, 90%, or 99%, Compound T inhibited 92 (23.3%), 31 (7.8%) or 6 (1.5%) of 395 non-mutant kinases respectively.

In addition to CDK4 kinase activity, several compounds were also tested against CDK6 kinase activity. The results of the CDK6/CycD3 kinase assays, along with the CDK4/cyclinD1, CDK2/CycA and CDK2/cyclinE kinase assays, are shown for PD0332991 (Reference) and the compounds T, Q, GG, and U in Table 3. The IC$_{50}$ of 10 nM for CDK4/cyclinD1 and 10 uM for CDK12/CyclinE agrees well with previously published reports for PD0332991 (Fry et al. Molecular Cancer Therapeutics (2004) 3(11)1427-1437; Toogood et al. Journal of Medicinal Chemistry (2005) 48, 2388-2406). Compounds T, Q, GG, and U are more potent (lower IC$_{50}$) with respect to the reference compound (PD0332991) and demonstrate a higher fold selectivity with respect to the reference compound (CDK2/CycE IC$_{50}$ divided by CDK4/CycD1 IC$_{50}$).

TABLE 3

Inhibition of CDK kinases by Compounds T, Q, GG, and U

| Formula | CDK4/ CycD1 IC$_{50}$(nM) | CDK2/ CycE IC$_{50}$(uM) | Fold Selectivity CDK2/ CDK4 | CDK2/ CycA IC$_{50}$(uM) | CDK6/ CycD3 IC$_{50}$(nM) |
|---|---|---|---|---|---|
| PD0332991 Reference | 10 | 10 | 1000 | Not determined | Not determined |
| Compound T | 0.821 | 1.66 | 2022 | 1.67 | 5.64 |
| Compound Q | 0.627 | 1.08 | 1722 | 3.03 | 4.38 |
| Compound GG | 1.060 | 3.58 | 3377 | 1.51 | 4.70 |
| Compound U | 0.655 | 1.46 | 2229 | .857 | 5.99 |

Example 151

G1 Arrest (Cellular G1 and S-Phase) Assay

For determination of cellular fractions in various stages of the cell cycle following various treatments, HS68 cells (human skin fibroblast cell line (Rb-positive)) were stained with propidium iodide staining solution and run on Dako Cyan Flow Cytometer. The fraction of cells in G0-G1 DNA cell cycle versus the fraction in S-phase DNA cell cycle was determined using FlowJo 7.2 0.2 analysis.

The compounds listed in Table 1 were tested for their ability to arrest HS68 cells at the G1 phase of the cell cycle. From the results of the cellular G1 arrest assay, the range of the inhibitory EC$_{50}$ values necessary for G1 arrest of HS68 cells was from 22 nM to 1500 nM (see column titled "Cellular G1 Arrest EC$_{50}$" in Table 4).

Example 152

Inhibition of Cellular Proliferation

Cellular proliferation assays were conducted using the following cancer cell lines: MCF7 (breast adenocarcinoma—Rb-positive), ZR-75-1 (breast ductal carcinoma—Rb-positive), H69 (human small cell lung cancer—Rb-negative) cells, or A2058 (human metastatic melanoma cells —Rb-negative). These cells were seeded in Costar (Tewksbury, Mass.) 3093 96 well tissue culture treated white walled/clear bottom plates. Cells were treated with the compounds of Table 1 as nine point dose response dilution series from 10 uM to 1 nM. Cells were exposed to compounds and then cell viability was determined after either four (H69) or six (MCF7, ZR75-1, A2058) days as indicated using the CellTiter-Glo® luminescent cell viability assay (CTG; Promega, Madison, Wis., United States of America) following the manufacturer's recommendations. Plates were read on BioTek (Winooski, Vt.) Syngergy2 multi-mode plate reader. The Relative Light Units (RLU) were plotted as a result of variable molar concentration and data was analyzed using Graphpad (LaJolla, Calif.) Prism 5 statistical software to determine the $EC_{50}$ for each compound.

The results of the cellular inhibition assays for the two Rb-positive breast cancer cell lines (MCF7 and ZR75-1) are shown in Table 4. The range of the inhibitory $EC_{50}$ values necessary for inhibition of MCF7 breast cancer cell proliferation was 28 nM to 257 nM. The range of the inhibitory $EC_{50}$ values necessary for inhibition of ZR75-1 breast cancer cell proliferation was 24 nM to 581 nM.

Figure 21:
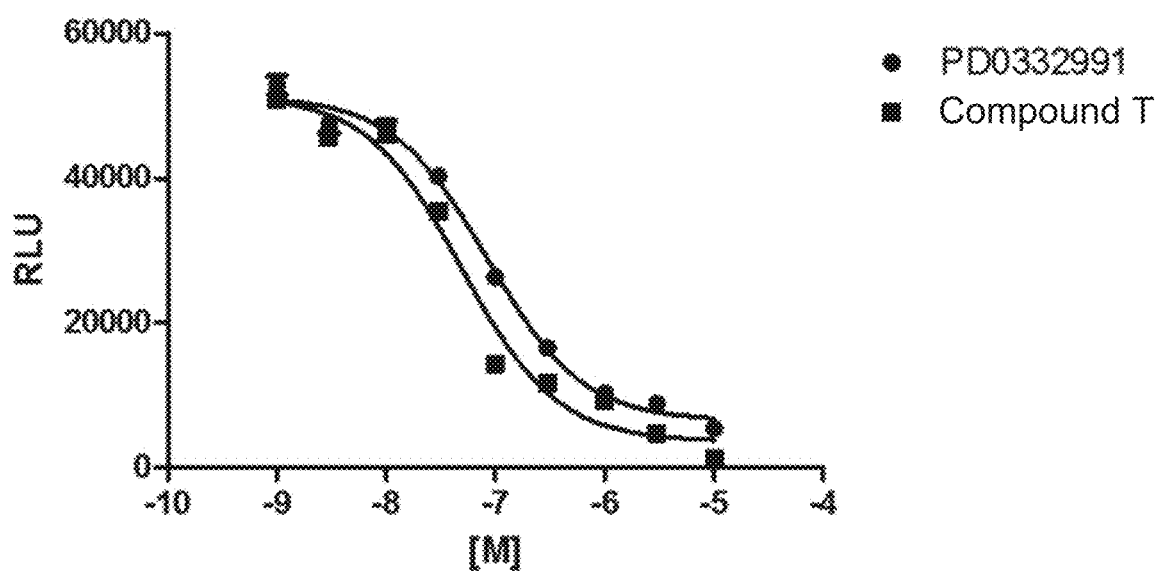
FIG. 21 is a graph of the cellular proliferation of MCF7 (Rb-positive) cells (breast adenocarcinoma) (as measured by Relative Light Units (RLU)) v. variable molar concentration (M) of treatment with either PD0332991 (circles) or Compound T (Table 1; squares). The MCF7 cells were seeded in Costar (Tewksbury, Mass.) 3903 96 well tissue culture treated white walled/clear bottom plates. A nine point dose response dilution series from 10 uM to 1 nM was performed and cell viability was determined after six days of compound treatment as indicated using the CellTiter-Glo® luminescent cell viability assay (CTG; Promega, Madison, Wis., United States of America) following the manufacturer's recommendations. Plates were read on a BioTek (Winooski, Vt.) Syngergy2 multi-mode plate reader. The Relative Light Units (RLU) were plotted as a result of variable molar concentration and data was analyzed using Graphpad (La-Jolla, Calif.) Prism 5 statistical software to determine the $EC_{50}$ for each compound.
Figure 22:
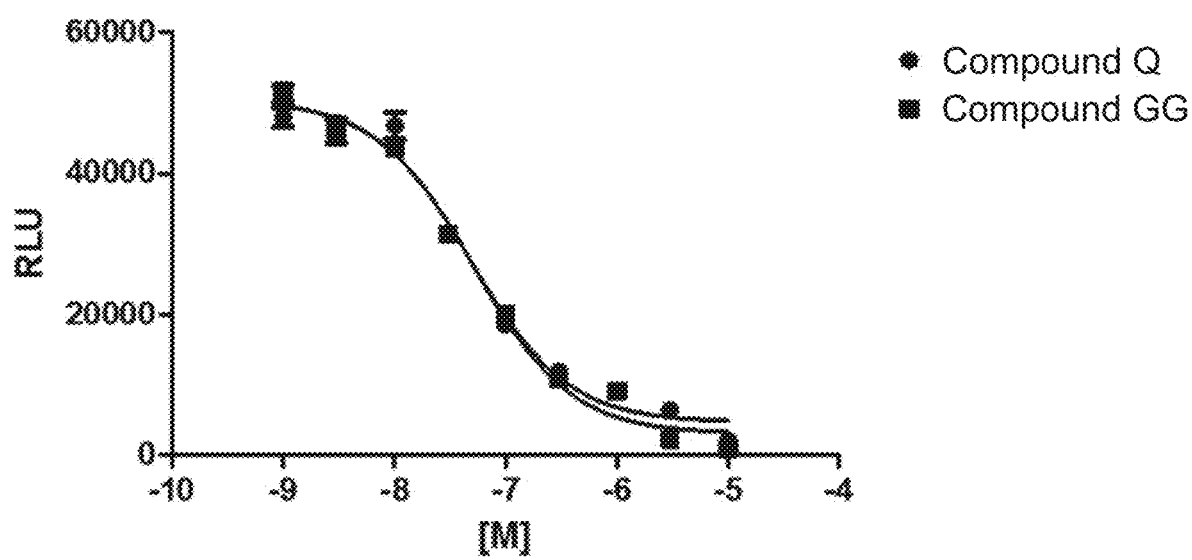
FIG. 22 is a graph of the cellular proliferation of MCF7 (Rb-positive) cells (breast adenocarcinoma) (as measured by Relative Light Units (RLU)) v. variable molar concentration (M) of treatment with either Compound Q (Table 1; circles) or Compound GG (Table 1; squares). Cellular proliferation was determined using the CellTiter-Glo® luminescent cell viability assay, as described in FIG. 21 and Example 152.
Figure 23:
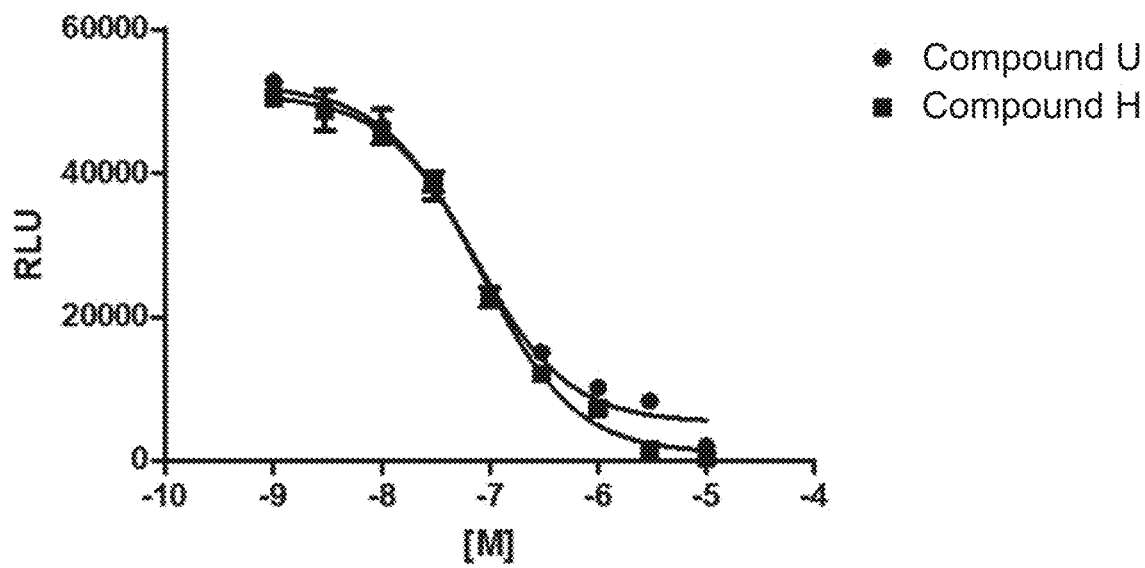
FIG. 23 is a graph of the cellular proliferation of MCF7 (Rb-positive) cells (breast adenocarcinoma) (as measured by Relative Light Units (RLU)) v. variable molar concentration (M) of treatment with either Compound U (Table 1; circles) or Compound H (Table 1; squares). Cellular proliferation was determined using the CellTiter-Glo® luminescent cell viability assay, as described in FIG. 21 and Example 152.
Figure 24:
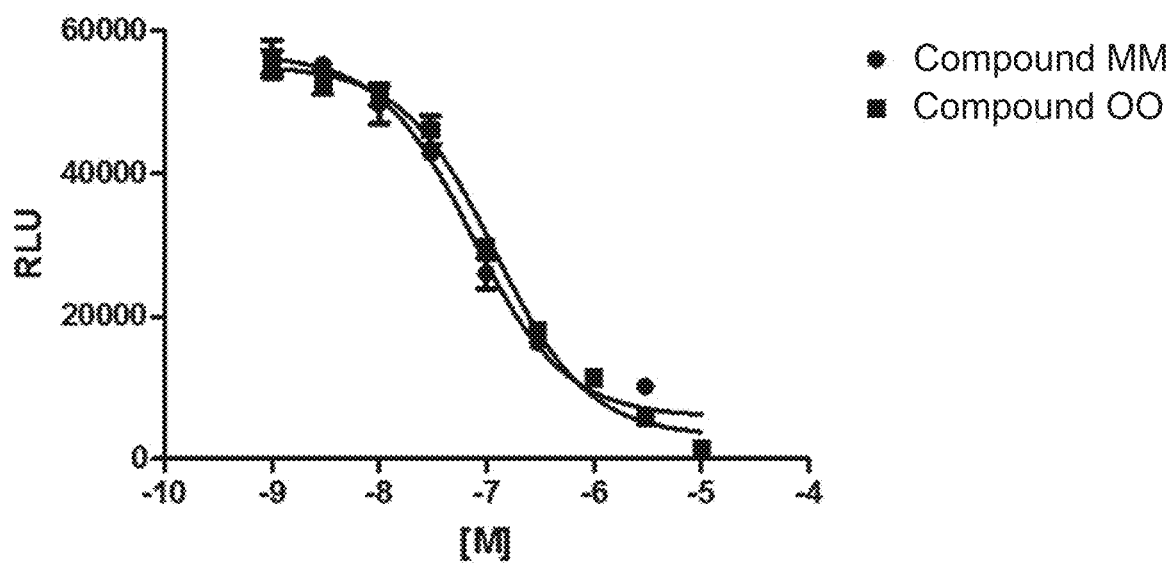
FIG. 24 is a graph of the cellular proliferation of MCF7 (Rb-positive) cells (breast adenocarcinoma) (as measured by Relative Light Units (RLU)) v. variable molar concentration (M) of treatment with either Compound MM (Table 1; circles) or Compound OO (Table 1; squares). Cellular proliferation was determined using the CellTiter-Glo® luminescent cell viability assay, as described in FIG. 21 and Example 152.

Examples of representative compounds highly active against the proliferation of MCF7 breast adenocarcinoma cells are shown in FIGS. 21-24. The compounds tested in FIGS. 21-24 (Compounds T, Q, GG, U, H, MM, OO, and PD-332991) all showed significant inhibition of cellular proliferation of MCF-7 cells. As can be seen in FIG. 21, compound T shows more potent activity against MCF-7 cells than PD0332991.

Figure 25:
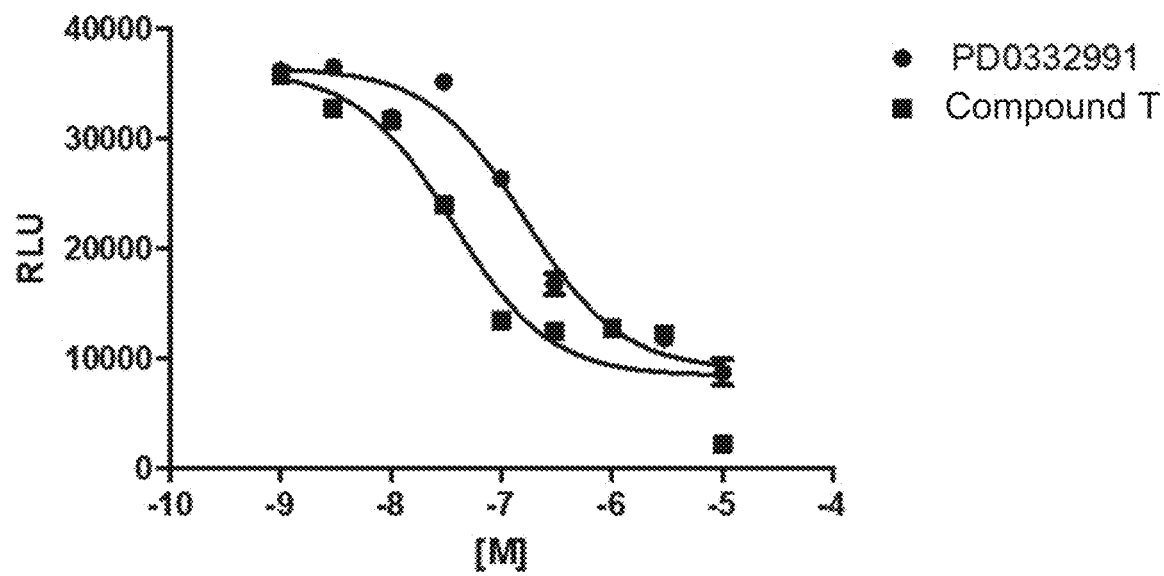
FIG. 25 is a graph of the cellular proliferation of ZR75-1 (Rb-positive) cells (breast adenocarcinoma) (as measured by Relative Light Units (RLU)) v. variable molar concentration (M) of treatment with either PD0332991 (circles) or Compound T (Table 1; squares). Cellular proliferation was determined using the CellTiter-Glo® luminescent cell viability assay, as described in FIG. 21 and Example 152.
Figure 26:
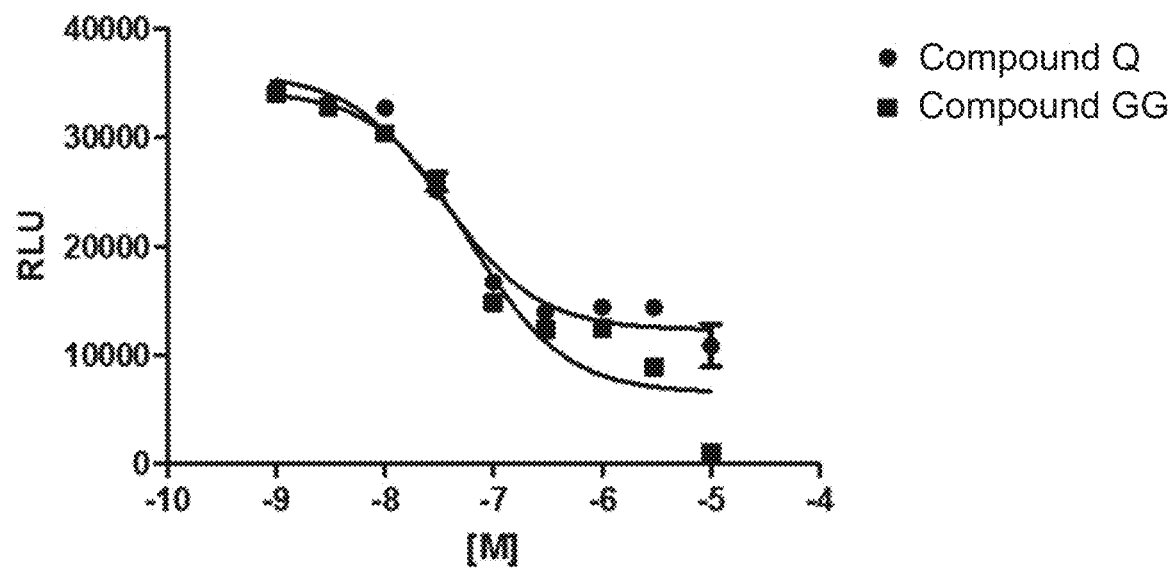
FIG. 26 is a graph of the cellular proliferation of ZR75-1 (Rb-positive) cells (breast adenocarcinoma) (as measured by Relative Light Units (RLU)) v. variable molar concentration (M) of treatment with either Compound Q (Table 1; circles) or Compound GG (Table 1; squares). Cellular proliferation was determined using the CellTiter-Glo® luminescent cell viability assay, as described in FIG. 21 and Example 152.
Figure 27:
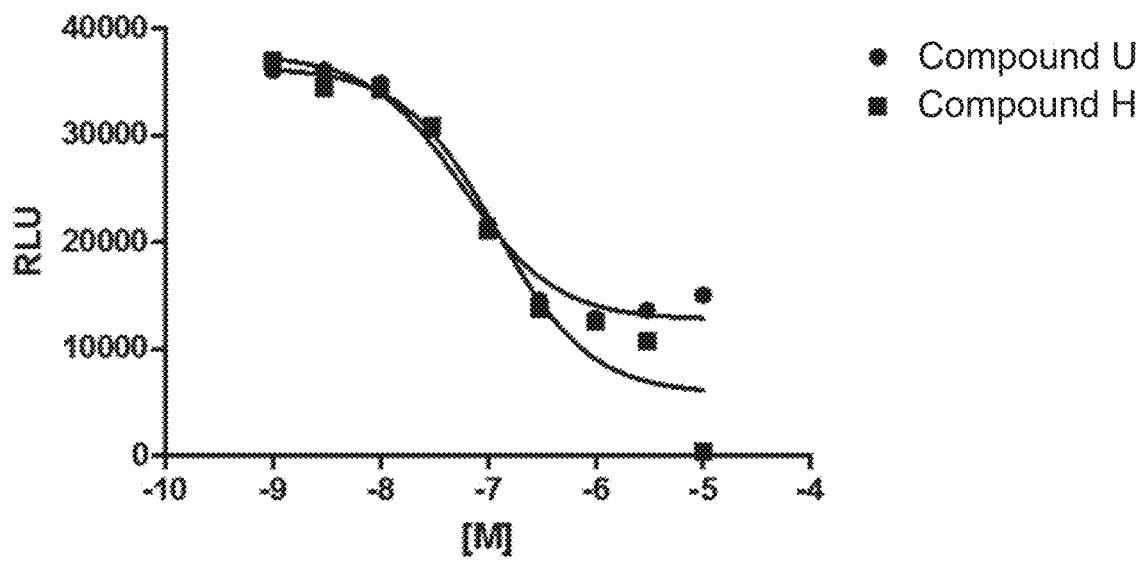
FIG. 27 is a graph of the cellular proliferation of ZR75-1 (Rb-positive) cells (breast adenocarcinoma) (as measured by Relative Light Units (RLU)) v. variable molar concentration (M) of treatment with either Compound U (Table 1; circles) or Compound H (Table 1; squares). Cellular proliferation was determined using the CellTiter-Glo® luminescent cell viability assay, as described in FIG. 21 and Example 152.
Figure 28:
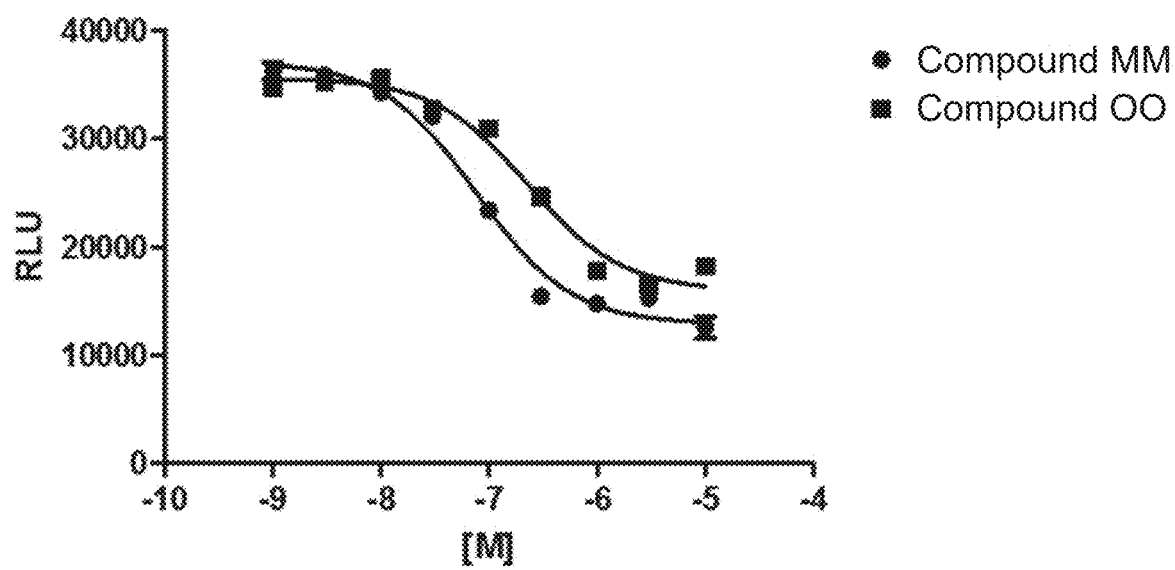
FIG. 28 is a graph of the cellular proliferation of ZR75-1 (Rb-positive) cells (breast adenocarcinoma) (as measured by Relative Light Units (RLU)) v. variable molar concentration (M) of treatment with either Compound MM (Table 1; circles) or Compound OO (Table 1; squares). Cellular proliferation was determined using the CellTiter-Glo® luminescent cell viability assay, as described in FIG. 21 and Example 152.

Examples of representative compounds highly active against the proliferation of ZR75-1 (breast ductal carcinoma (Rb-Positive)) cells are shown in FIGS. 25-28. The compounds tested in FIGS. 25-28 (Compounds T, Q, GG, U, H, MM, OO, and PD-332991) all showed significant inhibition of cellular proliferation of ZR75-1 cells. As can be seen in FIG. 25, compound T shows more potent activity against ZR75-1 cells than PD0332991.

In addition to breast cancer cell lines, a number of the compounds disclosed herein were also evaluated against a small cell lung cancer cell line (H69) and a human metastatic melanoma cell line (A2058), two Rb-deficient (Rb-negative) cell lines. The results of these cellular inhibition assays are shown in Table 4. The range of the inhibitory $EC_{50}$ values necessary for inhibition of H69 small cell lung cancer cells was 2040 nM to >3000 nM. The range of the inhibitory $EC_{50}$ values necessary for inhibition of A2058 malignant melanoma cell proliferation was 1313 nM to >3000 nM. In contrast to the significant inhibition seen on the two Rb-positive breast cancer cell lines, it was found that the compounds tested were not significantly effective at inhibiting proliferation of the small cell lung cancer or melanoma cells.

TABLE 4

Inhibition of Cancer Cell Proliferation

| Structure | Cellular G1 Arrest $EC_{50}$ (nM) | MCF7 Cellular $EC_{50}$ [nM] | ZR75-1 Cellular $EC_{50}$ [nM] | H69 Cellular $EC_{50}$ [nM] | A2058 Cellular $EC_{50}$ [nM] |
|---|---|---|---|---|---|
| A | 110 | 75 | 44 | >3000 | ND |
| B | 90 | 201 | 245 | ND | ND |
| C | 95 | 88 | 73 | ND | ND |
| D | 50 | 57 | 46 | 2911 | 1670 |
| E | 75 | 53 | 62 | 2580 | 1371 |
| F | 175 | ND | ND | ND | ND |
| G | 175 | ND | ND | ND | ND |
| H | 85 | 85 | 120 | 2040 | 1313 |
| I | 80 | 61 | 40 | 2950 | 1062 |
| J | 110 | 70 | 82 | >3000 | >3000 |
| K | 28 | 43 | ND | >3000 | 1787 |
| L | 65 | 506 | ND | 2161 | >3000 |
| M | 100 | ND | ND | ND | ND |
| N | 25 | 28 | 24 | >3000 | 1444 |
| O | 40 | 56 | 29 | >3000 | 2668 |
| P | 30 | 60 | 43 | >3000 | >3000 |
| Q | 100 | 49 | 35 | >3000 | 2610 |
| R | 70 | 36 | 50 | >3000 | 2632 |
| S | 150 | 76 | ND | >3000 | >3000 |
| T | 100 | 49 | 36 | >3000 | >3000 |
| U | 25 | 70 | 59 | >3000 | >3000 |
| V | 70 | 50 | 29 | >3000 | 1353 |
| W | 160 | 294 | ND | >3000 | >3000 |
| X | 65 | ND | ND | >3000 | >3000 |
| Y | 350 | ND | ND | ND | ND |
| Z | 110 | 141 | 54 | ND | ND |
| AA | 70 | 47 | 47 | >3000 | ND |
| BB | 75 | ND | ND | 2943 | 1635 |
| CC | 90 | 50 | 38 | >3000 | >3000 |
| DD | 100 | ND | ND | ND | ND |
| EE | 125 | 216 | 203 | ND | ND |
| FF | 80 | 140 | ND | ND | ND |
| GG | 80 | 52 | 62 | 2920 | 2691 |
| HH | 110 | ND | ND | ND | ND |
| II | 40 | 94 | 33 | >3000 | >3000 |
| JJ | 90 | 122 | ND | >3000 | >3000 |
| KK | 22 | 333 | ND | 2421 | 1379 |
| LL | 125 | 96 | ND | >3000 | >3000 |
| MM | 100 | 73 | 77 | >3000 | >3000 |
| NN | 110 | ND | ND | ND | ND |
| OO | 95 | 120 | 229 | >3000 | >3000 |
| PP | 100 | 164 | 66 | ND | ND |
| QQ | 120 | ND | ND | >3000 | >3000 |
| RR | 90 | 72 | ND | 2888 | 1617 |
| SS | 80 | 94 | 53 | 2948 | 1658 |
| TT | 75 | ND | ND | ND | ND |
| UU | 300 | ND | ND | ND | ND |
| VV | 200 | ND | ND | ND | ND |
| WW | 400 | ND | ND | ND | ND |
| XX | 225 | ND | ND | ND | ND |
| YY | 175 | 257 | 581 | ND | ND |
| ZZ | 500 | ND | ND | ND | ND |
| AAA | 275 | 320 | ND | >3000 | >3000 |
| BBB | 230 | 123 | ND | >3000 | >3000 |
| CCC | 250 | ND | ND | ND | ND |
| DDD | 350 | ND | ND | ND | ND |
| EEE | 250 | 453 | ND | >3000 | >3000 |
| FFF | 650 | ND | ND | ND | ND |
| GGG | 350 | ND | ND | ND | ND |
| HHH | 250 | ND | ND | ND | ND |
| III | 250 | ND | ND | ND | ND |
| JJJ | 240 | ND | ND | ND | ND |
| KKK | 190 | ND | ND | ND | ND |
| LLL | 250 | ND | ND | ND | ND |
| MMM | 200 | 134 | 141 | >3000 | >3000 |
| NNN | 210 | ND | ND | ND | ND |
| OOO | 200 | 138 | ND | >3000 | >3000 |
| PPP | 275 | ND | ND | ND | ND |
| QQQ | 500 | ND | ND | ND | ND |
| RRR | 400 | ND | ND | ND | ND |
| SSS | 1500 | ND | ND | ND | ND |
| TTT | 350 | ND | ND | ND | ND |
| UUU | 300 | ND | ND | ND | ND |
| VVV | 300 | ND | ND | ND | ND |
| WWW | 300 | ND | ND | ND | ND |
| XXX | 300 | ND | ND | ND | ND |

Example 153

HSPC Growth Suppression Studies

Figure 2:
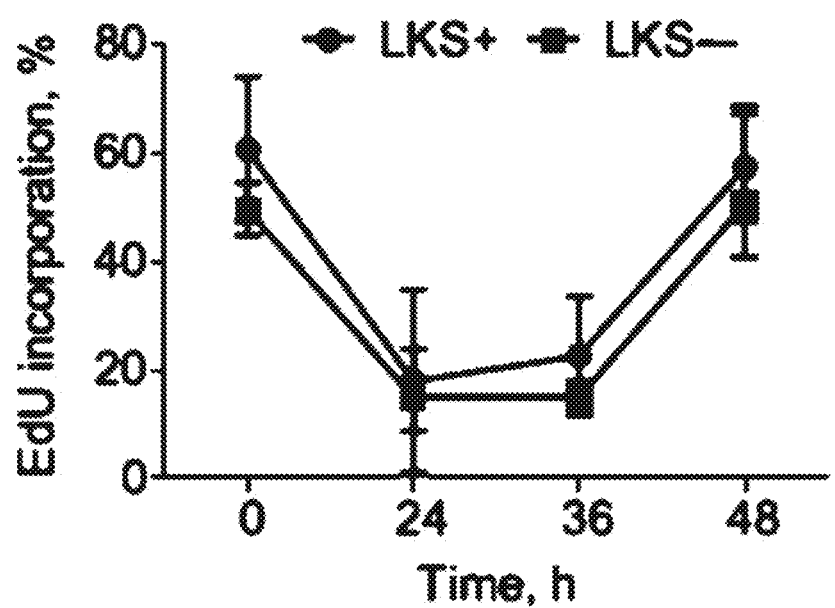
FIG. 2 is a graph of EdU incorporation vs. time after administration (hours) of PD0332991 to healthy mice HSPCs and healthy myeloid progenitor cells. PD0332991 (150 mg/kg) was administered by oral gavage to assess the temporal effect of transient CDK4/6 inhibition on bone marrow arrest as reported in Roberts et al. Multiple Roles of Cyclin-Dependent Kinase 4/6 Inhibitors in Cancer Therapy. JCNI 2012; 104(6):476-487 (FIG. 2A). As described in Example 153, a single oral dose of PD0332991 results in a sustained reduction in HSPC EdU incorporation (circles; LKS+) and myeloid progenitor cells EdU incorporation (squares; LKS−) for greater than 36 hours.
Figure 3A:
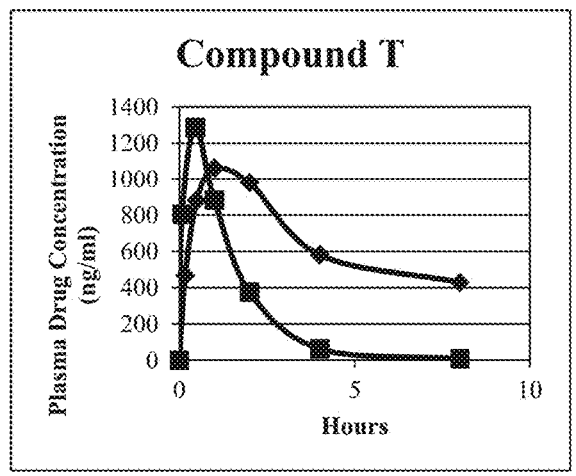
FIG. 3A is a graph of plasma drug concentration (ng/ml) vs. time after administration (hours) of compound T.
Figure 3B:
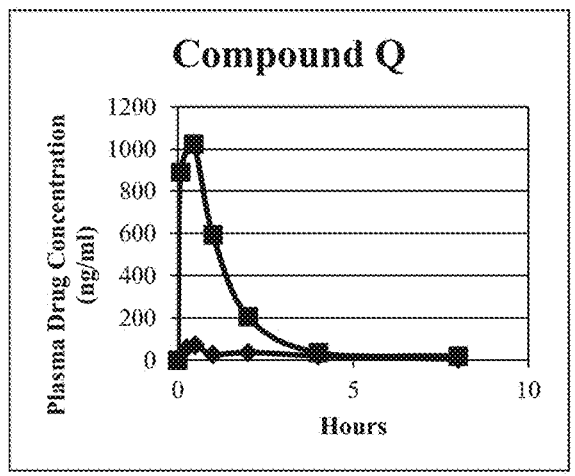
FIG. 3B is a graph of plasma drug concentration (ng/ml) vs. time after administration (hours) of compound Q.
Figure 3C:
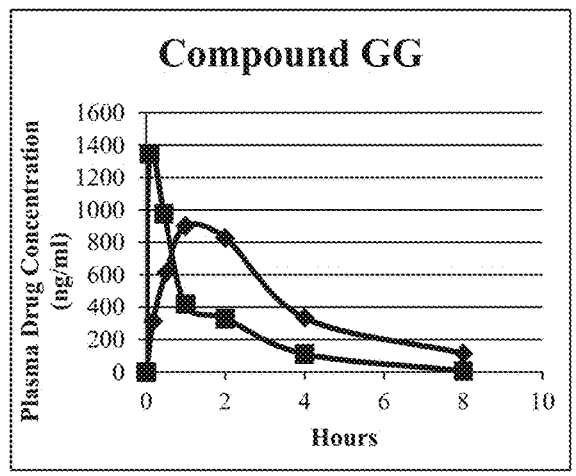
FIG. 3C is a graph of plasma drug concentration (ng/ml) vs. time after administration (hours) of compound GG.
Figure 3D:
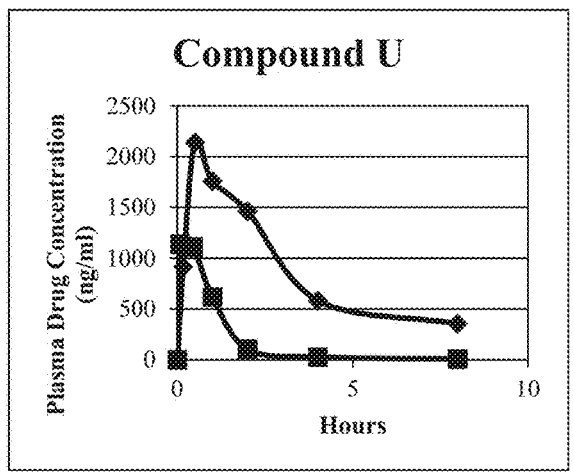
FIG. 3D is a graph of plasma drug concentration (ng/ml) vs. time after administration (hours) of compound U. Compounds were dosed to mice at 30 mg/kg by oral gavage (diamonds) or 10 mg/kg by intravenous injection (squares). Blood samples were taken at 0, 0.25, 0.5, 1.0, 2.0, 4.0, and 8.0 hours post dosing and the plasma concentrations were determined by HPLC.
Figure 4A:
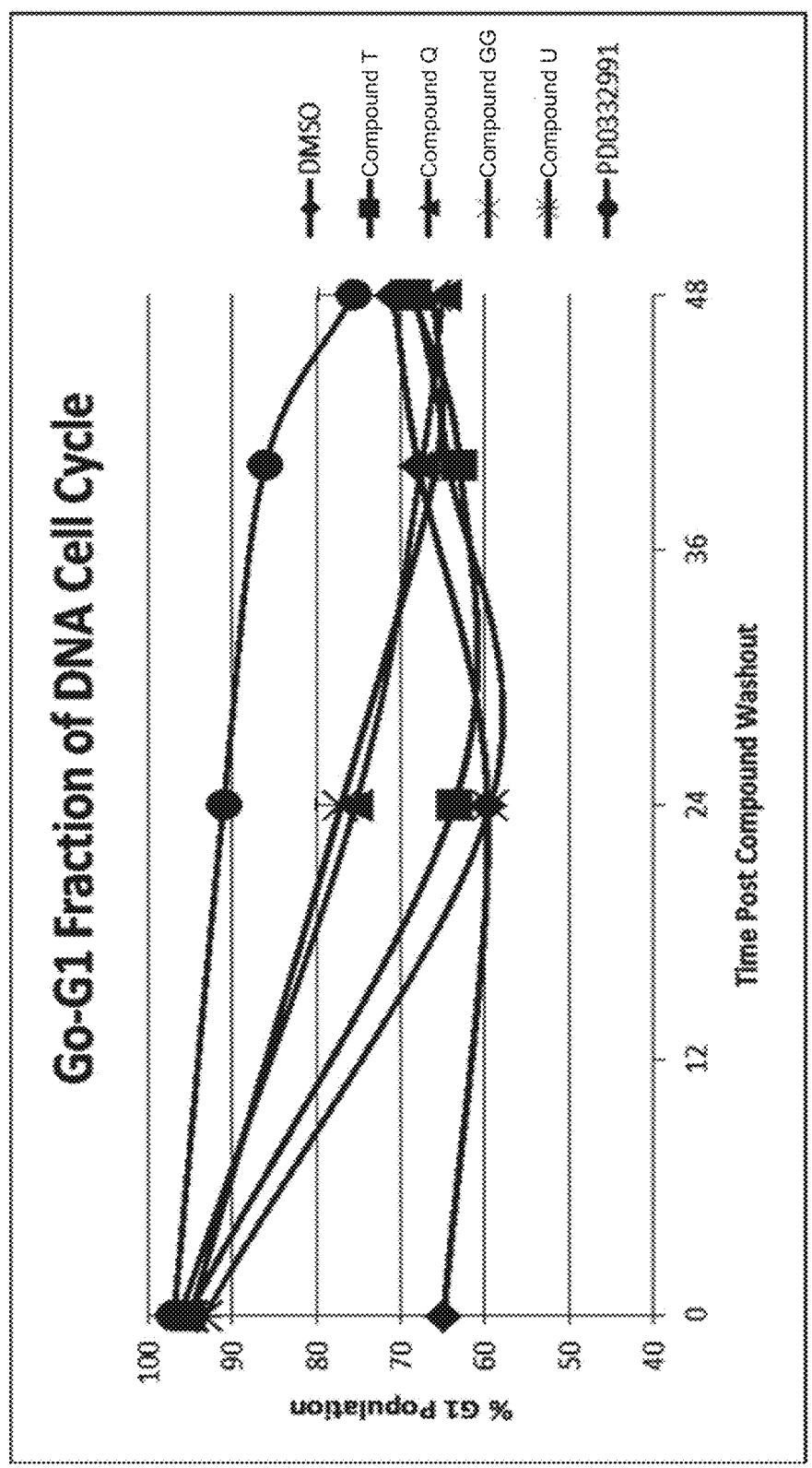
FIG. 4A is a graph of the percentage of cells in the G0-G1 phase of the cell cycle vs. time after washout of the compound (hours) in human fibroblast (Rb-positive) cells.
Figure 4B:
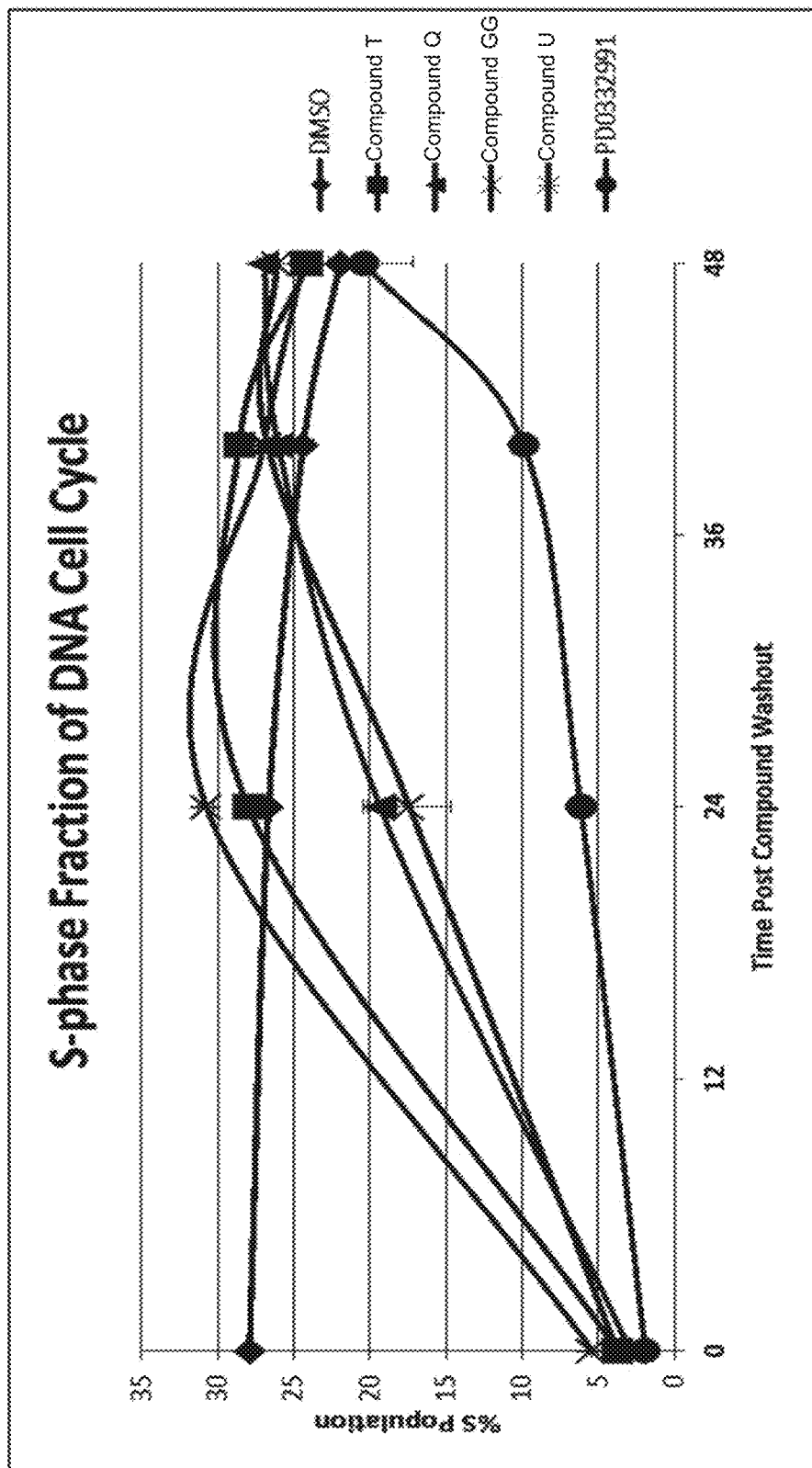
FIG. 4B is a graph of the percentage of cells in the S phase of the cell cycle vs. time after washout of the compound (hours) in human fibroblast (Rb-positive) cells.
Figure 4C:
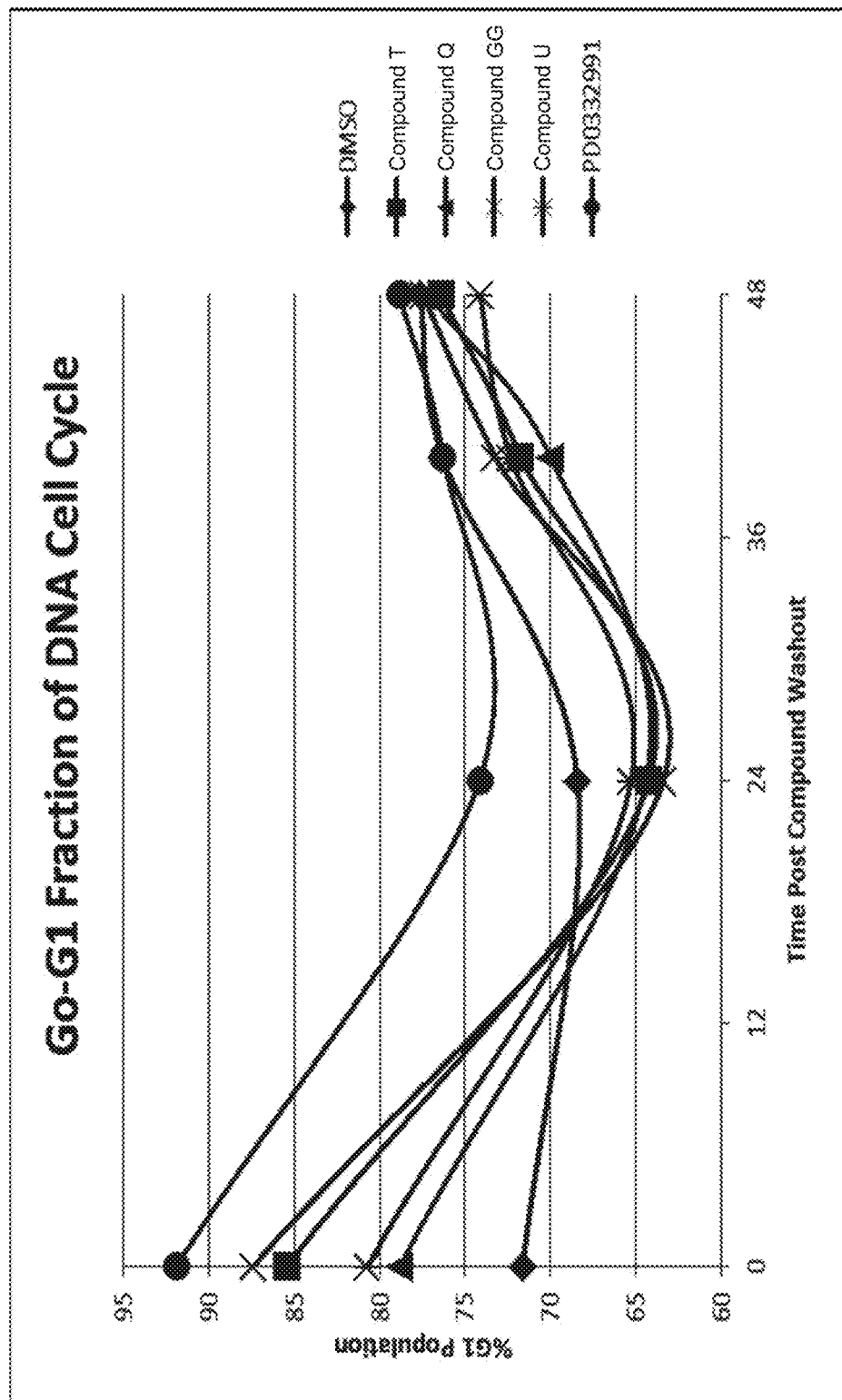
FIG. 4C is a graph of the percentage of cells in the G0-G1 phase of the cell cycle vs. time after washout of the compound (hours) in human renal proximal tubule epithelial (Rb-positive) cells.
Figure 4D:
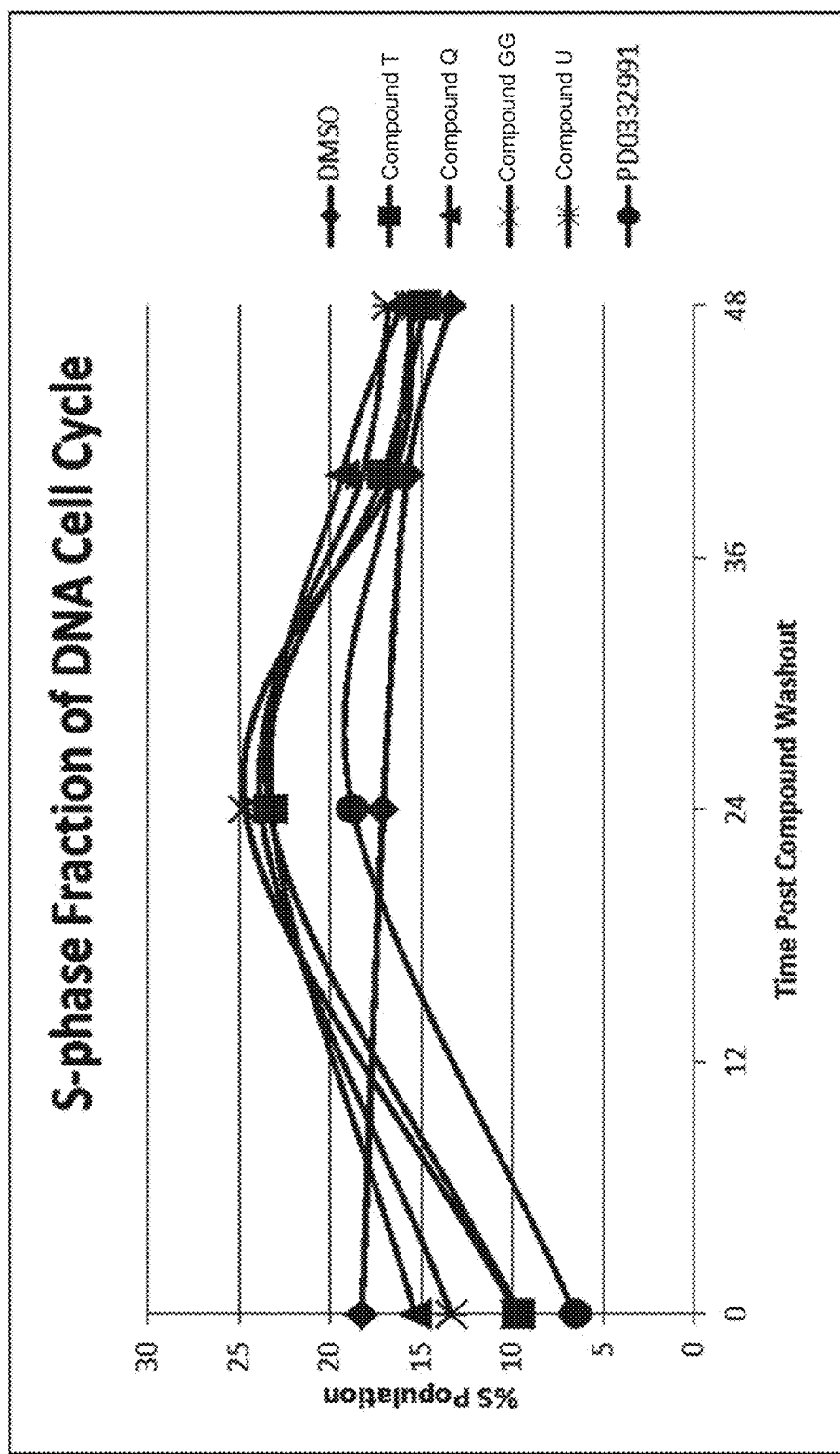
FIG. 4D is a graph of the percentage of cells in the S phase of the cell cycle vs. time after washout of the compound (hours) in human renal proximal tubule epithelial (Rb-positive) cells. These cellular wash out experiments demonstrated that the inhibitor compounds of the present invention have a short, transient G1-arresting effect in different cell types. The effect on the cell cycle following washing out of the compounds was determined at 24, 36, 40, and 48 hours. As described in Example 155, the results show that cells treated with PD0332991 (circles) took significantly longer to reach baseline levels of cell division (see cells treated only with DMSO (diamonds)), than cells treated with compound T (squares), compound Q (triangles), compound GG (X), or compound U (X with cross).

The effect of PD0332991 on HSPCs has been previously demonstrated. FIG. 2 shows the EdU incorporation of mice HSPC and myeloid progenitor cells following a single dose of 150 mg/kg PD0332991 by oral gavage to assess the temporal effect of transient CDK4/6 inhibition on bone marrow arrest as reported in Roberts et al. Multiple Roles of Cyclin-Dependent Kinase 4/6 Inhibitors in Cancer Therapy. JCNI 2012; 104(6):476-487 (FIG. 2A). As can be seen in FIG. 2, a single oral dose of PD0332991 results in a sustained reduction in HSPC (LKS+) and myeloid progenitor cells (LKS−) for greater than 36 hours. Not until 48 hours post oral dosing do HSPC and myeloid progenitor cells return to baseline cell division.

Example 154

Pharmacokinetic and Pharmacodynamic Properties of Anti-Neoplastic Compounds

Compounds of the present invention demonstrate good pharmacokinetic and pharmacodynamic properties. Compound T, Q, GG, and U were dosed to mice at 30 mg/kg by oral gavage or 10 mg/kg by intravenous injection. Blood samples were taken at 0, 0.25, 0.5, 1.0, 2.0, 4.0, and 8.0 hours post dosing and the plasma concentration of compound T, Q, GG, or U were determined by HPLC. Compound T, GG, and U were demonstrated to have excellent oral pharmacokinetic and pharmacodynamic properties as shown in Table 5. This includes very high oral bioavailability (F (%)) of 52% to 80% and a plasma half-life of 3 to 5 hours following oral administration. Compound T, Q, GG, and U were demonstrated to have excellent pharmacokinetic and pharmacodynamic properties when delivered by intravenous administration. Representative IV and oral PK curves for all four compounds are shown in FIG. 3.

TABLE 5

Pharmacokinetic and pharmacodynamic properties of anti-neoplastic compounds

| Mouse PK | Compound T | Compound Q | Compound GG | Compound U |
|---|---|---|---|---|
| CL (mL/min/kg) | 35 | 44 | 82 | 52 |
| Vss (L/kg) | 2.7 | 5.2 | 7.5 | 3.4 |
| $t_{1/2}$ (h) p.o. | 5 | 0.8 | 3.5 | 3 |
| $AUC_{0-inf}$ (uM*h) i.v. | 1.3 | 0.95 | 1.1 | 0.76 |
| AUC (uM*h) p.o. | 2.9 | 0.15 | 1.9 | 3.3 |
| $C_{max}$ (uM) p.o. | 2.5 | 0.16 | 1.9 | 4.2 |
| $T_{max}$ (h) p.o. | 1 | 0.5 | 1 | 0.5 |
| F (%) | 80 | 2 | 52 | 67 |

Example 155

Cellular Wash-Out Experiment

HS68 cells were seeded out at 40,000 cells/well in 60 mm dish on day 1 in DMEM containing 10% fetal bovine serum, 100 U/ml penicillin/streptomycin and 1× Glutamax (Invitrogen) as described (Brookes et al. EMBO J, 21(12)2936-2945 (2002) and Ruas et al. Mol Cell Biol, 27(12)4273-4282 (2007)). 24 hrs post seeding, cells are treated with compound T, compound Q, compound GG, compound U, PD0332991, or DMSO vehicle alone at 300 nM final concentration of test compounds. On day 3, one set of treated cell samples were harvested in triplicate (0 Hour sample). Remaining cells were washed two times in PBS-CMF and returned to culture media lacking test compound. Sets of samples were harvested in triplicate at 24, 40, and 48 hours.

Alternatively, the same experiment was done using normal Renal Proximal Tubule Epithelial Cells (Rb-positive) obtained from American Type Culture Collection (ATCC, Manassas, Va.). Cells were grown in an incubator at 37° C. in a humidified atmosphere of 5% CO2 in Renal Epithelial Cell Basal Media (ATCC) supplemented with Renal Epithelial Cell Growth Kit (ATCC) in 37° C. humidified incubator.

Upon harvesting cells, samples were stained with propidium iodide staining solution and samples run on Dako Cyan Flow Cytometer. The fraction of cells in G0-G1 DNA cell cycle versus the fraction in S-phase DNA cell cycle was determined using FlowJo 7.2 0.2 analysis.

FIG. 4 shows cellular wash-out experiments which demonstrate the inhibitor compounds of the present invention have a short, transient G1-arresting effect in different cell types. Compounds T, Q, GG, and U were compared to PD0332991 in either human fibroblast cells (Rb-positive) (FIGS. 4A & 4B) or human renal proximal tubule epithelial cells (Rb-positive) (FIGS. 4C & 4D) and the effect on cell cycle following washing out of the compounds was determined at 24, 36, 40, and 48 hours.

As shown in FIG. 4 and similar to results in vivo as shown in FIG. 2, PD0332991 required greater than 48 hours post wash out for cells to return to normal baseline cell division. This is seen in FIG. 4A and FIG. 4B as values equivalent to those for the DMSO control for either the G0-G1 fraction or the S-phase of cell division, respectively, were obtained. In contrast, HS68 cells treated with compounds of the present invention returned to normal baseline cell division in as little as 24 hours or 40 hours, distinct from PD0332991 at these same time points. The results using human renal proximal tubule epithelial cells (FIGS. 4C & 4D) also show that PD0332991-treated cells took significantly longer to return to baseline levels of cell division as compared to cells treated with compounds T, Q, GG, or U.

Example 156

Bone Marrow Proliferation as Evaluated Using EdU Incorporation and Flow Cytometry Analysis For HSPC proliferation experiments, young adult female FVB/N mice were treated with a single dose as indicated of compound T, compound Q, compound GG or PD0332991 by oral gavage. Mice were then sacrificed at the indicated times (0, 12, 24, 36, or 48 hours following compound administration), and bone marrow was harvested (n=3 mice per time point), as previously described (Johnson et al. J. Clin. Invest. (2010) 120(7), 2528-2536). Four hours before the bone marrow was harvested, mice were treated with 100 μg of EdU by intraperitoneal injection (Invitrogen). Bone marrow mononuclear cells were harvested and immunophenotyped using previously described methods and percent EdU positive cells were then determined (Johnson et al. J. Clin. Invest. (2010) 120(7), 2528-2536). In brief, HSPCs were identified by expression of lineage markers (Lin−), Sca1 (S+), and c-Kit (K+).

Figure 5A:
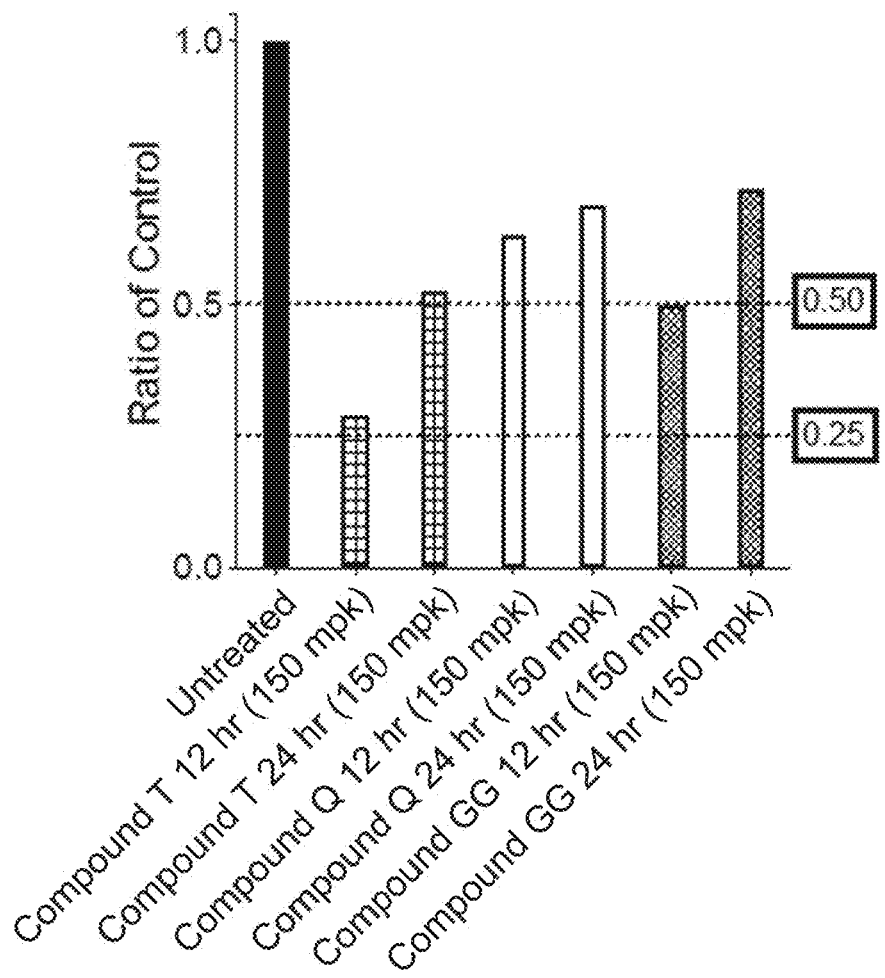
FIG. 5A is a graph of the ratio of EdU incorporation into HSPCs (compared to untreated control mice) following oral gavage of compounds T, Q, or GG at 150 mg/kg at either 12 or 24 hours post administration.

Analysis in mice determined that Compound T, Compound Q, and Compound GG demonstrated dose dependent, transient, and reversible G1-arrest of bone marrow stem cells (HSPC) (FIG. 5). Six mice per group were dosed by oral gavage at 150 mg/kg of Compound T, Compound Q, Compound GG, or vehicle only. Four hours before animals were sacrificed and the bone marrow was harvested, mice were treated with 100 μg of EdU by intraperitoneal injection. Three mice per group were sacrificed at 12 hours and the remaining three animals per group were sacrificed at 24 hours. Results are shown in FIG. 5A as the ratio of EdU positive cells for treated animals at 12 or 24 hour time points compared to control. Compound T and GG demonstrated a reduction in EdU incorporation at 12 hours which was starting to return to normal at 24 hours. Compound Q also demonstrated some reduction at 12 hours and started to return to baseline at 24 hours despite the fact that oral bioavailability of Compound Q is low.

Figure 5B:
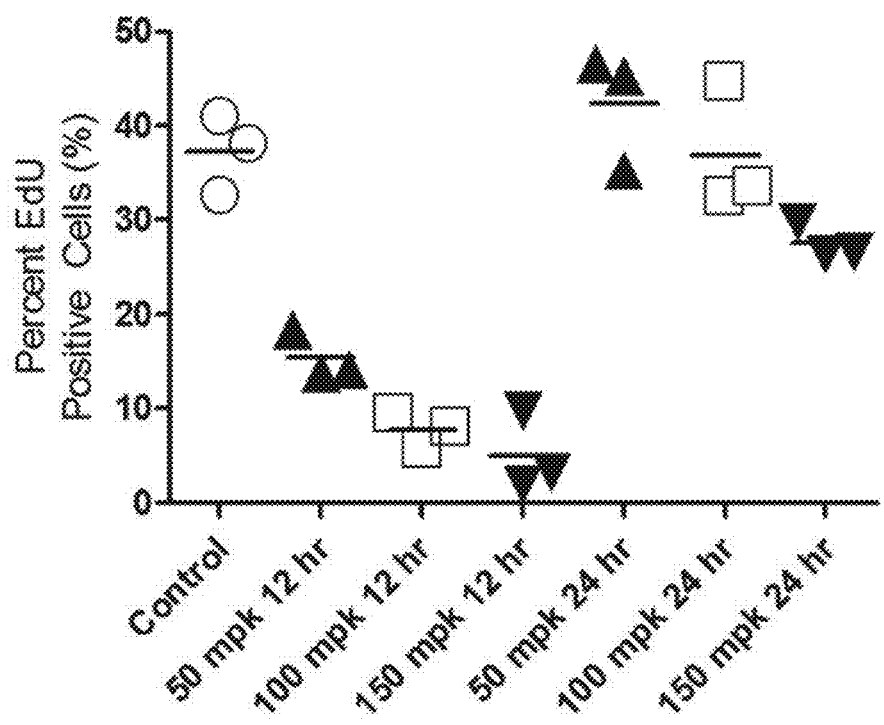
FIG. 5B is a graph of the percentage of EdU positive HSPC cells for mice treated with compound T at either 12 or 24 hours. Mice were dosed with 50 mg/kg (triangles), 100 mg/kg (squares), or 150 (upside down triangles) mg/kg by oral gavage.
Figure 5C:
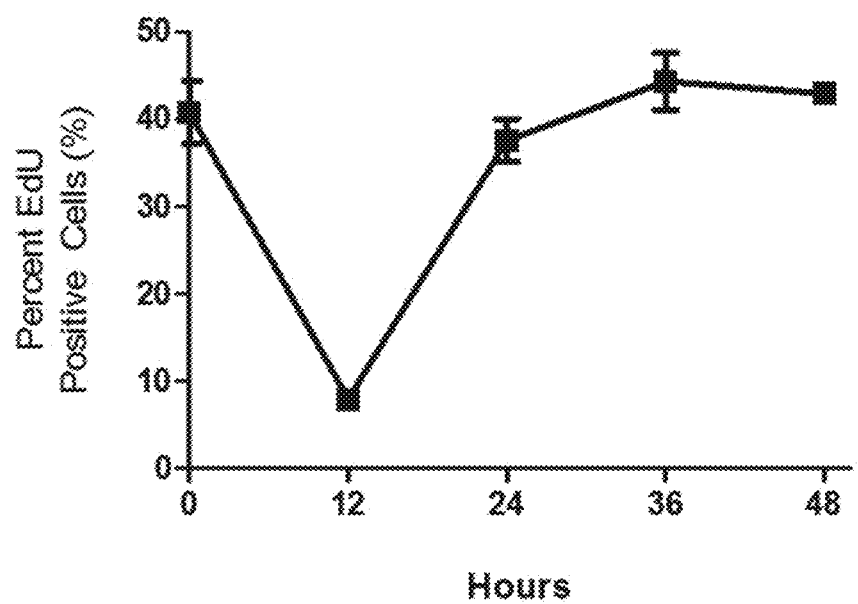
FIG. 5C is a graph of the percentage of EdU positive HSPC cells for mice treated with compound T (150 mg/kg by oral gavage) at either 12, 24, 36 and 48 hours. As described in Example 156, compound T and GG demonstrated a reduction in EdU incorporation at 12 hours, and started to return to normal levels of cell division by 24 hours.

Further experiments were completed with Compound T examining dose response and longer periods of compound treatment. Compound T was dosed by oral gavage at 50, 100 or 150 mg/kg and EdU incorporation into bone marrow was determined at 12 and 24 hours as described above. Alternatively, Compound T was dosed by oral gavage at 150 mg/kg and EdU incorporation into bone marrow was determined at 12, 24, 36 and 48 hours. As can be seen in FIGS. 5B and 5C, and similar to the cellular washout experiments, bone marrow cells, and in particular HSPCs were returning to normal cell division as determined by EdU incorporation in 24 hours following oral gavage at a number of doses. The 150 mg/kg oral dose of Compound T in FIG. 5C can be compared directly to the results of the same dose of PD0332991 shown in FIG. 2 where cells were still non-dividing (as determined by low EdU incorporation) at 24 and 36 hours, only returning to normal values at 48 hours.

Example 157

HSPC Growth Suppression Studies Comparing Compound T and PD0332991

Figure 6:
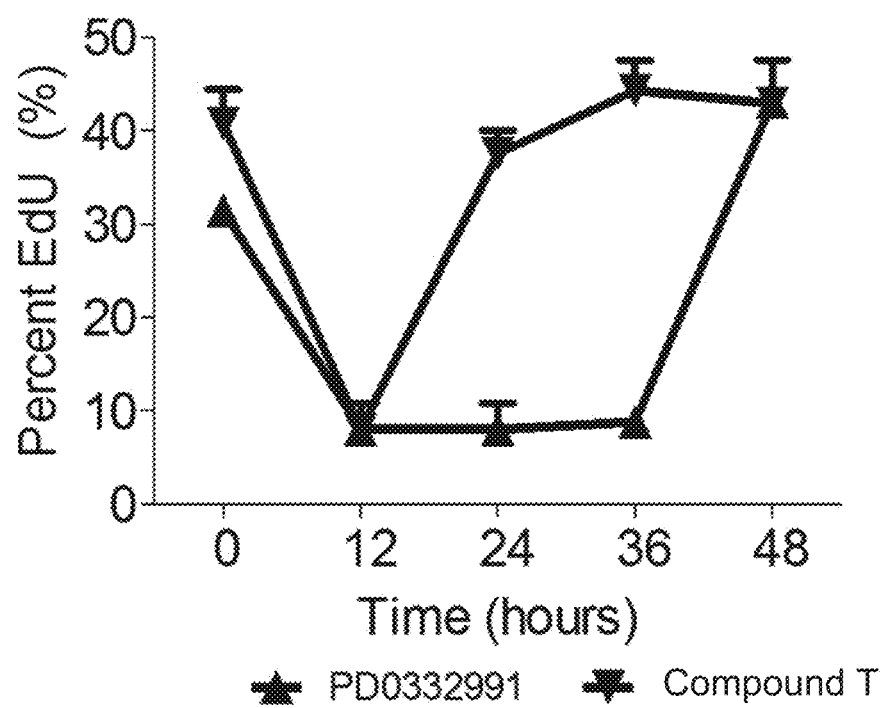
FIG. 6 is a graph of the percentage of EdU positive HSPC cells for mice treated with either PD0332991 (triangles) or compound T (upside down triangles) v. time after administration (hours) of the compound. Both compounds were administered at 150 mg/kg by oral gavage and the percentage of EdU positive HSPC cells was measured at 12, 24, 36 or 48 hours. As described in Example 157, a single oral dose of PD0332991 results in a sustained reduction of HSPC proliferation for greater than 36 hours. In contrast, a single oral dose of Compound T results in an initial reduction of HSPC proliferation at 12 hours, but proliferation of HSPCs resumes by 24 hours after dosage of Compound T.

FIG. 6 is a graph of the percentage of EdU positive HSPC cells for mice treated with either PD0332991 (triangles) or compound T (upside down triangles) v. time after administration (hours) of the compound. Both compounds were administered at 150 mg/kg by oral gavage. One hour prior to harvesting bone marrow, EdU was IP injected to label cycling cells. Bone marrow was harvested at 12, 24, 36, and 48 hours after compound treatment and the percentage of EdU positive HSPC cells was determined at each time point.

As seen in FIG. 6, a single oral dose of PD0332991 results in a sustained reduction in HSPCs for greater than 36 hours. In contrast, a single oral dose of Compound T results in an initial reduction of HSPC proliferation at 12 hours, but proliferation of HSPCs resumes by 24 hours after dosage of Compound T.

Example 158

Metabolic Stability

The metabolic stability of Compound T in comparison to PD0332991 was determined in human, dog, rat, monkey, and mouse liver microsomes. Human, mouse, and dog liver microsomes were purchased from Xenotech, and Sprague-Dawley rat liver microsomes were prepared by Absorption Systems. The reaction mixture comprising 0.5 mg/mL of liver microsomes, 100 mM of potassium phosphate, pH 7.4, 5 mM of magnesium chloride, and 1 uM of test compound was prepared. The test compound was added into the reaction mixture at a final concentration of 1 uM. An aliquot of the reaction mixture (without cofactor) was incubated in shaking water bath at 37 deg. C. for 3 minutes. The control compound, testosterone, was run simultaneously with the test compound in a separate reaction. The reaction was initiated by the addition of cofactor (NADPH), and the mixture was then incubated in a shaking water bath at 37 deg. C. Aliquots (100 µL) were withdrawn at 0, 10, 20, 30, and 60 minutes for the test compound and 0, 10, 30, and 60 minutes for testosterone. Test compound samples were immediately combined with 100 µL of ice-cold acetonitrile containing internal standard to terminate the reaction. Testosterone samples were immediately combined with 800 µL of ice cold 50/50 acetonitrile/dH2O containing 0.1% formic acid and internal standard to terminate the reaction. The samples were assayed using a validated LC-MS/MS method. Test compound samples were analyzed using the Orbitrap high resolution mass spectrometer to quantify the disappearance of parent test compound and detect the appearance of metabolites. The peak area response ration (PARR) to internal standard was compared to the PARR at time 0 to determine the percent of test compound or positive control remaining at time-point. Half-lives were calculated using GraphPad software, fitting to a single-phase exponential decay equation.

Half-life was calculated based on $t1/2=0.693k$, where k is the elimination rate constant based on the slope plot of natural logarithm percent remaining versus incubation time. When calculated half-life was longer than the duration of the experiment, the half-life was expressed as >the longest incubation time. The calculated half-life is also listed in parentheses. If the calculated half-life is >2× the duration of the experiment, no half-life was reported. The timely resumption of cellular proliferation is necessary for tissue repair, and therefore an overly long period of arrest is undesirable in healthy cells such as HSPCs. The characteristics of a CDK4/6 inhibitor that dictate its arresting duration are its pharmacokinetic (PK) and enzymatic half-lives. Once initiated, a G1-arrest in vivo will be maintained as long as circulating compound remains at an inhibitory level, and as long as the compound engages the enzyme. PD032991, for example, possesses an overall long PK half-life and a fairly slow enzymatic off-rate. In humans, PD0332991 exhibits a PK half-life of 27 hours (see Schwartz, G K et al. (2011) BJC, 104:1862-1868). In humans, a single administration of PD0332991 produces a cell cycle arrest of HSPC lasting approximately one week. This reflects the 6 days to clear the compound (5 half-lives×27 hour half-life), as well as an additional 1.5 to 2 days of inhibition of enzymatic CDK4/6 function. This calculation suggests that it takes a total of 7+days for normal bone marrow function to return, during which time new blood production is reduced. These observations may explain the severe granulocytopenia seen with PD0332991 in the clinic.

Further experiments were completed with Compound T and PD0332991 to compare the metabolic stability (half-life) in human, dog, rat, monkey, and mouse liver microsomes. As shown in FIG. 7, when analyzing the stability of the compounds in liver microsomes across species, the determinable half-life of Compound T is shorter in each species compared to that reported for PD0332991. Furthermore, as previously described above and in FIG. 4, it appears that PD0332991 also has an extended enzymatic half-life, as evidenced by the production of a pronounced cell cycle arrest in human cells lasting more than forty hours even after compound is removed from the cell culture media (i.e., in an in vitro wash-out experiment). As further shown in FIG. 4, removal of the compounds described herein from the culture media leads to a rapid resumption of proliferation, consistent with a rapid enzymatic off rate. These differences in enzymatic off rates translate into a marked difference in pharmacodynamic (PD) effect, as shown in FIGS. 2, 5C, and 6. As shown, a single oral dose of PD0332991 produces a 36+hour growth arrest of hematopoietic stem and progenitor cells (HSPCs) in murine bone marrow, which is greater than would be explained by the 6 hour PK half-life of PD0332991 in mice. In contrast, the effect of Compound T is much shorter, allowing a rapid re-entry into the cell cycle, providing exquisite in vivo control of HSPC proliferation.

Example 159

Efficacy of the CDK4/6 Inhibitor, Compound T) in HER2-Driven Breast Tumors

A HER2-driven model (Rb-positive) of breast cancer (Muller W J, Sinn E, Pattengale P K, Wallace R, Leder P. Single-step induction of mammary adenocarcinoma in transgenic mice bearing the activated c-neu oncogene. Cell 1988; 54: 105-15), that expresses c-neu (the mouse ortholog of human HER2) driven by the MMTV promoter was used in the following example. This model was chosen because previous studies in murine (Yu Q, Geng Y, Sicinski P. Specific protection against breast cancers by cyclin D1 ablation. Nature 2001; 411: 1017-21; Landis M W, Pawlyk B S, Li T, Sicinski P, Hinds P W. Cyclin D1-dependent kinase activity in murine development and mammary tumorigenesis. Cancer Cell 2006; 9: 13-22; Reddy H K, Mettus R V, Rane S G, Grana X, Litvin J, Reddy E P. Cyclin-dependent kinase 4 expression is essential for neu-induced breast tumorigenesis. Cancer Res 2005; 65: 10174-8; Yu Q, Sicinska E, Geng Y, Ahnstrom M, Zagozdzon A, Kong Y, et al. Requirement for CDK4 kinase function in breast cancer. Cancer Cell 2006; 9: 23-32.) and human HER2-positive breast cancer (An H X, Beckmann M W, Reifenberger G, Bender H G, Niederacher D. Gene amplification and overexpression of CDK4 in sporadic breast carcinomas is associated with high tumor cell proliferation. Am J Pathol 1999; 154: 113-8; Samady L, Dennis J, Budhram-Mahadeo V, Latchman D S. Activation of CDK4 gene expression in human breast cancer cells by the Brn-3b POU family transcription factor. Cancer Biol Ther 2004; 3: 317-23; Takano Y, Takenaka H, Kato Y, Masuda M, Mikami T, Saegusa M, et al. Cyclin D1 overexpression in invasive breast cancers: correlation with cyclin-dependent kinase 4 and oestrogen receptor overexpression, and lack of correlation with mitotic activity. J Cancer Res Clin Oncol 1999; 125: 505-12) suggest that these tumors require CDK4/6 and CCND1 for progression and maintenance.

MMTV-neu mice were generated and observed post-lactation, with tumors observed with a median latency of approximately 25 weeks. Mice were enrolled in therapy studies when tumors reached a standard size (50-60 mm3) that permitted easy serial assessment. Tumor-bearing mice were continuously treated with Compound T added to their chow (100 mg/kg/d or 150 mg/kg/d). MMTV-c-neu (control, n=9; Compound T 100 mg/kg, n=7; Compound T 150 mg/kg, n=6) mice were examined weekly to assess tumor development by palpation. Tumor volumes were calculated by the formula, Volume=[(width)$^2$×length]/2. Tumor-bearing mice were euthanized at the indicated times due to predefined morbidity, tumor ulceration, or a tumor size of more than 1.5 cm in diameter.

Figure 8:
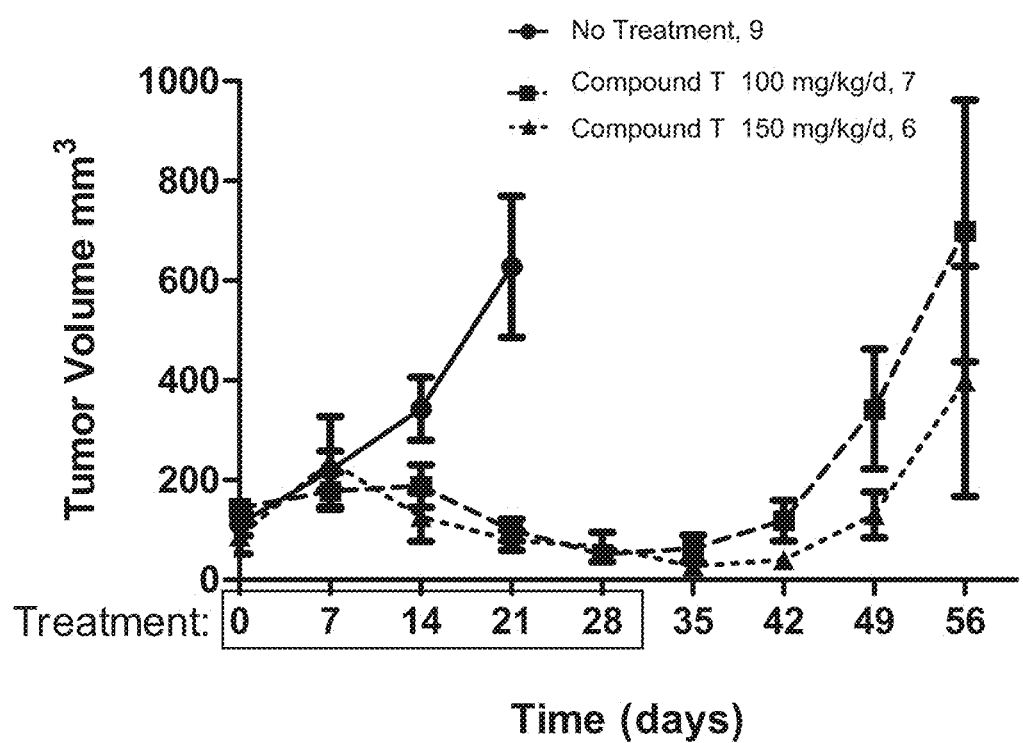
FIG. 8 is a graph showing the tumor volume ($mm^3$) in MMTV-c-neu (Rb-positive) tumor bearing mice treated with Compound T at 100 mg/kg/day (squares) or 150 mg/kg/day (triangles) v. time after administration (days) of Compound T. Tumor-bearing MMTV-c-neu mice (control, n=9; compound T, 100 mg/kg, n=7; compound T, 150 mg/kg, n=6) were treated with either compound T delivered in chow or standard chow (circles). Day 0 represents the first day of compound treatment. Mice were treated with compound T for 28 days (as represented by the box around the numbers on the x-axis indicating days of treatment administration). After 28 days, all mice were fed standard chow. Tumor volumes were recorded weekly (up to 56 days) and graphed as mean±standard error of the mean. As described in Example 159, continuous treatment with Compound T (100 mg/kg/d or 150 mg/kg/d) led to a marked reduction in tumor volume during a 28 day course of therapy compared to control.
Figure 9:
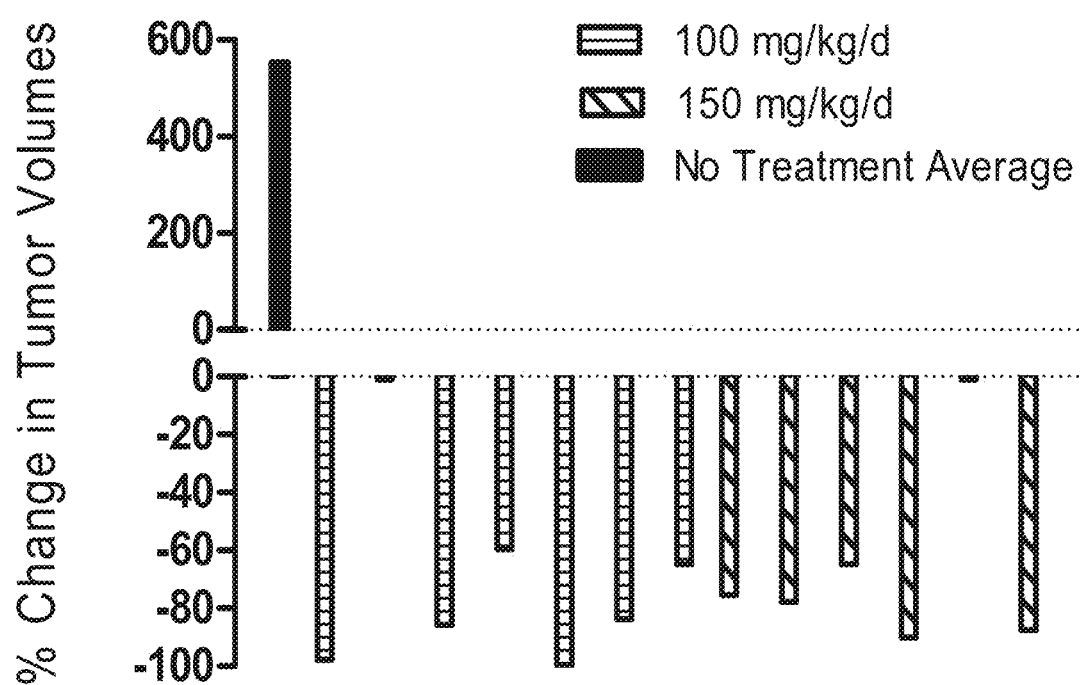
FIG. 9 is a waterfall plot of the percentage change in MMTV-c-neu mice (Rb-positive) tumor volumes for each mouse treated with Compound T at either 100 mg/kg (horizontal lined box) or 150 mg/kg (slanted lined box). Tumor volumes were compared to the average tumor size of untreated animals on day 21. Tumor volumes for mice treated with compound T represent the best response seen on day 28 or beyond. Negative values indicate tumor shrinkage.

As shown in FIGS. 8 and 9, continuous treatment with Compound T (100 mg/kg/d or 150 mg/kg/d) led to a marked reduction in tumor volume during a 28 day course of therapy. Several tumors displayed complete tumor regression and no resistance to Compound T was noted during the 28 day course of therapy. These data show that this HER2-driven mouse model is 'addicted' to CDK4/6 activity for proliferation and Compound T is an effective agent in CDK4/6 dependent, Rb-positive tumors.

Example 160

Efficacy of CDK4/6 Inhibitors (Compound T, Compound GG, and Compound U) in HER2-Driven Breast Tumors Preclinical characterization of compound T, compound GG, and compound U indicates that they inhibit CDK4 and CDK6 with an IC$_{50}$ of 0.7-1.0 nM and 5-6 nM, respectively. In tumor cells with functional Rb protein, these compounds potently inhibit Rb phosphorylation resulting in a G1 arrest. The in vivo efficacy of the CDK4/6 inhibitors compound T, compound GG, and compound U was tested in the genetically engineered mouse model of luminal breast cancer. Tumors were serially assessed weekly using caliper measurements. Therapeutic intervention began once tumors reached 40-64 mm$^3$. Tumor volume was calculated using the formula ((Width)×Length)/2. All three compounds were administered orally via medicated diets (100 mg/kg/d). Medicated diets were administered for 28 consecutive days and then stopped. RECIST criteria were used to assess objective response rates. The objective response rates were categorized based on the percentage change in tumor volume, using the following categories: CR (complete response)=100% response; PR (partial response)=at least a 30% decrease; SD (stable disease)=no change (not a PR and not a PD); and PD (progressive disease)=20% increase.

Figure 11:
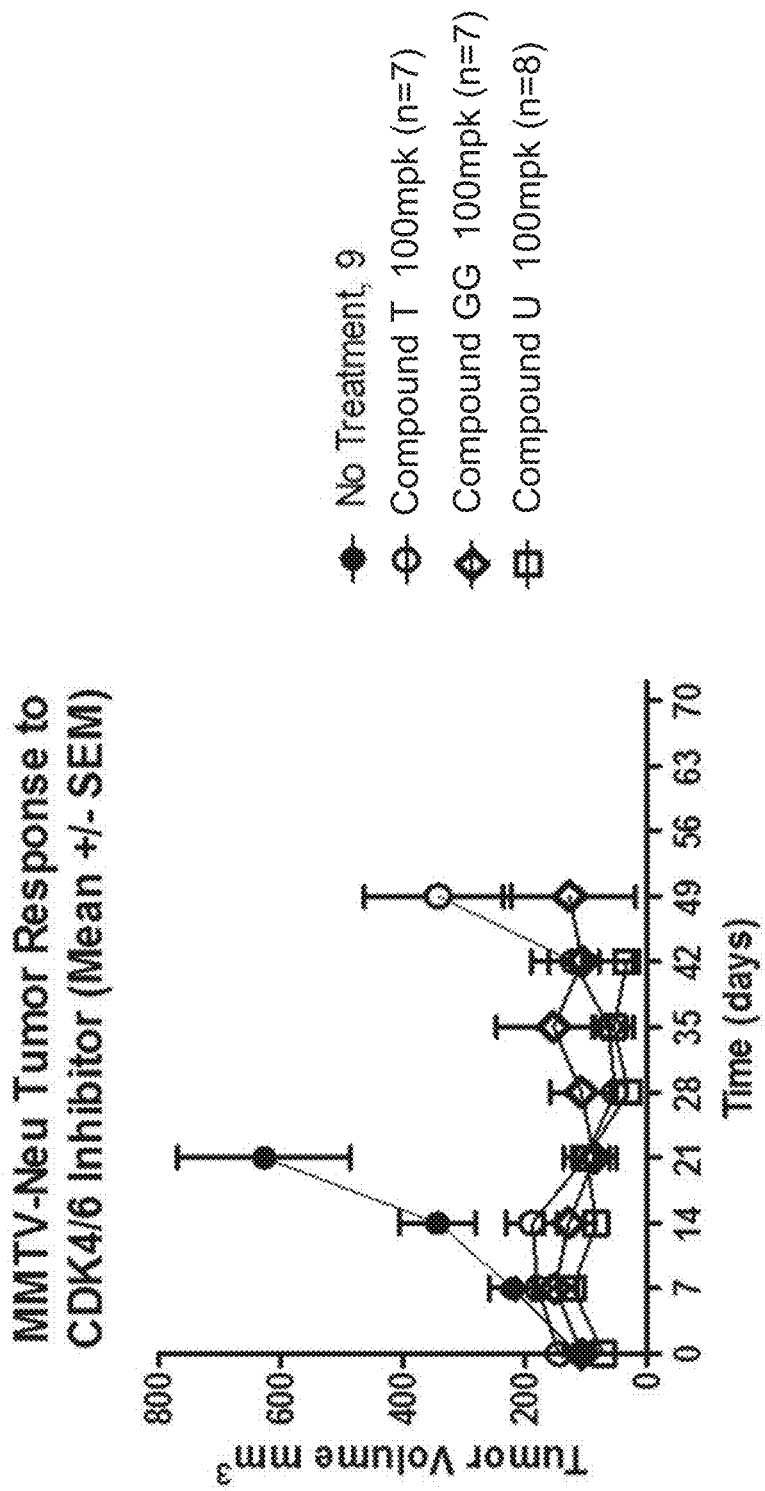
FIG. 11 is a graph showing the tumor volume ($mm^3$) in MMTV-c-neu (Rb-positive) tumor bearing mice treated with Compound T (open circles), Compound GG (diamonds), or Compound U (squares) v. time after administration of each compound (days). Tumor-bearing MMTV-c-neu mice (control, n=9; compound T, 100 mg/kg, n=7; compound GG, 100 mg/kg, n=7; compound U, 100 mg/kg, n=8) were treated with compound delivered in chow or standard chow (closed circles). Day 0 represents the first day of compound treatment. Mice were treated with compound for 28 days (as represented by the box around the numbers on the x-axis indicating days of treatment administration). After 28 days, all mice were fed standard chow. Tumor volumes were recorded weekly (up to 56 days) and graphed as mean±standard error of the mean. As described in Example 160, continuous treatment with compounds T, GG, or U led to a marked reduction in tumor volume during a 28 day course of therapy, with compounds T and U showing a 100% objective response rate, while compound GG showed an 85% objective response rate.
Figure 12:
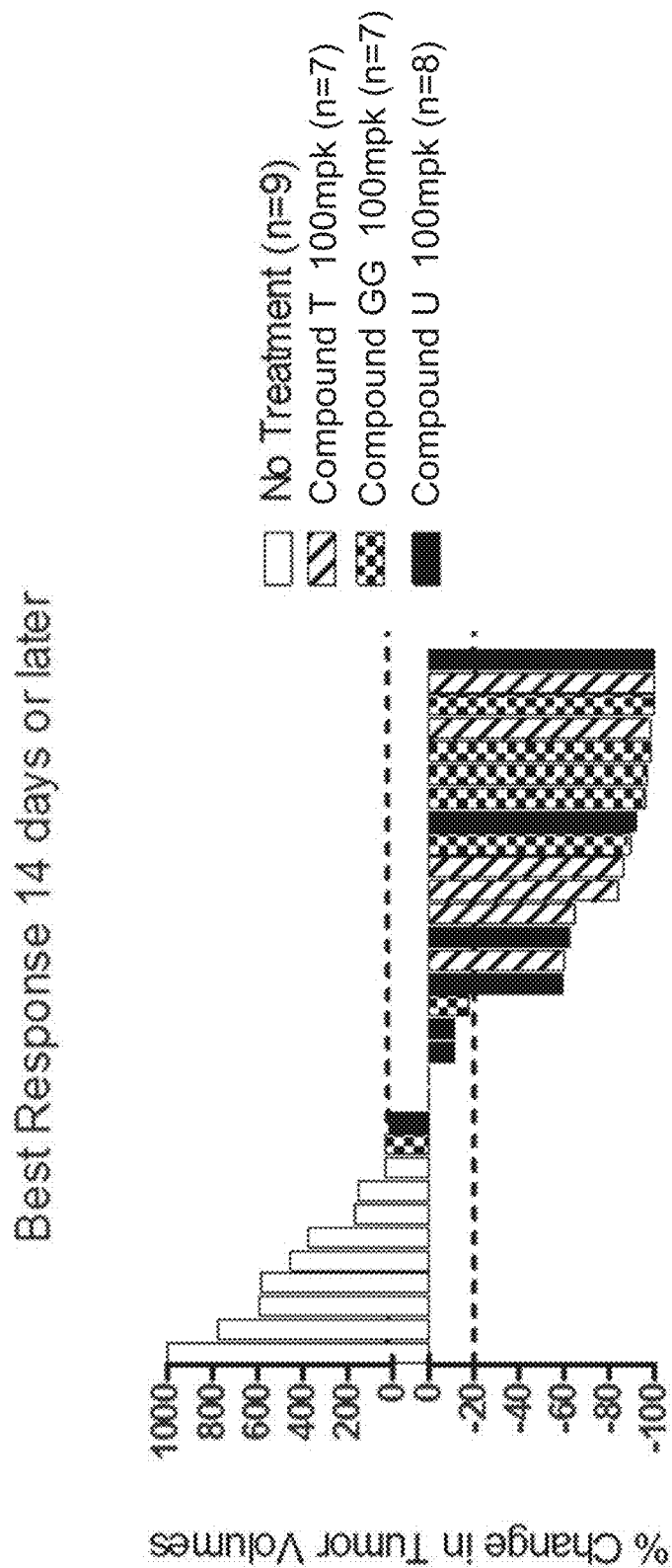
FIG. 12 is a waterfall plot of the percentage change in MMTV-c-neu (Rb-positive) tumor volumes for each mouse treated with 100 mg/kg compound T (bars with diagonal lines, n=7), 100 mg/kg compound GG (black and white boxed bars, n=7), 100 mg/kg compound U (filled bars, n=8), or no treatment (open bars, n=9). Tumor volumes were compared to the average tumor size of untreated animals on day 21. Tumor volumes for mice treated with compound T, GG, or U represent the best response seen on day 14 or beyond. Negative values indicate tumor shrinkage. Negative values indicate tumor shrinkage. As described in Example 160, continuous treatment with compounds T, GG, or U led to a marked reduction in tumor volume during a 28 day course of therapy.

As shown in FIG. 10, objective responses were noted in mice treated with compound T, compound GG, and compound U. Treatment groups were well tolerated with no clinical signs of toxicity, no weight loss and no deaths associated with toxicity. The linear regression t-test was used to determine statistical significance of tumor volume growth over time. All three cohorts were statistically significant compared to non-treated cohorts; compound T, $p<0.0001$; compound GG, $p=0.0001$; compound U, $p<0.0001$. As shown in FIG. 10, the number of animals in each objective category was determined. Compound T was found to have a 100% objective response rate (n=7), Compound GG was found to have an 85% objective response rate (n=7), and Compound U was found to have a 100% objective response rate (n=8). In FIG. 11, the tumor volumes from the MMTV-Neu mice treated with compound T, compound GG, and compound U are shown, with tumor volumes being measured every seven days. In FIG. 12, the data for the best response (14 days or later) is shown for each individual tumor. Taken together, these data show that continuous treatment with compound T (100 mg/kg), compound GG, (100 mg/kg), or compound U (100 mg/kg) led to a marked decrease in tumor volume during a 28 day course of therapy.

Example 161

Cell Cycle Arrest by Compound T in CDK4/6-Dependent Cells

To test the ability of CDK4/6 inhibitors to induce a clean G1-arrest, a cell based screening method was used consisting of two CDK4/6-dependent cell lines (tHS68 and WM2664; Rb-positive) and one CDK4/6-independent (A2058; Rb-negative) cell line. Twenty-four hours after plating, each cell line was treated with Compound T in a dose dependent manner for 24 hours. At the conclusion of the experiment, cells were harvested, fixed, and stained with propidium iodide (a DNA intercalator), which fluoresces strongly red (emission maximum 637 nm) when excited by 488 nm light. Samples were run on Dako Cyan flow cytometer and >10,000 events were collected for each sample. Data were analyzed using FlowJo 2.2 software developed by TreeStar, Inc.

Figure 29A:
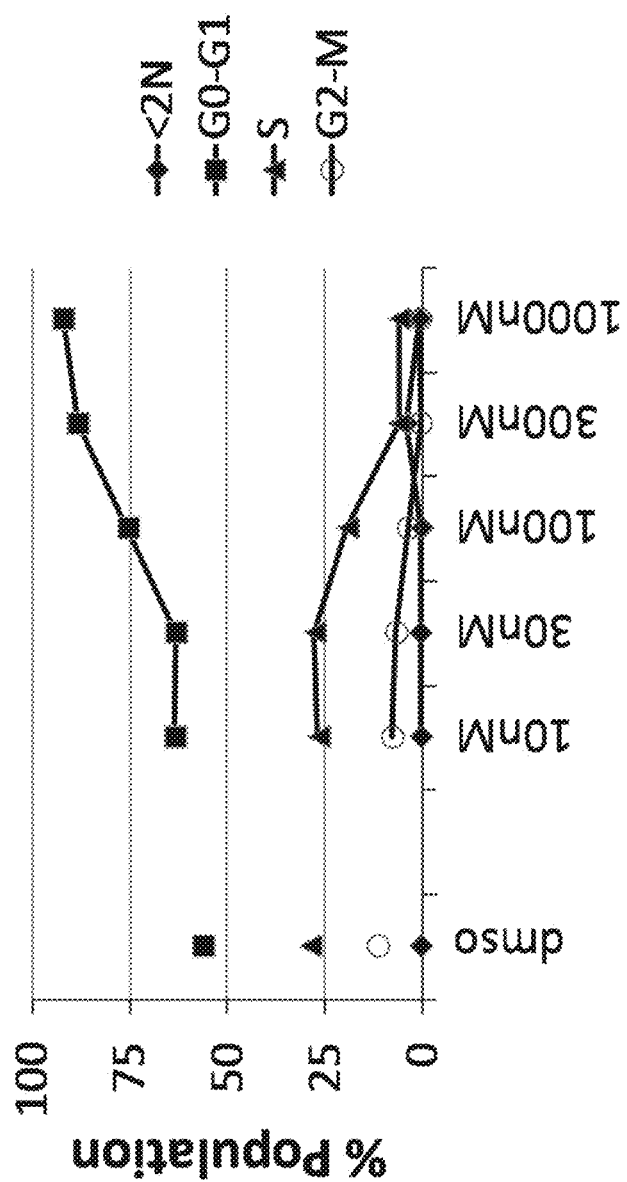
FIG. 29A is a graph of the percentage of cells in G2-M phase (open circles), S phase (triangles), G0-G1 phase (squares), <2N (diamonds) vs. variable concentration (nM) of compound T in tHS68 cells. The CDK4/6-dependent cell line (tHS68) was treated with the indicated concentrations of Compound T for 24 hours. Following treatment of Compound T, cells were harvested and analyzed for cell cycle distribution. As described in Example 161, tHS68 cells show a clean G1 arrest accompanied by a corresponding decrease in the number of cells in S-phase.
Figure 29C:
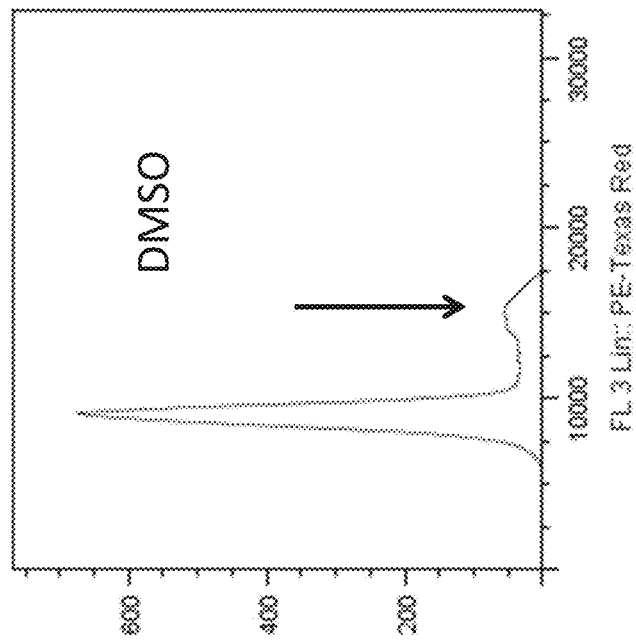
FIG. 29C is a graph of the number of WM2664 cells (CDK4/6-dependent cell line) vs. the DNA content of the cells (as measured by propidium iodide). Cells were treated with DMSO for 24 hours, harvested, and analyzed for cell cycle distribution.
Figure 29B:
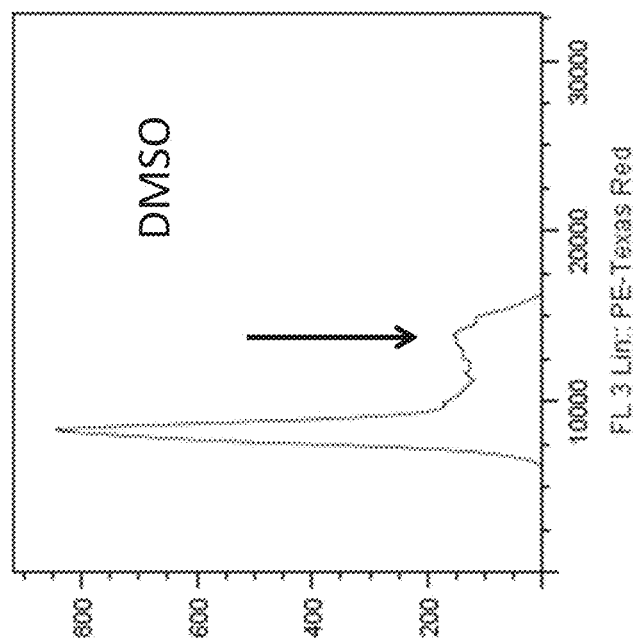
FIG. 29B is a graph of the number of tHS68 cells (CDK4/6-dependent cell line) vs. the DNA content of the cells (as measured by propidium iodide). Cells were treated with DMSO for 24 hours, harvested, and analyzed for cell cycle distribution.
Figures 29F, 29G:
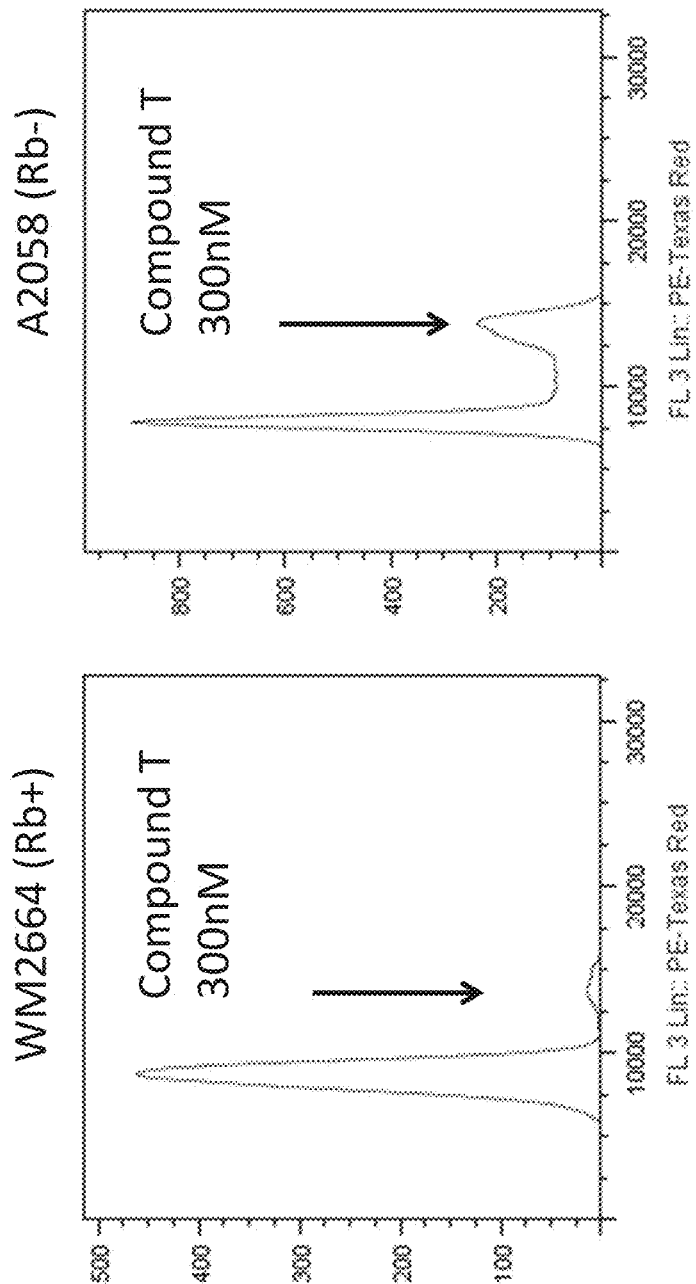
FIG. 29F is a graph of the number of WM2664 cells (CDK4/6-dependent cell line) vs. the DNA content of the cells (as measured by propidium iodide) after treatment with Compound T. Cells were treated with Compound T (300 nM) for 24 hours, harvested, and analyzed for cell cycle distribution. As described in Example 161, treatment of WM2664 cells with Compound T causes a loss of the S-phase peak (indicated by arrow).
FIG. 29G is a graph of the number of A2058 cells (CDK4/6-independent cell line) vs. the DNA content of the cells (as measured by propidium iodide) after treatment with Compound T. Cells were treated with Compound T (300 nM) for 24 hours, harvested, and analyzed for cell cycle distribution. As described in Example 161, treatment of A2058 cells with Compound T does not cause a loss of the S-phase peak (indicated by arrow).

In FIG. 29A, results show that Compound T induces a robust G1 cell cycle arrest, as nearly all cells are found in the G0-G1 phase upon treatment with increasing amounts of Compound T. In FIG. 29A, the results show that in CDK4/6-dependent cell lines, Compound T induced a robust G1 cell cycle arrest with an EC$_{50}$ of 80 nM in tHS68 cells with a corresponding reduction in S-phase ranging from 28% at baseline to 6% at the highest concentration shown. Upon treatment with Compound T (300 nM), there was a similar reduction in the S-phase population and an increase in G1-arrested cells in both CDK4/6-dependent cell lines (tHS68 (Compare FIGS. 29B and 29E) and WM2664 (Compare FIGS. 29C and 29F)), but not in the CDK4/6-independent (A2058; Compare FIGS. 29D and 29G) cell line. The CDK4/6-independent cell line shows no effect in the presence of inhibitor.

Example 162

Compound T Inhibits Phosphorylation of RB

Figure 30:
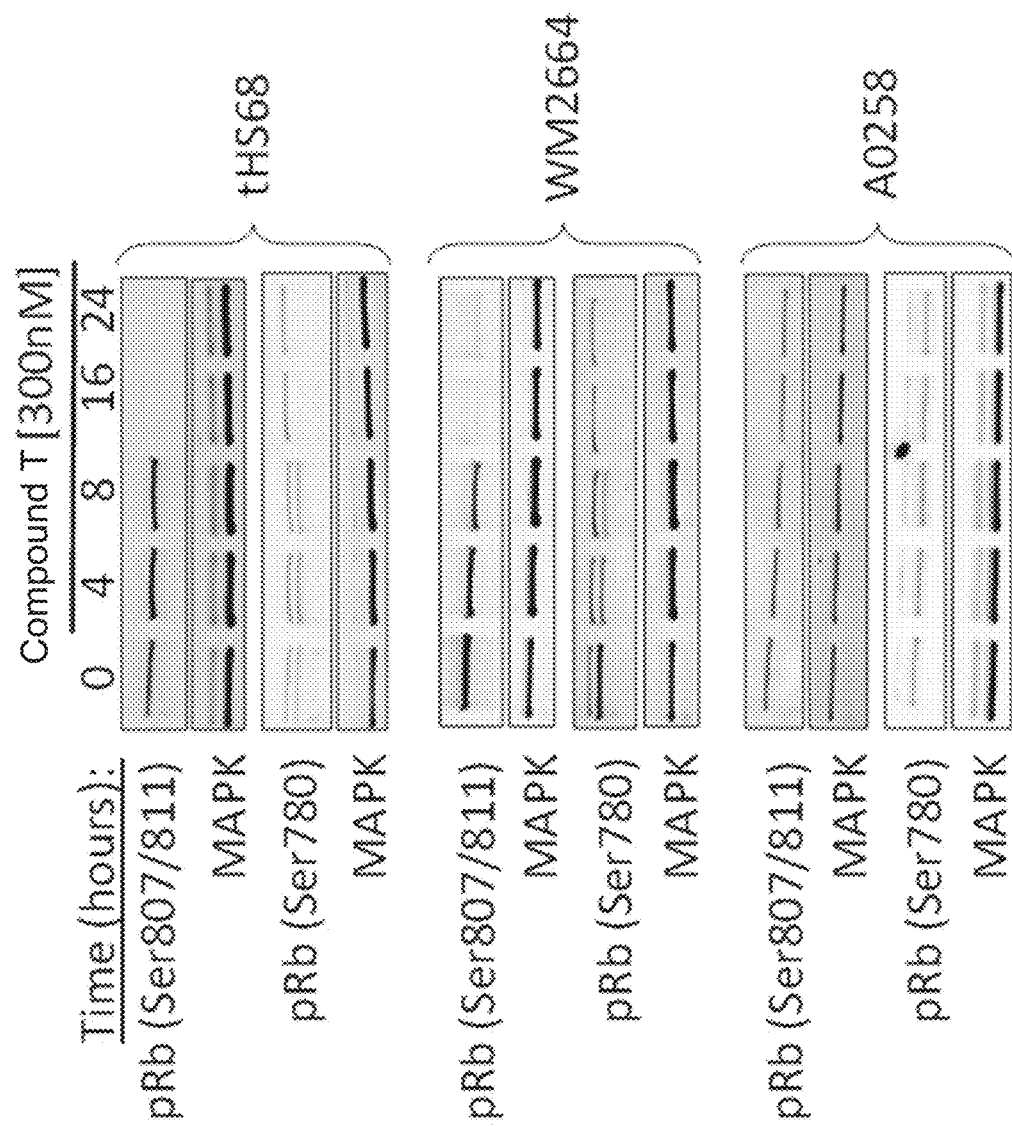
FIG. 30 is a Western blot showing the phosphorylation levels of Rb at Ser807/811 and Ser780 after treatment with Compound T. CDK4/6-dependent (tHS68 or WM2664) and CDK4/6-independent cell lines (A2058) were treated with Compound T (300 nM) for the indicated times (0, 4, 8, 16, and 24 hours). MAPK levels are shown as a control for protein levels. Following treatment, cells were harvested and analyzed for Rb-phosphorylation by western blot analysis. As described in Example 162, Compound T treatment resulted in reduced Rb-phosphorylation starting 16 hours after treatment in CDK4/6-dependent cell lines (tHS68 and WM2664), but not in the CDK4/6-independent cell line (A2058).

The CDK4/6-cyclin D complex is essential for progression from G1 to the S-phase of the DNA cell cycle. This complex phosphorylates the retinoblastoma tumor suppressor protein (Rb). To demonstrate the impact of CDK4/6 inhibition on Rb phosphorylation (pRb), Compound T was exposed to three cell lines, two CDK4/6 dependent (tHS68, WM2664; Rb-positive) and one CDK4/6 independent (A2058; Rb-negative). Twenty four hours after seeding, cells were treated with Compound T at 300 nM final concentration for 4, 8, 16, and 24 hours. Samples were lysed and protein was assayed by western blot analysis. Rb phosphorylation was measured at two sites targeted by the CDK4/6-cyclin D complex, Ser780 and Ser807/811 using species specific antibodies. Results demonstrate that Compound T blocks Rb phosphorylation in Rb-dependent cell lines by 16 hours post exposure, while having no effect on Rb-independent cells (FIG. 30).

This specification has been described with reference to embodiments of the invention. The invention has been described with reference to assorted embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the invention.

We claim:

1. A method for the treatment of a human with cancer, wherein the cancer is Retinoblastoma-positive (Rb) and selected from the group consisting of breast cancer, colorectal cancer, ovarian cancer, non-small cell lung cancer, and prostate cancer, comprising administering to the human an effective amount of a cyclin dependent kinase 4/6 (CDK4/6) inhibitor having the structure:

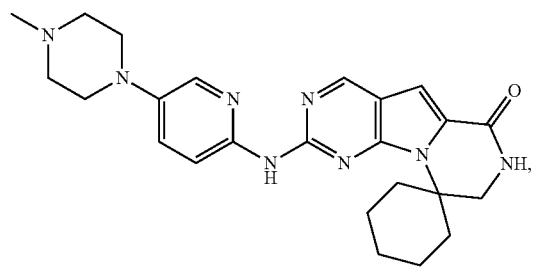 [SMILES: CN1CCN(c2ccc(Nc3ncc4cc5n(c4n3)C3(CCCCC3)CNC5=O)nc2)CC1]

or a pharmaceutically acceptable salt thereof, and administering to the human an effective amount of a chemotherapeutic agent, wherein the CDK4/6 inhibitor is administered 24 hours or less prior to administration of the chemotherapeutic agent.

2. The method of claim 1, wherein the cancer is breast cancer.

3. The method of claim 1, wherein the cancer is colorectal cancer.

4. The method of claim 1, wherein the cancer is ovarian cancer.

5. The method of claim 1, wherein the cancer is non-small cell lung cancer.

6. The method of claim 1, wherein the cancer is prostate cancer.

7. The method of claim 1, wherein the CDK4/6 inhibitor is administered 4 hours or less prior to administration of the chemotherapeutic agent.

8. A method for treating a human with Retinoblastoma-positive breast cancer comprising administering to the human an effective amount of a cyclin dependent kinase 4/6 (CDK4/6) inhibitor having the structure:

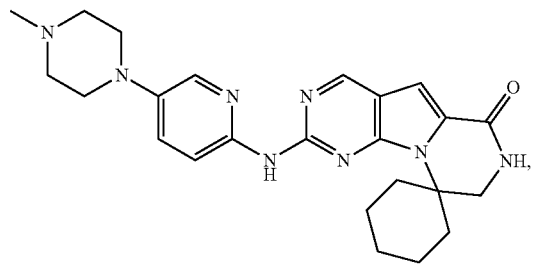 [SMILES: CN1CCN(c2ccc(Nc3ncc4cc5n(c4n3)C3(CCCCC3)CNC5=O)nc2)CC1]

or a pharmaceutically acceptable salt thereof, and administering to the human an effective amount of a chemotherapeutic agent, wherein the CDK4/6 inhibitor is administered 24 hours or less prior to administration of the chemotherapeutic agent.

9. The method of claim 8, wherein the chemotherapeutic agent is doxorubicin.

10. The method of claim 8, wherein the chemotherapeutic agent is paclitaxel.

11. The method of claim 8, wherein the chemotherapeutic agent is carboplatin.

12. The method of claim 8, wherein the chemotherapeutic agent is gemcitabine.

13. The method of claim 8, wherein the chemotherapeutic agent is cisplatin.

14. The method of claim 8, wherein the CDK4/6 inhibitor is administered 4 hours or less prior to administration of the chemotherapeutic agent.

15. The method of claim 8, wherein the breast cancer is estrogen-receptor positive.

16. A method for treating a human with Retinoblastoma (Rb)-positive non-small cell lung cancer comprising administering to the human an effective amount of a cyclin dependent kinase 4/6 (CDK4/6) inhibitor having the structure

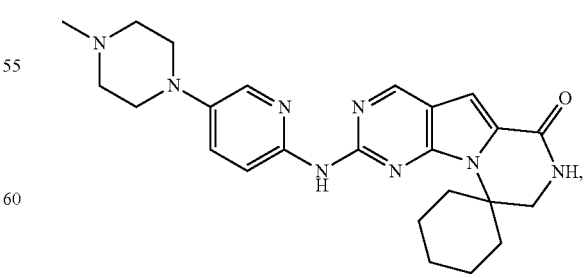

or a pharmaceutically acceptable salt thereof, and administering to the human an effective amount of a chemotherapeutic agent, wherein the CDK4/6 inhibitor is administered 24 hours or less prior to administration of the chemotherapeutic agent.

17. The method of claim 16, wherein the chemotherapeutic agent is docetaxel.

18. The method of claim 16, wherein the chemotherapeutic agent is doxorubicin.

19. The method of claim 16, wherein the chemotherapeutic agent is paclitaxel.

20. The method of claim 16, wherein the chemotherapeutic agent is etoposide.

21. The method of claim 16, wherein the chemotherapeutic agent is vinblastine sulfate.

22. The method of claim 16, wherein the chemotherapeutic agent is carboplatin.

23. The method of claim 16, wherein the chemotherapeutic agent is gemcitabine.

24. The method of claim 16, wherein the chemotherapeutic agent is cisplatin.

25. A method for treating a human with Retinoblastoma-positive colorectal cancer comprising administering to the human an effective amount of a cyclin dependent kinase 4/6 (CDK4/6) inhibitor having the structure

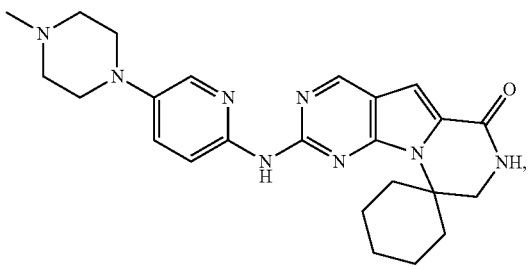 [SMILES: CN1CCN(c2ccc(Nc3ncc4cc5n(c4n3)C3(CCCCC3)CNC5=O)nc2)CC1]

or a pharmaceutically acceptable salt thereof, and administering to the human an effective amount of a chemotherapeutic agent, wherein the CDK4/6 inhibitor is administered 24 hours or less prior to administration of the chemotherapeutic agent.

26. The method of claim 25, wherein the chemotherapeutic agent is 5-fluorouracil.

27. The method of claim 25, wherein the chemotherapeutic agent is capecitabine.

28. The method of claim 25, wherein the colorectal cancer is metastatic colorectal cancer.

29. The method of claim 25, wherein the CDK4/6 inhibitor is administered 4 hours or less prior to administration of the chemotherapeutic agent.

30. The method of claim 1, wherein the cancer is colorectal cancer.

31. The method of claim 1, wherein the chemotherapeutic agent is topotecan HC1.

32. The method of claim 1, wherein the chemotherapeutic agent is docetaxel.

33. The method of claim 1, wherein the chemotherapeutic agent is doxorubicin.

34. The method of claim 1, wherein the chemotherapeutic agent is doxorubicin HC1.

35. The method of claim 1, wherein the chemotherapeutic agent is paclitaxel.

36. The method of claim 1, wherein the chemotherapeutic agent is etoposide.

37. The method of claim 1, wherein the chemotherapeutic agent is vinblastine sulfate.

38. The method of claim 1, wherein the chemotherapeutic agent is carboplatin.

39. The method of claim 1, wherein the chemotherapeutic agent is gemcitabine.

40. The method of claim 1, wherein the chemotherapeutic agent is cisplatin.

41. The method of claim 1, wherein the chemotherapeutic agent is 5-fluorouracil.

42. The method of claim 1, wherein the chemotherapeutic agent is capecitabine.

43. The method of claim 1, wherein the chemotherapeutic agent is cyclophosphamide.

44. The method of claim 8, wherein the chemotherapeutic agent is doxorubicin HC1.

45. The method of claim 8, wherein the chemotherapeutic agent is cyclophosphamide.

46. The method of claim 8, wherein the breast cancer is advanced breast cancer.

47. The method of claim 8, wherein the breast cancer is HER2-negative breast cancer.

48. The method of claim 8, wherein the breast cancer is HER2-positive breast cancer.

49. The method of claim 8, wherein the breast cancer is estrogen-receptor negative breast cancer.

50. The method of claim 8, wherein the breast cancer is estrogen-receptor positive, HER2-negative advanced breast cancer.

51. The method of claim 8, wherein the breast cancer is progesterone receptor-negative breast cancer.

52. The method of claim 8, wherein the breast cancer is progesterone receptor-positive breast cancer.

53. The method of claim 16, wherein the chemotherapeutic agent is topotecan HC1.

54. The method of claim 16, wherein the chemotherapeutic agent is cyclophosphamide.

55. The method of claim 16, wherein the chemotherapeutic agent is doxorubicin HC1.

56. The method of claim 16, wherein the CDK4/6 inhibitor is administered 4 hours or less prior to administration of the chemotherapeutic agent.

57. A method for the treatment of a human with cancer, wherein the cancer is Retinoblastoma-positive (Rb), comprising administering to the human an effective amount of a cyclin dependent kinase 4/6 (CDK4/6) inhibitor having the structure:

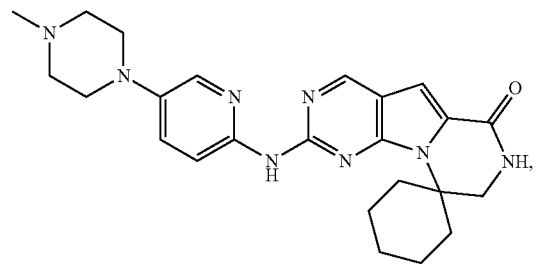 [SMILES: CN1CCN(c2ccc(Nc3ncc4cc5n(c4n3)C3(CCCCC3)CNC5=O)nc2)CC1]

or a pharmaceutically acceptable salt thereof, and administering to the human an effective amount of a chemotherapeutic agent, wherein the CDK4/6 inhibitor is administered 24 hours or less prior to administration of the chemotherapeutic agent.

58. The method of claim 57, wherein the CDK4/6 inhibitor is administered 4 hours or less prior to administration of the chemotherapeutic agent.

59. The method of claim 57, wherein the Rb-positive cancer is colon cancer.

60. The method of claim 57, wherein the RB-positive cancer is bladder cancer.

61. The method of claim 57, wherein the Rb-positive cancer is an adenocarcinoma.

62. The method of claim 57, wherein the Rb-positive cancer is stomach cancer.

63. The method of claim 57, wherein the RB-positive cancer is liver cancer.

64. The method of claim 63, wherein the RB-positive liver cancer is hepatocellular carcinoma.

65. The method of claim 63, wherein the Rb-positive liver cancer is cholangiocarcinoma.

66. The method of claim 57, wherein the Rb-positive cancer is pancreatic cancer.

67. The method of claim 57, wherein the Rb-positive cancer is cancer of the esophagus.

68. The method of claim 57, wherein the Rb-positive cancer is thyroid cancer.

69. The method of claim 57, wherein the Rb-positive cancer is kidney cancer.

70. The method of claim 69, wherein the Rb-positive cancer is renal cell carcinoma.

71. The method of claim 57, wherein the chemotherapeutic agent is topotecan HC1.

72. The method of claim 57, wherein the chemotherapeutic agent is docetaxel.

73. The method of claim 57, wherein the chemotherapeutic agent is doxorubicin.

74. The method of claim 57, wherein the chemotherapeutic agent is doxorubicin HC1.

75. The method of claim 57, wherein the chemotherapeutic agent is paclitaxel.

76. The method of claim 57, wherein the chemotherapeutic agent is etoposide.

77. The method of claim 57, wherein the chemotherapeutic agent is vinblastine sulfate.

78. The method of claim 57, wherein the chemotherapeutic agent is carboplatin.

79. The method of claim 57, wherein the chemotherapeutic agent is gemcitabine.

80. The method of claim 57, wherein the chemotherapeutic agent is cisplatin.

81. The method of claim 57, wherein the chemotherapeutic agent is 5-fluorouracil.

82. The method of claim 57, wherein the chemotherapeutic agent is capecitabine.

83. The method of claim 57, wherein the chemotherapeutic agent is cyclophosphamide.

84. The method of claim 57, wherein the chemotherapeutic agent is selected from the group consisting of daunorubicin, daunorubicin HC1, and daunorubicin citrate.

85. The method of claim 57, wherein the chemotherapeutic agent is methotrexate.

* * * * *